(12) United States Patent
Tang et al.

(10) Patent No.: US 8,367,710 B2
(45) Date of Patent: Feb. 5, 2013

(54) BICYCLO-SUBSTITUTED PYRAZOLON AZO DERIVATIVES, PREPARATION PROCESS AND PHARMACEUTICAL USE THEREOF

(75) Inventors: Peng Cho Tang, Shanghai (CN); Hejun Lü, Shanghai (CN); Hao Zheng, Shanghai (CN); Yiqian Chen, Shanghai (CN); Hongbo Fei, Shanghai (CN); Shenglan Wang, Shanghai (CN); Li Wang, Shanghai (CN)

(73) Assignees: Jiangsu Hengrui Medicine Co. Ltd., Jiangsu (CN); Shanghai Hengrui Pharmaceutical Co. Ltd., Shanghai (CN)

( * ) Notice: Subject to any disclaimer, the term of this patent is extended or adjusted under 35 U.S.C. 154(b) by 158 days.

(21) Appl. No.: 12/812,119
(22) PCT Filed: Jan. 4, 2009
(86) PCT No.: PCT/CN2009/000001
§ 371 (c)(1),
(2), (4) Date: Jul. 8, 2010

(87) PCT Pub. No.: WO2009/092276
PCT Pub. Date: Jul. 30, 2009

(65) Prior Publication Data
US 2010/0316601 A1 Dec. 16, 2010

(30) Foreign Application Priority Data
Jan. 10, 2008 (CN) .......................... 2008 1 0000346

(51) Int. Cl.
*A61K 31/4196* (2006.01)
*A61K 31/41* (2006.01)
*A61K 38/20* (2006.01)
*C07D 231/46* (2006.01)
*C07D 403/12* (2006.01)
*C07D 405/10* (2006.01)
*C07D 231/26* (2006.01)
*A61P 7/00* (2006.01)

(52) U.S. Cl. ..... 514/381; 514/404; 548/253; 548/364.1; 548/364.4; 548/365.7; 548/371.1

(58) Field of Classification Search .................. None
See application file for complete search history.

(56) References Cited

U.S. PATENT DOCUMENTS
2009/0131659 A1 5/2009 Miyaji et al.

FOREIGN PATENT DOCUMENTS
| JP | 11001477 | 1/1999 |
| WO | WO 96/40750 | 12/1996 |
| WO | WO 98/25965 | 6/1998 |
| WO | WO 99/11262 | 3/1999 |
| WO | WO 00/28987 | 5/2000 |
| WO | WO 00/35446 | 6/2000 |
| WO | WO 01/07423 A1 | 1/2001 |
| WO | WO 01/17349 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |
| WO | WO 2006/064957 A1 | 6/2006 |
| WO | WO 2007/044982 A2 | 4/2007 |

OTHER PUBLICATIONS

Byrn et al. Solid-State Chemistry of Drugs, 2d, 1999, Chapter 11 Hydrates and Solvates/hydrates, 233-247, 233.*
Wendling; F., et al. "Mpl ligand or Thrombopoietin: Biological activities", Biotherapy 10, 1998, pp. 269-277.
Kuter, D. J., "Thrombopoietin: Biology and Clinical Applications", The Oncologist 1996, pp. 98-106.
Metcalf, D., "Thrombopoietin—at last", Nature—vol. 369, Jun. 16, 1997, pp. 519-520.
Vigon, I. et al., "Molecular cloning and charaterizatino of MPL, the human homolog of the v-mpl oncogene: Identification of a member of the hemotopoietic growth factor receptor superfamily", Proc. Natl. Acad. Sci, vol. 89, Jun. 1992, pp. 5640-5644.
Kuter, D. J. et al., "The purification of megapoietin: A physiological regulator of megakaryocyte growth and platelet production", Proc. Natl. Acad. Sci., vol. 91, Nov. 1994, pp. 11104-11108.
Bartley, T. D. et al., "Identification and Cloning of a Megakaryocyte Growth and Development Factor That is a Ligand for the cytokine Receptor Mpl", Cell, vol. 77, Jul. 1, 1994, pp. 1117-1124.
Kaushansky, K. et al., "Promotion of megakaryocyte progenitor expansion and differentiation by the c-Mpl ligand thrombopoietin", Nature—vol. 369, Jun. 16, 1994, pp. 568-571.
Wendling, F. et al., c-Mpl ligand is a humoral regulator of megakaryocytopoiesis, Nature—vol. 369, Jun. 16, 1994, pp. 571-574.
De Sauvage, F.J. et al., "Stimulation of megakaryocytopoiesis and thrombopoiesis by the c-Mpl ligand", Nature—vol. 369, Jun. 16, 1994, pp. 533-538.

* cited by examiner

*Primary Examiner* — Kamal Saeed
(74) *Attorney, Agent, or Firm* — Ryan L. Marshall; Brinks Hofer Gilson & Lione

(57) ABSTRACT

The bicyclo-substituted pyrazolon-azo derivatives of formula (I) or pharmaceutical acceptable salts, hydrates or solvates thereof, methods for their preparation, pharmaceutical compositions containing the same and their use as a therapeutic agent, especially as thrombopoietin (TPO) mimetics and their use as agonists of thrombopoietin receptor are disclosed. The definition of substituents in formula (I) are the same as defined in the description.

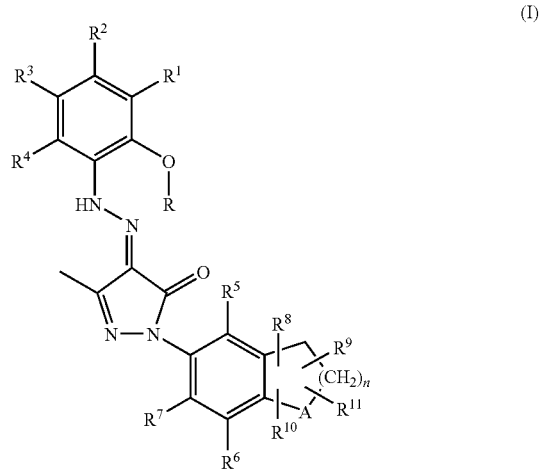

25 Claims, No Drawings

BICYCLO-SUBSTITUTED PYRAZOLON AZO DERIVATIVES, PREPARATION PROCESS AND PHARMACEUTICAL USE THEREOF

The present application is the national phase application of PCT Application No. PCT/CN2009/000001, filed Jan. 4, 2009, which claims priority to Chinese Patent Application No. 200810000346.6, filed Jan. 10, 2008, the entireties of both of which are hereby incorporated by references.

FIELD

This disclosure relates to novel bicyclo-substituted pyrazolon-azo derivatives represented by formula (I), methods for their preparation, pharmaceutical compositions containing the same, and their use as a therapeutic agent, particularly as thrombopoietin (TPO) mimetics and their use as agonists of the thrombopoietin receptor.

BACKGROUND

Thrombopoietin (TPO), also called megakaryocyte growth and development factor (MGDF), thrombocytopoiesis stimulating factor (TSF), c-myeloproliferative leukemia ligand (c-Mpl), mpl ligand, or megapoietin, is a glycoprotein that has been shown to be involved in the production of platelets. See Wendling, F., et. al., Biotherapy 10(4): 269-77 (1998); Kuter D. I. et al., The Oncologist, 1: 98-106 (1996); Metcalf, Nature 369: 519-520 (1994).

Under certain circumstances, the activity of TPO results from the binding of TPO with the TPO receptor (also called MPL). The TPO receptor has been cloned and its amino acid sequence has been described. See Vigon et al., Proc. Nat. Acad. Sci., 89: 5640-5644 (1992).

TPO is a 332-amino acid glycosylated polypeptide that plays a key role in the regulation of megakaryocytopoiesis, and in the process in which platelets are produced by bone marrow megakaryocytes. See Kuter et al., Proc. Natl. Acad. Sci. USA 91: 11104-11108 (1994); Barley et al., Cell 77:1117-1124 (1994); Kaushansky et al., Nature 369:568-571 (1994); Wendling et al., Nature 369: 571-574 (1994); and Sauvage et al., Nature 369: 533-538 (1994). TPO is produced in the liver but functions mainly in the bone marrow, where it stimulates the differentiation of stem cells into megakaryocyte progenitors, and stimulates megakaryocyte proliferation, polyploidization and, ultimately, enters the platelet circulation in the body. TPO is also a primary regulator in situations involving thrombocytopenia and in a number of studies that include increasing platelet counts, platelet size and isotope incorporation into platelets of recipient animals. See, Metcalf Nature 369: 519-520 (1994). Specifically, TPO is considered to affect megakaryocytopoiesis by several ways: (1) it causes increase in megakaryocyte size and number; (2) it increases DNA contents, the forms of polyploidy, and the number of megakaryocytes; (3) it increases megakaryocyte endomitosis; (4) it increases the number of mature megakaryocytes; (5) it increases the percentage of precursor cells, the number of small acetylcholinesterase positive cells, the number of bone marrow cells.

Platelets are necessary for blood clotting. When platelet numbers are very low, a patient is at risk of death from catastrophic hemorrhage. Thus, TPO has been used for both the diagnosis and the treatment of various hematological disorders, for example, diseases primarily caused by platelet defects. Likewise, TPO may be useful for the treatment of thrombocytopenic conditions, especially those derived from chemotherapy, radiation therapy, or bone marrow transplantation for the treatment of cancer or lymphoma.

Because the slow recovery of platelet levels in patients suffering from thrombocytopenia is a serious problem, it would be desirable to provide a compound for the treatment of thrombocytopenia by acting as a TPO mimetic. A few years ago, the development of TPO peptide mimetics was reported (WO96/40750, WO98/25965). These peptides were designed to bind and activate the TPO receptor (TPO-R) but have no sequence homology to the natural TPO. In recent years, a number of active small-molecule TPO mimetics have been reported, including 1,4-benzodiazepin-2-ones (JP11001477), metal complexes derived from Schiff base ligands (WO99/11262), cyclic polyamine derivatives (WO00/28987), thiazol-2-yl-benzamides (WO01/07423, WO01/53267), azo-aryl derivatives (WO00/35446, WO01/17349), 2-aryl-naphthimidazoles (WO01/39773, WO01/53267), and semicarbazone derivatives (WO01/34585). In cell-based systems, all of these molecules can activate signal transduction pathways that are dependent on the presence of the TPO receptor on the cell membrane. Certain types of compounds can directly act on the TPO receptor itself. It has been reported that certain substituted thiosemicarbazone derivatives are actually effective agonists of the TPO receptor. Some of the most preferred compounds of this series were found to stimulate the proliferation and differentiation of TPO-responsive human cell lines and TPO in human bone marrow cultures that has a concentration below 100 nM.

Several patents assigned on their face to GlaxoSmithKline describe a thrombopoietin analog, eltrombopag (WO00/189457, WO01/089457, WO2006/064957), which shows good activity.

SUMMARY

The present disclosure describes compounds that are TPO receptor agonists and TPO mimetics.

The present disclosure is directed to compounds of bicyclo-substituted pyrazolon-azo derivatives of formula (I) and tautomers, enantiomers, diastereomers, racemics, pharmaceutically acceptable salts, hydrates or solvates, as well as their metabolites, metabolic precursors or prodrugs thereof.

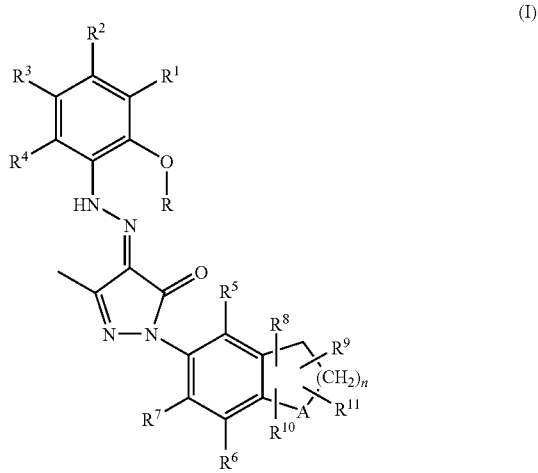

Wherein:

A is selected from the group consisting of carbon and oxygen;

R is selected from the group consisting of hydrogen and alkyl;

$R^1$, $R^2$, $R^3$ and $R^4$ are each independently selected from the group consisting of hydrogen, alkyl, alkoxy, halogen, aryl and heteroaryl, wherein the aryl or heteroaryl is each optionally substituted with one or more groups selected from the group consisting of alkyl, halogen, hydroxyl, tetrazolyl, imidazolyl, dihydroimidazolyl, carboxylic acid and carboxylic ester;

$R^5$, $R^6$ and $R^7$ are each independently selected from the group consisting of hydrogen, alkyl, alkoxy, halogen, hydroxyl, amino, nitro, cyano, carboxylic acid and carboxylic ester;

$R^8$, $R^9$, $R^{10}$ and $R^{11}$ are each independently selected from the group consisting of hydrogen and alkyl; and n is 0, 1 or 2.

In some preferred embodiments of present disclosure:

A is selected from the group consisting of carbon and oxygen;

R is selected from the group consisting of hydrogen and alkyl;

$R^1$ is selected from the group consisting of aryl and heteroaryl, wherein the aryl or heteroaryl is each optionally substituted with one or more groups selected from the group consisting of alkyl, halogen, hydroxyl, tetrazolyl, imidazolyl, dihydroimidazolyl, carboxylic acid and carboxylic ester;

$R^2$, $R^3$ and $R^4$ are each independently selected from the group consisting of hydrogen, alkyl, alkoxy and halogen;

$R^5$, $R^6$ and $R^7$ are each independently selected from the group consisting of hydrogen, alkyl, alkoxy, halogen, hydroxyl, amino, nitro, cyano, carboxylic acid and carboxylic ester;

$R^8$, $R^9$, $R^{10}$ and $R^{11}$ are each independently selected from the group consisting of hydrogen and alkyl; and n is 0, 1 or 2.

The compounds of formula (I) of the present disclosure preferably include, but are not limited to:

| Example No. | Structure | Name |
|---|---|---|
| 1 | 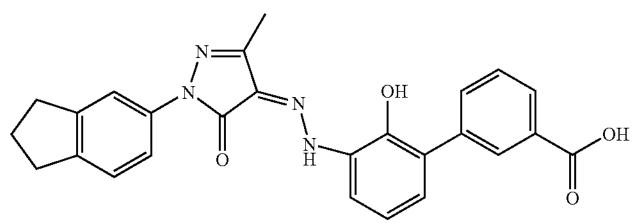 [SMILES: CC1=NN(c2ccc3c(c2)CCC3)C(=O)/C1=N\Nc1cccc(-c2cccc(C(=O)O)c2)c1O] | 2'-Hydroxy-3'-[N'-(1-indan-5-yl-3-methyl-5-oxo-1,5-dihydro-pyrazol-4-ylidene)-hydrazino]-biphenyl-3-carboxylic acid |
| 2 | 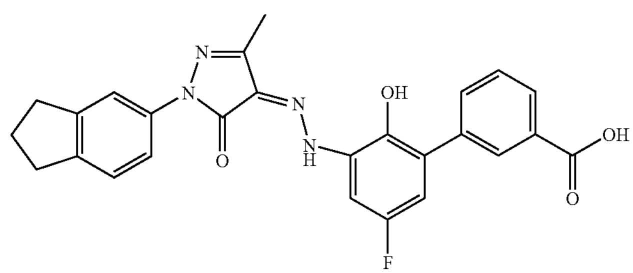 [SMILES: CC1=NN(c2ccc3c(c2)CCC3)C(=O)/C1=N\Nc1cc(F)cc(-c2cccc(C(=O)O)c2)c1O] | 5'-Fluoro-2'-hydroxy-3'-[N'-(1-indan-5-yl-3-methyl-5-oxo-1,5-dihydro-pyrazol-4-ylidene)-hydrazino]-biphenyl-3-carboxylic acid |
| 3 | 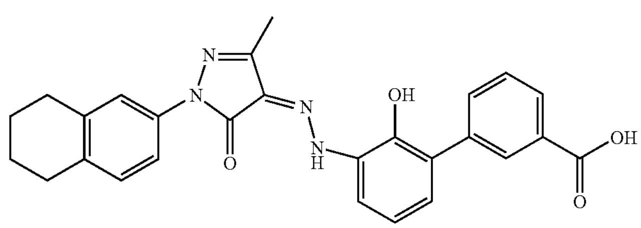 [SMILES: CC1=NN(c2ccc3c(c2)CCCC3)C(=O)/C1=N\Nc1cccc(-c2cccc(C(=O)O)c2)c1O] | 2'-Hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid |
| 4 | 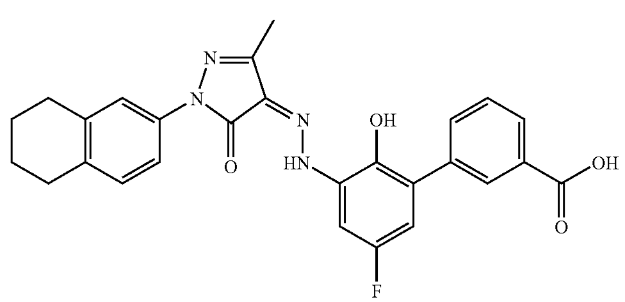 [SMILES: CC1=NN(c2ccc3c(c2)CCCC3)C(=O)/C1=N\Nc1cc(F)cc(-c2cccc(C(=O)O)c2)c1O] | 5'-Fluoro-2'-hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid |

| Example No. | Structure | Name |
|---|---|---|
| 5 | 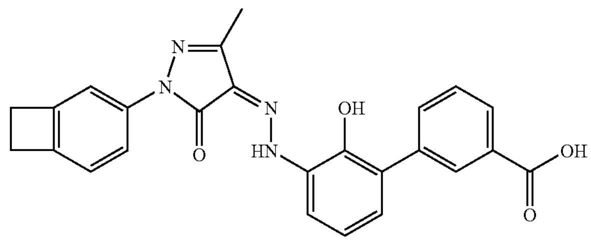 [SMILES: CC1=NN(c2ccc3c(c2)CC3)C(=O)/C1=N\Nc1cccc(-c2cccc(C(=O)O)c2)c1O] | 3'-[N'-(1-Bicyclo[4.2.0]octa-1(6),2,4-trien-3-yl-3-methyl-5-oxo-1,5-dihydro-pyrazol-4-ylidene)-hydrazino]-2'-hydroxy-biphenyl-3-carboxylic acid |
| 6 | 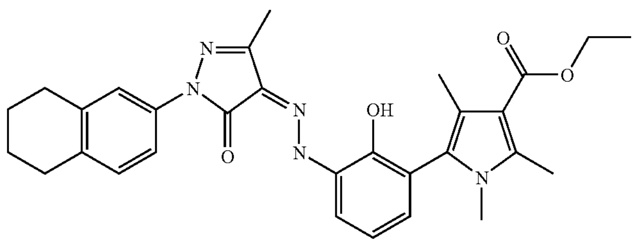 [SMILES: CCOC(=O)c1c(C)c(-c2cccc(N/N=C3\C(=O)N(c4ccc5c(c4)CCCC5)N=C3C)c2O)n(C)c1C] | 5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1,2,4-trimethyl-1H-pyrrole-3-carboxylic acid ethyl ester |
| 7 | 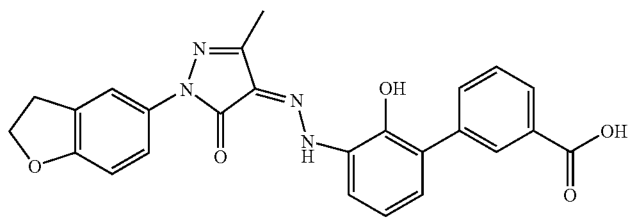 [SMILES: CC1=NN(c2ccc3c(c2)CCO3)C(=O)/C1=N\Nc1cccc(-c2cccc(C(=O)O)c2)c1O] | 3'-{N'-[1-(2,3-Dihydro-benzofuran-5-yl)-3-methyl-5-oxo-1,5-dihydro-pyrazol-4-ylidene]-hydrazino}-2'-hydroxy-biphenyl-3-carboxylic acid |
| 8 | 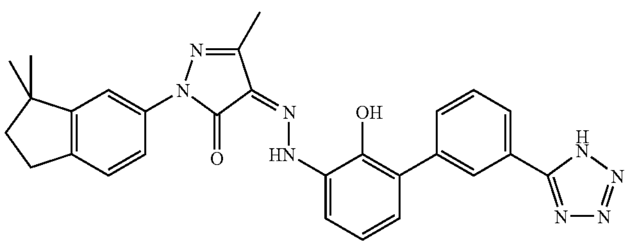 [SMILES: CC1=NN(c2ccc3c(c2)C(C)(C)CC3)C(=O)/C1=N\Nc1cccc(-c2cccc(-c3nnn[nH]3)c2)c1O] | 2-(3,3-Dimethyl-indan-5-yl)-4-{[2-hydroxy-3'-(1H-tetrazol-5-yl)-biphenyl-3-yl]-hydrazono}-5-methyl-2,4-dihydro-pyrazol-3-one |
| 9 | 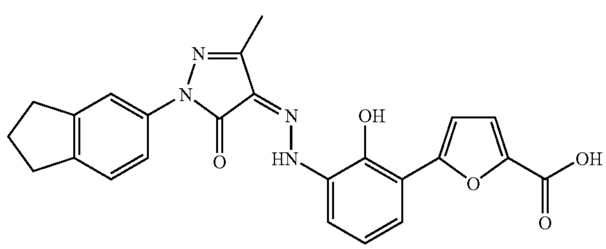 [SMILES: CC1=NN(c2ccc3c(c2)CCC3)C(=O)/C1=N\Nc1cccc(-c2ccc(C(=O)O)o2)c1O] | 5-{2-Hydroxy-3-[N'-(1-indan-5-yl-3-methyl-5-oxo-1,5-dihydro-pyrazol-4-ylidene)-hydrazino]-phenyl}-furan-2-carboxylic acid |
| 10 | 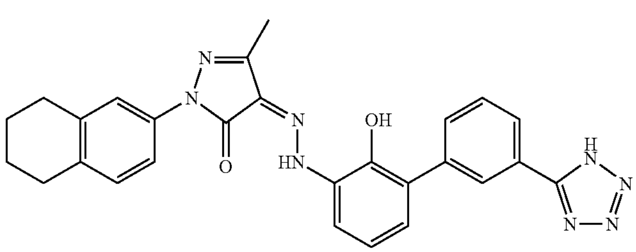 [SMILES: CC1=NN(c2ccc3c(c2)CCCC3)C(=O)/C1=N\Nc1cccc(-c2cccc(-c3nnn[nH]3)c2)c1O] | 4-{[2-Hydroxy-3'-(1H-tetrazol-5-yl)-biphenyl-3-yl]-hydrazono}-5-methyl-2-(5,6,7,8-tetrahydro-naphthalen-2-yl)-2,4-dihydro-pyrazol-3-one |

-continued

| Example No. | Structure | Name |
|---|---|---|
| 11 | 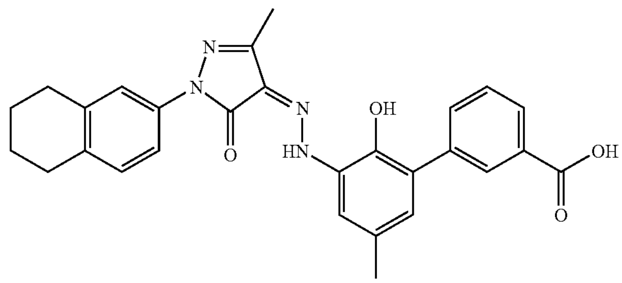 [SMILES: CC1=NN(c2ccc3c(c2)CCCC3)C(=O)/C1=N\Nc1cc(C)cc(-c2cccc(C(=O)O)c2)c1O] | 2'-Hydroxy-5'-methyl-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid |
| 12 | 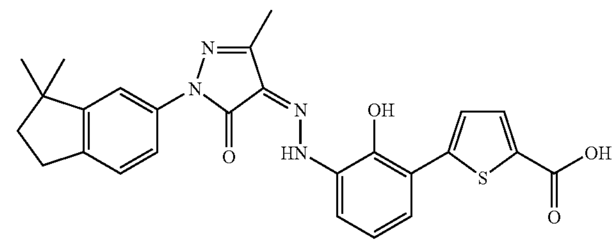 [SMILES: CC1=NN(c2ccc3c(c2)C(C)(C)CC3)C(=O)/C1=N\Nc1cccc(-c2ccc(C(=O)O)s2)c1O] | 5-(3-{N'-[1-(3,3-Dimethyl-indan-5-yl)-3-methyl-5-oxo-1,5-dihydro-pyrazol-4-ylidene]-hydrazino}-2-hydroxy-phenyl)-thiophene-2-carboxylic acid |
| 13 | 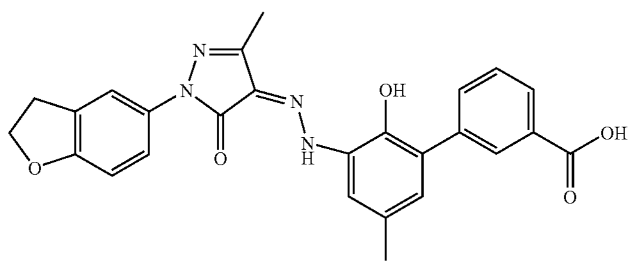 [SMILES: CC1=NN(c2ccc3c(c2)CCO3)C(=O)/C1=N\Nc1cc(C)cc(-c2cccc(C(=O)O)c2)c1O] | 3'-{N'-[1-(2,3-Dihydro-benzofuran-5-yl)-3-methyl-5-oxo-1,5-dihydro-pyrazol-4-ylidene]-hydrazino}-2'-hydroxy-5'-methyl-biphenyl-3-carboxylic acid |
| 14 | 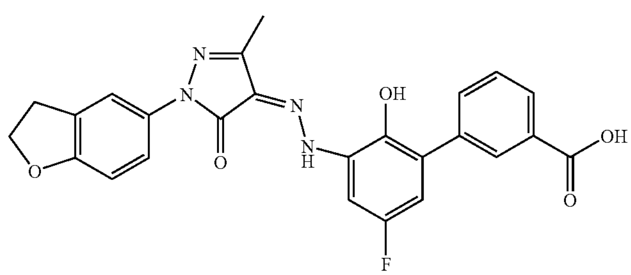 | 3'-{N'-[1-(2,3-Dihydro-benzofuran-5-yl)-3-methyl-5-oxo-1,5-dihydro-pyrazol-4-ylidene]-hydrazino}-5'-fluoro-2'-hydroxy-biphenyl-3-carboxylic acid |
| 15 | 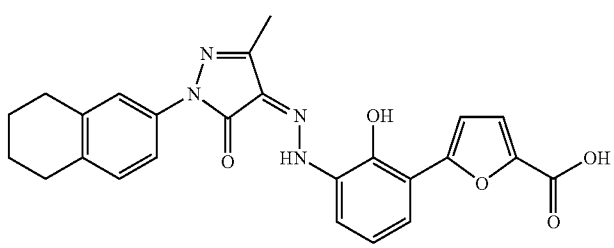 [SMILES: CC1=NN(c2ccc3c(c2)CCCC3)C(=O)/C1=N\Nc1cccc(-c2ccc(C(=O)O)o2)c1O] | 5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid |
| 16 | 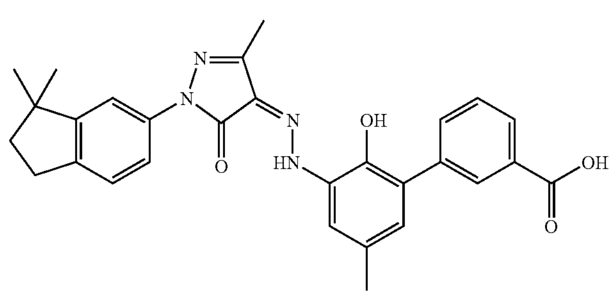 [SMILES: CC1=NN(c2ccc3c(c2)C(C)(C)CC3)C(=O)/C1=N\Nc1cc(C)cc(-c2cccc(C(=O)O)c2)c1O] | 3'-{N'-[1-(3,3-Dimethyl-indan-5-yl)-3-methyl-5-oxo-1,5-dihydro-pyrazol-4-ylidene]-hydrazino}-2'-hydroxy-5'-methyl-biphenyl-3-carboxylic acid |

| Example No. | Structure | Name |
|---|---|---|
| 17 | 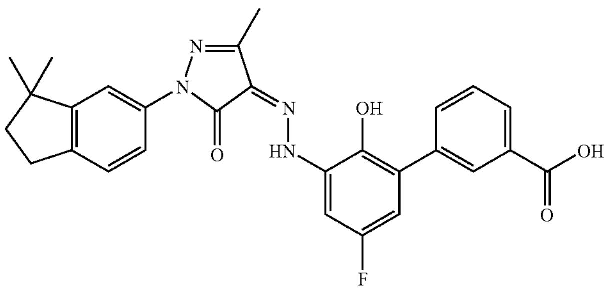 [SMILES: CC1=NN(c2ccc3c(c2)C(C)(C)CC3)C(=O)/C1=N\Nc1cc(F)cc(-c2cccc(C(=O)O)c2)c1O] | 3'-{N'-[1-(3,3-Dimethyl-indan-5-yl)-3-methyl-5-oxo-1,5-dihydro pyrazol-4-ylidene]-hydrazino}-5'-fluoro-2'-hydroxy-biphenyl-3-carboxylic acid |
| 18 | 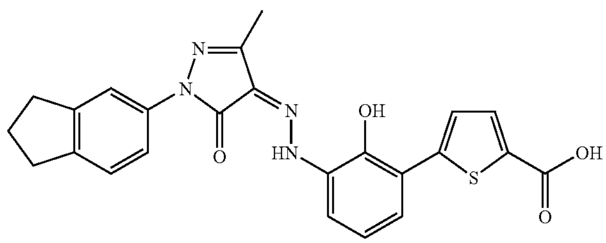 | 5-{2-Hydroxy-3-[N'-(1-indan-5-yl-3-methyl-5-oxo-1,5-dihydro-pyrazol-4-ylidene)-hydrazino]-phenyl}-thiophene-2-carboxylic acid |
| 19 | 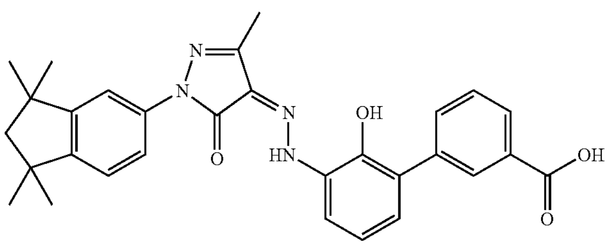 [SMILES: CC1=NN(c2ccc3c(c2)C(C)(C)CC3(C)C)C(=O)/C1=N\Nc1cccc(-c2cccc(C(=O)O)c2)c1O] | 2'-Hydroxy-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid |
| 20 | 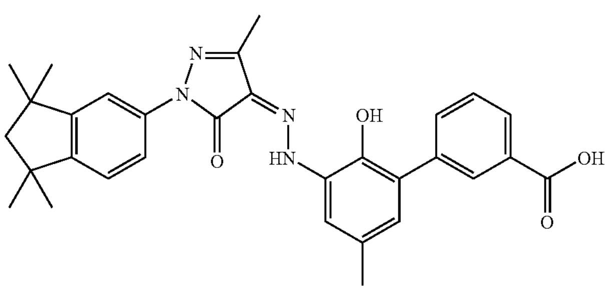 [SMILES: CC1=NN(c2ccc3c(c2)C(C)(C)CC3(C)C)C(=O)/C1=N\Nc1cc(C)cc(-c2cccc(C(=O)O)c2)c1O] | 2'-Hydroxy-5'-methyl-3'-{N'-[3-methyl-5-oxo-1-(1,1,3,3-tetramethyl-indan-5-yl)-1,5-dihydro-pyrazol-4-ylidenej-hydrazino}-biphenyl-3-carboxylic acid |
| 21 | 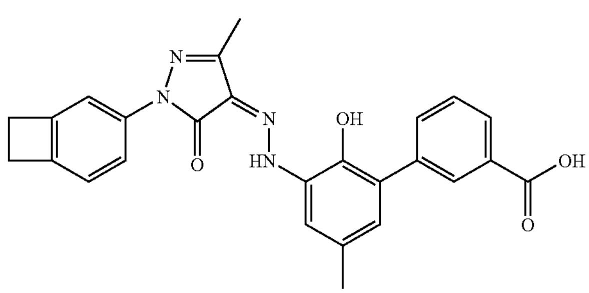 [SMILES: CC1=NN(c2ccc3c(c2)CC3)C(=O)/C1=N\Nc1cc(C)cc(-c2cccc(C(=O)O)c2)c1O] | 3'-[N'-(1-Bicyclo[4.2.0]octa-1(6),2,4-trien-3-yl-3-methyl-5-oxo-1,5-dihydro-pyrazol-4-ylidene)-hydrazino]-2'-hydroxy-5'-methyl-biphenyl-3-carboxylic acid |

| Example No. | Structure | Name |
|---|---|---|
| 22 | 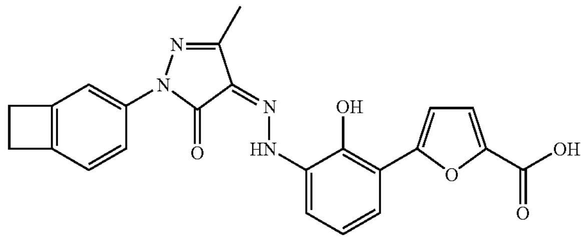 [SMILES: CC1=NN(c2ccc3c(c2)CC3)C(=O)/C1=N\Nc1cccc(-c2ccc(C(=O)O)o2)c1O] | 5-{3-[N'-(1-Bicyclo[4.2.0]octa-1(6),2,4-trien-3-yl-3-methyl-5-oxo-1,5-dihydro-pyrazol-4-ylidene)-hydrazino]-2-hydroxy-phenyl}-furan-2-carboxylic acid |
| 23 | 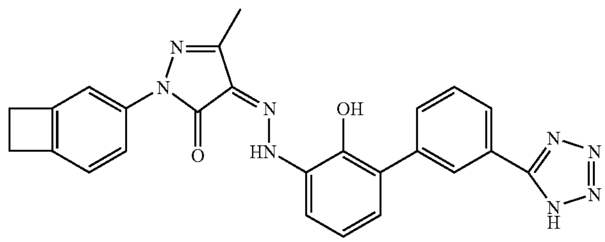 [SMILES: CC1=NN(c2ccc3c(c2)CC3)C(=O)/C1=N\Nc1cccc(-c2cccc(-c3nnn[nH]3)c2)c1O] | 2-Bicyclo[4.2.0]octa-1(6),2,4-trien-3-yl-4-{[2-hydroxy-3'-(1H-tetrazol-5-yl)-biphenyl-3-yl]-hydrazono}-5-methyl-2,4-dihydro-pyrazol-3-one |
| 24 | 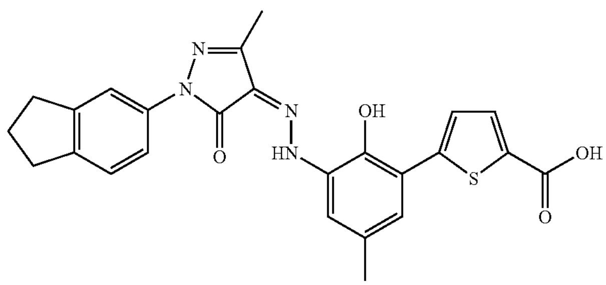 | 5-{2-Hydroxy-3-[N'-(1-indan-5-yl-3-methyl-5-oxo-1,5-dihydro-pyrazol-4-ylidene)-hydrazino]-5-methyl-phenyl}-thiophene-2-carboxylic acid |
| 25 | 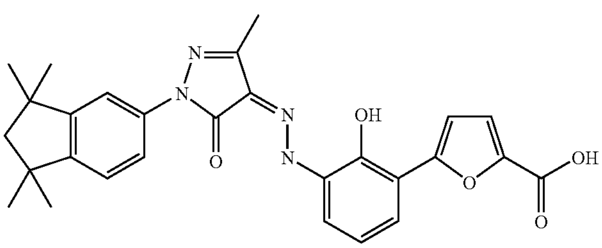 | 5-(2-Hydroxy-3-{N'-[3-methyl-5-oxo-1-(1,1,3,3-tetramethyl-indan-5-yl)-1,5-dihydro-pyrazol-4-ylidene]-hydrazino}-phenyl)-furan-2-carboxylic acid |
| 26 | 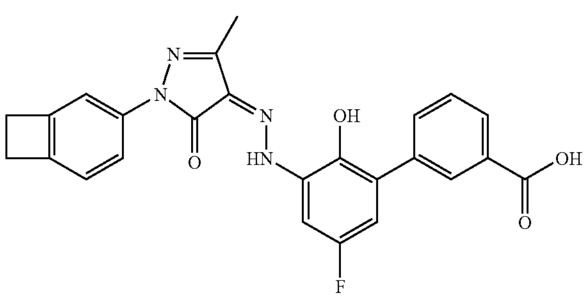 [SMILES: CC1=NN(c2ccc3c(c2)CC3)C(=O)/C1=N\Nc1cc(F)cc(-c2cccc(C(=O)O)c2)c1O] | 3'-[N'-(1-Bicyclo[4.2.0]octa-1(6),2,4-trien-3-yl-3-methyl-5-oxo-1,5-dihydro-pyrazol-4-ylidene)-hydrazino]-5'-fluoro-2'-hydroxy-biphenyl-3-carboxylic acid |
| 27 | 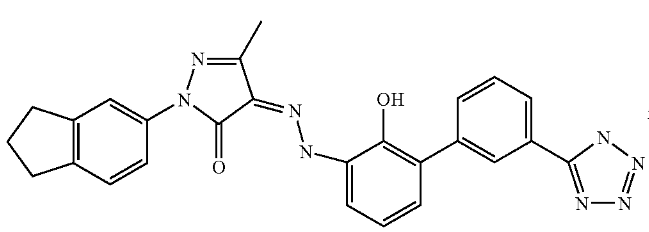 [SMILES: CC1=NN(c2ccc3c(c2)CCC3)C(=O)/C1=N\Nc1cccc(-c2cccc(-c3nnn[nH]3)c2)c1O] | 4-{[2-Hydroxy-3'-(1H-tetrazol-5-yl)-biphenyl-3-yl]-hydrazono}-2-indan-5-yl-5-methyl-2,4-dihydro-pyrazol-3-one |

-continued

| Example No. | Structure | Name |
|---|---|---|
| 28 | 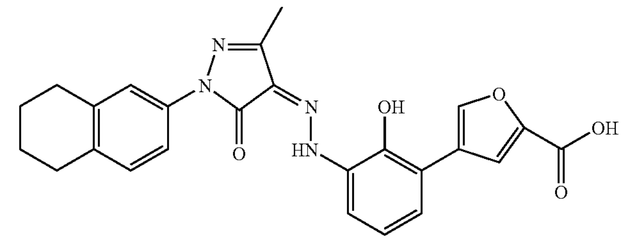 [SMILES: CC1=NN(c2ccc3c(c2)CCCC3)C(=O)/C1=N\Nc1cccc(-c2coc(C(=O)O)c2)c1O] | 4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid |
| 29 | 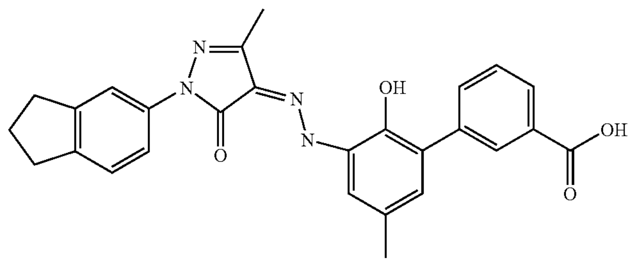 [SMILES: CC1=NN(c2ccc3c(c2)CCC3)C(=O)/C1=N\Nc1cc(C)cc(-c2cccc(C(=O)O)c2)c1O] | 2'-Hydroxy-3'-[N'-(1-indan-5-yl-3-methyl-5-oxo-1,5-dihydro-pyrazol-4-ylidene)-hydrazino]-5'-methyl-biphenyl-3-carboxylic acid |
| 30 | 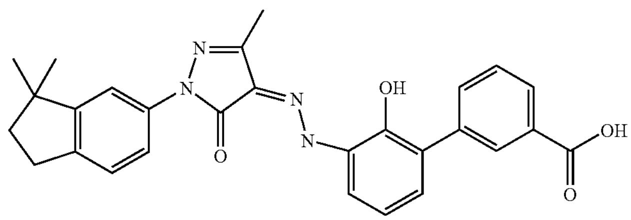 [SMILES: CC1=NN(c2ccc3c(c2)C(C)(C)CC3)C(=O)/C1=N\Nc1cccc(-c2cccc(C(=O)O)c2)c1O] | 3'-{N'-[1-(3,3-Dimethyl-indan-5-yl)-3-methyl-5-oxo-1,5-dihydro-pyrazol-4-ylidene]-hydrazino}-2'-hydroxy-biphenyl-3-carboxylic acid |
| 31 | 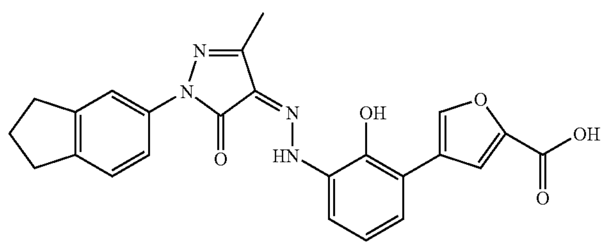 [SMILES: CC1=NN(c2ccc3c(c2)CCC3)C(=O)/C1=N\Nc1cccc(-c2coc(C(=O)O)c2)c1O] | 4-{2-Hydroxy-3-[N'-(1-indan-5-yl-3-methyl-5-oxo-1,5-dihydro-pyrazol-4-ylidene)-hydrazino]-phenyl}-furan-2-carboxylic acid |
| 32 | 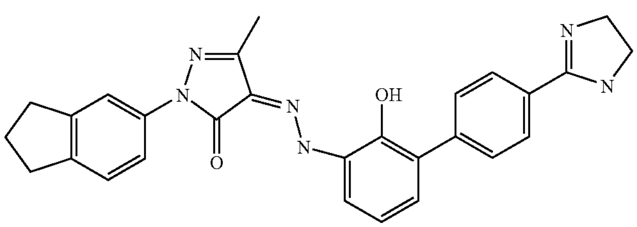 [SMILES: CC1=NN(c2ccc3c(c2)CCC3)C(=O)/C1=N\Nc1cccc(-c2ccc(C3=NCCN3)cc2)c1O] | 4-{[4'-(4,5-Dihydro-1H-imidazol-2-yl)-2-hydroxy-biphenyl-3-yl]-hydrazono}-2-indan-5-yl-5-methyl-2,4-dihydro-pyrazol-3-one |
| 33 | 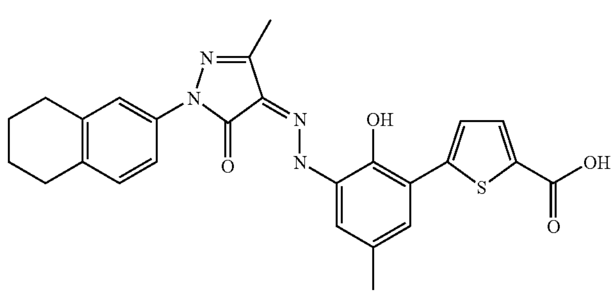 [SMILES: CC1=NN(c2ccc3c(c2)CCCC3)C(=O)/C1=N\Nc1cc(C)cc(-c2ccc(C(=O)O)s2)c1O] | 5-(2-Hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid |

-continued

| Example No. | Structure | Name |
|---|---|---|
| 34 | 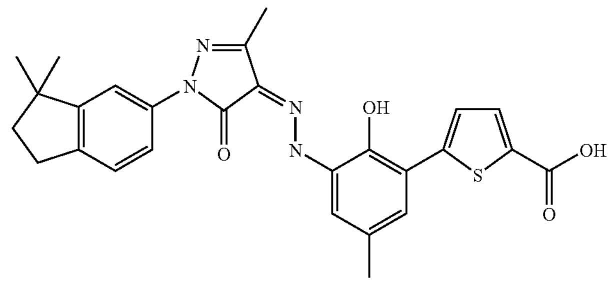 [SMILES: CC1=NN(c2ccc3c(c2)C(C)(C)CC3)C(=O)/C1=N\Nc1cc(C)cc(-c2ccc(C(=O)O)s2)c1O] | 5-(3-{N'-[1-(3,3-Dimethyl-indan-5-yl)-3-methyl-5-oxo-1,5-dihydro-pyrazol-4-ylidene]-hydrazino}-2-hydroxy-5-methyl-phenyl)-thiophene-2-carboxylic acid |
| 35 | 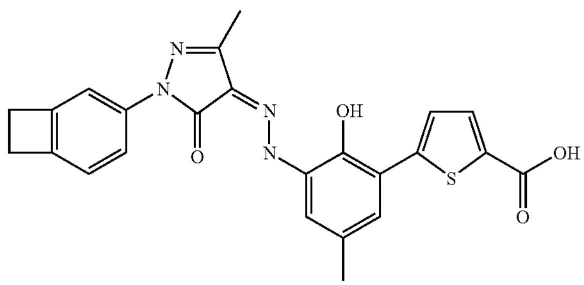 [SMILES: CC1=NN(c2ccc3c(c2)CC3)C(=O)/C1=N\Nc1cc(C)cc(-c2ccc(C(=O)O)s2)c1O] | 5-{3-[N'-(1-Bicyclo[4.2.0]octa-1(6),2,4-trien-3-yl-3-methyl-5-oxo-1,5-dihydro-pyrazol-4-ylidene)-hydrazino]-2-hydroxy-5-methyl-phenyl}-thiophene-2-carboxylic acid |
| 36 | 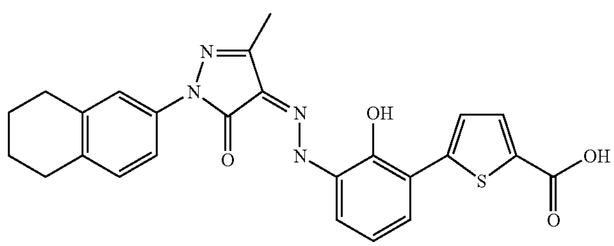 [SMILES: CC1=NN(c2ccc3c(c2)CCCC3)C(=O)/C1=N\Nc1cccc(-c2ccc(C(=O)O)s2)c1O] | 5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid |
| 37 | 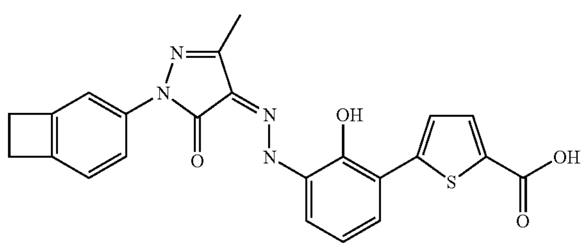 [SMILES: CC1=NN(c2ccc3c(c2)CC3)C(=O)/C1=N\Nc1cccc(-c2ccc(C(=O)O)s2)c1O] | 5-{3-[N'-(1-Bicyclo[4.2.0]octa-1(6),2,4-trien-3-yl-3-methyl-5-oxo-1,5-dihydro-pyrazol-4-ylidene)-hydrazino]-2-hydroxy-phenyl}-thiophene-2-carboxylic acid |
| 38 | 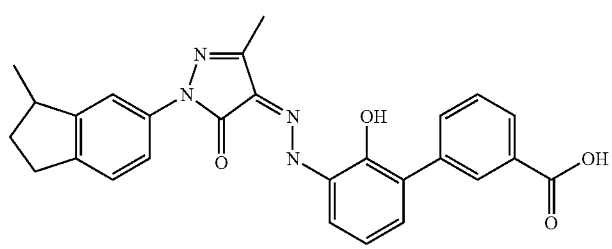 [SMILES: CC1=NN(c2ccc3c(c2)C(C)CC3)C(=O)/C1=N\Nc1cccc(-c2cccc(C(=O)O)c2)c1O] | 2'-Hydroxy-3'-{N'-[3-methyl-1-(3-methyl-indan-5-yl)-5-oxo-1,5-dihydro-pyrazol-4-ylidene]-hydrazino}-biphenyl-3-carboxylic acid |
| 39 | 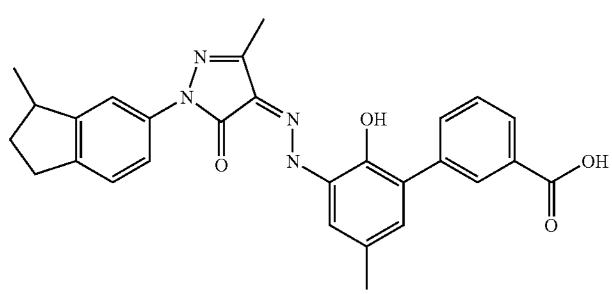 [SMILES: CC1=NN(c2ccc3c(c2)C(C)CC3)C(=O)/C1=N\Nc1cc(C)cc(-c2cccc(C(=O)O)c2)c1O] | 2'-Hydroxy-5'-methyl-3'-{N'-[3-methyl-1-(3-methyl-indan-5-yl)-5-oxo-1,5-dihydro-pyrazol-4-ylidene]-hydrazino}-biphenyl-3-carboxylic acid |

-continued

| Example No. | Structure | Name |
|---|---|---|
| 40 | 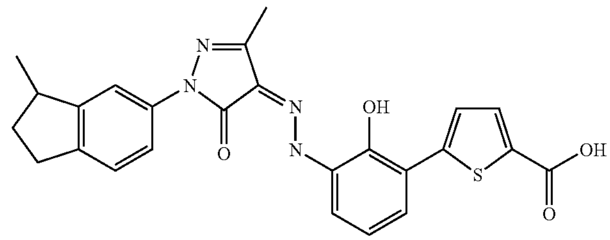 | 5-(2-Hydroxy-3-{N'-[3-methyl-1-(3-methyl-indan-5-yl)-5-oxo-1,5-dihydro-pyrazol-4-ylidene]-hydrazino}-phenyl)-thiophene-2-carboxylic acid |
| 41 | 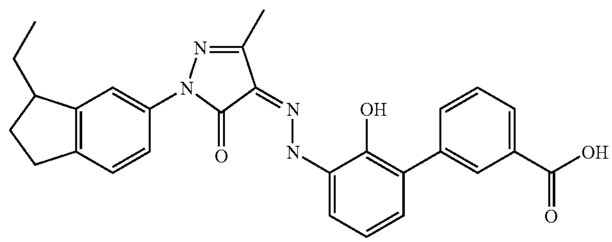 [SMILES: CCC1CCc2ccc(N3N=C(C)/C(=N/Nc4cccc(-c5cccc(C(=O)O)c5)c4O)C3=O)cc21] | 3'-{N'-[1-(3-Ethyl-indan-5-yl)-3-methyl-5-oxo-1,5-dihydro-pyrazol-4-ylidene]-hydrazino}-2-hydroxy-biphenyl-3-carboxylic acid |
| 42 | 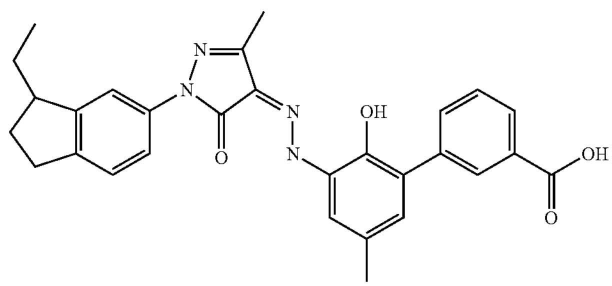 [SMILES: CCC1CCc2ccc(N3N=C(C)/C(=N/Nc4cc(C)cc(-c5cccc(C(=O)O)c5)c4O)C3=O)cc21] | 3'-{N'-[1-(3-Ethyl-indan-5-yl)-3-methyl-5-oxo-1,5-dihydro-pyrazol-4-ylidene]-hydrazino}-2-hydroxy-5'-methyl-biphenyl-3-carboxylic acid |
| 43 | 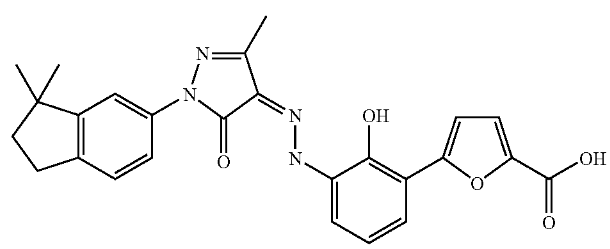 [SMILES: CC1=NN(c2ccc3c(c2)C(C)(C)CC3)C(=O)/C1=N\Nc1cccc(-c2ccc(C(=O)O)o2)c1O] | 5-(3-{N'-[1-(3,3-Dimethyl-indan-5-yl)-3-methyl-5-oxo-1,5-dihydro-pyrazol-4-ylidene]-hydrazino}-2-hydroxy-phenyl)-furan-2-carboxylic acid |
| 44 | 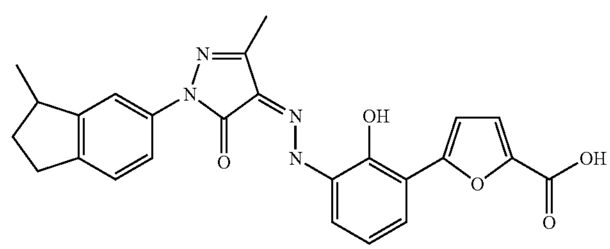 [SMILES: CC1=NN(c2ccc3c(c2)C(C)CC3)C(=O)/C1=N\Nc1cccc(-c2ccc(C(=O)O)o2)c1O] | 5-(2-Hydroxy-3-{N'-[3-methyl-1-(3-methyl-indan-5-yl)-5-oxo-1,5-dihydro-pyrazol-4-ylidene]-hydrazino}-phenyl)-furan-2-carboxylic acid |
| 45 | 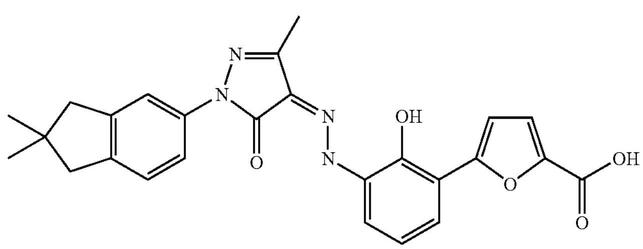 [SMILES: CC1=NN(c2ccc3c(c2)CC(C)(C)C3)C(=O)/C1=N\Nc1cccc(-c2ccc(C(=O)O)o2)c1O] | 5-(3-{N'-[1-(2,2-Dimethyl-indan-5-yl)-3-methyl-5-oxo-1,5-dihydro-pyrazol-4-ylidene]-hydrazino}-2-hydroxy-phenyl)-furan-2-carboxylic acid |

-continued

| Example No. | Structure | Name |
| --- | --- | --- |
| 46 | 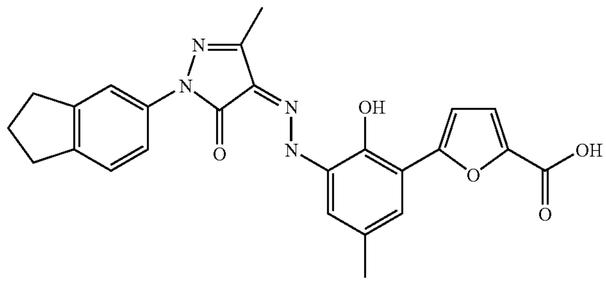 [SMILES: CC1=NN(c2ccc3c(c2)CCC3)C(=O)/C1=N\Nc1cc(C)cc(-c2ccc(C(=O)O)o2)c1O] | 5-{2-Hydroxy-3-[N'-(1-indan-5-yl-3-methyl-5-oxo-1,5-dihydro-pyrazol-4-ylidene)-hydrazino]-5-methyl-phenyl}-furan-2-carboxylic acid |
| 47 | 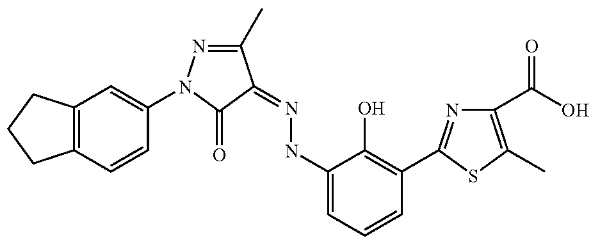 [SMILES: CC1=NN(c2ccc3c(c2)CCC3)C(=O)/C1=N\Nc1cccc(-c2nc(C(=O)O)c(C)s2)c1O] | 2-{2-Hydroxy-3-[N'-(1-indan-5-yl-3-methyl-5-oxo-1,5-dihydro-pyrazol-4-ylidene)-hydrazino]-phenyl}-5-methyl-thiazole-4-carboxylic acid |
| 48 | 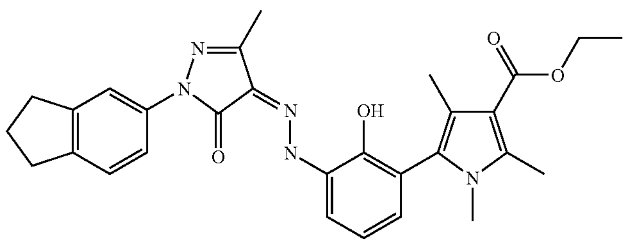 [SMILES: CCOC(=O)c1c(C)c(-c2cccc(N/N=C3\C(=O)N(c4ccc5c(c4)CCC5)N=C3C)c2O)n(C)c1C] | 5-{2-Hydroxy-3-[N'-(1-indan-5-yl-3-methyl-5-oxo-1,5-dihydro-pyrazol-4-ylidene)-hydrazino]-phenyl}-1,2,4-trimethyl-1H-pyrrole-3-carboxylic acid ethyl ester |
| 49 | 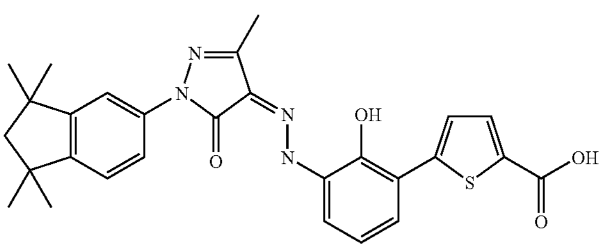 [SMILES: CC1=NN(c2ccc3c(c2)C(C)(C)CC3(C)C)C(=O)/C1=N\Nc1cccc(-c2ccc(C(=O)O)s2)c1O] | 5-(2-Hydroxy-3-{N'-[3-methyl-5-oxo-1-(1,1,3,3-tetramethyl-indan-5-yl)-1,5-dihydro-pyrazol-4-ylidene]-hydrazino}-phenyl)-thiophene-2-carboxylic acid |
| 50 | 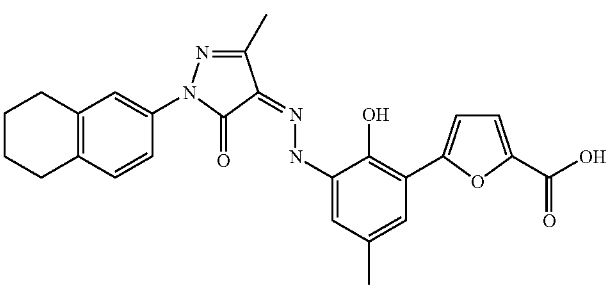 [SMILES: CC1=NN(c2ccc3c(c2)CCCC3)C(=O)/C1=N\Nc1cc(C)cc(-c2ccc(C(=O)O)o2)c1O] | 5-(2-Hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid |
| 51 | 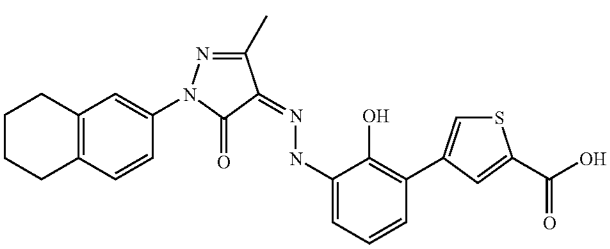 [SMILES: CC1=NN(c2ccc3c(c2)CCCC3)C(=O)/C1=N\Nc1cccc(-c2csc(C(=O)O)c2)c1O] | 4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid |

-continued

| Example No. | Structure | Name |
|---|---|---|
| 52 | 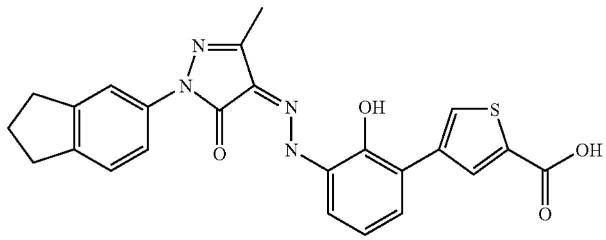 [SMILES: CC1=NN(c2ccc3c(c2)CCC3)C(=O)/C1=N\Nc1cccc(-c2csc(C(=O)O)c2)c1O] | 4-{2-Hydroxy-3-[N'-(1-indan-5-yl-3-methyl-5-oxo-1,5-dihydro-pyrazol-4-ylidene)-hydrazino]-phenyl}-thiophene-2-carboxylic acid |
| 53 | 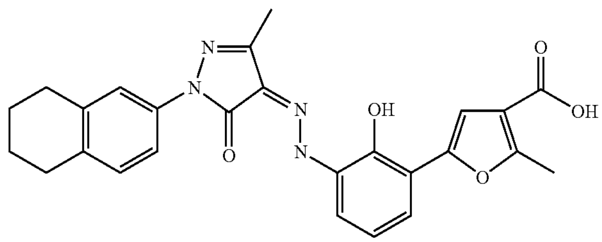 [SMILES: CC1=NN(c2ccc3c(c2)CCCC3)C(=O)/C1=N\Nc1cccc(-c2cc(C(=O)O)c(C)o2)c1O] | 5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-2-methyl-furan-3-carboxylic acid |
| 54 | 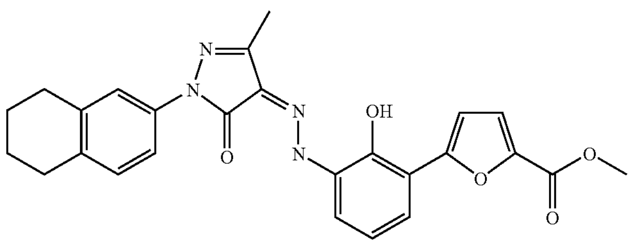 [SMILES: COC(=O)c1ccc(-c2cccc(N/N=C3\C(=O)N(c4ccc5c(c4)CCCC5)N=C3C)c2O)o1] | 5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid methyl ester |
| 55 | 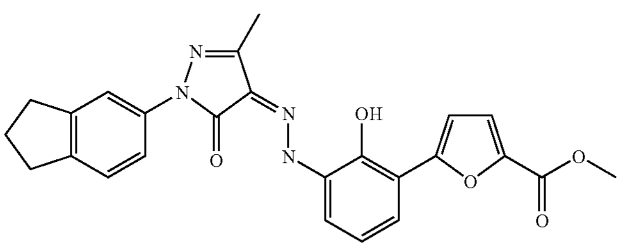 [SMILES: COC(=O)c1ccc(-c2cccc(N/N=C3\C(=O)N(c4ccc5c(c4)CCC5)N=C3C)c2O)o1] | 5-{2-Hydroxy-3-[N'-(1-indan-5-yl-3-methyl-5-oxo-1,5-dihydro-pyrazol-4-ylidene)-hydrazino]-phenyl}-furan-2-carboxylic acid methyl ester |
| 56 | 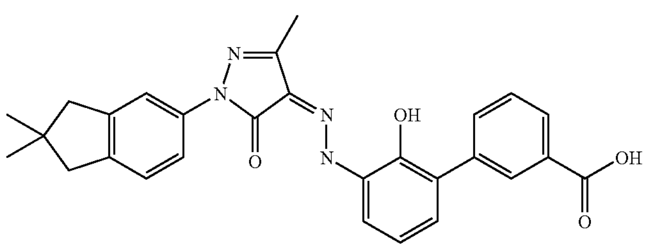 [SMILES: CC1=NN(c2ccc3c(c2)CC(C)(C)C3)C(=O)/C1=N\Nc1cccc(-c2cccc(C(=O)O)c2)c1O] | 3'-{N'-[1-(2,2-Dimethyl-indan-5-yl)-3-methyl-5-oxo-1,5-dihydro-pyrazol-4-ylidene]-hydrazino}-2'-hydroxy-biphenyl-3-carboxylic acid |
| 57 | 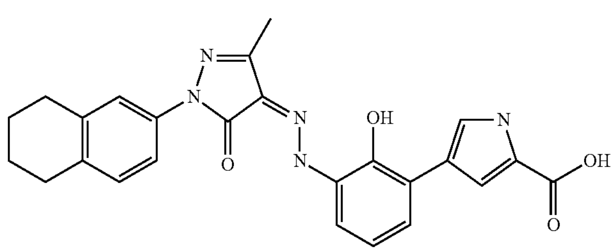 | 4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1H-pyrrole-2-carboxylic acid |

| Example No. | Structure | Name |
|---|---|---|
| 58 | | 4-{2-Hydroxy-3-[N'-(1-indan-5-yl-3-methyl-5-oxo-1,5-dihydro-pyrazol-4-ylidene)-hydrazino]-phenyl}-1H-pyrrole-2-carboxylic acid | or pharmaceutical acceptable salts, hydrates or solvates thereof.

The present disclosure further provides the compounds of formula (IA), as intermediates in the synthesis of the compounds having formula (I):

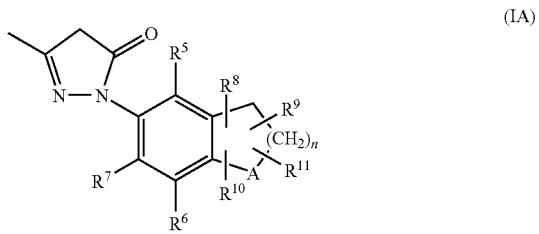

wherein:

A is selected from the group consisting of carbon and oxygen;

$R^5$, $R^6$ and $R^7$ are each independently selected from the group consisting of hydrogen, alkyl, alkoxy, halogen, hydroxyl, amino, nitro, cyano, carboxylic acid and carboxylic ester;

$R^8$, $R^9$, $R^{10}$ and $R^{11}$ are each independently selected from the group consisting of hydrogen and alkyl; and n is 0, 1 or 2.

The compounds of formula (IA) of the present disclosure preferably include, but are not limited to:

| No. | Structure | Name |
|---|---|---|
| 1 | | 2-Bicyclo[4.2.0]octa-1(6),2,4-trien-3-yl-5-methyl-2,4-dihydro-pyrazol-3-one |
| 2 | | 2-Indan-5-yl-5-methyl-2,4-dihydro-pyrazol-3-one |
| 3 | 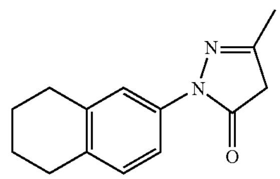 | 5-Methyl-2-(5,6,7,8-tetrahydro-naphthalen-2-yl)-2,4-dihydro-pyrazol-3-one |
| 4 | 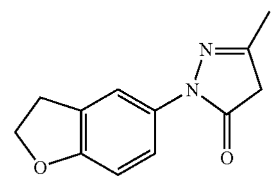 [SMILES: CC1=NN(c2ccc3c(c2)CCC3)C(=O)C1] | 2-(2,3-Dihydro-benzofuran-5-yl)-5-methyl-2,4-dihydro-pyrazol-3-one |
| 5 | 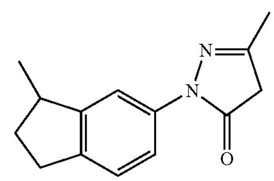 [SMILES: CC1=NN(c2ccc3c(c2)C(C)CC3)C(=O)C1] | 5-Methyl-2-(3-methyl-indan-5-yl)-2,4-dihydro-pyrazol-3-one |
| 6 | 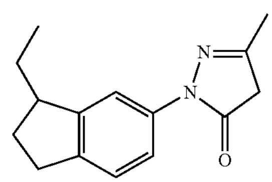 [SMILES: CCC1CCc2ccc(N3N=C(C)CC3=O)cc21] | 2-(3-Ethyl-indan-5-yl)-5-methyl-2,4-dihydro-pyrazol-3-one |
| 7 | 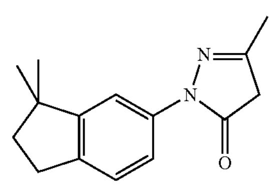 [SMILES: CC1=NN(c2ccc3c(c2)C(C)(C)CC3)C(=O)C1] | 2-(3,3-Dimethyl-indan-5-yl)-5-methyl-2,4-dihydro-pyrazol-3-one |
| 8 | 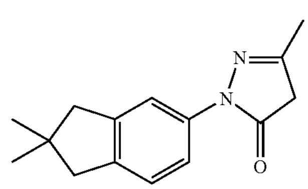 | 2-(2,2-Dimethyl-indan-5-yl)-5-methyl-2,4-dihydro-pyrazol-3-one |

| No. | Structure | Name |
|---|---|---|
| 9 | 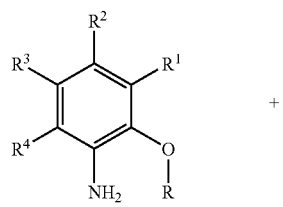 | 5-Methyl-2-(1,1,3,3-tetramethyl-indan-5-yl)-2,4-dihydro-pyrazol-3-one |

In another embodiment, the present disclosure provides a process for the preparation of the compounds of formula (IA), comprising the following steps of:

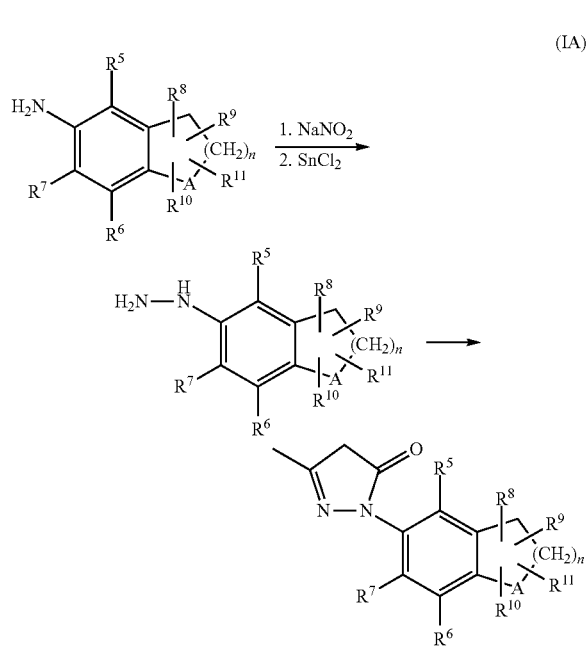

reacting an amino substituted benzocycle and sodium nitrite in an acidic solution via a diazo reaction; reducing the resulting intermediate by tin dichloride to obtain a hydrazine; heating the hydrazine and an electrophilic carbonyl compound, such as ethyl acetoacetate, in an suitable solvent, such as acetic acid, ethanol and the like, via a coupling reaction to obtain the compound of formula (IA).

In a further embodiment, the present disclosure provides a process for the preparation of the compounds of formula (I), comprising the following steps of:

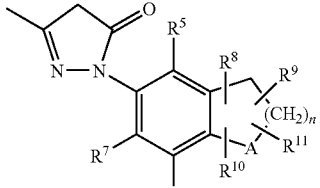

+

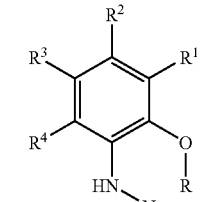

reacting a substituted aniline compound and sodium nitrite in a suitable acid, such as nitric acid, sulfuric acid, hydrochloric acid, via a diazo-reaction; reacting the resulting intermediate and the compound of formula (IA) in a suitable base, such as sodium bicarbonate, potassium hydrogen carbonate, via a coupling reaction to obtain the compound of formula (I).

The present disclosure relates to a use of the compounds of formula (I) and formula (IA) in the preparation of TPO receptor agonists.

The present disclosure relates to a use of the compounds of formula (I) and formula (IA) in the preparation of a medicament for the treatment of thrombocytopenia. Further, the said medicament can be co-administered with a therapeutically effective amount of one or more drugs selected from the group consisting of a colony stimulating factor, a cytokine, a chemokine, an interleukin or cytokine receptor agonist or antagonist, a soluble receptor, a receptor agonist or antagonist antibody, or one or more peptides or small molecule compounds which have the same mechanism of the said drugs.

The present disclosure relates to a pharmaceutical composition comprising a therapeutically effective amount of the compounds of formula (I) and formula (IA), or pharmaceutically acceptable salts, hydrates or solvates thereof. Further, the said composition can be co-administered with a therapeutically effective amount of one or more drugs selected from the group consisting of a colony stimulating factor, a cytokine, a chemokine, an interleukin or cytokine receptor agonist. The present disclosure also relates to a use of the said pharmaceutical composition in the preparation of a medicament for the treatment of thrombocytopenia.

The term "co-administering" means either simultaneous administration or separate sequential administration of the compounds of the present disclosure.

The present disclosure relates to a process for the preparation of a pharmaceutical composition comprising a pharmaceutically acceptable carrier or diluent and a therapeutically effective amount of the compounds of formula (I) and formula (IA), as well as their pharmaceutically acceptable salts, hydrates or solvates, wherein the process comprises combining the compounds of formula (I) and formula (IA) with carriers and diluents.

DETAILED DESCRIPTION OF THE PREFERRED EMBODIMENTS

Unless otherwise stated, the following terms used in the specification and claims have the meanings defined as below.

The term "alkyl" refers to a saturated aliphatic radical including straight chain or branched chain hydrocarbon radical having 1 to 20 carbon atoms. The alkyl group is preferably an alkyl having 1 to 10 carbon atoms, such as methyl, ethyl, propyl, 2-propyl, n-butyl, iso-butyl, tert-butyl or pentyl and the like. The alkyl group is more preferably a lower alkyl having 1 to 4 carbon atoms, such as methyl, ethyl, propyl, 2-propyl, n-butyl, iso-butyl or tert-butyl and the like. The alkyl group may be substituted or unsubstituted. When substituted, the substituent is preferably one or more groups independently selected from the group consisting of alkyl, alkoxy, halogen, hydroxyl, amino, nitro, cyano, aryl, heteroaryl, carboxylic acid or carboxylic ester.

The term "aryl" refers to a radical having at least one aromatic ring, i.e. having a conjugated pi-electron system, including all-carbon cyclic aryl, heteroaryl and biaryl. The aryl group may be substituted or unsubstituted. When substituted, the substituent is preferably one or more groups independently selected from the group consisting of alkyl, alkoxy, halogen, hydroxyl, amino, nitro, cyano, aryl, heteroaryl, carboxylic acid or carboxylic ester.

The term "heteroaryl" refers to an aryl having 1 to 4 heteroatoms selected from the group consisting of N, O, and S as ring atoms, the remaining ring atoms being C. The said ring may be a 5- or 6-membered ring. Examples of heteroaryl groups include furyl, thienyl, pyridyl, pyrrolyl, N-alkyl pyrrolyl, pyrimidinyl, pyrazinyl, imidazolyl, tetrazolyl, and the like. The heteroaryl group may be substituted or unsubstituted. When substituted, the substituent is preferably one or more groups independently selected from the group consisting of alkyl, alkoxy, halogen, hydroxyl, amino, nitro, cyano, aryl, heteroaryl, carboxylic acid or carboxylic ester.

The term "hydroxy" refers to an —OH radical.

The term "alkoxyl" refers to both an —O-(alkyl) and an —O— (unsubstituted cycloalkyl) radical. Representative examples include, but are not limited to, methoxy, ethoxy, propoxy, butoxy, cyclopropyloxy, cyclobutyloxy, cyclopentyloxy, cyclohexyloxy, and the like. The alkoxyl group may be substituted or unsubstituted. When substituted, the substituent is preferably one or more groups independently selected from the group consisting of alkyl, alkoxy, halogen, hydroxyl, amino, nitro, cyano, aryl, heteroaryl, carboxylic acid or carboxylic ester.

The term "halogen" refers to fluoro, chloro, bromo or iodo.

The term "amino" refers to a —NH$_2$ radical.

The term "cyano" refers to a —CN radical.

The term "nitro" refers to a —NO$_2$ radical.

The term "carboxylic acid" refers to a (alkyl) C(=O)OH radical.

The term "carboxylic ester" refers to a (alkyl) C(=O)O (alkyl).

The term "pharmaceutical composition" refers to a mixture of one or more of the compounds described herein, or physiologically/pharmaceutically acceptable salts or prodrugs thereof, with other chemical components such as physiologically/pharmaceutically acceptable carriers and excipients. The purpose of a pharmaceutical composition is to facilitate administration of a compound to an organism.

Synthesis Methods of the Disclosed Compounds

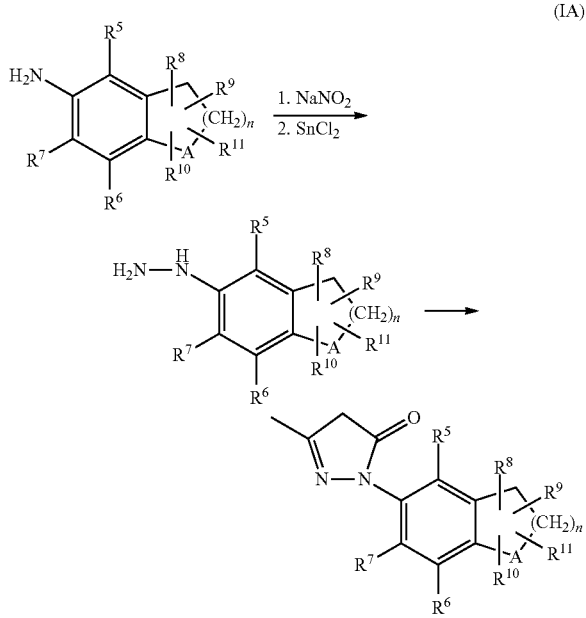

Scheme I reacting an amino substituted benzocycle and sodium nitrite in an acidic solution via a diazo-reaction; reducing the resulting intermediate by tin dichloride to obtain a hydrazine; heating the hydrazine and an electrophilic carbonyl compound, such as ethyl acetoacetate, in a suitable solvent, such as acetic acid, ethanol and the like, via a coupling reaction to obtain the compound of formula (IA).

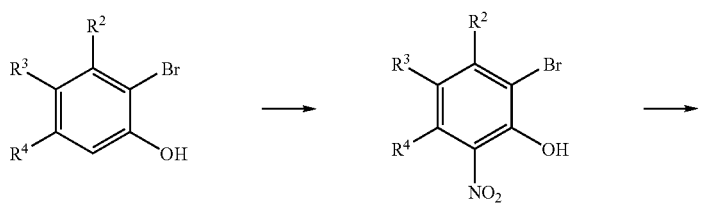

Scheme II

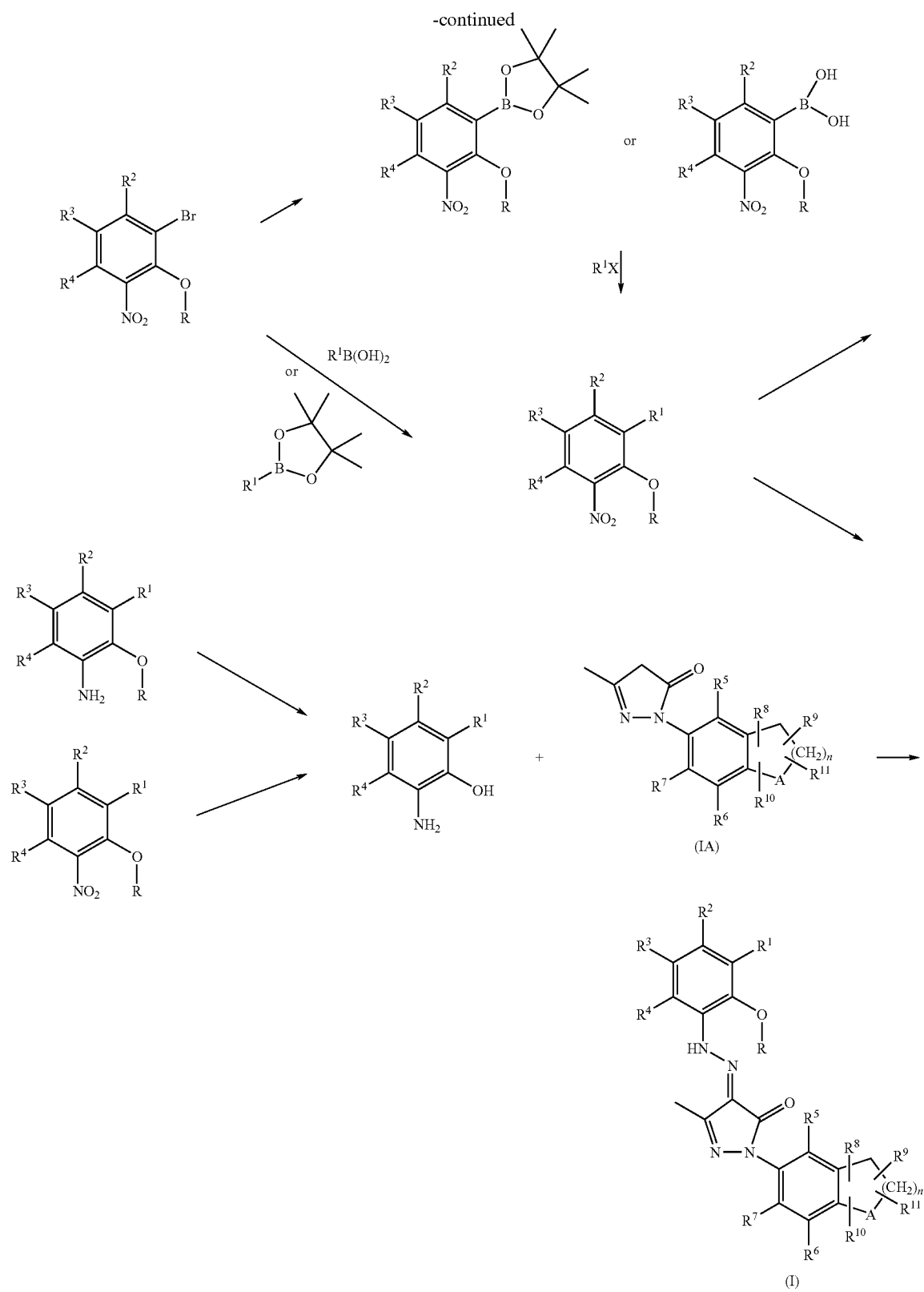

nitrating a substituted 2-bromophenol by sodium nitrate to obtain a nitrophenol, which is converted to a hydroxyl protected nitrophenol via a alkylation reaction at a suitable temperature, in the presence of a haloalkyl, such as methyl iodide;

reacting the hydroxyl protected nitrophenol and a substituted arylboronic acid via a Suzuki coupling reaction in the presence of the catalyst tetrakis(triphenylphosphine)palladium; or reacting the hydroxyl protected nitrophenol and a boronic acid derivative to obtain an arylboronic acid compound, which is reacted with a halogenated compound $R^1X$ via a Suzuki coupling reaction to obtain a $R^1$ substituted aryl compound; reducing the $R^1$ substituted aryl compound by palladium on carbon under hydrogen atmosphere to obtain arylaniline; removing the alkyl protecting group in the presence of hydrobromic acid to obtain the unprotected aniline; or removing the alkyl protecting group of the substituted aryl compound in the presence of hydrobromic acid to obtain a nitro compound, which is reduced by palladium on carbon under hydrogen atmosphere to obtain the unprotected arylaniline.

Reacting the substituted aniline compound and sodium nitrite in a suitable acid, such as nitric acid, sulfuric acid, hydrochloric acid, via a diazo-reaction; reacting the resulting intermediate and the compound of formula (IA) in a suitable base, such as sodium bicarbonate, potassium hydrogen carbonate, via a coupling reaction to obtain the compound of formula (I).

The present disclosure is further described by the following examples which are not intended to limit the scope of the disclosure.

EXAMPLES

The structures of all compounds were identified by nuclear magnetic resonance ($^1$H NMR) or mass spectrometry (MS). $^1$H NMR chemical shifts were recorded on ppm ($10^{-6}$). $^1$H NMR was performed on a Bruker AVANCE-400 spectrometer. The appropriate solvents were deuterated-methanol ($CD_3OD$), deuterated-chloroform ($CDCl_3$) and deuterated-dimethyl sulfoxide (DMSO-$d_6$) with tetramethylsilane (TMS) as the internal standard and chemical shifts were recorded on ppm ($10^{-6}$).

MS was determined by a FINNIGAN LCQ Ad (ESI) mass spectrometer (Thermo, Model: Finnigan LCQ advantage MAX).

$IC_{50}$ was determined by a NovoStar ELIASA (BMG Co. German).

The type of thin-layer silica gel was Yantai Huanghai HSGF254 or Qingdao GF254 silica gel plate.

Column chromatography studies generally used Yantai Huanghai 200~300 mesh silica gel as carrier.

HPLC was determined by an Agilent 1200DAD high pressure liquid chromatography spectrometer (Sunfire C18 150× 4.6 mm chromatographic column) and a Waters 2695-2996 high pressure liquid chromatography spectrometer (Gimini C18 150×4.6 mm chromatographic column).

Hydrogenation reactions under pressure were performed with a Pau 3916EKX hydrogenation spectrometer and a QL hydrogen generator. Microwave reactions were performed with a CEM Discover-S 908860 microwave reactor.

Unless otherwise stated, the following reactions were placed under nitrogen atmosphere.

The term "nitrogen atmosphere" refers to that a reaction flask is equipped with an about 1 L nitrogen balloon.

The term "hydrogen atmosphere" refers to that a reaction flask is equipped with an about 1 L hydrogen balloon.

Unless otherwise stated, the solution used in following reaction refers to an aqueous solution.

The term "TLC" refers to thin layer chromatography.

Example 1

2'-Hydroxy-3'-[N'-(1-indan-5-yl-3-methyl-5-oxo-1,5-dihydro-pyrazol-4-ylidene)-hydrazino]-biphenyl-3-carboxylic acid

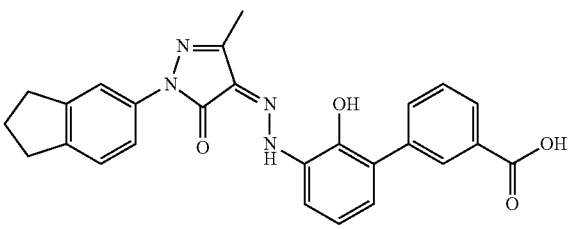

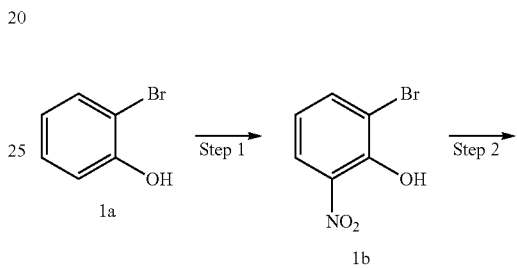

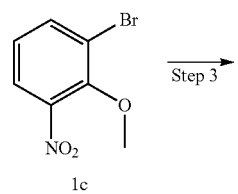

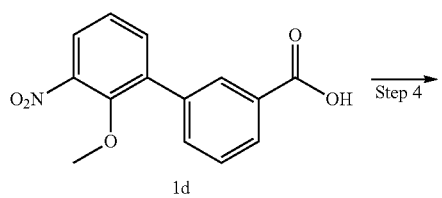

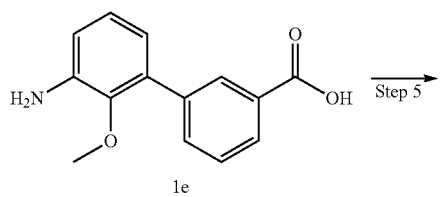

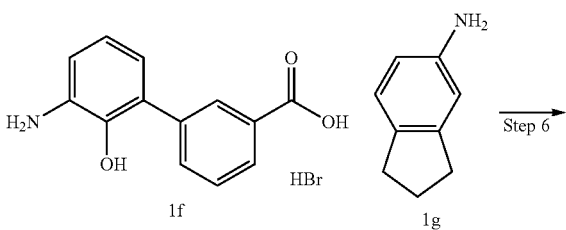

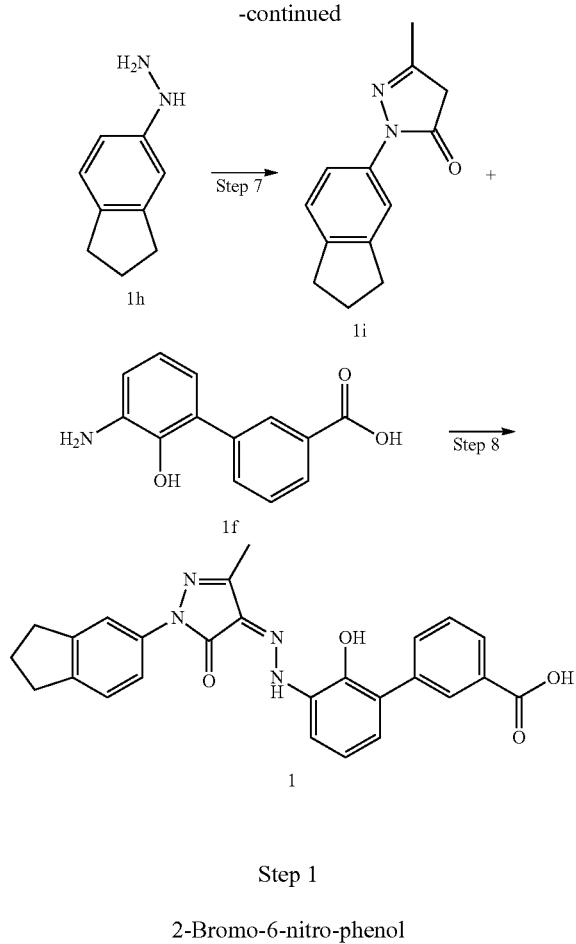

Step 1

2-Bromo-6-nitro-phenol

A solution of 60 mL of concentrated sulfuric acid diluted with 186 mL of water was cooled to room temperature. Sodium nitrate (79.2 g, 0.932 mol) was added to the solution. 2-Bromo-phenol 1a (60 mL, 0.516 mol) was added dropwise at such a rate that the reaction temperature was kept below 25° C. The reaction mixture was reacted at room temperature for 2 hours and monitored by thin layer chromatography (TLC) until the disappearance of the starting materials. The precipitate was dissolved in 320 mL of ethyl acetate. The mixture was washed with saturated brine, dried over anhydrous magnesium sulfate, filtered and concentrated under reduced pressure. The resulting residue was purified by silica gel column chromatography to obtain the title compound 2-bromo-6-nitro-phenol 1b (48.2 g, yield 42.8%) as a yellow solid.

MS m/z (ESI): 218 [M+1]

$^1$H NMR (400 MHz, CDCl$_3$): δ 6.88~7.02 (m, 1H), 7.89~7.91 (d, J=8 Hz, 1H), 8.12~8.15 (m, 1H), 11.18 (s, 1H)

Step 2

1-Bromo-2-methoxy-3-nitro-benzene

2-Bromo-6-nitro-phenol 1b (46.55 g, 0.214 mol) was dissolved in 500 mL of acetone followed by addition of potassium carbonate (35.36 g, 0.256 mol) and iodomethane (20.1 mL, 0.32 mol). The reaction mixture was heated to reflux at 70° C. for 40 hours. The reaction was monitored by TLC until the disappearance of the starting materials. The reaction mixture was concentrated under reduced pressure and diluted with 1300 mL of ethyl acetate and 500 mL of water. The aqueous layer was extracted with ethyl acetate (300 mL×2). The combined organic extracts were washed with 4 N hydrochloric acid and saturated aqueous sodium bicarbonate and then dried over anhydrous magnesium sulfate, filtered and concentrated under reduced pressure. The resulting residue was purified by silica gel column chromatography to obtain the title compound 1-bromo-2-methoxy-3-nitro-benzene 1c (44.59 g, yield 90.0%) as a brown solid.

MS m/z (ESI): 234 [M+1]

Step 3

2'-Methoxy-3'-nitro-biphenyl-3-carboxylic acid

1-Bromo-2-methoxy-3-nitro-benzene 1c (23.25 g, 0.10 mol), 3-carboxyphenylboronic acid (19.5 g, 0.117 mol) and tetrakis(triphenylphosphine)palladium (8.86 g, 7.7 mol) were dissolved in a solvent mixture of 100 mL of 2 N aqueous sodium carbonate and 500 mL of 1,4-dioxane. The reaction mixture was heated to reflux at 105° C. for 43 hours. The reaction was monitored by TLC until the disappearance of the starting materials. The mixture was concentrated under reduced pressure and then 300 mL of 6 N hydrochloric acid and 400 mL of ethyl acetate were added. The aqueous layer was extracted with ethyl acetate (200 mL×2). The combined organic extracts were dried over anhydrous magnesium sulfate, filtered and concentrated under reduced pressure to obtain the title compound 2'-methoxy-3'-nitro-biphenyl-3-carboxylic acid 1d (53.93 g) as a light yellow solid.

MS m/z (ESI): 272 [M−1]

$^1$H NMR (400 MHz, CDCl$_3$): δ 3.44~3.46 (d, J=8 Hz, 3H), 7.42~7.46 (m, 1H), 7.63~7.67 (m, 1H), 7.21~7.75 (m, 1H), 7.82~7.84 (m, 1H), 7.90~7.92 (m, 1H), 8.01~8.03 (d, J=8 Hz, 1H), 8.11 (s, 1H)

Step 4

2'-Methoxy-3'-amino-biphenyl-3-carboxylic acid

2'-Methoxy-3'-nitro-biphenyl-3-carboxylic acid 1d (0.48 g, 1.74 mmol) was dissolved in 60 mL of ethanol followed by addition of 0.5 g of palladium on carbon and ammonium formate (1.1 g, 17.4 mmol). The reaction mixture was heated to reflux at 80° C. for 20 minutes. The reaction was monitored by TLC until the disappearance of the starting materials. The mixture was filtered and the filtrate was concentrated under reduced pressure and dried to obtain the title compound 2'-methoxy-3'-amino-biphenyl-3-carboxylic acid 1e (0.42 g, yield 93.3%) as a white solid.

MS m/z (ESI): 242 [M−1]

Step 5

3'-Amino-2'-hydroxy-biphenyl-3-carboxylic acid hydrobromide

2'-Methoxy-3'-amino-biphenyl-3-carboxylic acid 1e (2.5 g, 10.3 mmol) was dissolved in 100 mL of hydrobromic acid (40%). The reaction mixture was heated to reflux at 120° C. overnight, and the reaction was monitored by TLC until the disappearance of the starting materials. The mixture was concentrated under reduced pressure and the resulting residue was purified by silica gel column chromatography to obtain the title compound 3'-amino-2'-hydroxy-biphenyl-3-carboxylic acid hydrobromide 1f (2.4 g, 88.8%) as a khaki solid.

MS m/z (ESI): 230 [M+1]

[Reference: WO01/89457]

Step 6

Indan-5-yl-hydrazine

Indan-5-ylamine 1g (3.59 g, 27.0 mmol) was dissolved in 20 mL of concentrated hydrochloric acid upon cooling by an ice-water bath and the mixture was stirred for 10 minutes. 10 mL of aqueous sodium nitrite (1.86 g, 27.0 mmol) was added dropwise and the mixture was stirred for another 15 minutes and used in the following reaction.

Upon cooling by an ice-salt bath, stannous chloride dihydrate (24.4 g, 108.0 mmol) was dissolved in 10 mL of concentrated hydrochloric acid followed by addition of above mentioned spare mixture. The reaction mixture was warmed up to room temperature and reacted for 1.5 hours. Then the mixture was adjusted to pH 9 with 40% aqueous sodium hydroxide upon cooling by an ice-water bath. The mixture was extracted with 400 mL of ethyl acetate and the combined organic extracts were concentrated under reduced pressure and dried to obtain the title compound indan-5-yl-hydrazine 1h (2.05 g, yield 51.3%) as a rufous solid.

MS m/z (ESI): 149 [M+1]

Step 7

2-Indan-5-yl-5-methyl-2,4-dihydro-pyrazol-3-one

Indan-5-yl-hydrazine 1h (2.05 g, 13.8 mmol) was dissolved in 50 mL of acetic acid followed by addition of ethyl acetoacetate (1.76 mL, 13.8 mmol). The reaction mixture was heated at 100° C. overnight and the reaction was monitored by TLC until the disappearance of the starting materials. The mixture was concentrated under reduced pressure and the resulting residue was purified by silica gel column chromatography to obtain the title compound 2-indan-5-yl-5-methyl-2,4-dihydro-pyrazol-3-one 1i (1.84 g, yield 62.3%) as a yellow solid.

MS m/z (ESI): 215 [M+1]

$^1$H NMR (400 MHz, CDCl$_3$): δ 7.69 (s, 1H), 7.60 (d, J=8.0 Hz, 1H), 7.24 (d, J=8 Hz, 1H), 3.44 (s, 2H), 2.90~2.97 (m, 4H), 3.21 (s, 3H), 2.07~2.14 (m, 2H)

Step 8

2'-Hydroxy-3'-[N'-(1-indan-5-yl-3-methyl-5-oxo-1,5-dihydro-pyrazol-4-ylidene)-hydrazino]-biphenyl-3-carboxylic acid Upon cooling by an ice-salt bath, 3'-amino-2'-hydroxy-biphenyl-3-carboxylic acid hydrobromide 1f (267 mg, 1.16 mmol) was dissolved in 10 mL of hydrochloric acid (1 N) followed by addition of 10 mL of aqueous sodium nitrite (88 mg, 1.28 mmol) and 2-indan-5-yl-5-methyl-2,4-dihydro-pyrazol-3-one 1i (249 mg, 1.16 mmol). The mixture was adjusted to pH 8 with saturated aqueous sodium bicarbonate, followed by addition of 10 mL of ethanol. The reaction mixture was warmed up to room temperature overnight. The reaction was monitored by TLC until the disappearance of the starting materials. The mixture was filtered, dried and recrystallized from methanol to obtain the title compound 2'-hydroxy-3'-[N'-(1-indan-5-yl-3-methyl-5-oxo-1,5-dihydro-pyrazol-4-ylidene)-hydrazino]-biphenyl-3-carboxylic acid 1 (60 mg, yield 11.4%) as a yellow solid.

MS m/z (ESI): 453 [M−1]

$^1$H NMR (400 MHz, DMSO-d$_6$): δ 2.03~2.10 (m, 2H), 2.34 (s, 3H), 2.86~2.93 (m, 4H), 7.13~7.17 (m, 2H), 7.28~7.30 (d, J=8.1 Hz, 1H), 7.60~7.82 (m, 5H), 7.96~7.98 (d, J=8.1 Hz, 1H), 8.13 (s, 1H), 9.66 (s, 1H), 13.03 (s, 1H), 13.76 (s, 1H)

Example 2

5'-Fluoro-2'-hydroxy-3'-[N'-(1-indan-5-yl-3-methyl-5-oxo-1,5-dihydro-pyrazol-4-ylidene)-hydrazino]-biphenyl-3-carboxylic acid

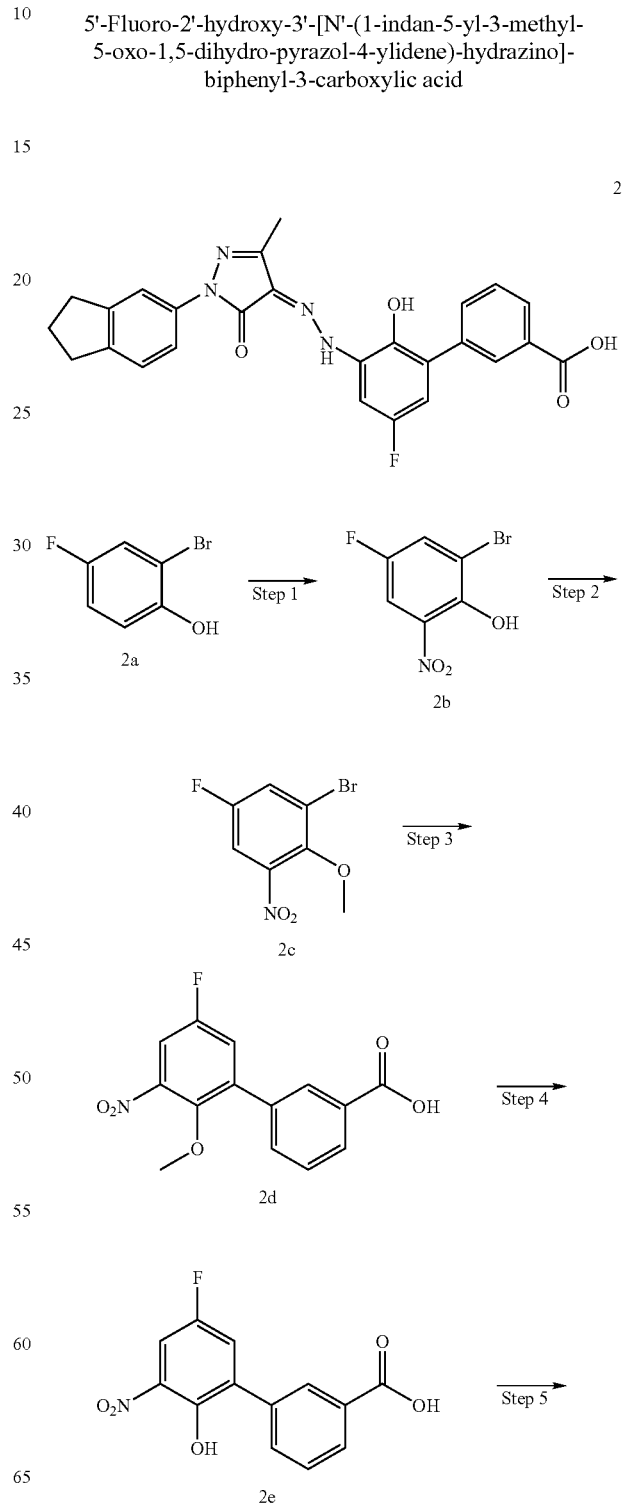

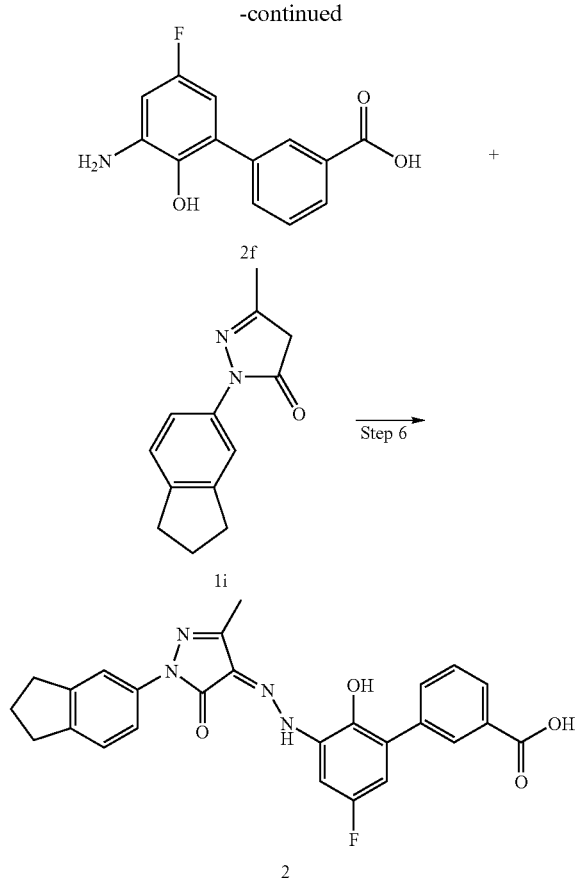

Step 1

2-Bromo-4-fluoro-6-nitro-phenol

2-Bromo-4-fluoro-phenol 2a (8.0 g, 41.9 mmol) was dissolved in 10 mL of sulfuric acid (50%) followed by addition of a solution of sodium nitrate (7.1 g, 83.5 mmol) in 24 mL of sulfuric acid (25%), upon cooling by an ice-water bath. The reaction mixture was reacted at room temperature for 1.5 hours and the reaction was monitored by TLC until the disappearance of the starting materials. The mixture was diluted with 50 mL of water and extracted with ethyl acetate (50 mL×2). The combined organic extracts were washed with water and saturated aqueous sodium bicarbonate and dried over anhydrous magnesium sulfate, filtered and concentrated under reduced pressure to obtain the title compound 2-bromo-4-fluoro-6-nitro-phenol 2b (8.0 g, yield 80.8%) as a red solid, which was directly used in the next step.

Step 2

1-Bromo-5-fluoro-2-methoxy-3-nitro-benzene

2-Bromo-4-fluoro-6-nitro-phenol 2b (24.7 g, 104.7 mmol) and potassium carbonate (17.34 g, 125.6 mmol) were dissolved in 300 mL of acetone followed by addition of iodomethane (9.8 mL, 157.1 mmol). The reaction mixture was heated to reflux at 80° C. for 22 hours. The reaction was monitored by TLC until the disappearance of the starting materials. The mixture was concentrated under reduced pressure and diluted with 200 mL of ethyl acetate and 200 mL of water. The aqueous layer was extracted with ethyl acetate (100 mL×2). The combined organic extracts were washed with 4 N hydrochloric acid and saturated aqueous sodium bicarbonate and dried over anhydrous magnesium sulfate, filtered and concentrated under reduced pressure. The resulting residue was purified by silica gel column chromatography to obtain the title compound 1-bromo-5-fluoro-2-methoxy-3-nitro-benzene 2c (16.18 g, yield 61.8%) as a white solid.

MS m/z (ESI): 252 [M+1]

$^1$H NMR (CDCl$_3$): δ 3.99 (s, 3H), 7.81 (d, J=8.0 Hz, 1H), 7.28 (q, J=8.0 Hz, 4.0 Hz, 1H), 7.89 (q, J=8.0 Hz, 4.0 Hz, 1H)

Step 3

5'-Fluoro-2'-methoxy-3'-nitro-biphenyl-3-carboxylic acid

1-Bromo-5-fluoro-2-methoxy-3-nitro-benzene 2c (16.18 g, 64.7 mmol), 3-carboxyphenylboronic acid (13.88 g, 77.7 mmol) and tetrakis(triphenylphosphine)palladium (3.73 g, 3.2 mmol) were dissolved in the solvent mixture of 65 mL of aqueous sodium carbonate (2 N) and 300 mL of 1,4-dioxane. The reaction mixture was heated to reflux at 120° C. for 24 hours. The reaction was monitored by TLC until the disappearance of the starting materials. The mixture was concentrated under reduced pressure and diluted with 150 mL of hydrochloric acid (6 N) and 200 mL of ethyl acetate. The aqueous layer was extracted with ethyl acetate (100 mL×2). The combined organic extracts were dried over anhydrous magnesium sulfate, filtered and concentrated under reduced pressure to obtain the title compound 5'-fluoro-2'-methoxy-3'-nitro-biphenyl-3-carboxylic acid 2d (7.86 g, yield 41.7%) as a yellow solid.

MS m/z (ESI): 290 [M−1]

Step 4

3'-Nitro-5'-fluoro-2'-hydroxy-biphenyl-3-carboxylic acid

5'-Fluoro-2'-methoxy-3'-nitro-biphenyl-3-carboxylic acid 2d (2.91 g, 10.0 mmol) was dissolved in 10 mL of hydrobromic acid (40%). The reaction mixture was heated to reflux at 120° C. overnight. The reaction was monitored by TLC until the disappearance of the starting materials. The mixture was concentrated under reduced pressure and the resulting residue was purified by silica gel column chromatography to obtain the title compound 3'-nitro-5'-fluoro-2'-hydroxy-biphenyl-3-carboxylic acid 2e (2.38 g, yield 85.7%) as a yellow solid, which was directly used in the next step.

MS m/z (ESI): 277 [M−1]

Step 5

3'-Amino-5'-fluoro-2'-hydroxy-biphenyl-3-carboxylic acid

3'-Nitro-5'-fluoro-2'-hydroxy-biphenyl-3-carboxylic acid hydrobromide 2e (417 mg, 1.5 mmol) was dissolved in 60 mL of ethanol followed by addition of 0.5 g of palladium on carbon and ammonium formate (0.95 g, 1.5 mmol). The reaction mixture was heated to reflux at 80° C. for 20 minutes. The reaction was monitored by TLC until the disappearance of the starting materials. The mixture was filtered and the filtrate was concentrated under reduced pressure and dried to obtain the title compound 3'-amino-5'-fluoro-2'-hydroxy-biphenyl-3-carboxylic acid 2f (339 mg, yield 91.5%) as a purple solid.

MS m/z (ESI): 246 [M−1]

Step 6

5'-Fluoro-2'-hydroxy-3'-[N'-(1-indan-5-yl-3-methyl-5-oxo-1,5-dihydro-pyrazol-4-ylidene)-hydrazino]-biphenyl-3-carboxylic acid Upon cooling by an ice-water bath, 3'-amino-5'-fluoro-2'-hydroxy-biphenyl-3-carboxylic acid 2f (296 mg, 1.20 mmol) was dissolved in 10 mL of hydrochloric acid (1 N) followed by addition of 10 mL of aqueous sodium nitrite (91 mg, 1.32 mmol) and 2-indan-5-yl-5-methyl-2,4-dihydro-pyrazol-3-one 1i (257 mg, 1.20 mmol). The mixture was adjusted to pH 8 with saturated aqueous sodium bicarbonate, followed by addition of 10 mL of ethanol. The mixture was warmed up to room temperature overnight. The reaction was monitored by TLC until the disappearance of the starting materials. The mixture was filtered, dried and recrystallized from methanol to obtain the title compound 5'-fluoro-2'-hydroxy-3'-[N'-(1-indan-5-yl-3-methyl-5-oxo-1,5-dihydro-pyrazol-4-ylidene)-hydrazino]-biphenyl-3-carboxylic acid 2 (87 mg, yield 14.1%) as a red solid.

MS m/z (ESI): 471 [M−1]

$^1$H NMR (400 MHz, DMSO-d$_6$): δ 2.02 (m, 2H), 2.34 (s, 3H), 2.87 (m, 4H), 7.03 (dd, J$_1$=9.2 Hz, J$_2$=2.8 Hz, 1H), 7.28 (d, J=8.0 Hz, 1H), 7.48 (m, 1H), 7.61 (m, 2H), 7.76 (s, 1H), 7.83 (d, J=7.6 Hz, 1H), 7.98 (d, J=8.0 Hz, 1H), 8.17 (s, 1H), 9.59 (s, 1H), 13.03 (s, 1H), 13.62 (s, 1H)

Example 3

2'-Hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid

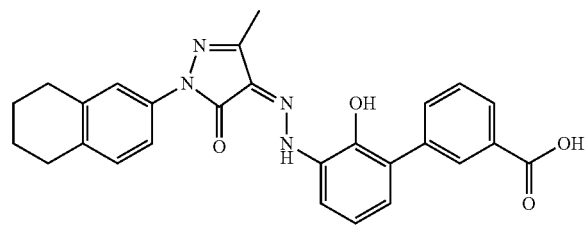

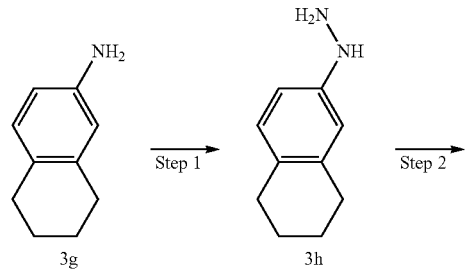

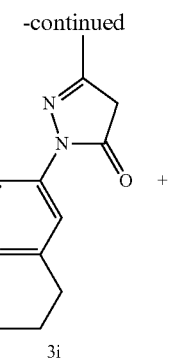

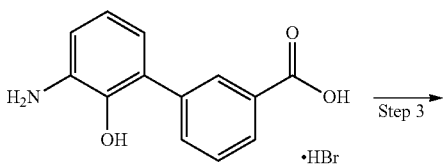

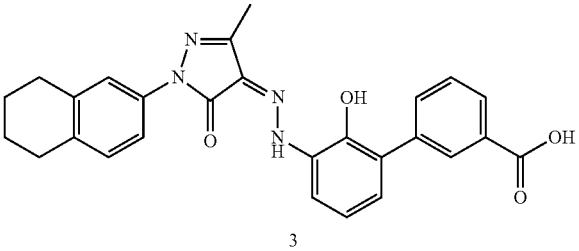

Step 1

(5,6,7,8-Tetrahydro-naphthalen-2-yl)-hydrazine 5,6,7,8-Tetrahydro-naphthalen-2-ylamine 3g (3.68 g, 25.0 mmol) was dissolved in 20 mL of concentrated hydrochloric acid and the mixture was stirred for 10 minutes upon cooling by an ice-water bath. 10 mL of aqueous sodium nitrite (1.72 g, 25.0 mmol) was added dropwise and the mixture was stirred for another 15 minutes and used in the following reaction.

Upon cooling by an ice-salt bath, stannous chloride dihydrate (22.6 g, 100 mmol) was dissolved in 10 mL of concentrated hydrochloric acid followed by addition of above mentioned spare mixture. The reaction mixture was warmed up to room temperature and reacted for 1.5 hours. Then the mixture was adjusted to pH 9 with 40% aqueous sodium hydroxide. The mixture was extracted with 400 mL of ethyl acetate and the combined organic extracts were concentrated under reduced pressure and dried to obtain the title compound (5,6,7,8-tetrahydro-naphthalen-2-yl)-hydrazine 3h (2.19 g, yield 53.7%) as a yellow oil.

MS m/z (ESI): 163 [M+1]

Step 2

5-Methyl-2-(5,6,7,8-tetrahydro-naphthalen-2-yl)-2,4-dihydro-pyrazol-3-one (5,6,7,8-Tetrahydro-naphthalen-2-yl)-hydrazine 3h (2.0 g, 12.3 mmol) was dissolved in 50 mL of acetic acid followed by addition of ethyl acetoacetate (1.57 mL, 12.3 mmol). The reaction mixture was heated to 100° C. overnight. The reaction was monitored by TLC until the disappearance of the starting materials. The mixture was concentrated under reduced pressure and the resulting residue was purified by silica gel column chromatography to obtain the title compound 5-methyl-2-(5,6,7,8-tetrahydro-naphthalen-2-yl)-2,4-dihydro-pyrazol-3-one 3i (1.58 g, yield 56.2%) as a colourless oil.

MS m/z (ESI): 457 [2M+1]

¹H NMR (400 MHz, CDCl₃): δ 7.54~7.58 (m, 2H), 7.08~7.10 (d, J=8 Hz, 1H), 3.43 (s, 2H), δ 2.77~2.81 (m, 4H), 2.21 (s, 3H), 1.80~1.83 (m, 4H).

Step 3

2'-Hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid Upon cooling by an ice-water bath, 3'-amino-2'-hydroxy-biphenyl-3-carboxylic acid hydrobromide 1f (250 mg, 1.09 mmol) was dissolved in 10 mL of hydrochloric acid (1 N) followed by addition of 10 mL of aqueous sodium nitrite (82 mg, 1.2 mmol) and 5-methyl-2-(5,6,7,8-tetrahydro-naphthalen-2-yl)-2,4-dihydro-pyrazol-3-one 3i (249 mg, 1.09 mmol). Then the mixture was adjusted to pH 8 with saturated aqueous sodium bicarbonate, followed by addition of 10 mL of ethanol. The reaction was warmed up to room temperature overnight. The reaction was monitored by TLC until the disappearance of the starting materials. The mixture was filtered, dried and recrystallized from methanol to obtain the title compound 2'-hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid 3 (59 mg, yield 11.6%) as a yellow solid.

MS m/z (ESI): 467 [M−1]

¹H NMR (400 MHz, DMSO-d₆): δ 1.75 (m, 4H), 2.33 (s, 3H), 2.70 (m, 4H), 7.13 (m, 3H), 7.36 (m, 1H), 7.60 (m, 2H), 7.71 (m, 1H), 7.75 (m, 1H), 7.97 (d, J=7.6 Hz, 1H), 8.14 (s, 1H), 9.66 (s, 1H), 13.03 (br, 1H), 13.76 (s, 1H)

Example 4

5'-Fluoro-2'-hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid

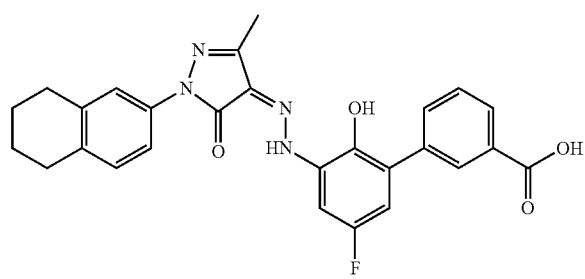

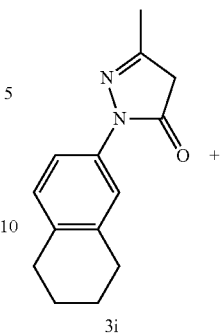

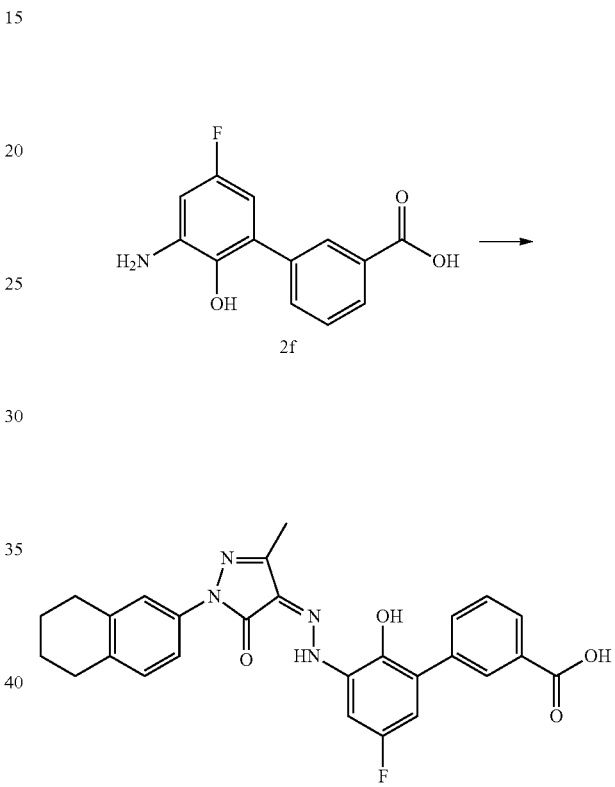

Upon cooling by an ice-water bath, 3'-amino-5'-fluoro-2'-hydroxy-biphenyl-3-carboxylic acid 2f (250 mg, 1.01 mmol) was dissolved in 10 mL of hydrochloric acid (1 N) followed by addition of 10 mL of aqueous sodium nitrite (77 mg, 1.12 mmol) and 5-methyl-2-(5,6,7,8-tetrahydro-naphthalen-2-yl)-2,4-dihydro-pyrazol-3-one 4i (230 mg, 1.01 mmol). The mixture was adjusted to pH 8 with saturated aqueous sodium bicarbonate, followed by addition of 10 mL of ethanol. The reaction was warmed up to room temperature overnight and monitored by TLC until the disappearance of the starting materials. The mixture was filtered, dried and recrystallized from methanol to obtain the title compound 5'-fluoro-2'-hydroxy-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid 4 (64 mg, yield 13.1%) as a red solid.

MS m/z (ESI): 485 [M−1]

¹H NMR (400 MHz, DMSO-d₆): δ 1.74 (m, 4H), 2.33 (s, 1H), 2.73 (m, 4H), 7.02 (dd, J₁=9.2 Hz, J₂=2.0 Hz, 1H), 7.11

(d, d=8.0 Hz, 1H), 7.47 (m, 1H), 7.63 (m, 3H), 7.82 (d, J=7.6 Hz, 1H), 7.98 (d, J=7.6 Hz, 1H), 8.18 (s, 1H), 9.58 (s, 1H), 13.05 (s, 1H), 13.62 (s, 1H)

Example 5

3'-[N'-(1-Bicyclo[4.2.0]octa-1(6),2,4-trien-3-yl-3-methyl-5-oxo-1,5-dihydro-pyrazol-4-ylidene)-hydrazino]-2'-hydroxy-biphenyl-3-carboxylic acid

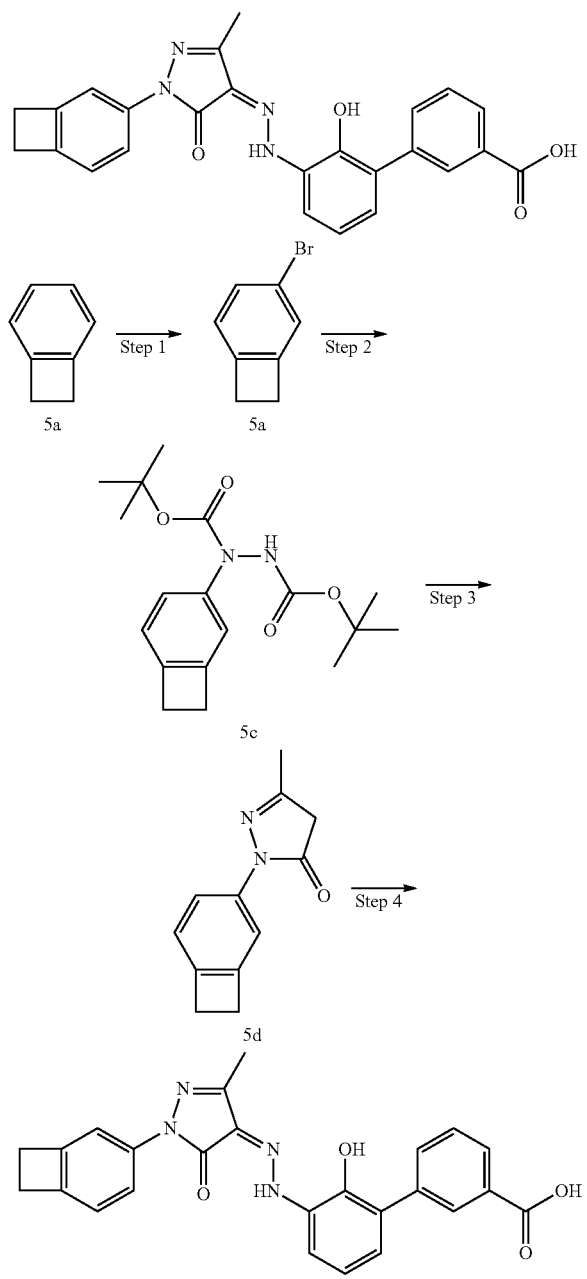

Step 1

3-Bromo-bicyclo[4.2.0]octa-1(6),2,4-triene

Bicyclo[4.2.0]octa-1(6),2,4-triene 5a (7.9 g, 76 mmol) was dissolved in 80 mL of water at room temperature. Upon cooling by an ice-water, 3.9 mL of bromine was added dropwise. Upon completion of the addition, the ice-water bath was removed and the reaction mixture was warmed up to room temperature and stirred overnight. The reaction was monitored by TLC until the disappearance of the starting materials. The mixture was diluted with 50 mL of n-hexane and sodium sulfite (3 g, 23.8 mmol) was added. Upon completion of the addition, the mixture was stirred at room temperature for 30 minutes. Then the separated organic layer was dried over anhydrous sodium sulfate, filtered to remove the drying agent and concentrated under reduced pressure to obtain the title compound 3-bromo-bicyclo[4.2.0]octa-1(6),2,4-triene 5b (13.53 g) as a colourless oil, which was directly used in the next step.

MS m/z (ESI): 181.8 [M−1]

Step 2

N-(bicyclo[4.2.0]octa-1(6),2,4-trienyl-3-yl)-N'-(tert-butoxycarbonyl-hydrazino)-tert-butyl-carbonate 3-Bromo-bicyclo[4.2.0]octa-1(6),2,4-triene 5b (13.5 g, 73.8 mmol) was dissolved in 100 mL of dry tetrahydrofuran. The mixture was cooled to −78° C. in a dry ice-ethanol bath and then n-butyllithium (66 mL, 165 mmol) was added. A solution of di-tert-butyl azodicarboxylate (20.1 g, 87.4 mmol) in 80 mL of dry tetrahydrofuran was added dropwise under stirring at the same temperature. Upon completion of the addition, the dry ice-ethanol bath was removed and the mixture was warmed up to room temperature and stirred overnight. The reaction was monitored by TLC until the disappearance of the starting materials. The reaction was quenched with 100 mL of water and the layers were separated. The aqueous layer was extracted with ethyl acetate (100 mL×2). The combined organic extracts were washed with saturated brine (150 mL×1), dried over anhydrous sodium sulfate and filtered to remove the drying agent. The filtrate was purified by silica gel column chromatography to obtain the title compound N-(bicyclo[4.2.0]octa-1(6),2,4-trienyl-3-yl)-N'-(tert-butoxycarbonyl-hydrazino)-tert-butyl-carbonate 5c (4.07 g, 16.5%) as a yellow oil.

Step 3

2-Bicyclo[4.2.0]octa-1(6),2,4-trienyl-3-yl-5-methyl-2,4-dihydro-pyrazol-3-one

N-(bicyclo[4.2.0]octa-1(6),2,4-trienyl-3-yl)-N'-(tert-butoxycarbonyl-hydrazino)-tert-butyl-carbonate 5c (4.0 g, 12 mmol) was dissolved in 30 mL of acetic acid followed by addition of 30 mL of trifluoroacetic acid and the mixture was stirred at room temperature for 30 minutes followed by addition of 3-oxo-butanoic acid methyl ester (1.6 mL, 15 mmol). The reaction mixture was stirred at 100° C. for 1.5 hours upon warming by an oil bath. The reaction was monitored by TLC until the disappearance of the starting materials. The reaction solvent was evaporated under reduced pressure to dryness. Then 100 mL of water, 60 mL of ethyl acetate and sodium carbonate (3 g) were added in batch. Upon completion of the addition, the layers were separated. The aqueous layer was extracted with ethyl acetate (40 mL×2). The combined organic extracts were washed with saturated brine (100 mL×1), dried over anhydrous sodium sulfate, filtered to remove the drying agent and concentrated under reduced pressure. The residue was purified by silica gel column chromatography to obtain the title compound 2-bicyclo[4.2.0]octa-1(6),2,4-trienyl-3-yl-5-methyl-2,4-dihydro-pyrazol-3-one 5d (910 mg, 37.9%) as a yellow solid.

MS m/z (ESI): 201.2 [M+1]

Step 4

3'-[N'-(1-Bicyclo[4.2.0]octa-1(6),2,4-trien-3-yl-3-methyl-5-oxo-1,5-dihydro-pyrazol-4-ylidene)-hydrazino]-2'-hydroxy-biphenyl-3-carboxylic acid 3'-Amino-2'-hydroxy-biphenyl-3-carboxylic acid hydrobromide 1f (258 mg, 0.83 mmol) was dissolved in 10 mL of hydrochloric acid (1 N), followed by addition of 10 mL of aqueous sodium nitrite (63 mg, 0.92 mmol) and 2-bicyclo[4.2.0]octa-1(6),2,4-trienyl-3-yl-5-methyl-2,4-dihydro-pyrazol-3-one 5d (150 mg, 0.75 mmol) upon cooling by an ice-water bath. The mixture was adjusted to pH 8 with saturated aqueous sodium bicarbonate, followed by addition of 10 mL of ethanol. The reaction mixture was warmed up to room temperature overnight and monitored by TLC until the disappearance of the starting materials. The mixture was filtered and the filter cake was dissolved in 30 mL of water and adjusted pH about 3~4 with concentrated hydrochloric acid. The mixture was then filtered and the filter cake was washed with dichloromethane (8 mL). The residue was dried to obtain the title compound 3'-[N'-(1-bicyclo[4.2.0]octa-1(6),2,4-trien-3-yl-3-methyl-5-oxo-1,5-dihydro-pyrazol-4-ylidene)-hydrazino]-2'-hydroxy-biphenyl-3-carboxylic acid 5 (198 mg, 60%) as a red solid.

MS m/z (ESI): 439.5 [M−1]

$^1$H NMR (400 MHz, DMSO-$d_6$): δ 2.33 (s, 3H), 3.16 (m, 4H), 7.14 (m, 3H), 7.64 (m, 2H), 7.79 (m, 2H), 7.80 (m, 1H), 7.98 (m, 1H), 8.18 (s, 1H), 9.61 (s, 1H), 12.93 (br, 1H), 13.75 (br, 1H)

Example 6

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1,2,4-trimethyl-1H-pyrrole-3-carboxylic acid ethyl ester

6

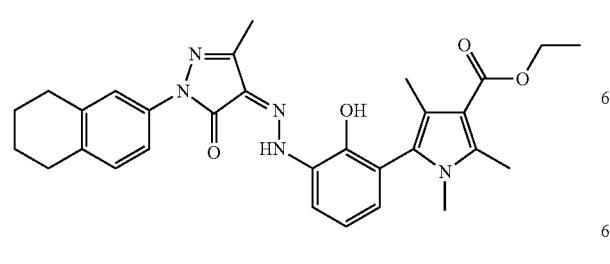

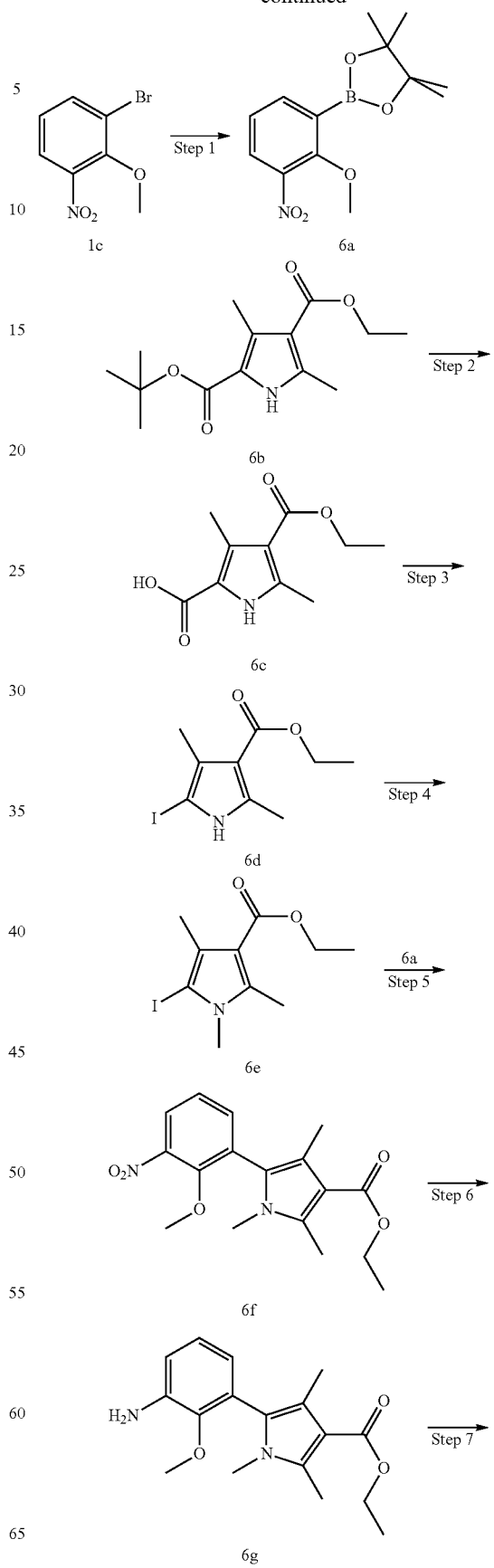

-continued

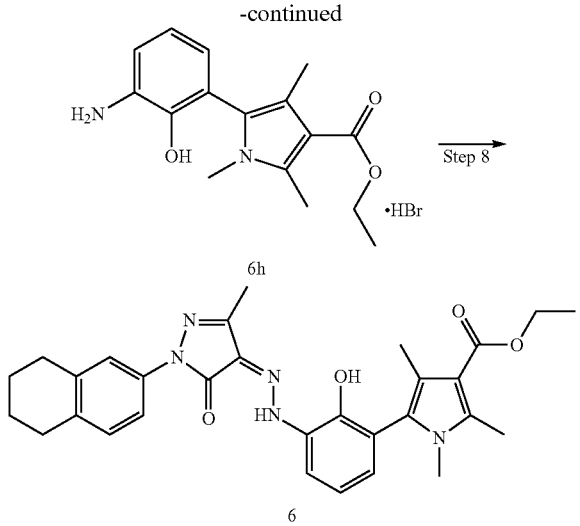

Step 1

2-(2-Methoxy-3-nitro-phenyl)-4,4,5,5-tetramethyl-[1,3,2]dioxaborolane

1-Bromo-2-methoxy-3-nitro-benzene 1c (67 g, 0.289 mol), 4,4,4',4',5,5,5',5'-octamethyl-2,2'-bi-1,3,2-dioxaborolane (110 g, 0.433 mol), tetrakis(triphenylphosphine)palladium (11.80 g, 14.44 mmol) and potassium acetate (71 g, 0.724 mol) were dissolved in 600 mL of ethylene glycol dimethyl ether. The mixture was heated to reflux for 17 hours. The reaction was monitored by TLC until the disappearance of the starting materials. The mixture was concentrated under reduced pressure and the residue was purified by silica gel column chromatography to obtain the title compound 2-(2-methoxy-3-nitro-phenyl)-4,4,5,5-tetramethyl-[1,3,2]dioxaborolane 6a (50.5 g, 61.9%) as a yellow crystal.

Step 2

3,5-Dimethyl-1H-pyrrole-2,4-dicarboxylic acid 4-ethyl ester 3,5-Dimethyl-1H-pyrrole-2,4-dicarboxylic acid 2-tert-butyl ester 4-ethyl ester 6b (5.34 g, 20 mmol) was dissolved in trifluoroacetic acid (7.4 mL, 100 mmol) and the mixture was stirred for 2 hours. The reaction was monitored by TLC until the disappearance of the starting materials. Then 40 mL of water was added. The mixture was filtered and the filter cake was washed with dichloromethane and dried to obtain the title compound 3,5-dimethyl-1H-pyrrole-2,4-dicarboxylic acid 4-ethyl ester 6c (3.65 g, yield 86.5%) as a pink solid.

MS m/z (ESI): 209.8 [M−1]

Step 3

5-Iodo-2,4-dimethyl-1H-pyrrole-3-carboxylic acid ethyl ester 3,5-dimethyl-1H-pyrrole-2,4-dicarboxylic acid 4-ethyl ester 6c (3.65 g, 17.3 mmol) was dissolved in the solvent mixture of 100 mL of dichloromethane and 10 mL of water followed by addition of potassium iodide (11.5 g, 69.2 mmol) and iodine (4.39 g, 17.3 mmol). Upon completion of the addition, the reaction mixture was heated to reflux for 2 hours. The reaction was monitored by TLC until the disappearance of the starting materials. The mixture was cooled to room temperature and then 20 mL of water and 10 mL of sodium thiosulfate (2 M) were added. The mixture was extracted with dichloromethane (30 mL×3). The combined organic extracts were washed with saturated brine, dried over anhydrous magnesium sulfate, filtered to remove the drying agent and concentrated under reduced pressure to obtain the title compound 5-iodo-2,4-dimethyl-1H-pyrrole-3-carboxylic acid ethyl ester 6d (4.1 g, yield 80.8%) as an orange solid.

Step 4

5-Iodo-1,2,4-trimethyl-1H-pyrrole-3-carboxylic acid ethyl ester

5-Iodo-2,4-dimethyl-1H-pyrrole-3-carboxylic acid ethyl ester 6d (4.1 g, 13.99 mmol) was dissolved in 80 mL of tetrahydrofuran followed by addition of 4-methyl-benzenesulfonic acid methyl ester (2.73 g, 14.69 mmol) and sodium tert-butoxide (2.02 g, 20.99 mmol). Upon completion of the addition, the reaction mixture was stirred for 0.5 hours and monitored by TLC until the disappearance of the starting materials. The mixture was filtered and the filter cake was washed with tetrahydrofuran. The filtrate was concentrated under reduced pressure to obtain the title compound 5-iodo-1,2,4-trimethyl-1H-pyrrole-3-carboxylic acid ethyl ester 6e (3.8 g, yield 88.6%) as a grey solid.

MS m/z (ESI): 308.1 [M+1]

$^1$H NMR (400 MHz, CDCl$_3$): δ 4.287~4.340 (q, 2H), 3.561 (s, 3H), 2.618 (s, 3H), 2.888 (s, 3H), 1.369-1.405 (t, 3H)

Step 5

5-(3-Nitro-2-methoxy-phenyl)-1,2,4-trimethyl-1H-pyrrole-3-carboxylic acid ethyl ester 5-Iodo-1,2,4-trimethyl-1H-pyrrole-3-carboxylic acid ethyl ester 6e (2.88 g, 9.38 mmol) was dissolved in 25 mL of 1,4-dioxane followed by addition of 2-(2-methoxy-3-nitro-phenyl)-4,4,5,5-tetramethyl-[1,3,2]dioxaborolane 6a (3.6 g, 10.3 mmol), tetrakis(triphenylphosphine)palladium (270 mg, 0.234 mmol), sodium carbonate (1.99 g, 18.77 mmol) and 10 mL of water. Upon completion of the addition, the reaction mixture was heated to reflux for 3 hours. The reaction was monitored by TLC until the disappearance of the starting materials. The mixture was cooled to room temperature followed by addition of 30 mL of water and extracted with ethyl acetate (30 mL×3). The combined organic extracts were washed with saturated brine, dried over anhydrous magnesium sulfate, filtered to remove the drying agent and concentrated under reduced pressure to obtain the title compound 5-(3-nitro-2-methoxy-phenyl)-1,2,4-trimethyl-1H-pyrrole-3-carboxylic acid ethyl ester 6f (1.25 g, yield 40.4%) as a yellow oil.

MS m/z (ESI): 333.2 [M+1]

$^1$H NMR (400 MHz, CDCl$_3$): δ 7.817~7.841 (m, 1H), 7.457~7.476 (m, 1H), 7.284~7.324 (m, 1H), 4.322~4.375 (q, 2H), 3.521 (s, 3H), 3.316 (s, 3H), 2.625 (s, 3H), 2.177 (s, 3H), 1.398~1.434 (t, 3H)

Step 6

5-(3-Amino-2-methoxy-phenyl)-1,2,4-trimethyl-1H-pyrrole-3-carboxylic acid ethyl ester 5-(3-Nitro-2-methoxy-phenyl)-1,2,4-trimethyl-1H-pyrrole-3-carboxylic acid ethyl ester 6f (300 mg, 0.9 mmol) was dissolved in 5 mL of ethyl acetate followed by addition of formamide (227 mg, 1.61 mmol) and 60 mg of palladium on carbon. The reaction mixture was heated to reflux for 1 hour. The reaction was monitored by TLC until the disappearance of the starting materials. The mixture was filtered and the filter cake was washed with ethyl acetate. The filtrate was concentrated under reduced pressure to obtain the title compound 5-(3-amino-2-methoxy-phenyl)-1,2,4-trimethyl-1H-pyrrole-3-carboxylic acid ethyl ester 6g (234 mg, yield 86%) as a white solid.

MS m/z (ESI): 303.4 [M+1]

$^1$H NMR (400 MHz, CDCl$_3$): δ 6.968~7.006 (m, 1H), 6.817~4.840 (m, 1H), 6.595~6.618 (m, 1H), 4.311~4.364 (q, 2H), 3.381 (s, 3H), 3.315 (s, 3H), 2.615 (s, 3H), 2.181 (s, 3H), 1.391~1.426 (t, 3H)

Step 7

5-(3-Amino-2-hydroxy-phenyl)-1,2,4-trimethyl-1H-pyrrole-3-carboxylic acid ethyl ester hydrobromide 5-(3-Amino-2-methoxy-phenyl)-1,2,4-trimethyl-1H-pyrrole-3-carboxylic acid ethyl ester 6g (210 mg, 0.69 mmol) was dissolved in 5 mL of dichloromethane followed by addition of boron tribromide (1.39 mL, 2.78 mmol). The reaction mixture was reacted at room temperature for 0.5 hours and monitored by TLC until the disappearance of the starting materials. The reaction was quenched with methanol, and the mixture was concentrated under reduced pressure followed by addition of 50 mL of ethyl acetate and 15 mL of saturated aqueous sodium bicarbonate. The mixture was mixed well and the layers were separated. The organic layer was washed with saturated brine, dried over anhydrous magnesium sulfate, filtered to remove the drying agent and concentrated under reduced pressure to obtain the title compound 5-(3-amino-2-hydroxy-phenyl)-1,2,4-trimethyl-1H-pyrrole-3-carboxylic acid ethyl ester hydrobromide 6h (165 mg, yield 82.5%) as a white solid.

MS m/z (ESI): 289.3 [M+1]

$^1$H NMR (400 MHz, DMSO-d$_6$): δ 7.313~7.396 (m, 1H), 7.098~7.117 (m, 1H), 6.993~7.032 (m, 1H), 4.173~4.227 (q, 2H), 3.221 (s, 3H), 1.979 (s, 3H), 1.242~1.295 (t, 3H)

Step 8

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1,2,4-trimethyl-1H-pyrrole-3-carboxylic acid ethyl ester 5-(3-Amino-2-hydroxy-phenyl)-1,2,4-trimethyl-1H-pyrrole-3-carboxylic acid ethyl ester hydrobromide 6h (140 mg, 0.51 mmol) was dissolved in 1.76 mL of hydrochloric acid (1 N) followed by addition of 1 mL of aqueous sodium nitrite (39 mg, 0.56 mmol) and the mixture was stirred for 20 minutes upon cooling by an ice-water bath. 5-Methyl-2-(5,6,7,8-tetrahydro-naphthalen-2-yl)-2,4-dihydro-pyrazol-3-one 3i (105 mg, 0.46 mmol) was then added. The mixture was adjusted to pH 8 with saturated aqueous sodium bicarbonate, followed by addition of 1 mL of ethanol. The reaction was warmed up to room temperature overnight. The reaction was monitored by TLC until the disappearance of the starting materials. The mixture was filtered and the filter cake was dried and then dissolved in dichloromethane. Then the mixture was washed with saturated brine and the organic layer was concentrated under reduced pressure. The residue was purified by silica gel column chromatography to obtain the title compound 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1,2,4-trimethyl-1H-pyrrole-3-carboxylic acid ethyl ester 6 (120 mg, 50.8%) as a red solid.

MS m/z (ESI): 514.1 [M+1]

$^1$H NMR (400 MHz, DMSO-d$_6$): δ 1.84 (m, 4H), 2.14 (s, 3H), 2.41 (s, 3H), 2.57 (s, 3H), 2.80 (m, 4H), 3.34 (s, 3H), 3.87 (s, 3H), 6.51 (m, 1H), 7.00 (d, J=7.6 Hz, 1H), 7.11 (m, 2H), 7.71 (m, 2H), 13.82 (br, 1H)

Example 7

3'-{N-[1-(2,3-Dihydro-benzofuran-5-yl)-3-methyl-5-oxo-1,5-dihydro-pyrazol-4-ylidene]-hydrazino}-2'-hydroxy-biphenyl-3-carboxylic acid

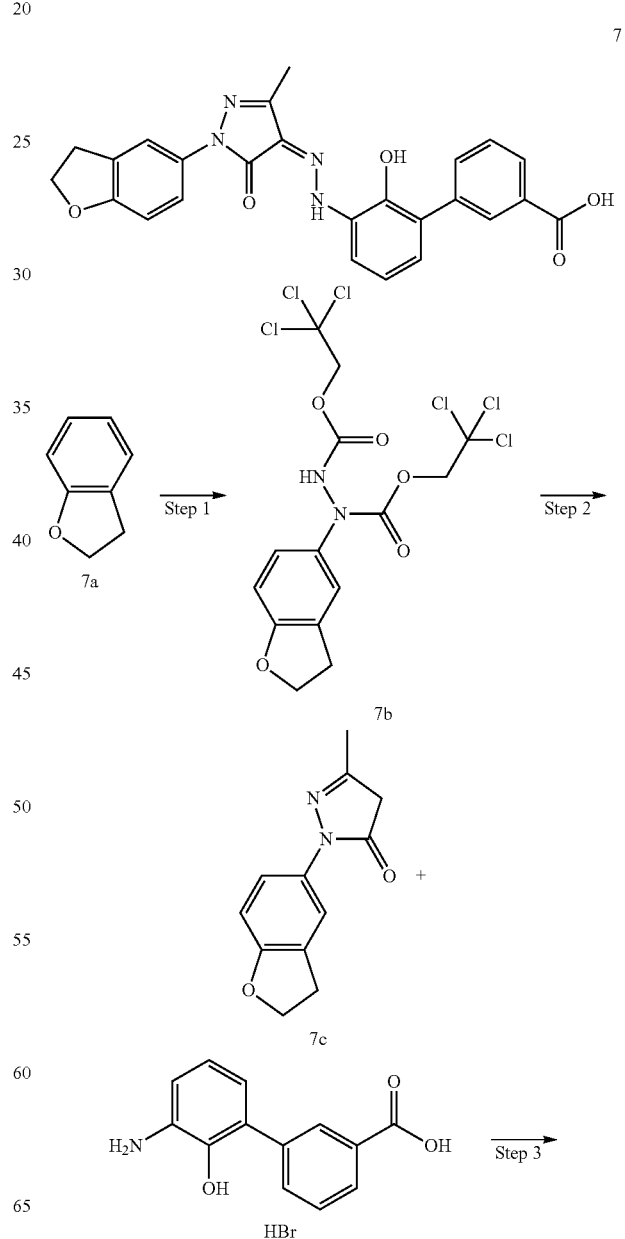

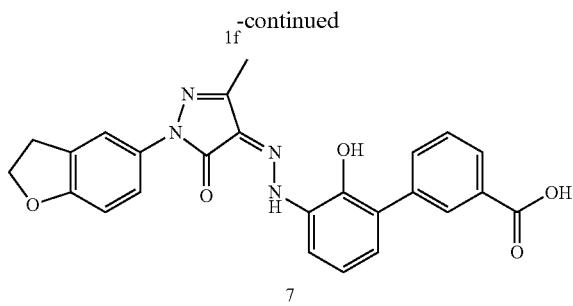

Step 1

Bis(2,2,2-trichloroethyl) 1-(2,3-dihydrobenzofuran-5-yl)hydrazine-1,2-dicarboxylate 2,3-Dihydro-benzofuran 7a (0.6 mL, 5.32 mmol), bis(2,2,2-trichloroethyl) hydrazine-1,2-dicarboxylate (1.96 g, 5.15 mmol) and zinc chloride (920 mg, 6.76 mmol) were dissolved in 40 mL of dichloromethane. The reaction was reacted overnight at room temperature and monitored by TLC until the disappearance of the starting materials. Then the mixture was purified by silica gel column chromatography to obtain the title compound bis(2,2,2-trichloroethyl) 1-(2,3-dihydrobenzofuran-5-yl)hydrazine-1,2-dicarboxylate 7b (2.5 g, yield 96.6%) as a white solid.

Step 2

2-(2,3-Dihydro-benzofuran-5-yl)-5-methyl-2,4-dihydro-pyrazol-3-one

Bis(2,2,2-trichloroethyl) 1-(2,3-dihydrobenzofuran-5-yl)hydrazine-1,2-dicarboxylate 7b (2.9 g, 5.8 mmol) was dissolved in 50 mL of ethanol and 5 mL of methanol followed by addition of zinc powder (10.8 g, 166 mmol) and aqueous ammonium acetate (15 mL, 1 mol/L) and the mixture was reacted at room temperature for 1 hour. Then ethyl acetoacetate (0.75 mL, 5.9 mmol) was added dropwise. The reaction mixture was heated to reflux for 2 hours. The reaction was monitored by TLC until the disappearance of the starting materials. The reaction was cooled to room temperature and filtered. The filtrate was concentrated under reduced pressure and the residue was purified by silica gel column chromatography to obtain the title compound 2-(2,3-dihydro-benzofuran-5-yl)-5-methyl-2,4-dihydro-pyrazol-3-one 7c (706 mg, yield 56.5%) as a yellow solid.

MS m/z (ESI): 217 [M+1]

$^1$H NMR (400 MHz, CDCl$_3$): δ 7.63 (s, 1H), 7.51 (d, J=1.2 Hz, 1H), 6.78 (d, J=8.8 Hz, 1H), 4.57 (t, J=8.8 Hz, 2H), 3.39 (s, 2H), 3.22 (t, J=8.4 Hz, 2H), 2.16 (s, 3H)

Step 3

3'-{N'-[1-(2,3-Dihydro-benzofuran-5-yl)-3-methyl-5-oxo-1,5-dihydro-pyrazol-4-ylidene]-hydrazino}-2'-hydroxy-biphenyl-3-carboxylic acid 3'-Amino-2'-hydroxy-biphenyl-3-carboxylic acid hydrobromide 1f (155 mg, 0.5 mmol) was dissolved in 1.7 mL of hydrochloric acid (1 N) followed by dropwise addition of 0.6 mL of aqueous sodium nitrite (36 mg, 0.53 mmol) and the mixture was stirred for 10 minutes upon cooling by an ice-water bath. Then 2-(2,3-dihydro-benzofuran-5-yl)-5-methyl-2,4-dihydro-pyrazol-3-one 7c (97 mg, 0.45 mmol) was added. The mixture was adjusted to pH 7 by batch addition of saturated aqueous sodium bicarbonate (630 mg, 7.5 mmol). The reaction mixture was warmed up to room temperature overnight. The reaction was monitored by TLC until the disappearance of the starting materials. The mixture was adjusted to pH<5 with concentrated hydrochloric acid. The mixture was filtered and dried to obtain the title compound 3'-{N'-[1-(2,3-dihydro-benzofuran-5-yl)-3-methyl-5-oxo-1,5-dihydro-pyrazol-4-ylidene]-hydrazino}-2'-hydroxy-biphenyl-3-carboxylic acid 7 (131 mg, yield 63.9%) as a brown solid.

MS m/z (ESI): 455 [M−1]

$^1$H NMR (400 MHz, DMSO-d$_6$): δ 2.33 (s, 3H), 3.24 (t, J=8.4 Hz, 2H), 4.56 (t, J=8.4 Hz, 2H), 6.82 (d, J=8.4 Hz, 1H), 7.16 (m, 2H), 7.61 (m, 2H), 7.72 (m, 2H), 7.80 (d, J=8.0 Hz, 1H), 7.96 (d, J=8.0 Hz, 1H), 8.13 (d, J=1.6 Hz, 1H), 9.64 (s, 1H), 13.01 (s, 1H), 13.75 (s, 1H)

Example 8

2-(3,3-Dimethyl-indan-5-yl)-4-{[2-hydroxy-3'-(1H-tetrazol-5-yl)-biphenyl-3-yl]-hydrazono}-5-methyl-2,4-dihydro-pyrazol-3-one

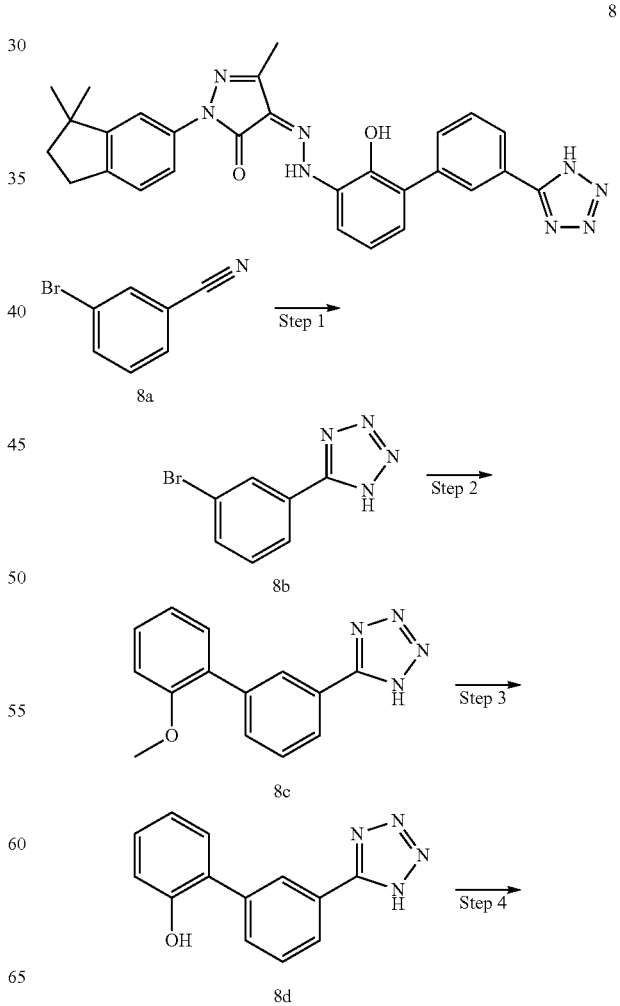

-continued

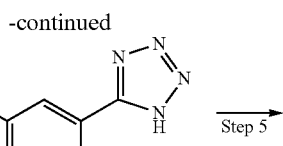

8e

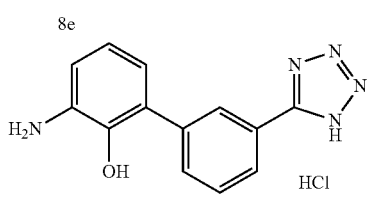

8f mixture was heated to 100° C. and reacted overnight. Then the mixture was cooled to 60° C. and concentrated under reduced pressure to remove N,N'-dimethylformamide. The residue was diluted with 100 mL of water and 4 mL of concentrated hydrochloric acid and stirred for 1 hour. The mixture was filtered and dried to obtain the title compound 5-(3-bromo-phenyl)-1H-tetrazole 8b (23 g) as a white solid.

Step 2

5-(2'-Methoxy-biphenyl-3-yl)-1H-tetrazole 5-(3-Bromo-phenyl)-1H-tetrazole 8b (20 g, 89 mmol) and 2-methoxybenzeneboronic acid (14.2 g, 93.3 mmol) were dissolved in 530 mL of 1,4-dioxane followed by addition of tetrakis(triphenylphosphine)palladium (1.84 g) and sodium carbonate (18.9 g, 178 mmol) under argon atmosphere. The reaction mixture was heated to reflux overnight. The reaction was monitored by TLC until the disappearance of the starting materials. The mixture was concentrated under reduced pressure to remove 1,4-dioxane and then hydrochloric acid (200 mL, 6 mol/L) was added. The mixture was cooled for 2 hours and the layers were separated. The organic layer was collected and concentrated. The residue was dissolved in 500 mL of ethyl acetate and washed with 250 mL of water. The mixture was dried over anhydrous sodium sulfate and concentrated under reduced pressure. The residue was dissolved in 25 mL of ethyl acetate and standing overnight. The mixture was filtered to obtain the title compound 5-(2'-methoxy-biphenyl-3-yl)-1H-tetrazole 8c (15 g, yield 68.2%) as a light yellow solid.

Step 3

3'-(1H-Tetrazol-5-yl)-biphenyl-2-ol 5-(2'-Methoxy-biphenyl-3-yl)-1H-tetrazole 8c (15.5 g, 61.5 mol) was dissolved in 195 mL of acetic acid followed by addition of 195 mL of hydrobromic acid under argon atmosphere. The reaction mixture was heated to reflux for 5 hours. The reaction was monitored by TLC until the disappearance of the starting materials. The mixture was cooled to room temperature overnight. The mixture was filtered and the filter cake was dissolved in 500 mL of ethyl acetate. The mixture was washed with water (500 mL×2), dried over anhydrous sodium sulfate, filtered and concentrated under reduced pressure. The residue was recrystallized from 100 mL of ethyl acetate to obtain the title compound 3'-(1H-tetrazol-5-yl)-biphenyl-2-ol 8d (12 g, yield 82.8%) as a white solid.

Step 4

3-Nitro-3'-(1H-tetrazol-5-yl)-biphenyl-2-ol

3'-(1H-Tetrazol-5-yl)-biphenyl-2-ol 8d (3.5 g, 14.7 mmol) was dissolved in 145 mL of ethanol under argon atmosphere. Fuming nitric acid (0.565 mL, 13.2 mmol) was added dropwise at 35° C. After the reaction mixture was reacted at room temperature for 1 hour, 150 mL of water was added. After standing overnight, the mixture was filtered. The filter cake was washed with 100 mL of water and dissolved in 500 mL of ethyl acetate and 250 mL of water. The separated organic layer was washed with saturated brine and dried over anhydrous magnesium sulfate. The mixture was purified by silica gel column chromatography to obtain the title compound 3-nitro-3'-(1H-tetrazol-5-yl)-biphenyl-2-ol 8e (1 g, yield 27.0%) as a yellow solid.

MS m/z (ESI): 282 [M−1]

Step 1

5-(3-Bromo-phenyl)-1H-tetrazole

3-Bromo-benzonitrile 8a (18.2 g, 0.1 mol) and ammonium chloride (5.9 g, 0.11 mol) were dissolved in 80 mL of N,N'-dimethylformamide followed by addition of sodium azide (7.16 g, 0.11 mol) under argon atmosphere. The reaction Step 5

3-Amino-3'-(1H-tetrazol-5-yl)-biphenyl-2-ol hydrochloride

3-Nitro-3'-(1H-tetrazol-5-yl)-biphenyl-2-ol 8e (2.5 g, 8.83 mmol) was dissolved in 118 mL of ethanol and 78.6 mL of water followed by addition of aqueous sodium hydroxide (2.95 mL, 3 mol/L) and 313 mg of palladium on carbon. The mixture was hydrogenated for 3 hours in a hydrogenator under 3 atm. of hydrogen. The reaction was monitored by TLC until the disappearance of the starting materials. The mixture was filtered and then hydrochloric acid (60 mL, 3 mol/L) was added to the filtrate. The filtrate was concentrated under reduced pressure. The residue was diluted with a small amount of water and filtered. The filter cake was washed with water and n-hexane and dried to obtain the title compound 3-amino-3'-(1H-tetrazol-5-yl)-biphenyl-2-ol hydrochloride 8f (2.33 g) as a brown solid.

MS m/z (ESI): 252 [M+1]

Step 6

Di-tert-butyl 1-(3,3-dimethyl-2,3-dihydro-1H-inden-5-yl)hydrazine-1,2-dicarboxylate 6-Bromo-1,1-dimethyl-indan (WO2005066115) 8g (4.32 g, 19.27 mmol) was dissolved in 40 mL of tetrahydrofuran and then butyllithium (15.67 mL, 1.6 mol/L, 25.05 mmol) was added dropwise at −78° C. After the reaction mixture was reacted for 40 minutes, a solution of di-tert-butyl azodicarboxylate (5.32 g, 23.12 mmol) in 30 mL of tetrahydrofuran was then added. The reaction mixture was reacted for another 3 hours at −78° C. The reaction was monitored by TLC until the disappearance of the starting materials and quenched with 5 mL of methanol. The mixture was warmed up to room temperature and filtered by silica gel. The filtrate was concentrated under reduced pressure and the residue was purified by silica gel column chromatography to obtain the title compound di-tert-butyl 1-(3,3-dimethyl-2,3-dihydro-1H-inden-5-yl)hydrazine-1,2-dicarboxylate 8h (2.70 g, yield 37.2%) as a yellow solid.

Step 7

2-(3,3-Dimethyl-indan-5-yl)-5-methyl-2,4-dihydro-pyrazol-3-one

Di-tert-butyl 1-(3,3-dimethyl-2,3-dihydro-1H-inden-5-yl)hydrazine-1,2-dicarboxylate 8h (2.70 g, 7.18 mmol) was dissolved in 100 mL of acetic acid followed by addition of 20 mL of trifluoroacetic acid. After the mixture was reacted at room temperature for 2 hours, ethyl acetoacetate (0.98 g, 7.54 mmol) was added. Then the mixture was heated to 100° C. and reacted for 2 hours. The reaction was monitored by TLC until the disappearance of the starting materials. The mixture was cooled to room temperature and concentrated under reduced pressure to remove acetic acid. The reaction mixture was neutralized by saturated aqueous sodium bicarbonate. Then the mixture was extracted with ethyl acetate. The combined organic extracts were washed with saturated brine, dried over anhydrous sodium sulfate, filtered and concentrated under reduced pressure. The resulting residue was purified by silica gel column chromatography to obtain the title compound 2-(3,3-dimethyl-indan-5-yl)-5-methyl-2,4-dihydro-pyrazol-3-one 8i (1.0 g, yield 47.7%) as a light brown solid.

MS m/z (ESI): 243 [M+1]

Step 8

2-(3,3-Dimethyl-indan-5-yl)-4-{[2-hydroxy-3'-(1H-tetrazol-5-yl)-biphenyl-3-yl]-hydrazono}-5-methyl-2,4-dihydro-pyrazol-3-one 3-Amino-3'-(1H-tetrazol-5-yl)-biphenyl-2-ol hydrochloride 8f (290 mg, 1.0 mmol) was dissolved in hydrochloric acid (3.4 mL, 1 mol/L) followed by dropwise addition of 1.2 mL of aqueous sodium nitrite (73 mg, 1.05 mmol) upon cooling by an ice-water bath. After the mixture was reacted at room temperature for 10 minutes, 2-(3,3-dimethyl-indan-5-yl)-5-methyl-2,4-dihydro-pyrazol-3-one 8i (218 mg, 0.9 mmol), sodium bicarbonate (1.26 g, 15 mmol) and 4.4 mL of ethanol were added successively. Then the reaction mixture was reacted for 10 hours. The reaction was monitored by TLC until the disappearance of the starting materials. The mixture was filtered and the filter cake was washed with 20 mL of water and then dissolved in 20 mL of water. Upon cooling by an ice-water bath, the mixture was adjusted to pH<5 with concentrated hydrochloric acid. The mixture was filtered and dried to obtain the title compound 2-(3,3-dimethyl-indan-5-yl)-4-{[2-hydroxy-3'-(1H-tetrazol-5-yl)-biphenyl-3-yl]-hydrazono}-5-methyl-2,4-dihydro-pyrazol-3-one 8 (336 mg, yield 73.8%) as a yellow solid.

MS m/z (ESI): 505 [M−1]

¹H NMR (400 MHz, DMSO-d₆): δ 1.24 (m, 6H), 1.92 (t, J=7.2 Hz, 2H), 2.36 (s, 3H), 2.87 (t, J=7.2 Hz, 2H), 7.21 (m, 3H), 7.73 (m, 5H), 8.08 (d, J=7.6 Hz, 1H), 8.25 (s, 1H), 9.77 (s, 1H), 13.80 (s, 1H)

Example 9

5-{2-Hydroxy-3-[N'-(1-indan-5-yl-3-methyl-5-oxo-1,5-dihydro-pyrazol-4-ylidene)-hydrazino]-phenyl}-furan-2-carboxylic acid

9

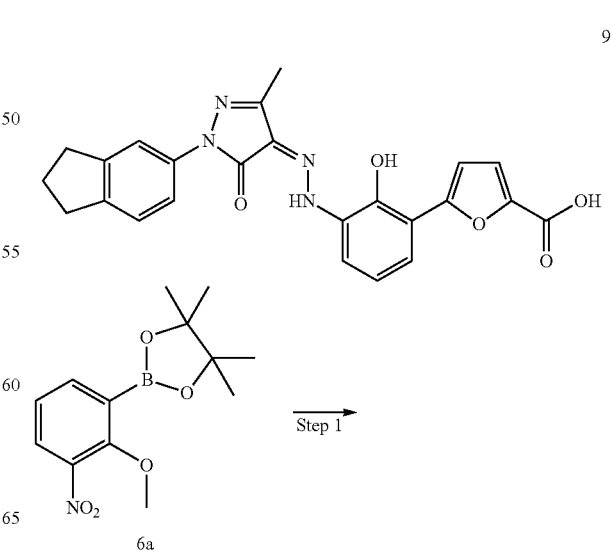

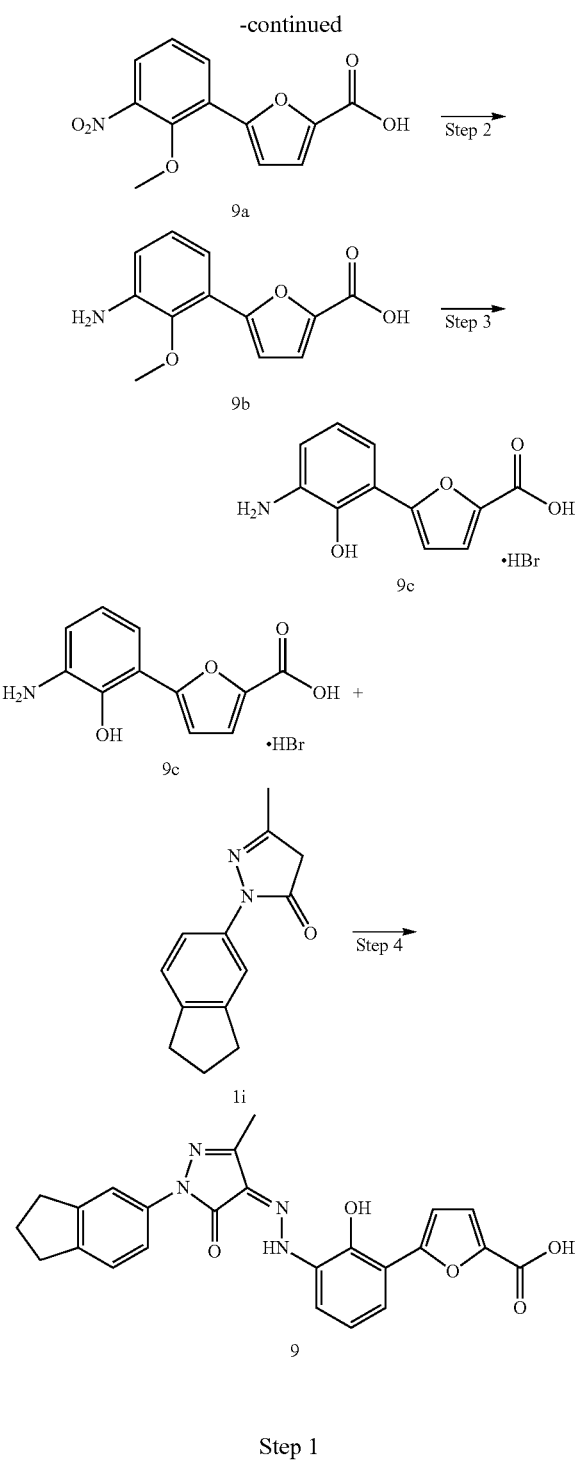

Step 1

5-(2-Methoxy-3-nitro-phenyl)furan-2-carboxylic acid 2-(2-Methoxy-3-nitro-phenyl)-4,4,5,5-tetramethyl-[1,3,2]dioxaborolane 6a (10 g, 35.85 mmol), 5-bromofuran-2-carboxylic acid (5.47 g, 28.66 mmol), tetrakis(triphenylphosphine)palladium (2.07 g, 1.79 mmol) and sodium carbonate (7.60 g, 71.66 mmol) were dissolved in the solvent mixture of 200 mL of 1,4-dioxane and 30 mL of water. The reaction mixture was heated to reflux for 2.5 hours. The reaction was monitored by TLC until the disappearance of the starting materials. The mixture was filtered and the filtrate was concentrated under reduced pressure. The residue was diluted with 150 mL of water and adjusted to pH 3 with 1 N hydrochloric acid. Then the mixture was filtered and the filter cake was washed with 50 mL of the solvent mixture of n-hexane/ethyl acetate (V/V=1:1). The residue was dried to obtain the title compound 5-(2-methoxy-3-nitro-phenyl)furan-2-carboxylic acid 9a (4.23 g, yield 56.1%) as a grey solid.

MS m/z (ESI): 262 [M−1]

Step 2

5-(3-Amino-2-methoxy-phenyl)-furan-2-carboxylic acid 5-(2-methoxy-3-nitro-phenyl)furan-2-carboxylic acid 9a (4.23 g, 16.09 mmol) was dissolved in 125 mL of ethyl acetate followed by addition of 423 mg of palladium on carbon and ammonium formate (4.054 g, 64.35 mmol). The reaction mixture was heated to reflux for 3.5 hours. The reaction was monitored by TLC until the disappearance of the starting materials. The mixture was concentrated under reduced pressure and the resulting residue was purified by silica gel column chromatography to obtain the title compound 5-(3-amino-2-methoxy-phenyl)-furan-2-carboxylic acid 9b (2.79 g, yield 74.4%) as a light green solid.

MS m/z (ESI): 232 [M−1]

Step 3

5-(3-Amino-2-hydroxy-phenyl)-furan-2-carboxylic acid hydrobromide 5-(3-Amino-2-methoxy-phenyl)-furan-2-carboxylic acid 9b (2.79 g, 11.97 mmol) was dissolved in 25 mL of dichloromethane followed by dropwise addition of boron tribromide (23.9 mL, 2.0 mol/L). The reaction mixture was reacted at room temperature for 1 hour. The reaction was monitored by TLC until the disappearance of the starting materials. The mixture was concentrated under reduced pressure after 5 mL of methanol was added. The residue was diluted with 100 mL of ethyl acetate and stirred for 1 hour. Then the mixture was filtered and the filter cake was dried to obtain the title compound 5-(3-amino-2-hydroxy-phenyl)-furan-2-carboxylic acid hydrobromide 9c (1.24 g, yield 47.2%) as a yellow solid.

MS m/z (ESI): 218 [M−1]

Step 4

5-(3-Amino-2-hydroxy-phenyl)-furan-2-carboxylic acid hydrobromide 9c (300 mg, 1.0 mmol) was dissolved in hydrochloric acid (3.4 mL, 1 mol/L) followed by dropwise addition of 1.2 mL of aqueous sodium nitrite (73 mg, 1.05 mmol) upon cooling by an ice-water bath. After the mixture was reacted for 10 minutes, 2-indan-5-yl-5-methyl-2,4-dihydro-pyrazol-3-one 1i (193 mg, 0.9 mmol), sodium bicarbonate (1.26 g, 15 mmol) and 4.4 mL of ethanol were added successively. The mixture was reacted at room temperature for 24 hours. The reaction was monitored by TLC until the disappearance of the starting materials. The mixture was filtered and the filter cake was washed with 20 mL of water and then dissolved in 20 mL of water. Upon cooling by an ice-water bath, the mixture was adjusted to pH<5 with concentrated hydrochloric acid, filtered and dried to obtain the title compound 5-{2-hydroxy-3-[N'-(1-indan-5-yl-3-methyl-5-oxo-1,5-dihydro-pyrazol-4-ylidene)-hydrazino]-phenyl}-furan-2-carboxylic acid 9 (287 mg, yield 71.8%) as a yellow solid.

MS m/z (ESI): 443 [M−1]

¹H NMR (400 MHz, DMSO-d₆): δ 2.03 (m, 2H), 2.32 (s, 3H), 2.89 (m, 4H), 7.15 (m, 1H), 7.22 (t, J=8.0 Hz, 1H), 7.29 (d, J=8.0 Hz, 1H), 7.36 (d, J=3.6 Hz, 1H), 7.57 (m, 1H), 7.70 (m, 2H), 7.78 (s, 1H), 9.97 (s, 1H), 13.73 (s, 1H)

Example 10

4-{[2-Hydroxy-3'-(1H-tetrazol-5-yl)-biphenyl-3-yl]-hydrazono}-5-methyl-2-(5,6,7,8-tetrahydro-naphtha-len-2-yl)-2,4-dihydro-pyrazol-3-one

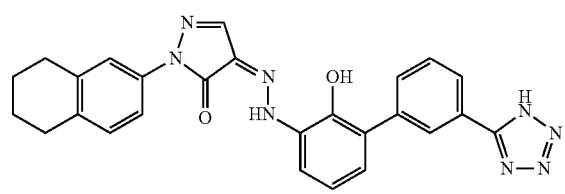

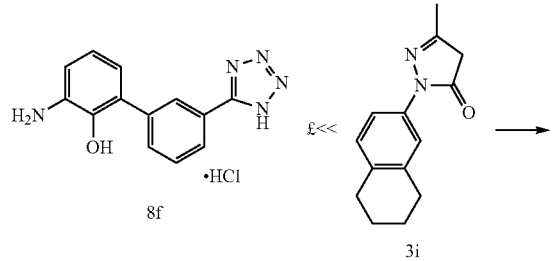

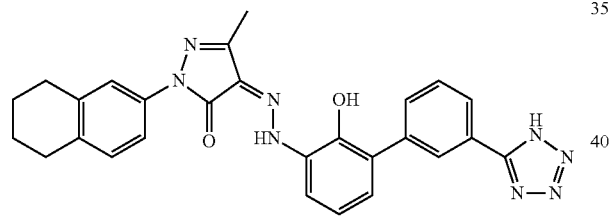

3-Amino-3'-(1H-tetrazol-5-yl)-biphenyl-2-ol hydrochloride 8f (340 mg, 1.34 mmol) was dissolved in 3 mL of 1 N hydrochloric acid followed by dropwise addition of 3 mL of aqueous sodium nitrite (98 mg, 1.41 mmol) upon cooling by an ice-water bath. After the mixture was reacted for 10 minutes, 5-methyl-2-(5,6,7,8-tetrahydro-naphthalen-2-yl)-2,4-dihydro-pyrazol-3-one 3i (276 mg, 1.21 mmol), sodium bicarbonate (1.69 g, 20 mmol) and 3 mL of ethanol were added successively. The reaction mixture was reacted at room temperature for 18 hours. The reaction was monitored by TLC until the disappearance of the starting materials. The mixture was filtered and the filter cake was washed with 20 mL of water and then dissolved in 20 mL of water. Upon cooling by an ice-water bath, the mixture was adjusted to pH 3~4 with concentrated hydrochloric acid. Then the mixture was filtered and dried to obtain the title compound 4-{[2-hydroxy-3'-(1H-tetrazol-5-yl)-biphenyl-3-yl]-hydrazono}-5-methyl-2-(5,6,7,8-tetrahydro-naphthalen-2-yl)-2,4-dihydro-pyrazol-3-one 10 (208 mg, 31.6%) as a yellow solid.

MS m/z (ESI): 491 [M−1]

¹H NMR (400 MHz, DMSO-d₆): δ 8.19 (1H, s), 7.99 (1H, s), 7.69 (2H, t, J=8.8), 7.49 (2H, d, J=7.6), 7.15 (3H, m), 2.75 (4H, m), 2.39 (3H, s), 1.75 (4H, m)

Example 11

2'-Hydroxy-5'-methyl-3'-{N'-[3-methyl-5-oxo-1-(5,6,7,8-tetrahydro-naphthalen-2-yl)-1,5-dihydro-pyra-zol-4-ylidene]-hydrazino}-biphenyl-3-carboxylic acid

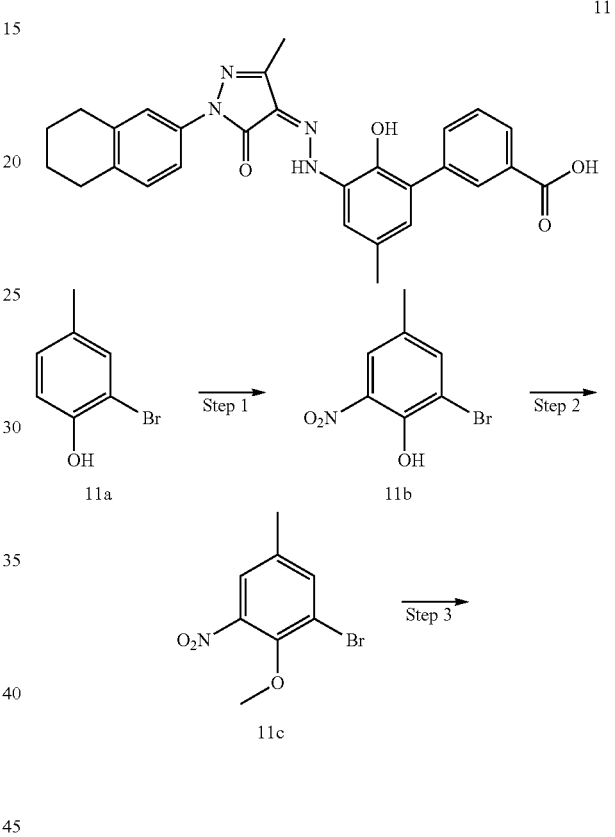

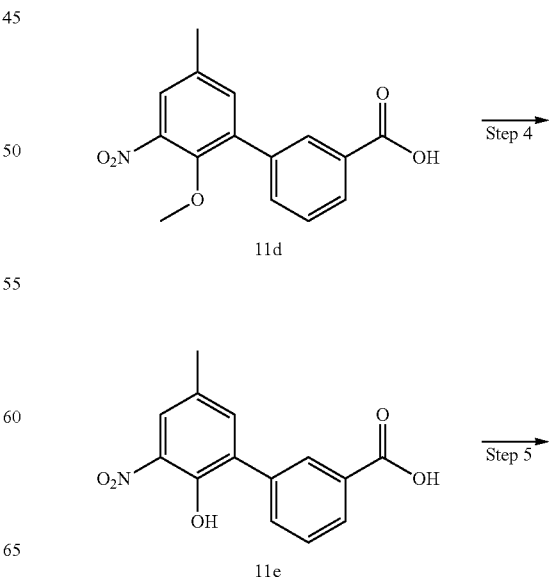

-continued

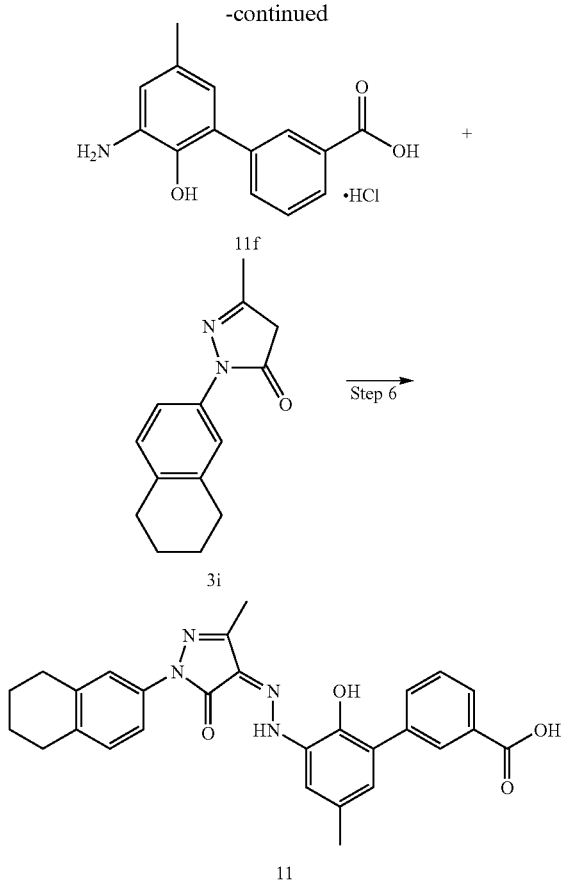

Step 1

2-Bromo-4-methyl-6-nitro-phenol

Sodium nitrate (28 g, 0.33 mmol) was dissolved in the solvent mixture of 70 mL of concentrated sulfuric acid and 210 mL of water at −5° C., followed by slowly dropwise addition of 2-bromo-4-methyl-phenol 11a (30.8 g, 0.165 mol). The reaction mixture was reacted for 2 hours upon cooling by an ice-water bath. The mixture was warmed up to room temperature and reacted for another 1 hour. The reaction was monitored by TLC until the disappearance of the starting materials. The mixture was extracted with 200 mL of ethyl acetate. The combined organic extracts were washed with water (100 mL×5), dried over anhydrous sodium sulfate, filtered and concentrated under reduced pressure. The residue was purified by silica gel column chromatography to obtain the title compound 2-bromo-4-methyl-6-nitro-phenol 11b (22.24 g, yield 58.1%) as a yellow solid.

$^1$H NMR (400 MHz, DMSO-$d_6$): δ 2.29 (s, 3H), 7.81 (m, 2H), 10.76 (s, 1H)

Step 2

1-Bromo-2-methoxy-5-methyl-3-nitro-benzene

2-Bromo-4-methyl-6-nitro-phenol 11b (22.24 g, 95.9 mmol) was dissolved in 150 mL of acetone, followed by addition of potassium carbonate (15.9 g, 115 mmol) and iodomethane (13.7 mL, 220.6 mmol). The reaction mixture was heated to reflux overnight. The reaction was monitored by TLC until the disappearance of the starting materials. The mixture was filtered and the filtrate was concentrated under reduced pressure. The residue was diluted with 100 mL of ethyl acetate and filtered. The mixture was concentrated under reduced pressure to obtain the title compound 1-bromo-2-methoxy-5-methyl-3-nitro-benzene 11c (23.1 g, yield 97.9%) as an orange solid.

Step 3

2'-Methoxy-5'-methyl-3-nitro-biphenyl-3-carboxylic acid

1-Bromo-2-methoxy-5-methyl-3-nitro-benzene 11c (15.0 g, 61 mmol) and 3-carboxyphenylboronic acid (11.6 g, 70.1 mmol) were dissolved in 200 mL of 1,4-dioxane followed by addition of tetrakis(triphenylphosphine)palladium (2.8 g, 2.44 mmol) and 61 mL of aqueous sodium carbonate (12.9 g, 122 mmol). The reaction mixture was heated to reflux overnight. The reaction was monitored by TLC until the disappearance of the starting materials. The mixture was concentrated under reduced pressure and the residue was diluted with 500 mL of water. The mixture was washed with the solvent mixture of 150 mL of n-hexane and 150 mL of ethyl acetate followed by ethyl acetate (300 mL×2). The aqueous layer was adjusted to pH 1~2 with concentrated hydrochloric acid. The mixture was filtered and the filter cake was dried to obtain the title compound 2'-methoxy-5'-methyl-3-nitro-biphenyl-3-carboxylic acid 11d (15.4 g, 88.1%) as a yellow solid.

$^1$H NMR (400 MHz, DMSO-$d_6$): δ 2.40 (s, 3H), 3.42 (s, 3H), 7.58 (s, 1H), 7.58~7.75 (m, 1H), 7.75 (d, J=1.6 Hz, 1H), 7.82~7.84 (m, 1H), 8.02 (d, J=8 Hz, 1H), 8.11 (d, J=1.6 Hz, 1H), 13.12 (s, 1H)

Step 4

2'-Hydroxy-5'-methyl-3'-nitro-biphenyl-3-carboxylic acid

2'-Methoxy-5'-methyl-3'-nitro-biphenyl-3-carboxylic acid 11d (11.2 g, 39.0 mmol) was dissolved in hydrobromic acid (250 mL, 40%). The reaction mixture was heated to reflux overnight. The reaction was monitored by TLC until the disappearance of the starting materials. The mixture was cooled to room temperature and filtered. The filter cake was washed with water and n-hexane and dried to obtain the title compound 2'-hydroxy-5'-methyl-3'-nitro-biphenyl-3-carboxylic acid 11e (9.15 g, yield 85.9%) as a yellow solid.

MS m/z (ESI): 272 [M−1]

$^1$H NMR (400 MHz, DMSO-$d_6$): δ 2.36 (s, 3H), 7.60 (m, 2H), 7.78 (d, J=8 Hz, 1H), 7.88 (d, J=1.2 Hz, 1H), 7.97 (d, J=8 Hz, 1H), 8.11 (s, 1H), 10.44 (s, 1H), 13.06 (s, 1H)

Step 5

3'-Amino-2'-hydroxy-5'-methyl-biphenyl-3-carboxylic acid hydrochloride

2'-Hydroxy-5'-methyl-3'-nitro-biphenyl-3-carboxylic acid 11e (9.15 g, 33.5 mmol) was dissolved in 200 mL of ethyl acetate followed by addition of 2 g of palladium on carbon and ammonium formate (8.45 g, 134 mmol). The reaction mixture was heated to reflux for 30 minutes. The reaction was monitored by TLC until the disappearance of the starting materials. The mixture was filtered and the filtrate was acidified by hydrochloric acid. The mixture was filtered and dried to obtain the title compound 3'-amino-2'-hydroxy-5'-methyl-biphenyl-3-carboxylic acid hydrochloride 11f (6.65 g, yield 71.0%) as a white solid.

MS m/z (ESI): 242 [M−1]

$^1$H NMR (400 MHz, DMSO-d$_6$): δ 2.29 (s, 3H), 7.09 (d, J=1.6 Hz, 1H), 7.14 (d, J=1.6 Hz, 1H), 7.59 (t, J=8 Hz, 1H), 7.74 (dd, J$_1$=6.4 Hz, J$_2$=1.6 Hz, 1H), 7.94 (dd, J$_1$=6.4 Hz, J$_2$=1.6 Hz, 1H), 8.07 (s, 1H)

Step 6

2'-Hydroxy-5'-methyl-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid 3'-Amino-2'-hydroxy-5'-methyl-biphenyl-3-carboxylic acid hydrochloride 11f (272 mg, 0.97 mmol) was dissolved in hydrochloric acid (3.3 mL, 1 mol/L) followed by dropwise addition of 1.3 mL of aqueous sodium nitrite (74 mg, 1.07 mmol) upon cooling by an ice-water bath. After the mixture was reacted for 20 minutes, 5-methyl-2-(5,6,7,8-tetrahydro-naphthalen-2-yl)-2,4-dihydro-pyrazol-3-one 3i (200 mg, 0.88 mmol), sodium bicarbonate (1.22 g, 14.6 mmol) and 2.1 mL of ethanol were added successively. The reaction mixture was reacted at room temperature for 4 hours. The reaction was monitored by TLC until the disappearance of the starting materials. The mixture was filtered and the filter cake was washed with 20 mL of water and then dissolved in 20 mL of water. Upon cooling by an ice-water bath, the mixture was adjusted to pH<5 with concentrated hydrochloric acid, filtered and dried to obtain the title compound 2'-hydroxy-5'-methyl-3'-{N'-[3-methyl-5-oxo-1-(5,6,7,8-tetrahydro-naphthalen-2-yl)-1,5-dihydro-pyrazol-4-ylidene]-hydrazino}-biphenyl-3-carboxylic acid 11 (170 mg, yield 40.2%) as a red solid.

MS m/z (ESI): 481 [M−1]

$^1$H NMR (400 MHz, DMSO-d$_6$): δ 1.75 (m, 4H), 2.30 (s, 3H), 2.34 (s, 3H), 2.74 (m, 4H), 7.00 (d, J=1.2 Hz, 1H), 7.11 (d, J=8.0 Hz, 1H), 7.53 (s, 1H), 7.62 (m, 3H), 7.80 (d, J=7.6 Hz, 1H), 7.95 (d, J=7.6 Hz, 1H), 8.14 (s, 1H), 9.39 (s, 1H), 13.03 (s, 1H), 13.77 (s, 1H)

Example 12

5-(3-{N'-[1-(3,3-Dimethyl-indan-5-yl)-3-methyl-5-oxo-1,5-dihydro-pyrazol-4-ylidene]-hydrazino}-2-hydroxy-phenyl)-thiophene-2-carboxylic acid

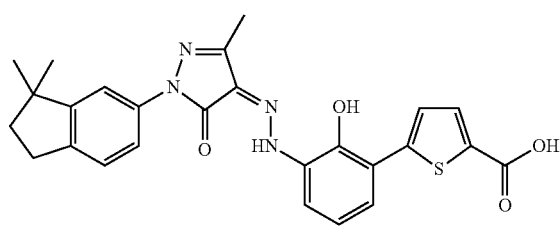

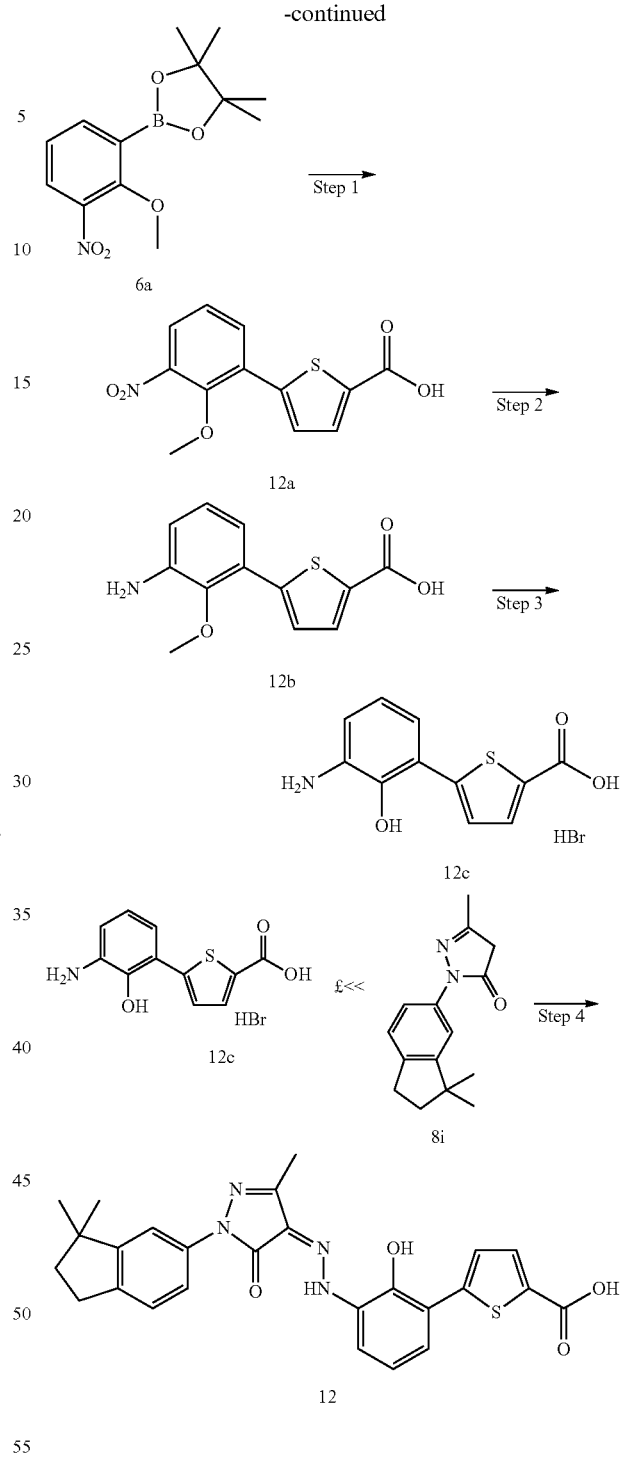

Step 1

5-(2-Methoxy-3-nitro-phenyl)thiophene-2-carboxylic acid 2-(2-Methoxy-3-nitro-phenyl)-4,4,5,5-tetramethyl-[1,3,2]dioxaborolane 6a (10 g, 35.85 mmol), 5-bromothiophene-2-carboxylic acid (6.68 g, 32.2 mmol), tetrakis(triphenylphosphine)palladium (2.07 g, 1.79 mmol) and sodium carbonate (7.59 g, 71.6 mmol) were dissolved in the solvent mixture of 200 mL of 1,4-dioxane and 30 mL of water. The reaction mixture was heated to reflux for 1 hour. The reaction was monitored by TLC until the disappearance of the starting materials. The mixture was filtered and the filtrate was concentrated under reduced pressure. The residue was diluted with 150 mL of water and adjusted to pH 3 with 1 N hydrochloric acid. The mixture was filtered and the filter cake was washed with 50 mL of the solvent mixture of n-hexane/ethyl acetate (V:V=1/1) and dried to obtain the title compound 5-(2-methoxy-3-nitro-phenyl)thiophene-2-carboxylic acid 12a (7.7 g, yield 77%) as a light yellow solid.

MS m/z (ESI): 277.9 [M−1]

Step 2

5-(3-Amino-2-methoxy-phenyl)-thiophene-2-carboxylic acid 5-(2-methoxy-3-nitro-phenyl)thiophene-2-carboxylic acid 12a (7.7 g, 27.6 mmol) was dissolved in 300 mL of ethyl acetate followed by addition of 500 mg of palladium on carbon and ammonium formate (6.96 g, 110 mmol). The reaction mixture was heated to reflux for 4 hours. The reaction was monitored by TLC until the disappearance of the starting materials. The mixture was concentrated under reduced pressure and the resulting residue was purified by silica gel column chromatography to obtain the title compound 5-(3-amino-2-methoxy-phenyl)-thiophene-2-carboxylic acid 12b (6.2 g, yield 90.1%) as a grey solid.

MS m/z (ESI): 248 [M−1]

Step 3

5-(3-Amino-2-hydroxy-phenyl)-thiophene-2-carboxylic acid hydrobromide 5-(3-Amino-2-methoxy-phenyl)-thiophene-2-carboxylic acid 12b (2.2 g, 8.83 mmol) was dissolved in 20 mL of dichloromethane followed by dropwise addition of boron tribromide (35 mL, 35.32 mmol/L). The reaction mixture was reacted at room temperature for 1.5 hours. The reaction was monitored by TLC until the disappearance of the starting materials. Then 5 mL of methanol was added and the mixture was concentrated under reduced pressure. The residue was diluted with 100 mL of ethyl acetate and stirred for 1.5 hours. The mixture was filtered and the filter cake was dried to obtain the title compound 5-(3-amino-2-hydroxy-phenyl)-thiophene-2-carboxylic acid hydrobromide 12c (1.2 g, yield 57.1%) as a grey solid.

MS m/z (ESI): 234 [M−1]

Step 4

5-(3-{N'-[1-(3,3-Dimethyl-indan-5-yl)-3-methyl-5-oxo-1,5-dihydro-pyrazol-4-ylidene]-hydrazino}-2-hydroxy-phenyl)-thiophene-2-carboxylic acid 5-(3-Amino-2-hydroxy-phenyl)-thiophene-2-carboxylic acid 12c (171 mg, 0.62 mmol) was dissolved in 3 mL of hydrochloric acid (1 N) upon cooling by an ice-water bath, followed by dropwise addition of 1 mL of aqueous sodium nitrite (47 mg, 0.68 mmol). After the mixture was stirred for 20 minutes, 2-(3,3-dimethyl-indan-5-yl)-5-methyl-2,4-dihydro-pyrazol-3-one 8i (150 mg, 0.62 mmol) was added. The mixture was adjusted to pH 8-9 by batch addition of aqueous sodium bicarbonate (781 mg, 9.3 mmol). The generated bubbles were quenched with 2 mL of ethanol and the mixture was warmed up to room temperature and stirred overnight. The reaction was monitored by TLC until the disappearance of the starting materials. The mixture was filtered and the filter cake was dissolved in 20 mL of water. The mixture was adjusted to pH 3~4 with concentrated hydrochloric acid, filtered and dried. The crude product was purified by HPLC to obtain the title compound 5-(3-{N'-[1-(3,3-dimethyl-indan-5-yl)-3-methyl-5-oxo-1,5-dihydro-pyrazol-4-ylidene]-hydrazino}-2-hydroxy-phenyl)-thiophene-2-carboxylic acid 12 (48 mg, yield 15.9%) as an orange solid.

MS m/z (ESI): 487 [M−1]

$^1$H NMR (400 MHz, DMSO-d$_6$): δ 1.24 (t, J=8.6, 6H), 1.93 (t, J=7.0, 2H), 2.87 (t, J=7.0, 2H), 7.16 (m, J=6.0, 1H), 7.27 (d, J=4.2, 2H), 7.57 (d, J=8.0, 1H), 7.64 (d, J=4.0, 1H), 7.70 (t, J=8.4, 2H), 7.75 (d, J=4.0, 1H)

Example 13

3'-{N'-[1-(2,3-Dihydro-benzofuran-5-yl)-3-methyl-5-oxo-1,5-dihydro-pyrazol-4-ylidene]-hydrazino}-2'-hydroxy-5'-methyl-biphenyl-3-carboxylic acid

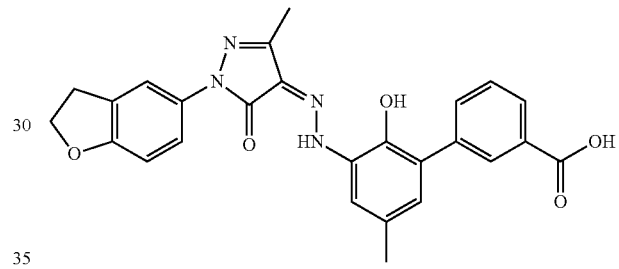

13

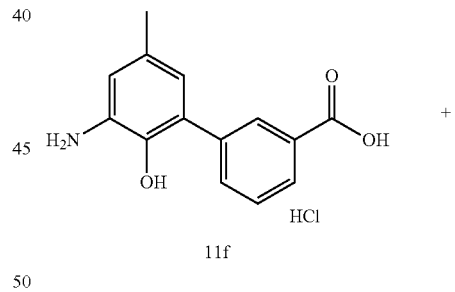

11f

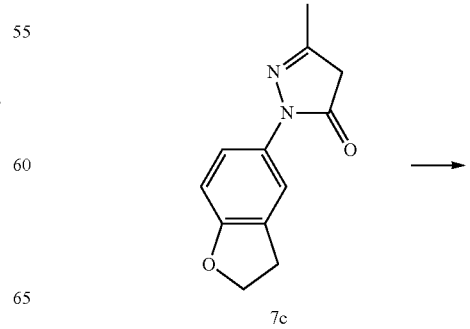

7c

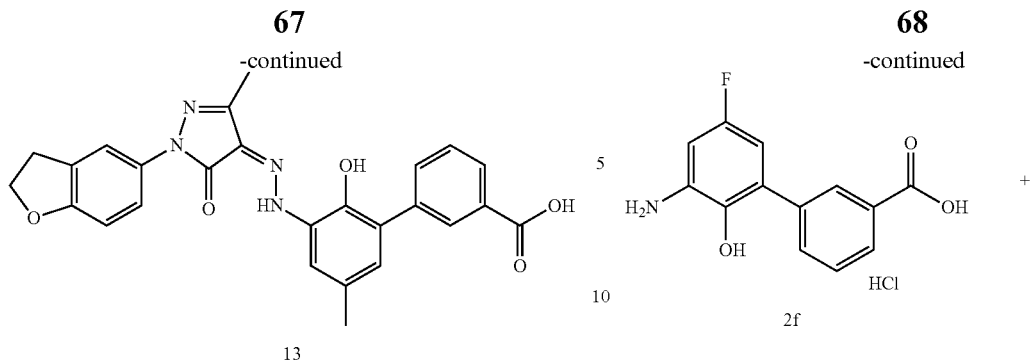

13

3'-Amino-2'-hydroxy-5'-methyl-biphenyl-3-carboxylic acid hydrochloride 11f (287 mg, 1.03 mmol) was dissolved in 3.5 mL of hydrochloric acid (1 N) upon cooling by an ice-water bath, followed by dropwise addition of 1.5 mL of aqueous sodium nitrite (78 mg, 1.13 mmol). After the mixture was stirred for 20 minutes, 2-(2,3-dihydro-benzofuran-5-yl)-5-methyl-2,4-dihydro-pyrazol-3-one 7c (200 mg, 0.93 mmol) was added. The mixture was adjusted to pH 8-9 by batch addition of aqueous sodium bicarbonate (1.298 g, 15.45 mmol). The generated bubbles were quenched with 2 mL of ethanol. The mixture was warmed up to room temperature and reacted overnight. The reaction was monitored by TLC until the disappearance of the starting materials. The mixture was filtered and then the filter cake was dissolved in 20 mL of water. After mixing well, the mixture was adjusted to pH 3~4 with concentrated hydrochloric acid, filtered and dried. The residue was washed with 10 mL of the solvent mixture of dichloromethane/methanol (V:V=1:1), and then the crude product was purified by HPLC to obtain the title compound 3'-{N'-[1-(2,3-dihydro-benzofuran-5-yl)-3-methyl-5-oxo-1,5-dihydro-pyrazol-4-ylidene]-hydrazino}-2'-hydroxy-5'-methyl-biphenyl-3-carboxylic acid 13 (100 mg, yield 23.0%) as a red solid.

MS m/z (ESI): 469 [M−1]

$^1$H NMR (400 MHz, DMSO-d$_6$): δ 2.34 (s, 3H), 2.36 (s, 3H), 3.24 (t, J=8.8 Hz, 2H), 4.57 (t, J=8.8 Hz, 2H), 6.82 (d, J=8.8 Hz, 1H), 7.00 (s, 1H), 7.54 (s, 1H), 7.61 (m, 2H), 7.74 (s, 1H), 7.80 (d, J=7.6 Hz, 1H), 7.95 (d, J=7.6 Hz, 1H), 8.13 (s, 1H), 9.38 (s, 1H), 13.02 (s, 1H), 13.76 (s, 1H)

Example 14

3'-{N'-[1-(2,3-Dihydro-benzofuran-5-yl)-3-methyl-5-oxo-1,5-dihydro-pyrazol-4-ylidene]-hydrazino}-5'-fluoro-2'-hydroxy-biphenyl-3-carboxylic acid

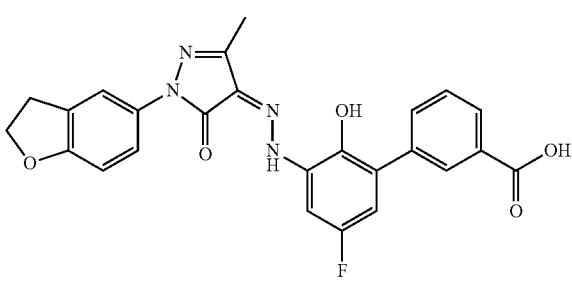

14

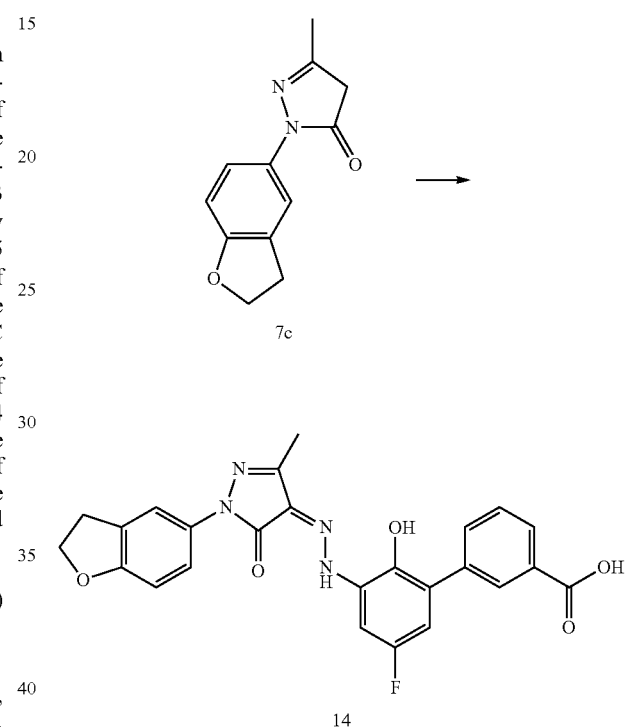

3'-Amino-5'-fluoro-2'-hydroxy-biphenyl-3-carboxylic acid hydrochloride 2f (219 mg, 0.772 mmol) was dissolved in 3 mL of hydrochloric acid (1 N) upon cooling by an ice-water bath, followed by dropwise addition of 1 mL of aqueous sodium nitrite (59 mg, 0.85 mmol). After the mixture was stirred for 20 minutes, 2-(2,3-dihydro-benzofuran-5-yl)-5-methyl-2,4-dihydro-pyrazol-3-one 7c (150 mg, 0.69 mmol) was added. The mixture was adjusted to pH 8~9 by batch addition of aqueous sodium bicarbonate (1.007 g, 11.57 mmol). The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 15 mL of water. After mixing well, the mixture was adjusted to pH 3~4 with concentrated hydrochloric acid, filtered and dried. The crude product was purified by HPLC to obtain the title compound 3'-{N'-[1-(2,3-dihydro-benzofuran-5-yl)-3-methyl-5-oxo-1,5-dihydro-pyrazol-4-ylidene]-hydrazino}-5'-fluoro-2'-hydroxy-biphenyl-3-carboxylic acid 14 (65 mg, yield 20.0%) as a red solid.

MS m/z (ESI): 473 [M−1]

$^1$H NMR (400 MHz, DMSO-d$_6$): δ 2.33 (s, 3H), 3.23 (t, J=8.8 Hz, 2H), 4.56 (t, J=8.8 Hz, 2H), 6.83 (d, J=8.4 Hz, 1H), 7.03 (m, 1H), 7.48 (m, 1H), 7.60 (m, 2H), 7.65 (s, 1H), 7.83

(d, J=8.0 Hz, 1H), 7.98 (d, J=8.0 Hz, 1H), 8.17 (s, 1H), 9.57 (s, 1H), 13.07 (s, 1H), 13.62 (s, 1H)

Example 15

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid

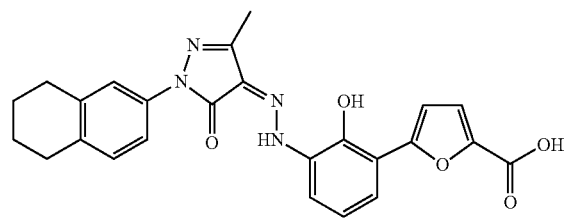

15

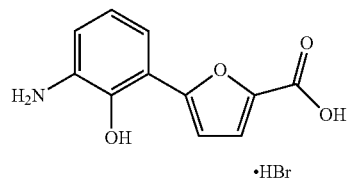

9c

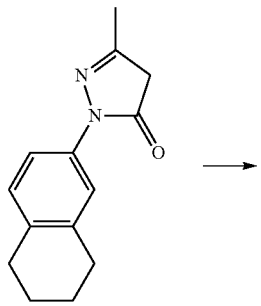

3i

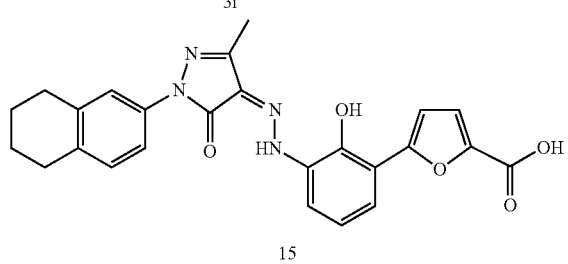

15

5-(3-Amino-2-hydroxy-phenyl)-furan-2-carboxylic acid hydrobromide 9c (292 mg, 0.975 mmol) was dissolved in 3.3 mL of hydrochloric acid (1 N) upon cooling by an ice-water bath, followed by dropwise addition of 1.3 mL of aqueous sodium nitrite (74 mg, 1.07 mmol). After the mixture was stirred for 20 minutes, 5-methyl-2-(5,6,7,8-tetrahydro-naphthalen-2-yl)-2,4-dihydro-pyrazol-3-one 3i (200 mg, 0.88 mmol) was added. The mixture was adjusted to pH 8-9 by batch addition of aqueous sodium bicarbonate (1.226 g, 14.6 mmol). The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 20 mL of water. After mixing well, the mixture was adjusted to pH 3~4 with concentrated hydrochloric acid, filtered and dried. The crude product was purified by HPLC to obtain the title compound 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 15 (160 mg, yield 39.8%) as a red solid.

MS m/z (ESI): 457 [M−1]

$^1$H NMR (400 MHz, DMSO-d$_6$): δ 1.76 (m, 4H), 2.33 (s, 3H), 2.75 (m, 4H), 7.13 (m, 2H), 7.22 (t, J=8.0 Hz, 1H), 7.37 (d, J=3.2 Hz, 1H), 7.56 (d, J=7.6 Hz, 1H), 7.63 (m, 2H), 7.71 (d, J=8.4 Hz, 1H)

Example 16

3'-{N'-[1-(3,3-Dimethyl-indan-5-yl)-3-methyl-5-oxo-1,5-dihydro-pyrazol-4-ylidene]-hydrazino}-2'-hydroxy-5'-methyl-biphenyl-3-carboxylic acid

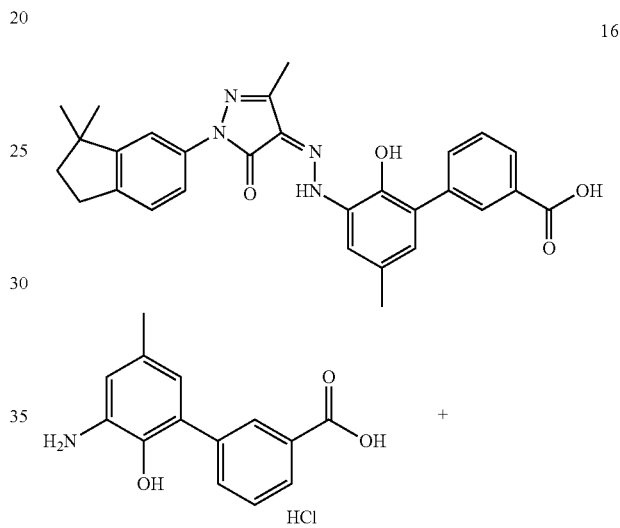

16

11f

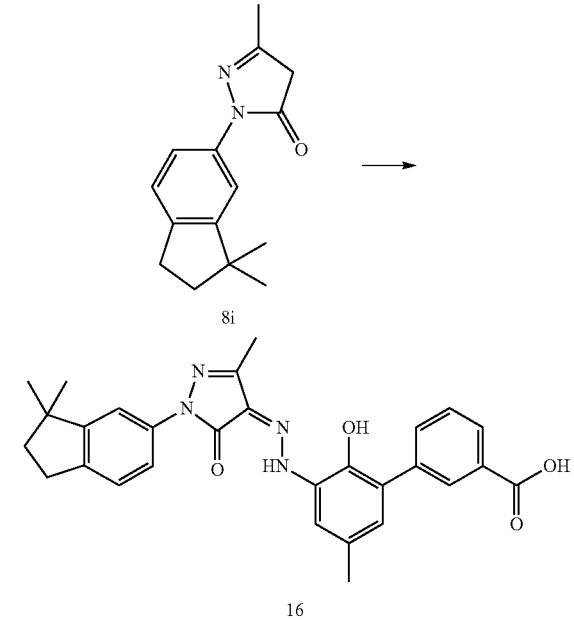

8i

16

3'-Amino-2'-hydroxy-5'-methyl-biphenyl-3-carboxylic acid hydrochloride 11f (257 mg, 0.92 mmol) was dissolved in 3.1 mL of hydrochloric acid (1 N) upon cooling by an ice-water bath, followed by dropwise addition of 1.2 mL of aqueous sodium nitrite (70 mg, 1.01 mmol). After the mixture was stirred for 20 minutes, 2-(3,3-dimethyl-indan-5-yl)-5-methyl-2,4-dihydro-pyrazol-3-one 8i (200 mg, 0.83 mmol) was added. The mixture was adjusted to pH 8~9 by batch addition of aqueous sodium bicarbonate (1.157 g, 13.8 mmol). The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 30 mL of water. After mixing well, the mixture was adjusted to pH 3~4 with concentrated hydrochloric acid, filtered and dried. The crude product was purified by HPLC to obtain the title compound 3'-{N'-[1-(3,3-dimethyl-indan-5-yl)-3-methyl-5-oxo-1,5-dihydro-pyrazol-4-ylidene]-hydrazino}-2'-hydroxy-5'-methyl-biphenyl-3-carboxylic acid 16 (160 mg, yield 39.0%) as an orange solid.

MS m/z (ESI): 495 [M−1]

$^1$H NMR (400 MHz, DMSO-d$_6$): δ 1.25 (s, 6H), 1.92 (t=7.2 Hz, 2H), 2.35 (s, 3H), 2.86 (t, J=7.6 Hz, 2H), 7.00 (s, 1H), 7.25 (d, J=8.8 Hz, 1H), 7.54 (s, 1H), 7.61 (t, J=8.0 Hz, 1H), 7.69 (m, 2H), 7.80 (d, J=7.6 Hz, 1H), 7.95 (d, J=7.6 Hz, 1H), 8.14 (s, 1H), 9.41 (s, 1H), 13.05 (br, 1H), 13.77 (s, 1H)

Example 17

3'-{N'-[1-(3,3-Dimethyl-indan-5-yl)-3-methyl-5-oxo-1,5-dihydro-pyrazol-4-ylidene]-hydrazino}-5'-fluoro-2'-hydroxy-biphenyl-3-carboxylic acid

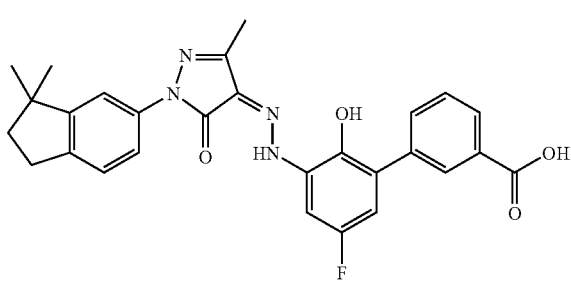

17

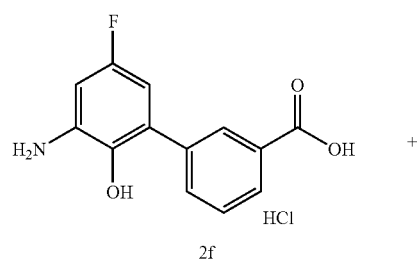

2f

+ HCl

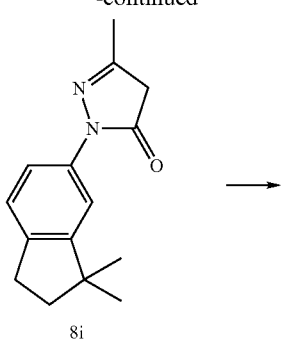

8i

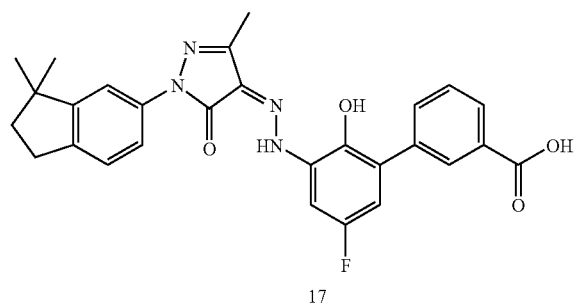

17

3'-Amino-5'-fluoro-2'-hydroxy-biphenyl-3-carboxylic acid hydrochloride 2f (200 mg, 0.71 mmol) was dissolved in 2.4 mL of hydrochloric acid (1 N) upon cooling by an ice-water bath, followed by dropwise addition of 1 mL of aqueous sodium nitrite (54 mg, 0.78 mmol). After the mixture was stirred for 20 minutes, 2-(3,3-dimethyl-indan-5-yl)-5-methyl-2,4-dihydro-pyrazol-3-one 8i (153 mg, 0.64 mmol) was added. The mixture was adjusted to pH 8-9 by batch addition of aqueous sodium bicarbonate (889 mg, 10.6 mmol). The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 20 mL of water. After mixing well, the mixture was adjusted to pH 3~4 with concentrated hydrochloric acid, filtered and dried. The crude product was purified by HPLC to obtain the title compound 3'-{N'-[1-(3,3-dimethyl-indan-5-yl)-3-methyl-5-oxo-1,5-dihydro-pyrazol-4-ylidene]-hydrazino}-5'-fluoro-2'-hydroxy-biphenyl-3-carboxylic acid 17 (120 mg, yield 38.0%) as a red solid.

MS m/z (ESI): 499 [M−1]

$^1$H NMR (400 MHz, DMSO-d$_6$): δ 1.25 (s, 6H), 1.92 (t, J=7.2 Hz, 2H), 2.34 (s, 3H), 2.86 (t, J=7.2 Hz, 2H), 7.03 (m, 1H), 7.25 (d, J=8.4 Hz, 1H), 7.47 (m, 1H), 7.63 (m, 3H), 7.83

(d, J=7.6 Hz, 1H), 7.98 (d, J=8.0 Hz, 1H), 8.18 (s, 1H), 9.60 (s, 1H), 13.07 (br, 1H), 13.64 (s, 1H)

Example 18

5-{2-Hydroxy-3-[N'-(1-indan-5-yl-3-methyl-5-oxo-1,5-dihydro-pyrazol-4-ylidene)-hydrazino]-phenyl}-thiophene-2-carboxylic acid

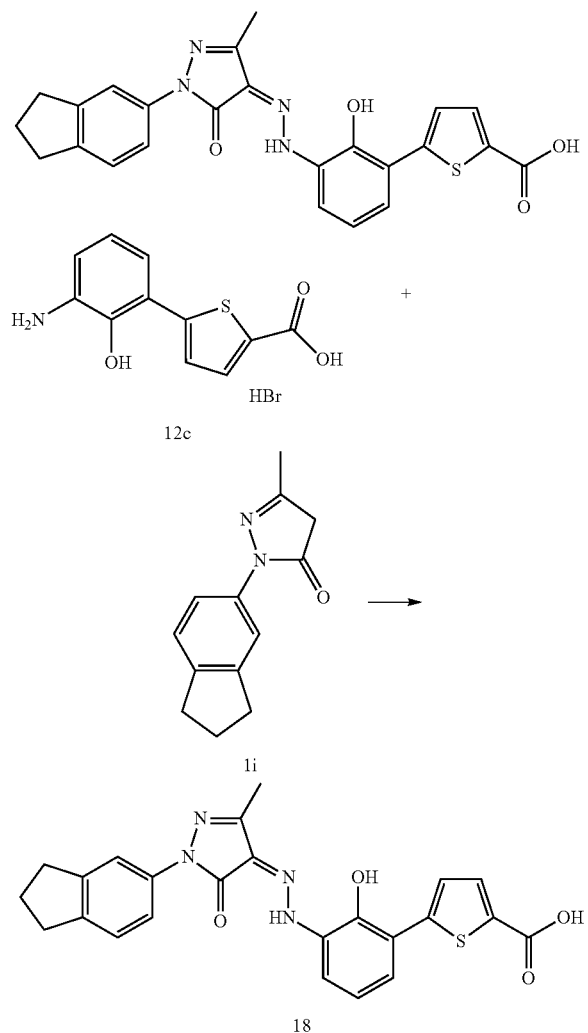

5-(3-Amino-2-hydroxy-phenyl)-thiophene-2-carboxylic acid hydrobromide 12c (380 mg, 1.2 mmol) was dissolved in 3.9 mL of hydrochloric acid (1 N) upon cooling by an ice-water bath, followed by dropwise addition of 1.5 mL of aqueous sodium nitrite (90 mg, 1.32 mmol). After the mixture was stirred for 20 minutes, 2-indan-5-yl-5-methyl-2,4-dihydro-pyrazol-3-one 1i (210 mg, 1 mmol) was added. The mixture was adjusted to pH 8~9 by batch addition of aqueous sodium bicarbonate (1.51 g, 18 mmol). The generated bubbles were quenched with 2 mL of ethanol and the reaction mixture was warmed up to room temperature and reacted overnight. The reaction was monitored by TLC until the disappearance of the starting materials. The mixture was filtered and the filter cake was dissolved in 20 mL of 5% aqueous sodium hydroxide. The layers were separated and then the aqueous layer was extracted with dichloromethane (50 mL×3). The aqueous layer was adjusted to pH 3~4 with concentrated hydrochloric acid, filtered and dried. The crude product was purified by HPLC to obtain the title compound 5-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 18 (15 mg, yield 3.3%) as an orange solid.

MS m/z (ESI): 459 [M−1]

$^1$H NMR (400 MHz, DMSO-$d_6$): δ 1.36-1.78 (m, 2H), 2.33 (s, 3H), 2.86-2.94 (m, 4H), 7.17 (t, J=8 Hz, 1H), 7.30 (d, J=8 Hz, 1H), 7.56 (dd, $J_1$=8 Hz, $J_2$=0.8 Hz, 1H), 7.56 (d, J=4 Hz, 1H), 7.70 (m, 2H), 7.75 (d, J=4 Hz, 1H), 7.79 (s, 1H)

Example 19

2'-Hydroxy-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid

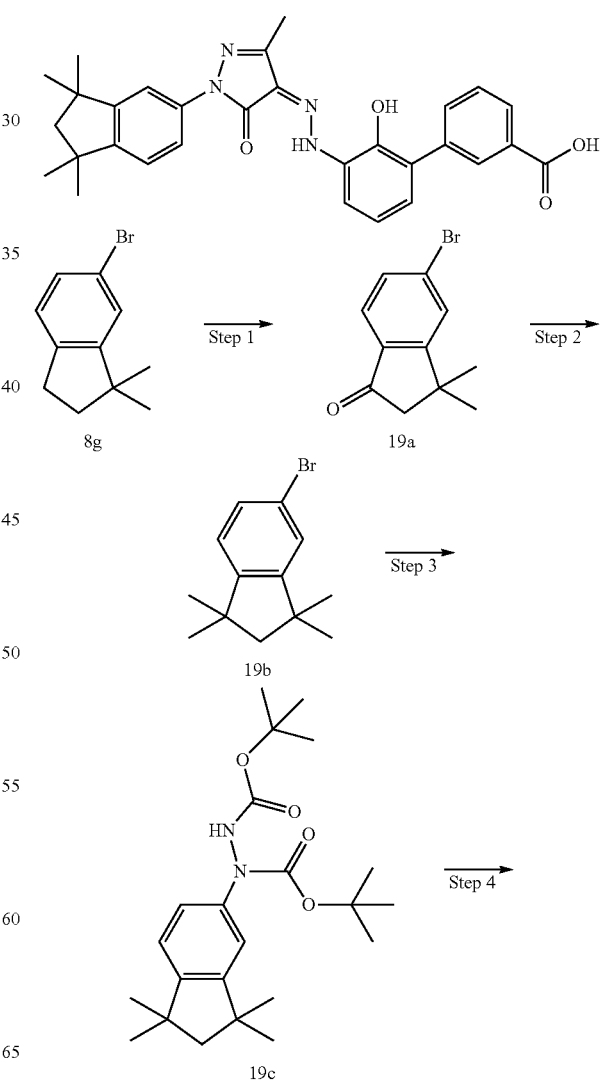

-continued

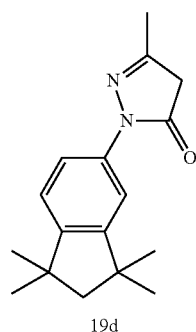

19d

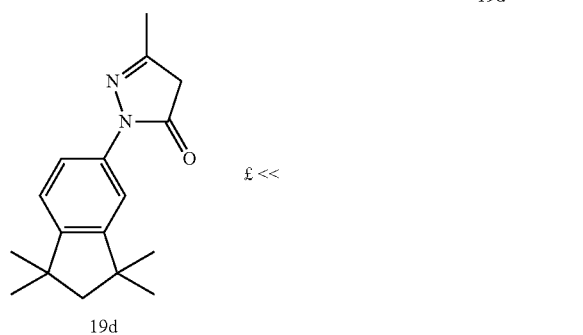

19d

HBr
1f

19

Step 1

5-Bromo-3,3-dimethyl-indan-1-one

6-Bromo-1,1-dimethyl-indan 8g (4 g, 17.8 mmol) was dissolved in 40 mL of anhydrous dichloromethane, followed by addition of chromium oxide (280 mg, 1.8 mmol) and slowly dropwise addition of tert-butyl hydroperoxide (19 mL, 190 mmol). The reaction system was sealed and stirred overnight at room temperature after the reaction solution was crimson and the generated gas was released. The reaction was monitored by TLC until the disappearance of the starting materials. The mixture was diluted with 50 mL of water and extracted with dichloromethane (100 mL×3). The combined organic extracts were dried over anhydrous sodium sulfate, filtered and concentrated under reduced pressure to obtain the title compound 5-bromo-3,3-dimethyl-indan-1-one 19a (3.5 g, 82.3%) as a white solid.

MS m/z (ESI): 238 [M−1]

Step 2

5-Bromo-1,1,3,3-tetramethyl-indan

Upon cooling by a dry ice-acetonitrile bath, 40 mL of dichloromethane was cooled to −40° C. followed by addition of titanium tetrachloride (2.7 mL, 24.6 mmol) through a syringe. The mixture was stirred for 20 minutes at the same temperature and a solution of dimethyl zinc (29.3 mL, 35.1 mmol) in toluene was added at such a rate that the reaction temperature was kept below −30° C. Upon completion of the addition, the reaction mixture was stirred at the same temperature for 30 minutes and then a solution of 5-bromo-3,3-dimethyl-indan-1-one 19a (2.8 g, 11.7 mmol) in 10 mL of dichloromethane was added. The reaction mixture was warmed up to room temperature and reacted overnight. The reaction was monitored by TLC until the disappearance of the starting materials. The mixture was concentrated under reduced pressure and then the resulting residue was purified by silica gel column chromatography to obtain the title compound 5-bromo-1,1,3,3-tetramethyl-indan 19b (1.55 g, 52.3%) as a colourless oil.

MS m/z (ESI): 252 [M−1]

Step 3

Di-tert-butyl 1-(1,1,3,3-tetramethyl-2,3-dihydro-1H-inden-5-yl)hydrazine-1,2-dicarboxylate 5-Bromo-1,1,3,3-tetramethyl-indan 19b (1.4 g, 5.53 mmol) was dissolved in 10 mL of tetrahydrofuran and cooled to −78° C. in a dry ice-acetone bath. t-Butyllithium (4.4 mL, 11.1 mmol) was added dropwise at the same temperature and the mixture was stirred for 40 minutes. A solution of di-tert-butyl azodicarboxylate (1.59 g, 6.92 mmol) in 10 mL of tetrahydrofuran was added dropwise by a constant-pressure addition funnel. The reaction mixture was stirred at −78° C. for 3 hours. The reaction was monitored by TLC until the disappearance of the starting materials. The reaction was quenched with 5 mL of methanol and was warmed up to room temperature. The mixture was extracted with ethyl acetate (20 mL×3). The combined organic extracts were dried over anhydrous sodium sulfate, filtered and concentrated under reduced pressure. The residue was purified by silica gel column chromatography to obtain the title compound di-tert-butyl 1-(1,1,3,3-tetramethyl-2,3-dihydro-1H-inden-5-yl)hydrazine-1,2-dicarboxylate 19c (1.326 g, yield 59.3%) as a yellow oil.

MS m/z (ESI): 403 [M+1]

Step 4

5-Methyl-2-(1,1,3,3-tetramethyl-indan-5-yl)-2,4-dihydro-pyrazol-3-one

Di-tert-butyl 1-(1,1,3,3-tetramethyl-2,3-dihydro-1H-inden-5-yl)hydrazine-1,2-dicarboxylate 19c (2.70 g, 7.18 mmol) was dissolved in 10 mL of acetic acid followed by addition of 13 mL of trifluoroacetic acid. After the mixture was reacted at room temperature for 30 minutes, ethyl acetoacetate (502 mg, 3.86 mmol) was added. The reaction mixture was heated to 100° C. and reacted for 2 hours. The reaction was monitored by TLC until the disappearance of the starting materials. The mixture was cooled to room temperature and concentrated under reduced pressure to remove acetic acid. The mixture was neutralized by saturated aqueous sodium bicarbonate. The mixture was extracted with ethyl acetate (20 mL×3). The combined organic extracts were washed with saturated brine, dried over anhydrous sodium sulfate, filtered and concentrated under reduced pressure. The resulting residue was purified by silica gel column chromatography to obtain the title compound 5-methyl-2-(1,1,3,3-tetramethyl-indan-5-yl)-2,4-dihydro-pyrazol-3-one 19d (130 mg, yield 13.6%) as a light yellow oil.

MS m/z (ESI): 269 [M+1]

Step 5

2'-Hydroxy-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid 3'-Amino-2'-hydroxy-biphenyl-3-carboxylic acid hydrobromide 1f (172 mg, 0.56 mmol) was dissolved in 1.9 mL of 1 N hydrochloric acid upon cooling by an ice-water bath, followed by dropwise addition of 0.7 mL of aqueous sodium nitrite (42 mg, 0.61 mmol) and 5-methyl-2-(1,1,3,3-tetramethyl-indan-5-yl)-2,4-dihydro-pyrazol-3-one 19d (135 mg, 0.5 mmol). The mixture was adjusted to pH 8~9 by batch addition of saturated sodium bicarbonate (700 mg, 8.33 mmol) followed by addition of 2 mL of ethanol. The reaction mixture was warmed up to room temperature overnight. The reaction was monitored by TLC until the disappearance of the starting materials. The mixture was filtered and the filter cake was dissolved in 20 mL of water. After mixing well, the mixture was adjusted to pH 3~4 with concentrated hydrochloric acid, filtered and dried. The crude product was purified by HPLC to obtain the title compound 2'-hydroxy-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid 19 (75 mg, yield 29.4%) as a red solid.

MS m/z (ESI): 509 [M−1]

$^1$H NMR (400 MHz, DMSO-d$_6$): δ 1.30 (m, 12H), 1.92 (s, 2H), 2.35 (s, 3H), 7.14 (m, 2H), 7.23 (d, J=8.0 Hz, 1H), 7.62 (m, 2H), 7.72 (m, 2H), 7.80 (d, J=7.6 Hz, 1H), 7.96 (d, J=8.0 Hz, 1H), 8.14 (s, 1H), 9.68 (s, 1H), 13.10 (br, 1H), 13.78 (s, 1H)

Example 20

2'-Hydroxy-5'-methyl-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid

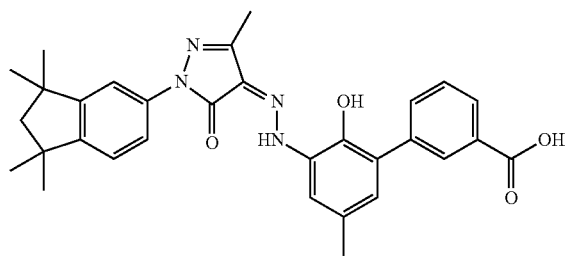

3'-Amino-2'-hydroxy-5'-methyl-biphenyl-3-carboxylic acid hydrochloride 11f (155 mg, 0.56 mmol) was dissolved in 1.9 mL of hydrochloric acid (1 N) upon cooling by an ice-water bath, followed by dropwise addition of 1.2 mL of aqueous sodium nitrite (42 mg, 0.61 mmol). After the mixture was stirred for 20 minutes, 5-methyl-2-(1,1,3,3-tetramethyl-indan-5-yl)-2,4-dihydro-pyrazol-3-one 19d (135 mg, 0.5 mmol) was added. The mixture was adjusted to pH 8~9 by batch addition of aqueous sodium bicarbonate (700 mg, 8.33 mmol). The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 30 mL of water. After mixing well, the mixture was adjusted to pH 3~4 with concentrated hydrochloric acid, filtered and dried. The crude product was purified by HPLC to obtain the title compound 2'-hydroxy-5'-methyl-3'-{N'-[3-methyl-5-oxo-1-(1,1,3,3-tetramethyl-indan-5-yl)-1,5-dihydro-pyrazol-4-ylidene]-hydrazino}-biphenyl-3-carboxylic acid 20 (50 mg, yield 19.1%) as a red solid.

MS m/z (ESI): 523 [M−1]

$^1$H NMR (400 MHz, DMSO-d$_6$): δ 1.30 (m, 12H), 1.92 (s, 2H), 2.35 (m, 6H), 7.00 (m, 1H), 7.23 (d, J=8.4 Hz, 1H), 7.59

(s, 1H), 7.65 (m, 2H), 7.74 (m, 1H), 7.80 (d, J=8.0 Hz, 1H), 7.95 (d, J=7.6 Hz, 1H), 8.14 (s, 1H), 9.41 (s, 1H), 13.05 (br, 1H), 13.78 (s, 1H)

Example 21

3'-[N'-(1-Bicyclo[4.2.0]octa-1(6),2,4-trien-3-yl-3-methyl-5-oxo-1,5-dihydro-pyrazol-4-ylidene)-hydrazino]-2'-hydroxy-5'-methyl-biphenyl-3-carboxylic acid

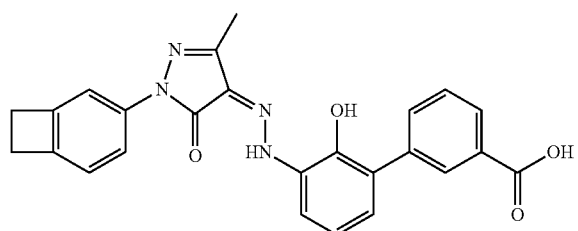

21

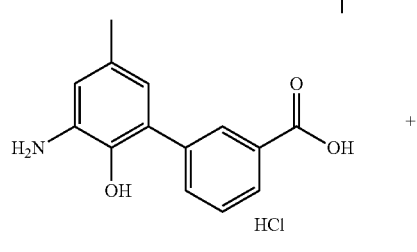

11f

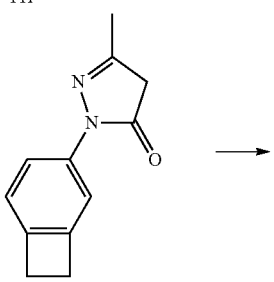

5d

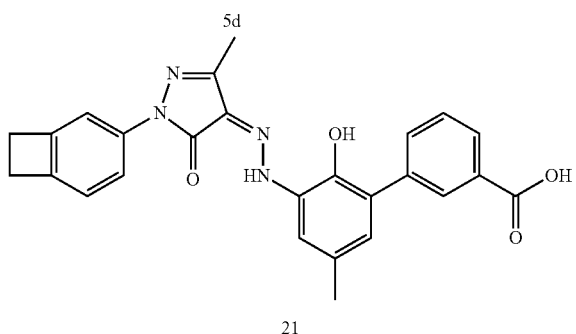

21

3'-Amino-2'-hydroxy-5'-methyl-biphenyl-3-carboxylic acid hydrochloride 11f (311 mg, 1.11 mmol) was dissolved in 3.7 mL of 1 N hydrochloric acid upon cooling by an ice-water bath, followed by dropwise addition of 1.5 mL of aqueous sodium nitrite (84 mg, 1.22 mmol) and 2-bicyclo[4.2.0]octa-1(6),2,4-trienyl-3-yl-5-methyl-2,4-dihydro-pyrazol-3-one 5d (200 mg, 1 mmol). The mixture was adjusted to pH 8~9 by batch addition of saturated sodium bicarbonate (1.4 g, 16.7 mmol) followed by addition of 2 mL of ethanol. The reaction mixture was warmed up to room temperature overnight. The reaction was monitored by TLC until the disappearance of the starting materials. The mixture was filtered and the filter cake was dissolved in 20 mL of water. After mixing well, the mixture was adjusted to pH 3~4 with concentrated hydrochloric acid, filtered and dried. The crude product was purified by HPLC to obtain the title compound 3'-[N'-(1-bicyclo[4.2.0]octa-1(6),2,4-trien-3-yl-3-methyl-5-oxo-1,5-dihydro-pyrazol-4-ylidene)-hydrazino]-2'-hydroxy-5'-methyl-biphenyl-3-carboxylic acid 21 (330 mg, yield 72.7%) as an orange solid.

MS m/z (ESI): 453 [M−1]

$^1$H NMR (400 MHz, DMSO-$d_6$): δ 2.34 (m, 6H), 3.16 (m, 4H), 7.00 (s, 1H), 7.15 (d, J=8.0 Hz, 1H), 7.54 (s, 1H), 7.62 (m, 2H), 7.71 (d, J=8.0 Hz, 1H), 7.80 (d, J=7.6 Hz, 1H), 7.95 (d, J=7.6 Hz, 1H), 8.13 (s, 1H), 9.40 (s, 1H), 13.02 (s, 1H), 13.75 (s, 1H)

Example 22

5-{3-[N'-(1-Bicyclo[4.2.0]octa-1(6),2,4-trien-3-yl-3-methyl-5-oxo-1,5-dihydro-pyrazol-4-ylidene)-hydrazino]-2-hydroxy-phenyl}-furan-2-carboxylic acid

22

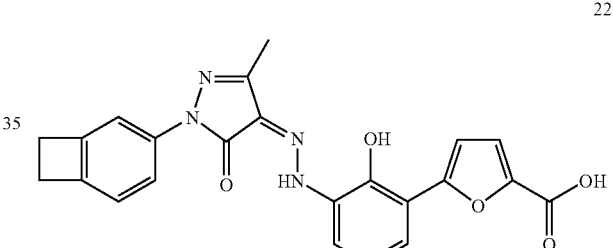

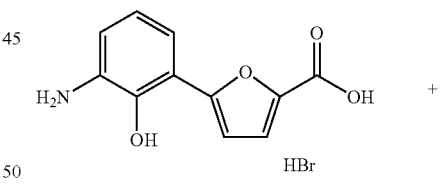

9c

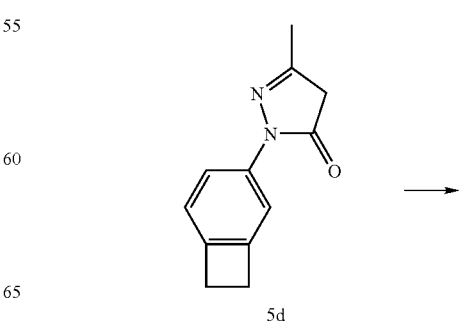

5d

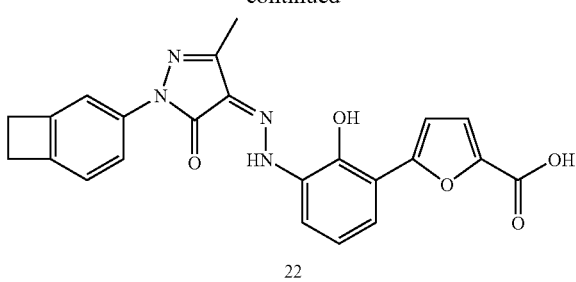

22

5-(3-Amino-2-hydroxy-phenyl)-furan-2-carboxylic acid hydrobromide 9c (333 mg, 1.11 mmol) was dissolved in 3.7 mL of 1 N hydrochloric acid upon cooling by an ice-water bath, followed by addition of 1.5 mL of aqueous sodium nitrite (84 mg, 1.22 mmol) and 2-bicyclo[4.2.0]octa-1(6),2,4-trienyl-3-yl-5-methyl-2,4-dihydro-pyrazol-3-one 5d (200 mg, 1 mmol). The mixture was adjusted to pH 8~9 by batch addition of saturated sodium bicarbonate (1.4 g, 16.7 mmol), followed by addition of 2 mL of ethanol. The reaction mixture was warmed up to room temperature overnight. The reaction was monitored by TLC until the disappearance of the starting materials. The mixture was filtered and the filter cake was dissolved in 20 mL of water. After mixing well, the mixture was adjusted to pH 3~4 with concentrated hydrochloric acid, filtered and dried. The crude product was purified by HPLC to obtain the title compound 5-{3-[N'-(1-bicyclo[4.2.0]octa-1(6),2,4-trien-3-yl-3-methyl-5-oxo-1,5-dihydro-pyrazol-4-ylidene)-hydrazino]-2-hydroxy-phenyl}-furan-2-carboxylic acid 22 (275 mg, yield 63.9%) as a red solid.

MS m/z (ESI): 429 [M−1]

$^1$H NMR (400 MHz, DMSO-$d_6$): δ 2.31 (s, 3H), 3.15 (m, 4H), 7.15 (m, 2H), 7.20 (t, J=8.0 Hz, 1H), 7.36 (d, J=3.6 Hz, 1H), 7.54 (m, 1H), 7.68 (m, 1H), 7.72 (m, 2H), 9.97 (s, 1H), 13.71 (s, 1H)

Example 23

2-Bicyclo[4.2.0]octa-1(6),2,4-trien-3-yl-4-{[2-hydroxy-3'-(1H-tetrazol-5-yl)-biphenyl-3-yl]-hydrazono}-5-methyl-2,4-dihydro-pyrazol-3-one

23

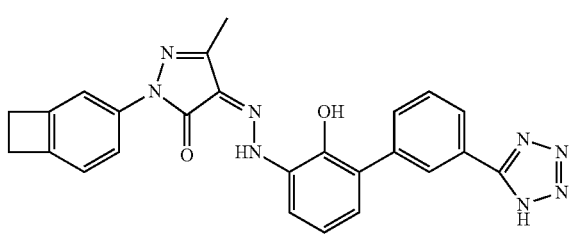

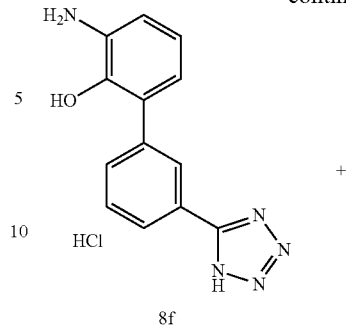

8f

5d

23

3-Amino-3'-(1H-tetrazol-5-yl)-biphenyl-2-ol hydrochloride 8f (321 mg, 1.11 mmol) was dissolved in 3.7 mL of 1 N hydrochloric acid upon cooling by an ice-water bath, followed by dropwise addition of 1.5 mL of aqueous sodium nitrite (85 mg, 1.22 mmol). After the mixture was reacted for 20 minutes, 2-bicyclo[4.2.0]octa-1(6),2,4-trienyl-3-yl-5-methyl-2,4-dihydro-pyrazol-3-one 5d (200 mg, 1 mmol), sodium bicarbonate (1.69 g, 20 mmol) and 3 mL of ethanol were added successively. The reaction mixture was warmed up to room temperature and stirred overnight. The reaction was monitored by TLC until the disappearance of the starting materials. The mixture was filtered and the filter cake was washed with 20 mL of water, and then dissolved in 20 mL of water. Upon cooling by an ice-water bath, the mixture was adjusted to pH 3-4 with concentrated hydrochloric acid. The mixture was filtered and dried to obtain the title compound 2-bicyclo[4.2.0]octa-1(6),2,4-trien-3-yl-4-{[2-hydroxy-3'-(1H-tetrazol-5-yl)-biphenyl-3-yl]-hydrazono}-5-methyl-2,4-dihydro-pyrazol-3-one 23 (150 mg, yield 32.3%) as a red solid.

MS m/z (ESI): 463 [M−1]

¹H NMR (400 MHz, DMSO-d₆): δ 2.34 (s, 3H), 3.16 (m, 4H), 7.18 (m, 3H), 7.68 (s, 1H), 7.73 (m, 4H), 8.08 (d, J=7.6 Hz, 1H), 8.25 (d, J=10 Hz, 1H), 9.71 (br, 1H), 13.77 (br, 1H)

Example 24

5-{2-Hydroxy-3-[N'-(1-indan-5-yl-3-methyl-5-oxo-1,5-dihydro-pyrazol-4-ylidene)-hydrazino]-5-methyl-phenyl}-thiophene-2-carboxylic acid

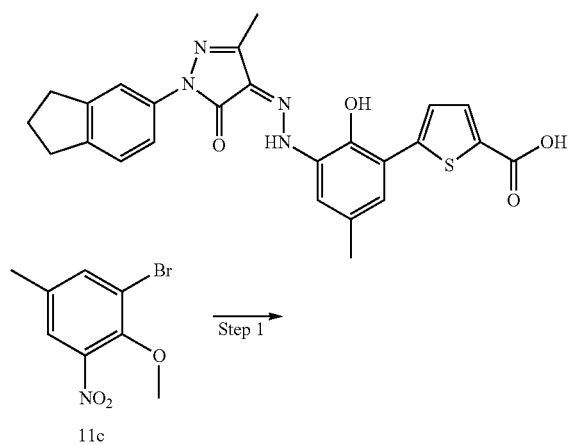

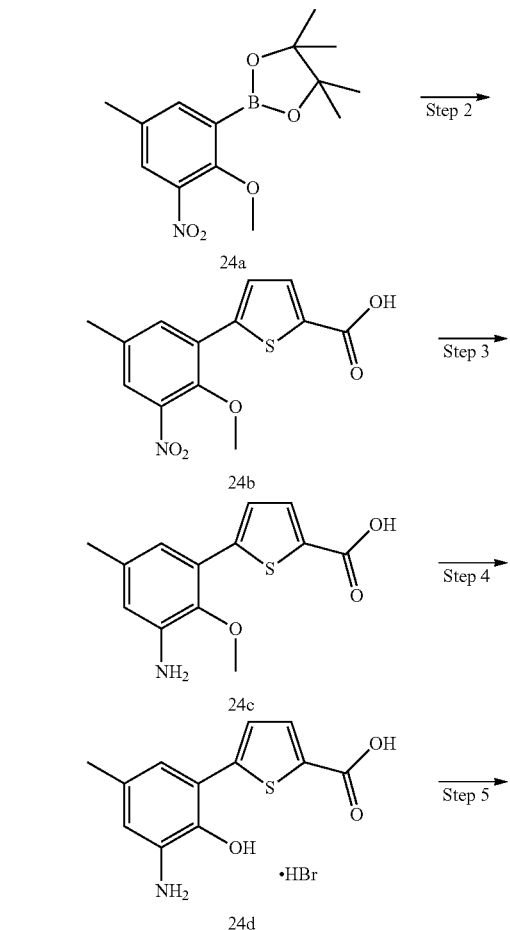

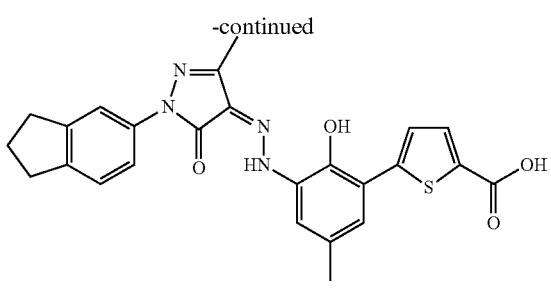

24

Step 1

2-(2-Methoxy-5-methyl-3-nitro-phenyl)-4,4,5,5-tetramethyl-1,3,2-dioxaborolane

3-Bromo-2-methoxy-5-methyl-nitrobenzene 11c (20 g, 81.3 mmol) and 4,4,4',4',5,5,5',5'-octamethyl-2,2'-bi-1,3,2-dioxaborolane (30.9 g, 112 mmol) were dissolved in 400 mL of dimethyl ether followed by addition of [1,1'-bis(diphenylphosphino)ferrocene]dichloropalladium(II) (3.3 g, 4.06 mmol) and potassium acetate (19.9 g, 203 mmol). Upon completion of the addition, the reaction mixture was heated to reflux for 3 hours. The mixture was filtered to remove [1,1'-bis(diphenylphosphino)ferrocene]dichloropalladium(II) and the filtrate was concentrated under reduced pressure. The residue was purified by silica gel column chromatography to obtain the title compound 2-(2-methoxy-5-methyl-3-nitro-phenyl)-4,4,5,5-tetramethyl-1,3,2-dioxaborolane 24a (13.1 g, 57.1%) as a yellow oil.
MS m/z

Step 2

5-(3-Nitro-2-methoxy-5-methyl-phenyl)thiophene-2-carboxylic acid 2-(2-Methoxy-5-methyl-3-nitro-phenyl)-4,4,5,5-tetramethyl-1,3,2-dioxaborolane 24a (4.0 g, 14.5 mmol), 5-bromothiophene-2-carboxylic acid (1.0 g, 4.8 mmol), tetrakis(triphenylphosphine)palladium (0.276 g, 0.24 mmol) and sodium carbonate (1.01 g, 9.6 mmol) were dissolved in 30 mL of 1,4-dioxane and 10 mL of water. The reaction mixture was heated to reflux for 1 hour. The reaction was monitored by TLC until the disappearance of the starting materials. The mixture was concentrated under reduced pressure and the residue was dissolved in water. The mixture was filtered to remove tetrakis(triphenylphosphine)palladium and the filtrate was extracted with ethyl acetate. The aqueous layer was acidified to form precipitates. The precipitates were dissolved in ethyl acetate, dried over anhydrous magnesium sulfate, filtered to remove the drying agent and concentrated under reduced pressure to obtain the title compound 5-(3-nitro-2-methoxy-5-methyl-phenyl)thiophene-2-carboxylic acid 24b (1.03 g, 73.6%) as a yellow solid.
MS m/z (ESI): 291.7 [M−1]
¹H NMR (400 MHz, CDCl₃): δ 2.41 (s, 3H), 3.73 (s, 3H), 7.73~7.79 (m, 3H), 8.00 (m, 1H), 13.20 (br, 1H)

Step 3

5-(3-Amino-2-methoxy-5-methyl-phenyl)-thiophene-2-carboxylic acid 5-(3-Nitro-2-methoxy-5-methyl-phenyl)thiophene-2-carboxylic acid 24b (0.29 g, 1 mmol) was dissolved in 30 mL of ethyl acetate followed by addition of 0.06 g of palladium on carbon and ammonium formate (0.25 g, 4 mmol). Upon completion of the addition, the reaction mixture was heated to reflux for 45 minutes. The reaction was monitored by TLC until the disappearance of the starting materials. The mixture was filtered to remove palladium on carbon. The filtrate was concentrated under reduced pressure and dried to obtain the title compound 5-(3-amino-2-methoxy-5-methyl-phenyl)-thiophene-2-carboxylic acid 24c (0.26 g, yield 99%) as a green solid.

MS m/z (ESI): 261.7 [M−1]

$^1$H NMR (400 MHz, CDCl$_3$): δ 2.18 (s, 3H), 3.58 (s, 3H), 6.54 (d, J=1.6 Hz, 1H), 6.78 (d, J=1.6 Hz, 1H), 7.53 (d, J=4 Hz, 1H), 7.68 (d, J=4 Hz, 1H)

Step 4

5-(3-Amino-2-hydroxy-5-methyl-phenyl)-thiophene-2-carboxylic acid hydrobromide 5-(3-Amino-2-methoxy-5-methyl-phenyl)-thiophene-2-carboxylic acid 24c (0.26 g, 1 mmol) was dissolved in 20 mL of dichloromethane followed by addition of boron tribromide (5 mL, 35.32 mmol/L). The mixture was reacted at room temperature for 1 hour. The reaction was monitored by TLC until the disappearance of the starting materials. The mixture was concentrated under reduced pressure. The residue was diluted with 30 mL of ethyl acetate and stirred for 0.5 hours. The mixture was filtered and the filter cake was washed with ethyl acetate and dried to obtain the title compound 5-(3-amino-2-hydroxy-5-methyl-phenyl)-thiophene-2-carboxylic acid hydrobromide 24d (0.15 g, yield 45.5%) as a grey solid.

MS m/z (ESI): 247.8 [M−1]

$^1$H NMR (400 MHz, CDCl$_3$): δ 2.29 (s, 3H), 7.02 (d, J=1.6 Hz, 1H), 7.41 (s, 1H), 7.59 (d, J=4 Hz, 1H), 7.73 (d, J=4 Hz, 1H)

Step 5

5-{2-Hydroxy-3-[N'-(1-indan-5-yl-3-methyl-5-oxo-1,5-dihydro-pyrazol-4-ylidene)-hydrazino]-5-methyl-phenyl}-thiophene-2-carboxylic acid 5-(3-Amino-2-hydroxy-5-methyl-phenyl)-thiophene-2-carboxylic acid hydrobromide 24d (138 mg, 0.42 mmol) was dissolved in 1.5 mL of 1 N hydrochloric acid upon cooling by an ice-water bath followed by dropwise addition of 1.5 mL of aqueous sodium nitrite (85 mg, 1.22 mmol). After the mixture was reacted for 20 minutes, 2-indan-5-yl-5-methyl-2,4-dihydro-pyrazol-3-one 1i (81 mg, 0.38 mmol), sodium bicarbonate (527 mg, 6.27 mmol) and 2 mL of ethanol were added successively. The reaction mixture was reacted overnight at room temperature. The reaction was monitored by TLC until the disappearance of the starting materials. The mixture was filtered and the filter cake was washed with 20 mL of water, and then dissolved in 10 mL of water. Upon cooling by an ice-water bath, the mixture was adjusted to pH 3-4 with concentrated hydrochloric acid, filtered and dried to obtain the title compound 5-{2-hydroxy-3-[N'-(1-indan-5-yl-3-methyl-5-oxo-1,5-dihydro-pyrazol-4-ylidene)-hydrazino]-5-methyl-phenyl}-thiophene-2-carboxylic acid 24 (30 mg, yield 16.7%) as a red solid.

MS m/z (ESI): 473 [M−1]

$^1$H NMR (400 MHz, DMSO-d$_6$): δ 2.03 (m, 2H), 2.32 (s, 3H), 2.36 (s, 3H), 2.89 (m, 4H), 7.29 (d, J=8.0 Hz, 1H), 7.38 (s, 1H), 7.50 (s, 1H), 7.63 (d, J=4.0 Hz, 1H), 7.68 (d, J=8.0 Hz, 1H), 7.74 (m, 2H), 9.78 (s, 1H), 13.72 (br, 1H)

Example 25

5-(2-Hydroxy-3-{N'-[3-methyl-5-oxo-1-(1,1,3,3-tetramethyl-indan-5-yl)-1,5-dihydro-pyrazol-4-ylidene]-hydrazino}-phenyl)-furan-2-carboxylic acid

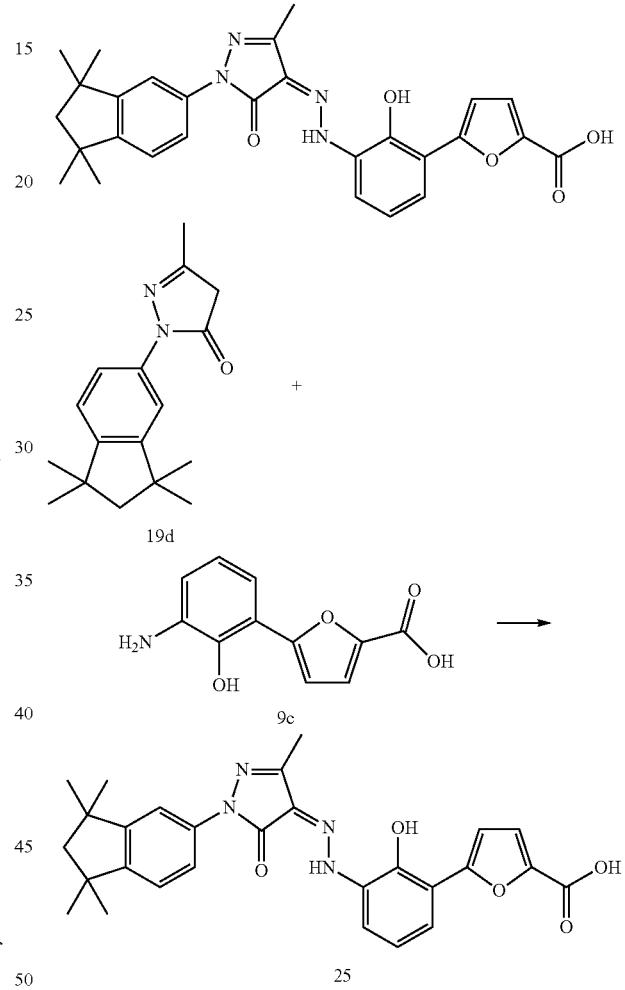

5-(3-Amino-2-hydroxy-phenyl)-furan-2-carboxylic acid hydrobromide 9c (124 mg, 0.41 mmol) was dissolved in 1.4 mL of hydrochloric acid (1 N) upon cooling by an ice-water bath, followed by dropwise addition of 0.5 mL of aqueous sodium nitrite (32 mg, 0.45 mmol). After the mixture was stirred for 20 minutes, 5-methyl-2-(1,1,3,3-tetramethyl-indan-5-yl)-2,4-dihydro-pyrazol-3-one 19d (100 mg, 0.37 mmol) was added. The mixture was adjusted to pH 8 with saturated aqueous sodium bicarbonate. The generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 10 mL of water. The mixture was adjusted to pH 3~4 with concentrated hydrochloric acid, filtered and dried. The residue was purified by silica gel column chromatography to obtain the title compound 5-(2-hydroxy-3-{N'-[3-methyl-5-oxo-1-(1,1,3,3-tetramethyl-indan-5-yl)-1,5-dihydro-pyrazol-4-ylidene]-hydrazino}-phenyl)-furan-2-carboxylic acid 25 (22 mg, yield 11.9%) as a red solid.

$^1$H NMR (400 MHz, DMSO-d$_6$): δ 1.30 (m, 12H), 1.92 (s, 2H), 2.34 (s, 3H), 7.15 (d, J=3.6 Hz, 1H), 7.22 (m, 2H), 7.36 (d, J=3.2 Hz, 1H), 7.56 (dd, J$_1$=8.0 Hz, J$_2$=1.2 Hz, 1H), 7.66 (d, J=2.0 Hz, 1H), 7.75 (m, 2H)

Example 26

3'-[N'-(1-Bicyclo[4.2.0]octa-1(6),2,4-trien-3-yl-3-methyl-5-oxo-1,5-dihydro-pyrazol-4-ylidene)-hydrazino]-5'-fluoro-2'-hydroxy-biphenyl-3-carboxylic acid

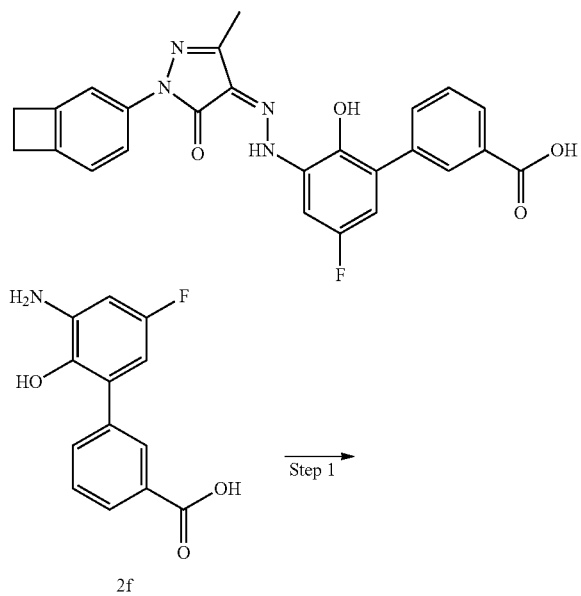

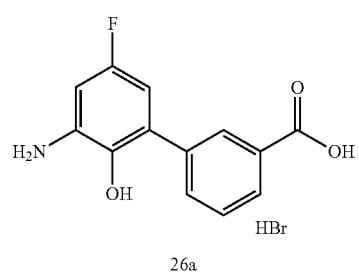

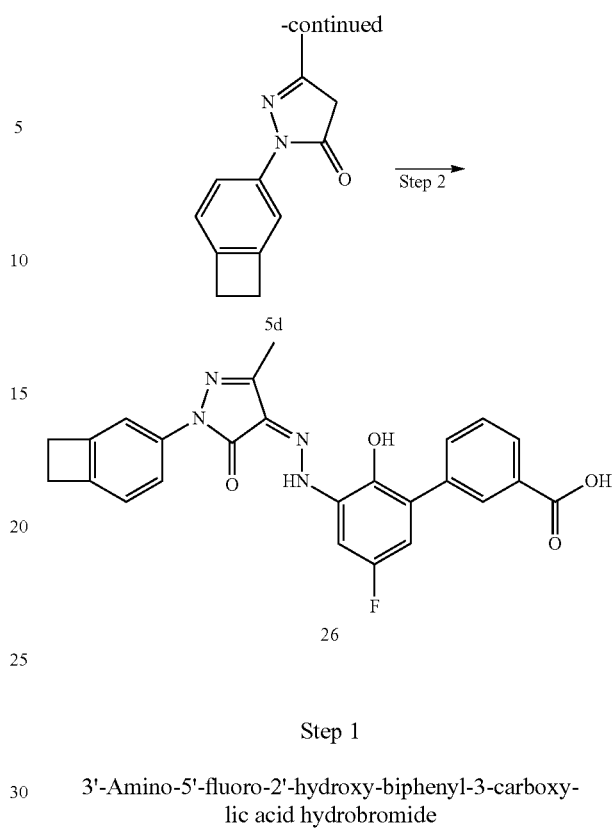

Step 1

3'-Amino-5'-fluoro-2'-hydroxy-biphenyl-3-carboxylic acid hydrobromide 20 mL of hydrobromic acid was added dropwise to 3'-amino-5'-fluoro-2'-hydroxy-biphenyl-3-carboxylic acid 2f (500 mg, 1.92 mmol) obtained from Step 5 of Example 2 to form white precipitates. The reaction solution was heated to reflux overnight, and then it became clear. The colour of the reaction solution finally was brown. The reaction was monitored by TLC until the disappearance of the starting materials. The mixture was concentrated under reduced pressure to obtain a brown solid which was dissolved in 20 mL of ethyl acetate. The mixture was stirred for 20 minutes and filtered to obtain the title compound 3'-amino-5'-fluoro-2'-hydroxy-biphenyl-3-carboxylic acid hydrobromide 26a (344 mg, yield 54.8%) as a grey solid.

MS m/z (ESI): 248 [M+1]

Step 2

3'-[N'-(1-Bicyclo[4.2.0]octa-1(6),2,4-trien-3-yl-3-methyl-5-oxo-1,5-dihydro-pyrazol-4-ylidene)-hydrazino]-5'-fluoro-2'-hydroxy-biphenyl-3-carboxylic acid 3'-Amino-5'-fluoro-2'-hydroxy-biphenyl-3-carboxylic acid hydrobromide 26a (328 mg, 1.11 mmol) was dissolved in 3.7 mL of 1 N hydrochloric acid upon cooling by an ice-water bath, followed by addition of 1.5 mL of aqueous sodium nitrite (84 mg, 1.22 mmol) and 2-bicyclo[4.2.0]octa-1(6),2,4-trienyl-3-yl-5-methyl-2,4-dihydro-pyrazol-3-one 5d (200 mg, 1 mmol). The mixture was adjusted to pH 8~9 by batch addition of saturated sodium bicarbonate (1.4 g, 16.7 mmol), followed by addition of 2 mL of ethanol. The reaction mixture was warmed up to room temperature overnight. The reaction was monitored by TLC until the disappearance of the starting materials. The mixture was filtered and then the filter cake was dissolved in 20 mL of water. After mixing well, the mixture was adjusted to pH 3~4 with concentrated hydrochloric acid, filtered and dried. The crude product was purified by HPLC to obtain the title compound 3'-[N'-(1-bicyclo[4.2.0]octa-1(6),2,4-trien-3-yl-3-methyl-5-oxo-1,5-dihydro-pyrazol-4-ylidene)-hydrazino]-5'-fluoro-2'-hydroxy-biphenyl-3-carboxylic acid 26 (335 mg, yield 73.1%) as a red solid.

MS m/z (ESI): 457 [M−1]

$^1$H NMR (400 MHz, DMSO-d$_6$): δ 2.32 (s, 3H), 3.22 (m, 4H), 7.02 (m, 1H), 7.14 (d, J=8.0 Hz, 1H), 7.46 (m, 1H), 7.61 (m, 2H), 7.69 (m, 1H), 7.82 (d, J=7, 6 Hz, 1H), 7.98 (d, J=7.6 Hz, 1H), 8.17 (s, 1H), 9.58 (s, 1H), 13.07 (s, 1H), 13.60 (s, 1H)

Example 27

4-{[2-Hydroxy-3'-(1H-tetrazol-5-yl)-biphenyl-3-yl]-hydrazono}-2-indan-5-yl-5-methyl-2,4-dihydro-pyrazol-3-one

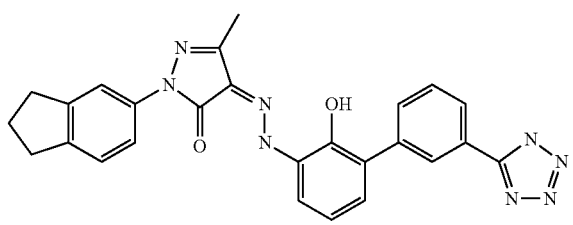

27

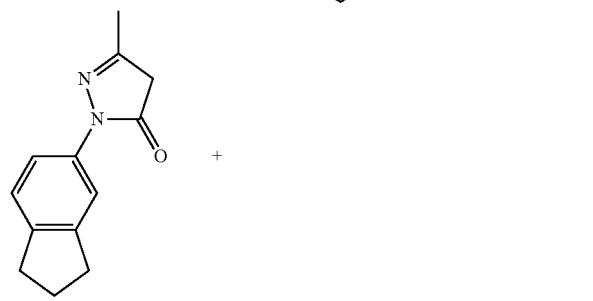

1i

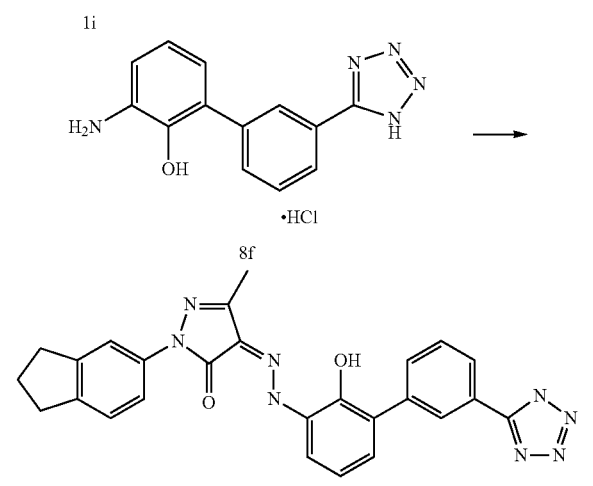

27

3-Amino-3'-(1H-tetrazol-5-yl)-biphenyl-2-ol hydrochloride 8f (188 mg, 0.74 mmol) was dissolved in 4 mL of 2 N hydrochloric acid upon cooling by an ice-water bath, followed by dropwise addition of 1 mL of aqueous sodium nitrite (57 mg, 0.82 mmol). After the mixture was reacted for 30 minutes, 2-indan-5-yl-5-methyl-2,4-dihydro-pyrazol-3-one 1i (159 mg, 0.74 mmol) was added. The mixture was adjusted to pH 8 with saturated sodium bicarbonate, followed by addition of 0.5 mL of ethanol. The reaction mixture was reacted overnight at room temperature. The reaction was monitored by TLC until the disappearance of the starting materials. The mixture was filtered and the filter cake was dissolved in aqueous sodium hydroxide (3 N). The mixture was washed three times with dichloromethane. The layers were separated and then the aqueous layer was adjusted to pH 3 with 2 N hydrochloric acid to form a copious amount of precipitates. The mixture was filtered and the filter cake was purified by silica gel column chromatography to obtain the title compound 4-{[2-hydroxy-3'-(1H-tetrazol-5-yl)-biphenyl-3-yl]-hydrazono}-2-indan-5-yl-5-methyl-2,4-dihydro-pyrazol-3-one 27 (67 mg, yield 18.8%) as an orange solid.

MS m/z (ESI): 477.2 [M−1]

$^1$H NMR (400 MHz, DMSO-d$_6$): δ 2.03 (m, 2H), 2.33 (s, 3H), 2.89 (m, 4H), 7.17 (m, 2H), 7.28 (d, J=8.0 Hz, 1H), 7.71 (m, 5H), 8.08 (d, J=8.0 Hz, 1H), 8.25 (s, 1H), 9.73 (br, 1H), 13.77 (s, 1H)

Example 28

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid

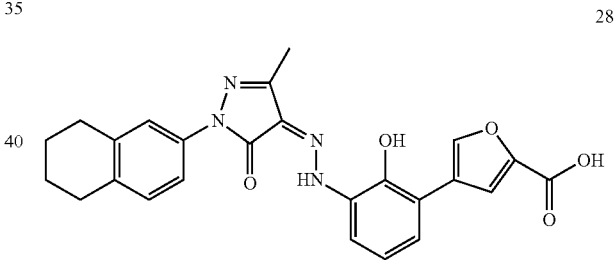

28

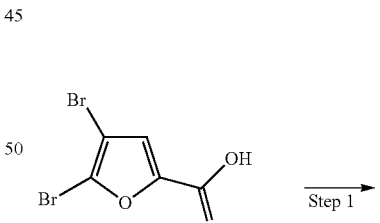

28a

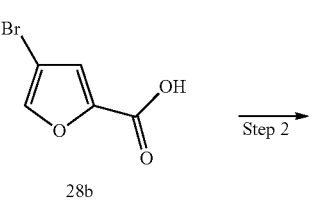

28b

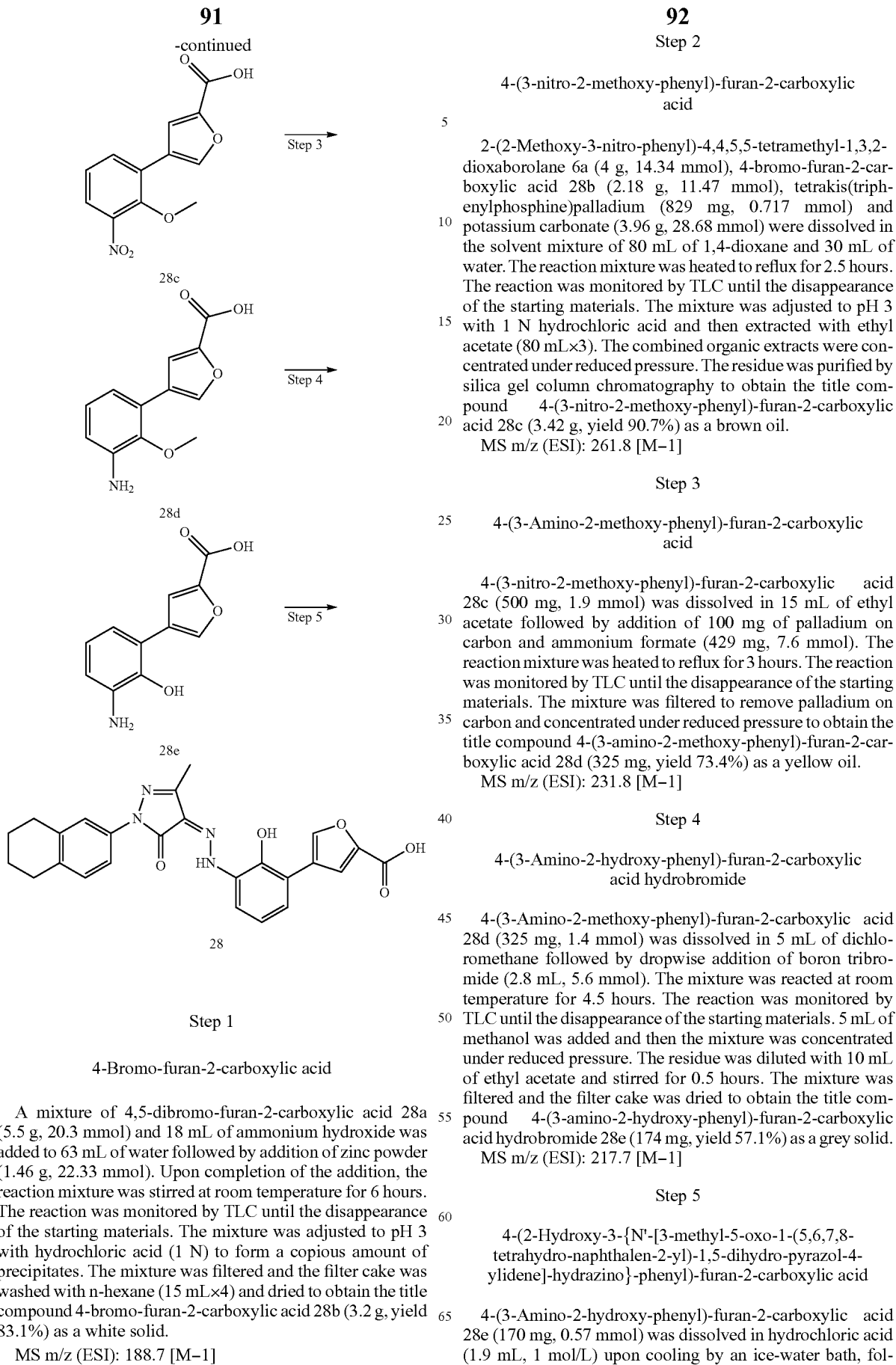

Step 1

4-Bromo-furan-2-carboxylic acid

A mixture of 4,5-dibromo-furan-2-carboxylic acid 28a (5.5 g, 20.3 mmol) and 18 mL of ammonium hydroxide was added to 63 mL of water followed by addition of zinc powder (1.46 g, 22.33 mmol). Upon completion of the addition, the reaction mixture was stirred at room temperature for 6 hours. The reaction was monitored by TLC until the disappearance of the starting materials. The mixture was adjusted to pH 3 with hydrochloric acid (1 N) to form a copious amount of precipitates. The mixture was filtered and the filter cake was washed with n-hexane (15 mL×4) and dried to obtain the title compound 4-bromo-furan-2-carboxylic acid 28b (3.2 g, yield 83.1%) as a white solid.

MS m/z (ESI): 188.7 [M−1]

Step 2

4-(3-nitro-2-methoxy-phenyl)-furan-2-carboxylic acid 2-(2-Methoxy-3-nitro-phenyl)-4,4,5,5-tetramethyl-1,3,2-dioxaborolane 6a (4 g, 14.34 mmol), 4-bromo-furan-2-carboxylic acid 28b (2.18 g, 11.47 mmol), tetrakis(triphenylphosphine)palladium (829 mg, 0.717 mmol) and potassium carbonate (3.96 g, 28.68 mmol) were dissolved in the solvent mixture of 80 mL of 1,4-dioxane and 30 mL of water. The reaction mixture was heated to reflux for 2.5 hours. The reaction was monitored by TLC until the disappearance of the starting materials. The mixture was adjusted to pH 3 with 1 N hydrochloric acid and then extracted with ethyl acetate (80 mL×3). The combined organic extracts were concentrated under reduced pressure. The residue was purified by silica gel column chromatography to obtain the title compound 4-(3-nitro-2-methoxy-phenyl)-furan-2-carboxylic acid 28c (3.42 g, yield 90.7%) as a brown oil.

MS m/z (ESI): 261.8 [M−1]

Step 3

4-(3-Amino-2-methoxy-phenyl)-furan-2-carboxylic acid 4-(3-nitro-2-methoxy-phenyl)-furan-2-carboxylic acid 28c (500 mg, 1.9 mmol) was dissolved in 15 mL of ethyl acetate followed by addition of 100 mg of palladium on carbon and ammonium formate (429 mg, 7.6 mmol). The reaction mixture was heated to reflux for 3 hours. The reaction was monitored by TLC until the disappearance of the starting materials. The mixture was filtered to remove palladium on carbon and concentrated under reduced pressure to obtain the title compound 4-(3-amino-2-methoxy-phenyl)-furan-2-carboxylic acid 28d (325 mg, yield 73.4%) as a yellow oil.

MS m/z (ESI): 231.8 [M−1]

Step 4

4-(3-Amino-2-hydroxy-phenyl)-furan-2-carboxylic acid hydrobromide 4-(3-Amino-2-methoxy-phenyl)-furan-2-carboxylic acid 28d (325 mg, 1.4 mmol) was dissolved in 5 mL of dichloromethane followed by dropwise addition of boron tribromide (2.8 mL, 5.6 mmol). The mixture was reacted at room temperature for 4.5 hours. The reaction was monitored by TLC until the disappearance of the starting materials. 5 mL of methanol was added and then the mixture was concentrated under reduced pressure. The residue was diluted with 10 mL of ethyl acetate and stirred for 0.5 hours. The mixture was filtered and the filter cake was dried to obtain the title compound 4-(3-amino-2-hydroxy-phenyl)-furan-2-carboxylic acid hydrobromide 28e (174 mg, yield 57.1%) as a grey solid.

MS m/z (ESI): 217.7 [M−1]

Step 5

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 4-(3-Amino-2-hydroxy-phenyl)-furan-2-carboxylic acid 28e (170 mg, 0.57 mmol) was dissolved in hydrochloric acid (1.9 mL, 1 mol/L) upon cooling by an ice-water bath, followed by dropwise addition of 0.7 mL of aqueous sodium nitrite (43 mg, 0.63 mmol). After the mixture was reacted for 20 minutes, 5-methyl-2-(5,6,7,8-tetrahydro-naphthalen-2-yl)-2,4-dihydro-pyrazol-3-one 3i (116 mg, 0.51 mmol) was added. The mixture was adjusted to pH 8~9 with saturated aqueous sodium bicarbonate followed by addition of 2 mL of ethanol. The mixture was reacted at room temperature for 24 hours. The reaction was monitored by TLC until the disappearance of the starting materials. The mixture was filtered and then 15 mL of water was added to the filter cake. Upon cooling by an ice-water bath, the mixture was adjusted to pH 2~3 with concentrated hydrochloric acid and filtered. The filter cake was washed with ethyl acetate and dried to obtain the title compound 4-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 28 (13 mg, yield 5.5%) as a red solid.

MS m/z (ESI): 456.7 [M−1]

$^1$H NMR (400 MHz, DMSO-d$_6$): δ 1.75 (m, 4H), 2.31 (s, 3H), 2.78 (m, 4H), 3.86 (s, 3H), 7.13 (m, 2H), 7.43 (d, J=7.6 Hz, 1H), 7.62 (m, 2H), 7.78 (s, 1H), 8.43 (s, 1H), 9.68 (br, 1H), 13.73 (br, 1H)

Example 29

2'-Hydroxy-3'-[N'-(1-indan-5-yl-3-methyl-5-oxo-1,5-dihydro-pyrazol-4-ylidene)-hydrazino]-5'-methyl-biphenyl-3-carboxylic acid

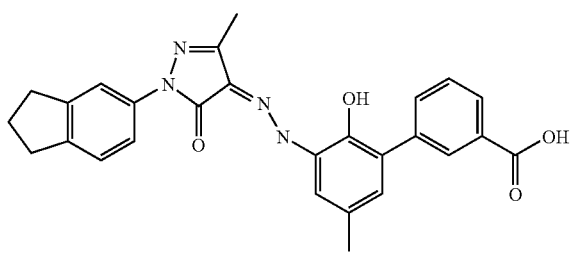

29

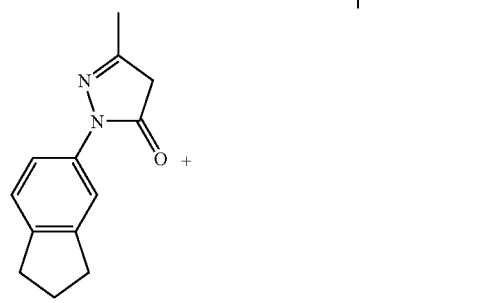

1i

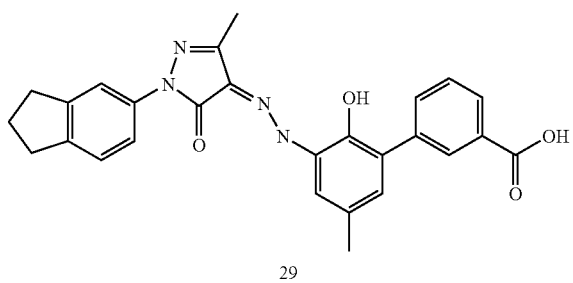

29

3'-Amino-2'-hydroxy-5'-methyl-biphenyl-3-carboxylic acid hydrochloride 11f (346 mg, 1.07 mmol) was dissolved in hydrochloric acid (5 mL, 2 mol/L) upon cooling by an ice-water, followed by addition of 2 mL of aqueous sodium nitrite (81 mg, 1.17 mmol). After the mixture was reacted for 30 minutes, 2-indan-5-yl-5-methyl-2,4-dihydro-pyrazol-3-one 1i (229 mg, 1.07 mmol) was added. The mixture was adjusted to pH 8 with saturated aqueous sodium bicarbonate, followed by addition of 5 mL of ethanol. The mixture was reacted overnight at room temperature. The reaction was monitored by TLC until the disappearance of the starting materials. The mixture was filtered and the filter cake was washed with ethanol. The filtrate was poured into a mixture of ice and water. The resulting mixture was adjusted to pH 4 with concentrated hydrochloric acid to form precipitates. The mixture was filtered and the filter cake was washed three times with ethyl acetate, and then dried to obtain the title compound 2'-hydroxy-3'-[N'-(1-indan-5-yl-3-methyl-5-oxo-1,5-dihydro-pyrazol-4-ylidene)-hydrazino]-5'-methyl-biphenyl-3-carboxylic acid 29 (75 mg, yield 15%) as a red solid.

MS m/z (ESI): 467.2 [M−1]

$^1$H NMR (400 MHz, DMSO-d$_6$): δ 2.01 (m, 2H), 2.35 (m, 6H), 2.88 (m, 4H), 6.97 (s, 1H), 7.30 (s, 1H), 7.70 (m, 5H), 8.02 (s, 1H), 8.15 (s, 1H), 9.42 (br, 1H), 13.03 (br, 1H), 13.77 (s, 1H)

Example 30

3'-{N'-[1-(3,3-Dimethyl-indan-5-yl)-3-methyl-5-oxo-1,5-dihydro-pyrazol-4-ylidene]-drazino}-2'-hydroxy-biphenyl-3-carboxylic acid

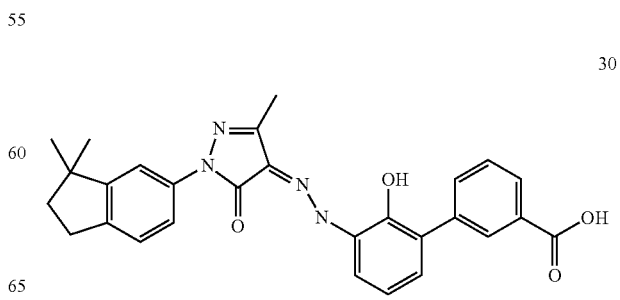

30

2H), 7.25 (d, J=8.8 Hz, 1H), 7.62 (t, J=7.6 Hz, 1H), 7.70 (m, 3H), 7.80 (d, J=7.6 Hz, 1H), 7.96 (d, J=7.2 Hz, 1H), 8.14 (s, 1H), 9.68 (s, 1H)

Example 31

4-{2-Hydroxy-3-[N'-(1-indan-5-yl-3-methyl-5-oxo-1,5-dihydro-pyrazol-4-ylidene)-hydrazino]-phenyl}-furan-2-carboxylic acid

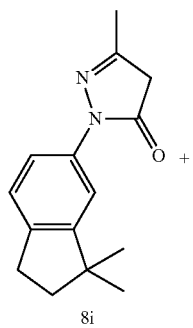

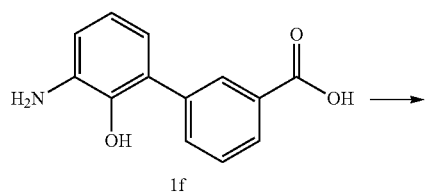

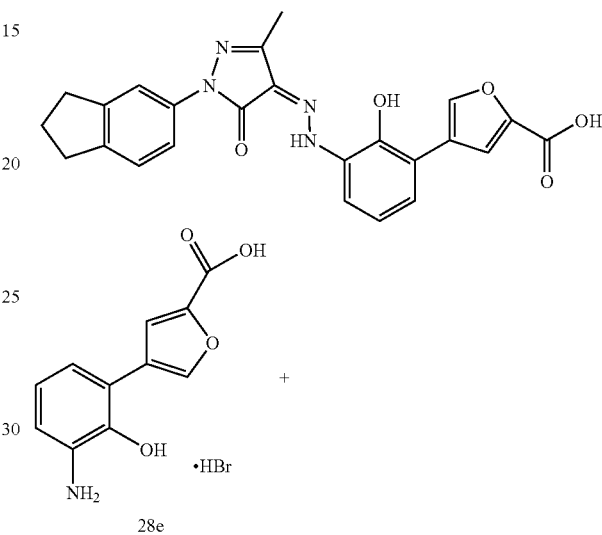

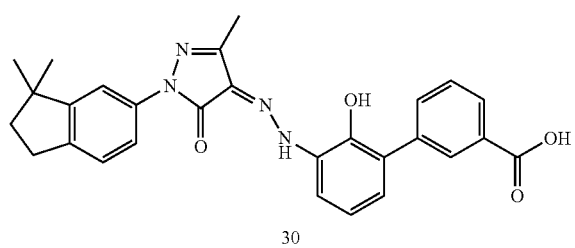

3'-Amino-2'-hydroxy-biphenyl-3-carboxylic acid hydrobromide 1f (310 mg, 1.0 mmol) was dissolved in hydrochloric acid (3.4 mL, 1 mol/L) upon cooling by an ice-water bath, followed by dropwise addition of 1.2 mL of aqueous sodium nitrite (73 mg, 1.05 mmol). After the mixture was reacted for 10 minutes, 2-(3,3-dimethyl-indan-5-yl)-5-methyl-2,4-dihydro-pyrazol-3-one 8i (218 mg, 0.9 mmol), sodium bicarbonate (1.26 g, 15 mmol) and 4.4 mL of ethanol were added successively. The reaction mixture was reacted at room temperature for 10 hours. The reaction was monitored by TLC until the disappearance of the starting materials. The mixture was filtered and the filter cake was washed with 20 mL of water and then dissolved in 20 mL of water. Upon cooling by an ice-water bath, the mixture was adjusted to pH<5 with concentrated hydrochloric acid, filtered and dried to obtain the title compound 3'-{N'-[1-(3,3-dimethyl-indan-5-yl)-3-methyl-5-oxo-1,5-dihydro-pyrazol-4-ylidene]-hydrazino}-2'-hydroxy-biphenyl-3-carboxylic acid 30 (500 mg, yield 94%) as a yellow solid.

MS m/z (ESI): 509.1 [M−1]

$^1$H NMR (400 MHz, DMSO-d$_6$): δ 1.24 (m, 6H), 1.92 (t, J=7.2 Hz, 2H), 2.34 (s, 3H), 2.86 (t, J=7.2 Hz, 2H), 7.16 (m,

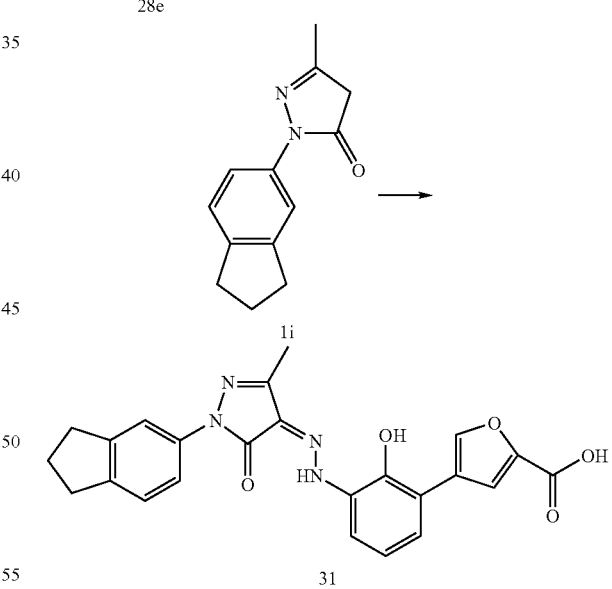

4-(3-Amino-2-hydroxy-phenyl)-furan-2-carboxylic acid hydrobromide 28e (170 mg, 0.57 mmol) was dissolved in hydrochloric acid (1.9 mL, 1 mol/L) upon cooling by an ice-water bath, followed by dropwise addition of 0.7 mL of aqueous sodium nitrite (43 mg, 0.63 mmol). After the mixture was reacted for 20 minutes, 2-indan-5-yl-5-methyl-2,4-dihydro-pyrazol-3-one 1i (109 mg, 0.51 mmol) was added. The mixture was adjusted to pH 8~9 with saturated aqueous sodium bicarbonate, followed by addition of 2 mL of ethanol. The reaction mixture was reacted at room temperature for 24 hours. The reaction was monitored by TLC until the disappearance of the starting materials. The mixture was filtered and 15 mL of water was added to the filter cake. Upon cooling by an ice-water bath, the mixture was adjusted to pH 2~3 with concentrated hydrochloric acid, filtered and the filter cake was washed with ethyl acetate, and then dried to obtain the title compound 4-{2-hydroxy-3-[N'-(1-indan-5-yl-3-methyl-5-oxo-1,5-dihydro-pyrazol-4-ylidene)-hydrazino]-phenyl}-furan-2-carboxylic acid 31 (83 mg, yield 36.7%) as a black solid.

MS m/z (ESI): 442.8 [M−1]

$^1$H NMR (400 MHz, DMSO-$d_6$): δ 2.08 (m, 2H), 2.32 (s, 3H), 2.89 (m, 4H), 7.13 (t, J=8.0 Hz, 1H), 7.28 (d, J=8.4 Hz, 1H), 7.41 (d, J=7.6 Hz, 1H), 7.65 (m, 3H), 7.75 (m, 1H), 8.37 (s, 1H), 9.68 (s, 1H), 13.22 (br, 1H), 13.74 (s, 1H)

Example 32

4-{[4'-(4,5-Dihydro-1H-imidazol-2-yl)-2-hydroxy-biphenyl-3-yl]-hydrazono}-2-indan-5-yl-5-methyl-2,4-dihydro-pyrazol-3-one

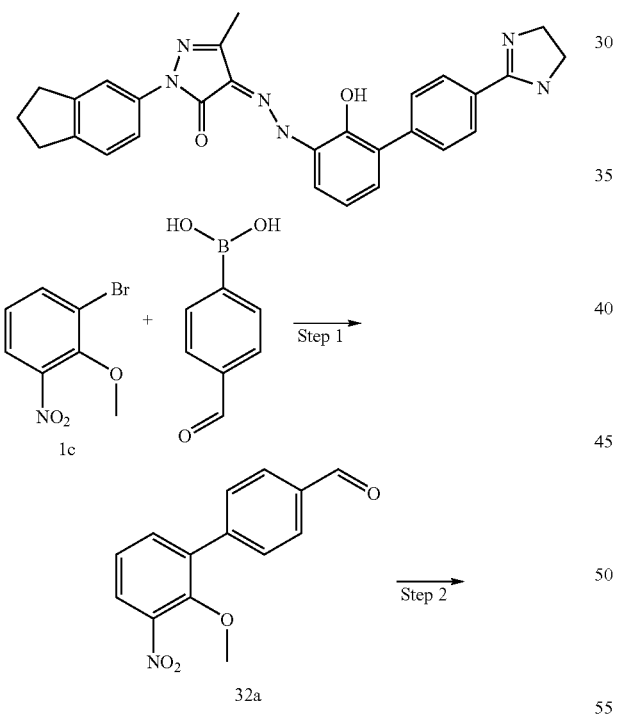

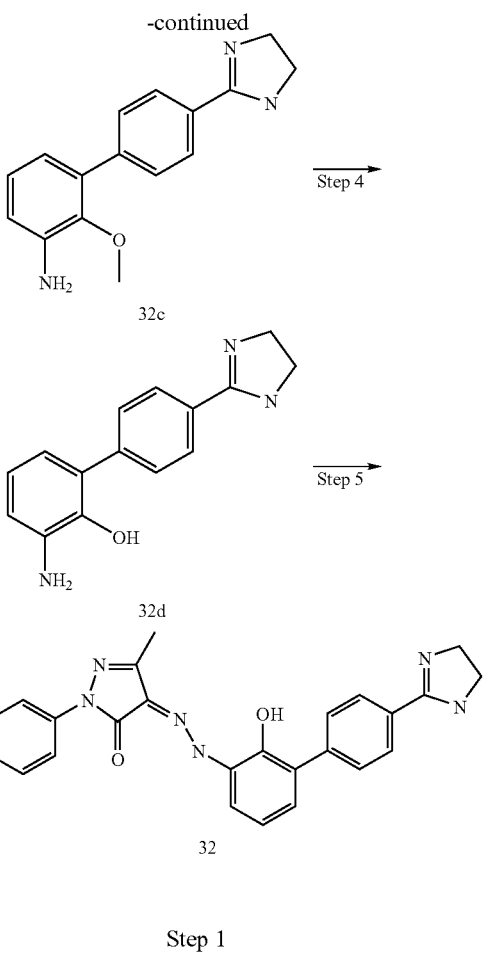

Step 1

3'-Nitro-2'-methoxy-biphenyl-4-carbaldehyde

To a solution of 60 mL of 1,4-dioxane and 10 mL of water was added 4-formylphenylboronic acid (3.0 g, 0.02 mol), followed by 1-bromo-2-methoxy-3-nitro-benzene 1c (4.64 g, 0.02 mol), tetrakis(triphenylphosphine)palladium (1.15 g, 1 mmol) and sodium carbonate (4.24 g, 0.04 mol). Upon completion of the addition, the mixture was heated to reflux for 5 hours. The reaction was monitored by TLC until the disappearance of the starting materials. The mixture was filtered and the filter cake was washed with ethyl acetate. The filtrate was concentrated under reduced pressure and the residue was purified by silica gel column chromatography to obtain the title compound 3'-nitro-2'-methoxy-biphenyl-4-carbaldehyde 32a (4.1 g, 80.4%) as a yellow solid.

Step 2

2-(2'-Methoxy-3'-nitro-biphenyl-4-yl)-4,5-dihydro-1H-imidazole

To a solution of 3'-nitro-2'-methoxy-biphenyl-4-carbaldehyde 32a (4.0 g, 15.5 mmol) in 40 mL of dichloromethane under stirring, upon cooling by an ice-water bath, was added 1,2-diaminoethane (981 mg, 16.3 mmol). After the mixture was stirred for another 0.5 hours, 1-bromo-pyrrolidine-2,5-dione (2.91 g, 16.33 mmol) was added. Upon completion of the addition, the ice-water bath was removed. The reaction mixture was stirred overnight at room temperature. The reaction was monitored by TLC until the disappearance of the starting materials. The mixture was concentrated under reduced pressure and the residue was purified by silica gel column chromatography to obtain the title compound 2-[(2'-methoxy-3'-nitro-biphenyl-4-yl]-4,5-dihydro-1H-imidazole 32b (4.0 g, 86.9%) as yellow solid.

MS m/z (ESI): 298.1 [M+1]

$^1$H NMR (400 MHz, DMSO-$d_6$): δ 8.11 (2H, d, J=8.4 Hz), 7.89 (1H, dd, $J_1$=8.0 Hz, $J_2$=1.6 Hz), 7.87 (2H, d, J=8.4 Hz), 7.79 (1H, m), 7.49 (1H, t, J=8.0 Hz), 4.04 (4H, m), 3.47 (3H, s)

Step 3

2-(2'-Methoxy-3'-amino-biphenyl-4-yl)-4,5-dihydro-1H-imidazol

To a solution of 2-[(2'-methoxy-3'-nitro-biphenyl-4-yl]-4, 5-dihydro-1H-imidazole 32b (1.5 g, 5.05 mmol) in 30 mL of methanol under stirring, was added ammonium formate (1.28 g, 20.2 mmol) followed by palladium on carbon (200 mg). Upon completion of the addition, the reaction mixture was heated to reflux for 1 hour. The reaction was monitored by TLC until the disappearance of the starting materials. The mixture was cooled to room temperature and filtered. The filtrate was concentrated under reduced pressure to obtain the title compound 2-(2'-methoxy-3'-amino-biphenyl-4-yl)-4,5-dihydro-1H-imidazol 32c (1.1 g, 81.5%) as a yellow solid.

MS m/z (ESI): 268.2 [M+1]

$^1$H NMR (400 MHz, DMSO-$d_6$): δ 8.42 (2H, s), 7.96 (2H, d, J=8.0 Hz), 6.89 (1H, t, J=7.6 Hz), 6.75 (1H, m), 6.54 (1H, dd, $J_1$=8.0 Hz, $J_2$=1.6 Hz), 3.80 (4H, m), 3.47 (3H, s)

Step 4

2-(2'-Hydroxy-3'-amino-biphenyl-4-yl-4,5-dihydro-1H-imidazol 2-(2'-Methoxy-3'-amino-biphenyl-4-yl)-4,5-dihydro-1H-imidazol 32c (1.1 g, 4.1 mmol) was dissolved in 50 mL of dichloromethane at room temperature, followed by addition of a solution of boron tribromide in dichloromethane (1 N, 16.5 mL). The reaction mixture was stirred at room temperature for 4 hours. The reaction was monitored by TLC until the disappearance of the starting materials and then quenched with methanol. The mixture was concentrated under reduced pressure. The residue was dissolved in 10 mL of ethyl acetate and stirred for 30 minutes. The mixture was filtered and the filter cake was washed with ethyl acetate (5 mL×2) and dried to obtained the title compound 2-(2'-hydroxy-3'-amino-biphenyl-4-yl)-4,5-dihydro-1H-imidazol 32d (900 mg, 89.6%) as a grey solid.

MS m/z (ESI): 254.3 [M+1]

$^1$H NMR (400 MHz, DMSO-$d_6$): δ 7.23 (2H, m), 7.01 (2H, t, J=6.8 Hz), 6.65 (1H, m), 6.62 (1H, dd, J=8.0 Hz, $J_2$=1.6 Hz), 6.36 (1H, t, J=7.6 Hz), 4.03 (4H, m)

Step 5

4-{[4'-(4,5-Dihydro-1H-imidazol-2-yl)-2-hydroxy-biphenyl-3-yl]-hydrazono}-2-indan-5-yl-5-methyl-2,4-dihydro-pyrazol-3-one 2-(2'-Hydroxy-3'-amino-biphenyl-4-yl-4,5-dihydro-1H-imidazol 32d (334 mg, 1.11 mmol) was dissolved in hydrochloric acid (3.7 mL, 1 mol/L) upon cooling by an ice-water bath, followed by dropwise addition of 1.5 mL of aqueous sodium nitrite (85 mg, 1.22 mmol). After the mixture was reacted for 20 minutes, 2-indan-5-yl-5-methyl-2,4-dihydro-pyrazol-3-one 1i (214 mg, 1 mmol) was added. The mixture was adjusted to pH 8 with saturated aqueous sodium bicarbonate, followed by addition of 5 mL of ethanol. The reaction mixture was reacted overnight at room temperature. The reaction was monitored by TLC until the disappearance of the starting materials. The mixture was filtered and 30 mL of water was added to the filter cake. After mixing well, the mixture was adjusted to pH 4 with concentrated hydrochloric acid to form precipitates. The mixture was filtered and the filter cake was purified by silica gel column chromatography to obtain the title compound 4-{[4'-(4,5-dihydro-1H-imidazol-2-yl)-2-hydroxy-biphenyl-3-yl]-hydrazono}-2-indan-5-yl-5-methyl-2,4-dihydro-pyrazol-3-one 32 (145 mg, yield 30.3%) as a red solid.

MS m/z (ESI): 476.9 [M−1]

$^1$H NMR (400 MHz, DMSO-$d_6$): δ 2.02 (m, 2H), 2.34 (s, 3H), 2.87 (m, 4H), 4.00 (s, 4H), 6.88 (m, 1H), 7.18 (m, 2H), 7.49 (m, 1H), 7.90 (m, 5H), 8.18 (s, 1H)

Example 33

5-(2-Hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid

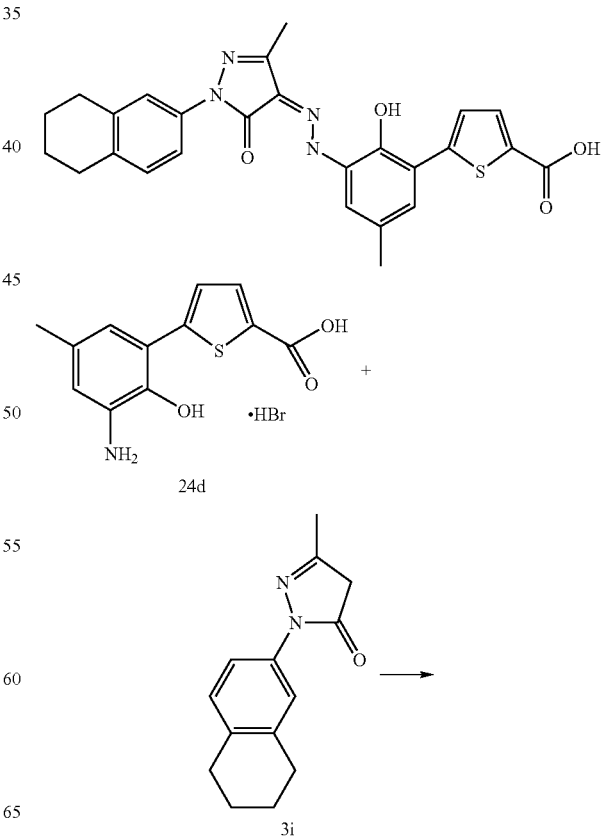

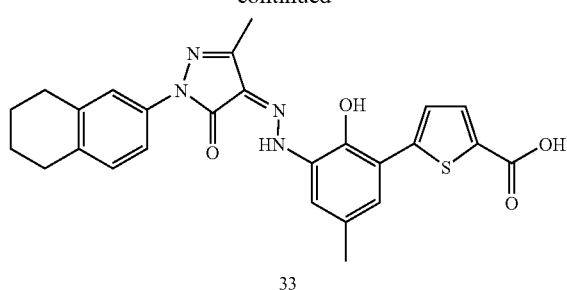

33

5-(3-Amino-2-hydroxy-5-methyl-phenyl)-thiophene-2-carboxylic acid hydrobromide 24d (366 mg, 1.11 mmol) was dissolved in 3.7 mL of 1 N hydrochloric acid upon cooling by an ice-water bath, followed by dropwise addition of 1.5 mL of aqueous sodium nitrite (85 mg, 1.22 mmol). After the mixture was reacted for 20 minutes, 5-methyl-2-(5,6,7,8-tetrahydro-naphthalen-2-yl)-2,4-dihydro-pyrazol-3-one 3i (228 mg, 1 mmol), sodium bicarbonate (1.4 g, 16.67 mmol) and 2 mL of ethanol were added successively. The reaction mixture was reacted overnight at room temperature. The reaction was monitored by TLC until the disappearance of the starting materials. The mixture was filtered and the filter cake was added to 30 mL of water. The mixture was adjusted to pH 3~4 with concentrated hydrochloric acid. The mixture was filtered and the filter cake was dried and purified by silica gel column chromatography to obtain the title compound 5-(2-hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid 33 (88 mg, yield 18.09%) as a red solid.

MS m/z (ESI): 486.7 [M−1]

$^1$H NMR (400 MHz, DMSO-d$_6$): δ 1.75 (m, 4H), 2.31 (s, 3H), 2.36 (s, 3H), 2.73 (m, 4H), 7.12 (d, J=8.4 Hz, 1H), 7.37 (s, 1H), 7.56 (s, 1H), 7.63 (m, 3H), 7.74 (d, J=3.6 Hz, 1H), 9.77 (s, 1H), 13.07 (br, 1H), 13.70 (s, 1H)

Example 34

5-(3-{N'-[1-(3,3-Dimethyl-indan-5-yl)-3-methyl-5-oxo-1,5-dihydro-pyrazol-4-ylidene]-hydrazino}-2-hydroxy-5-methyl-phenyl)-thiophene-2-carboxylic acid

34

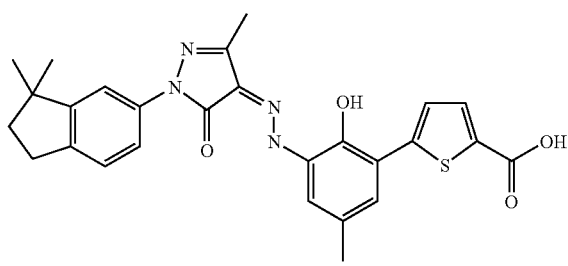

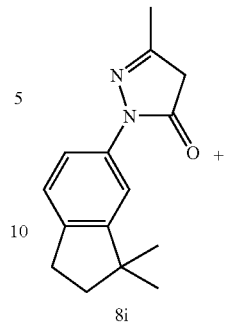

8i

24d

34

5-(3-Amino-2-hydroxy-5-methyl-phenyl)-thiophene-2-carboxylic acid hydrobromide 24d (366 mg, 1.11 mmol) was dissolved in 3.7 mL of 1 N hydrochloric acid upon cooling by an ice-water bath, followed by dropwise addition of 1.5 mL of aqueous sodium nitrite (85 mg, 1.22 mmol). After the mixture was reacted for 20 minutes, 2-(3,3-dimethyl-indan-5-yl)-5-methyl-2,4-dihydro-pyrazol-3-one 8i (242 mg, 1 mmol) was added. The mixture was adjusted to pH 8 with saturated aqueous sodium bicarbonate, followed by addition of 2 mL of ethanol. Upon completion of the addition, the ice-water bath was removed. The reaction mixture was reacted overnight at room temperature. The reaction was monitored by TLC until the disappearance of the starting materials. The mixture was filtered and the filter cake was added to 30 mL of water. The mixture was adjusted to pH 3~4 with concentrated hydrochloric acid. The mixture was filtered and the filter cake was dried and purified by silica gel column chromatography to obtain the title compound 5-(3-{N'-[1-(3,3-dimethyl-indan-5-yl)-3-methyl-5-oxo-1,5-dihydro-pyrazol-4-ylidene]-hydrazino}-2-hydroxy-5-methyl-phenyl)-thiophene-2-carboxylic acid 34 (308 mg, yield 61.4%) as a red solid.

MS m/z (ESI): 500.8 [M−1]

$^1$H NMR (400 MHz, DMSO-d$_6$): δ 1.25 (s, 6H), 1.93 (m, 2H), 2.36 (s, 3H), 2.38 (s, 3H), 2.87 (t, J=7.2 Hz, 2H), 7.27 (d, J=8.8 Hz, 1H), 7.40 (d, J=1.6 Hz, 1H), 7.53 (d, J=1.2 Hz, 1H), 7.65 (m, 1H), 7.71 (m, 2H), 7.74 (d, J=4.0 Hz, 1H), 9.82 (br, 1H), 13.06 (s, 1H), 13.71 (br, 1H)

Example 35

5-{3-[N'-(1-Bicyclo[4.2.0]octa-1(6),2,4-trien-3-yl-3-methyl-5-oxo-1,5-dihydro-pyrazol-4-ylidene)-hydrazino]-5-methyl-phenyl}-thiophene-2-carboxylic acid

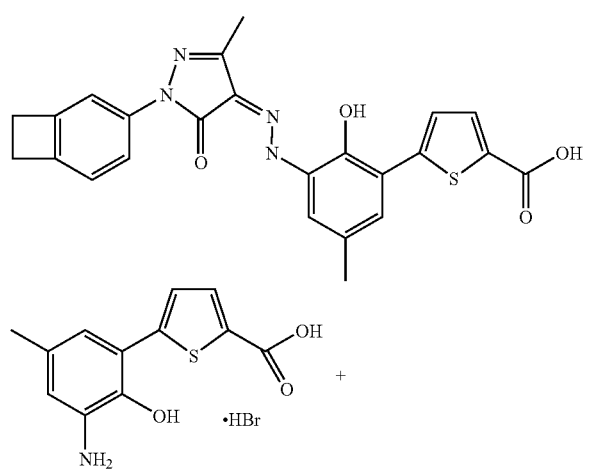

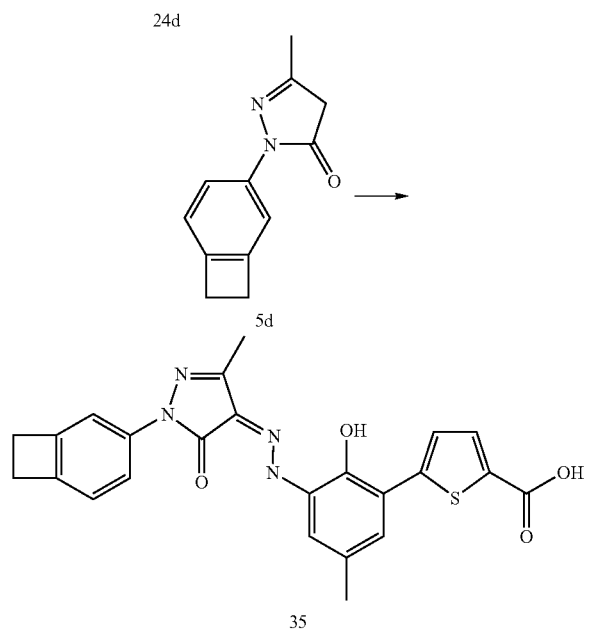

5-(3-Amino-2-hydroxy-5-methyl-phenyl)-thiophene-2-carboxylic acid hydrobromide 24d (366 mg, 1.11 mmol) was dissolved in 3.7 mL of 1 N hydrochloric acid upon cooling by an ice-water bath, followed by dropwise addition of 1.5 mL of aqueous sodium nitrite (85 mg, 1.22 mmol). After the mixture was reacted for 20 minutes, 2-bicyclo[4.2.0]octa-1(6),2,4-trienyl-3-yl-5-methyl-2,4-dihydro-pyrazol-3-one 5d (200 mg, 1 mmol) was added. The mixture was adjusted to pH 8 with saturated aqueous sodium bicarbonate, followed by addition of 2 mL of ethanol. Then the ice-water bath was removed and the reaction mixture was reacted at room temperature for 5 hours. The reaction was monitored by TLC until the disappearance of the starting materials. The mixture was filtered and the filter cake was added to 30 mL of water. The mixture was adjusted to pH 3~4 with concentrated hydrochloric acid and filtered. The filter cake was washed with 6 mL of dichloromethane and dried to obtain the title compound 5-{3-[N'-(1-bicyclo[4.2.0]octa-1(6),2,4-trien-3-yl-3-methyl-5-oxo-1,5-dihydro-pyrazol-4-ylidene)-hydrazino]-2-hydroxy-5-methyl-phenyl}-thiophene-2-carboxylic acid 35 (306 mg, yield 66.5%) as a red solid.

MS m/z (ESI): 459.2 [M−1]

$^1$H NMR (400 MHz, DMSO-d$_6$): δ 2.33 (s, 3H), 2.36 (s, 3H), 3.16 (m, 4H), 7.16 (d, J=8.0 Hz, 1H), 7.38 (s, 1H), 7.49 (s, 1H), 7.62 (m, 2H), 7.73 (m, 2H)

Example 36

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid

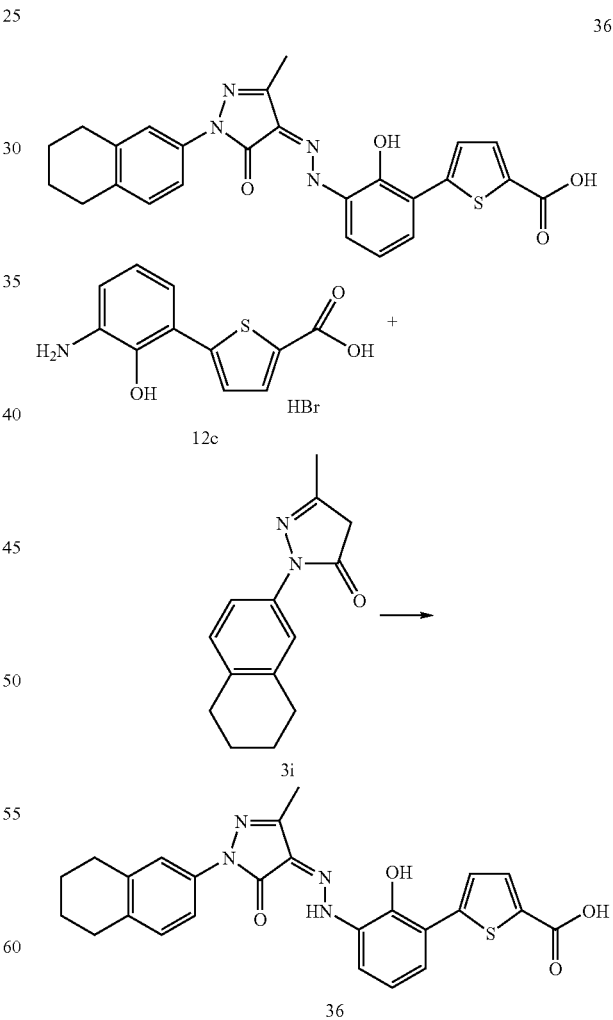

5-(3-Amino-2-hydroxy-phenyl)-thiophene-2-carboxylic acid hydrobromide 12c (351 mg, 1.11 mmol) was dissolved in 3.7 mL of hydrochloric acid (1 N) upon cooling by an ice-water bath, followed by dropwise addition of 1.5 mL of aqueous sodium nitrite (85 mg, 1.22 mmol). After the mixture was stirred for 20 minutes, 5-methyl-2-(5,6,7,8-tetrahydro-naphthalen-2-yl)-2,4-dihydro-pyrazol-3-one 3i (228 mg, 1 mmol) was added. The mixture was adjusted to pH 8 with saturated aqueous sodium bicarbonate. The generated bubbles were quenched with 2 mL of ethanol. The reaction was warmed up to room temperature and reacted for 3 hours. The reaction was monitored by TLC until the disappearance of the starting materials. The mixture was filtered and 30 mL of water was added to the filter cake. The mixture was adjusted to pH 3~4 with concentrated hydrochloric acid. The mixture was filtered and the filter cake was dried and purified by silica gel column chromatography to obtain the title compound 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid 36 (30 mg, yield 6.3%) as a red solid.

MS m/z (ESI): 472.8 [M−1]

$^1$H NMR (400 MHz, DMSO-d$_6$): δ 1.74 (m, 4H), 2.30 (s, 3H), 2.73 (m, 4H), 7.12 (d, J=8.0 Hz, 1H), 7.17 (m, 1H), 7.53 (d, J=7.6 Hz, 1H), 7.62 (m, 3H), 7.67 (d, J=8.0 Hz, 1H), 7.74 (d, J=4.0 Hz, 1H)

Example 37

5-{3-[N'-(1-Bicyclo[4.2.0]octa-1(6),2,4-trien-3-yl-3-methyl-5-oxo-1,5-dihydro-pyrazol-4-ylidene)-hydrazino]-2-hydroxy-phenyl}-thiophene-2-carboxylic acid

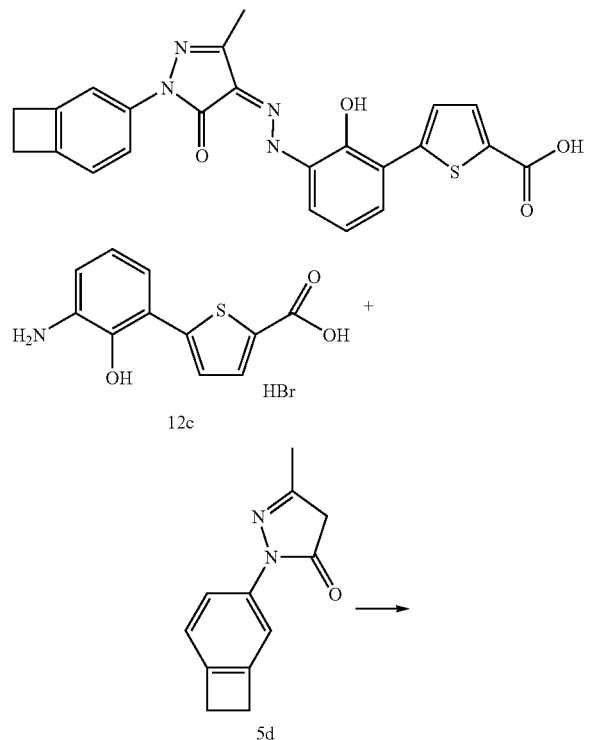

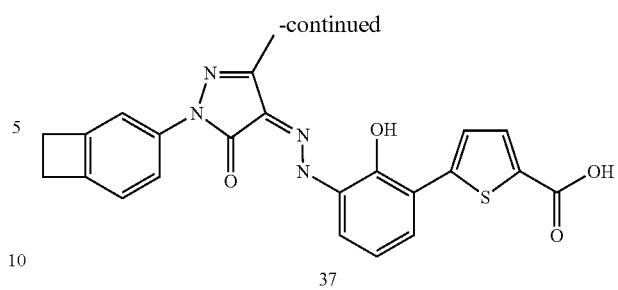

5-(3-Amino-2-hydroxy-phenyl)-thiophene-2-carboxylic acid 12c (298 mg, 0.94 mmol) was dissolved in 3.1 mL of hydrochloric acid (1 N) upon cooling by an ice-water bath, followed by dropwise addition of 1.3 mL of aqueous sodium nitrite (72 mg, 1.04 mmol). After the mixture was reacted for 20 minutes, 2-bicyclo[4.2.0]octa-1(6),2,4-trienyl-3-yl-5-methyl-2,4-dihydro-pyrazol-3-one 5d (170 mg, 0.85 mmol) was added. The mixture was adjusted to pH 8 with saturated aqueous sodium bicarbonate. The generated bubbles were quenched with 2 mL of ethanol. The mixture was warmed up to room temperature and reacted for 3 hours. The reaction was monitored by TLC until the disappearance of the starting materials. The mixture was filtered and 30 mL of water was added to the filter cake. The mixture was adjusted to pH 3~4 with concentrated hydrochloric acid and filtered. The filter cake was dried and purified by silica gel column chromatography to obtain the title compound 5-{3-[N'-(1-bicyclo[4.2.0]octa-1(6),2,4-trien-3-yl-3-methyl-5-oxo-1,5-dihydro-pyrazol-4-ylidene)-hydrazino]-2-hydroxy-phenyl}-thiophene-2-carboxylic acid 37 (57 mg, yield 15.01%) as a red solid.

MS m/z (ESI): 444.5 [M−1]

$^1$H NMR (400 MHz, DMSO-d$_6$): δ 2.31 (s, 3H), 3.15 (m, 4H), 7.15 (m, 2H), 7.54 (d, J=7.6 Hz, 1H), 7.63 (m, 2H), 7.67 (d, J=7.6 Hz, 1H), 7.73 (m, 2H)

Example 38

2'-Hydroxy-3'-{N'-[3-methyl-1-(3-methyl-indan-5-yl)-5-oxo-1,5-dihydro-pyrazol-4-ylidene]-hydrazino}-biphenyl-3-carboxylic acid

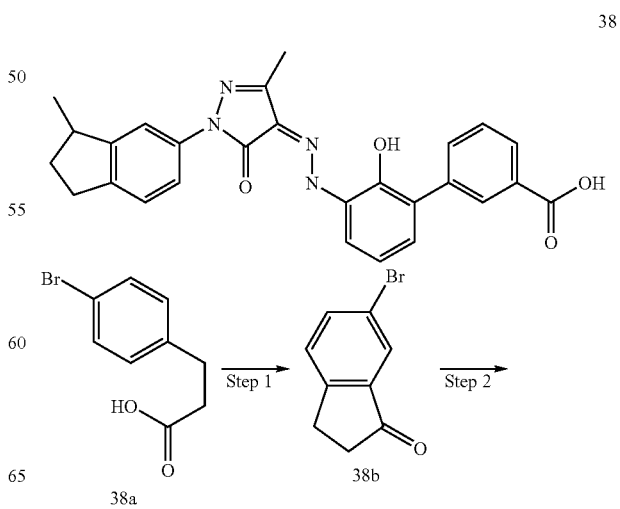

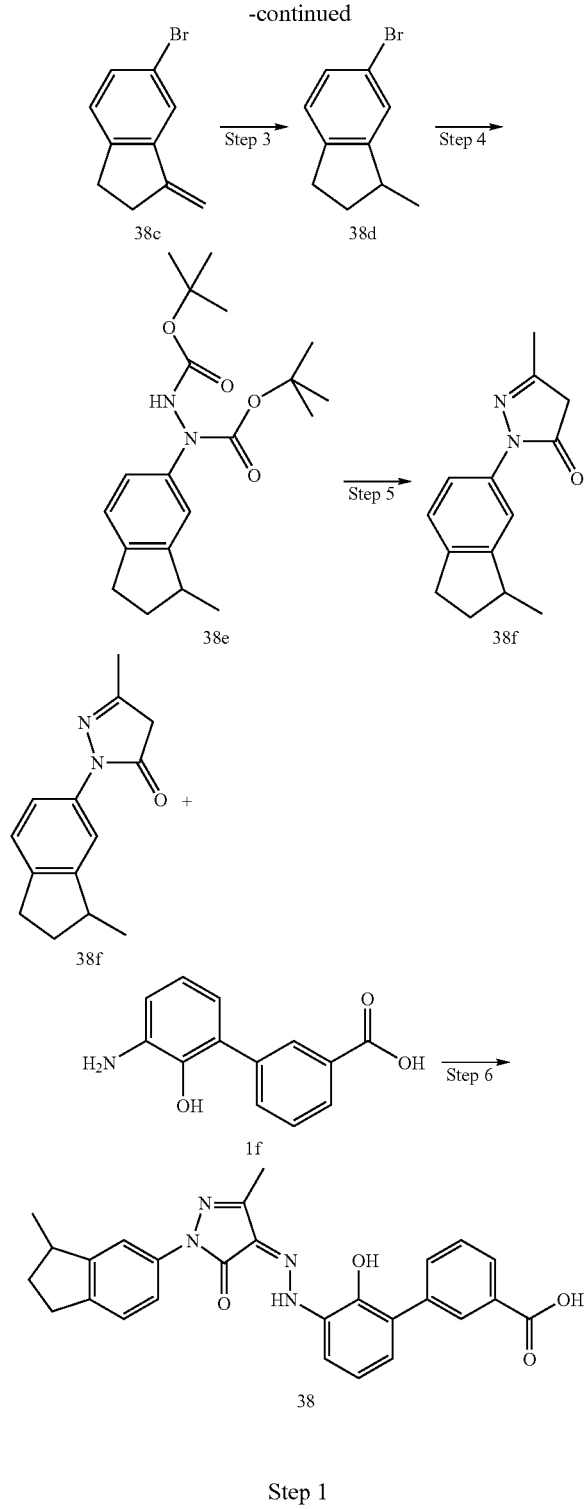

followed by addition of 100 mL of dichloromethane, and then aluminium trichloride (24.5 g, 25.8 mmol) was added. The generated gas was released. The mixture was warmed up to reflux and stirred overnight. The mixture was poured into 200 g of ice to form a copious amount of precipitates and filtered through silica gel. The filtrate was separated and the aqueous layer was extracted with 30 mL of dichloromethane. The combined organic extracts were dried over anhydrous magnesium sulfate and concentrated under reduced pressure to obtain the title compound 6-bromo-indan-1-one 38b (18.34 g, yield 96.6%) as a yellow solid.

MS m/z (ESI): 210 [M−1]

Step 2

6-Bromo-1-methylene-indan

Methytriphenyl phosphonium bromide (4.56 g, 12.76 mmol) was dissolved in 25 mL of tetrahydrofuran followed by addition of potassium tert-butoxide (1.5 g, 13.4 mmol). Upon completion of the addition, the mixture was stirred at room temperature for 35 minutes and used in the following reaction.

6-Bromo-indan-1-one 38b (898 mg, 4.25 mmol) was dissolved in 5 mL of tetrahydrofuran under stirring followed by addition of above mentioned mixture. The reaction mixture was stirred at room temperature for 1 hour prior to quenching by addition of 25 mL of water. The mixture was extracted with dichloromethane (25 mL×4). The combined organic extracts were washed with saturated brine (10 mL×2), dried over anhydrous sodium sulfate, filtered and concentrated under reduced pressure. The resulting residue was purified by silica gel column chromatography to obtain the title compound 6-bromo-1-methylene-indan 38c (830 mg, yield 93.4%) as a yellow oil.

MS m/z (ESI): 208 [M−1]

Step 3

6-Bromo-1-methyl-indan

6-Bromo-1-methylene-indan 38c (4.91 g, 23.5 mmol) was dissolve in ethyl acetate followed by addition of palladium on carbon (0.98 g). The reaction mixture was reacted at room temperature for 4 hours under hydrogen atmosphere. The reaction was monitored by TLC until the disappearance of the starting materials. The mixture was filtered and the filtrate was concentrated under reduced pressure. The residue was purified by silica gel column chromatography to obtain the title compound 6-bromo-1-methyl-indan 38d (3.11 g, yield 62.7%) as a colourless oil.

MS m/z (ESI): 209.8 [M−1]

Step 4

Di-tert-butyl 1-(3-methyl-inden-5-yl)hydrazine-1,2-dicarboxylate n-Butyllithium (8.6 mL, 13.76 mmol) was added to a three-neck flask under argon atmosphere. Upon cooling by a dry ice-acetone bath, 8 mL of tetrahydrofuran, 6-bromo-1-methyl-indan 38d (1.32 g, 6.26 mmol) were added successively under stirring. The reaction mixture was reacted in the dry ice-acetone bath for 2 hours followed by dropwise addition of a solution of di-tert-butyl azodicarboxylate (1.87 g, 8.14 mmol) in 10 mL of tetrahydrofuran. The mixture was stirred for another 30 minutes and the ice-acetone bath was removed.

Step 1

6-Bromo-indan-1-one

To a 250 mL of flask was added 3-(4-bromo-phenyl)-propionic acid 38a (20.6 g, 90 mmol, ABCR) and dried in vacuo for 20 minutes followed by addition of 110 mL of anhydrous dichloromethane under nitrogen atmosphere, and then thionyl chloride (20 mL, 276 mmol) was added. The reaction mixture was heated to reflux overnight. The mixture was concentrated under reduced pressure to remove most solvent The mixture was warmed up to room temperature and stirred for 20 hours. The reaction was quenched by addition of 20 mL of saturated ammonium chloride. The mixture was extracted with ethyl acetate (25 mL×3). The combined organic extracts were washed with saturated brine (10 mL×2), dried over anhydrous sodium sulfate, filtered and concentrated under reduced pressure. The residue was purified by silica gel column chromatography to obtain the title compound di-tert-butyl 1-(3-methyl-inden-5-yl)hydrazine-1,2-dicarboxylate 38e (1.05 g, yield 46.7%) as a yellow oil.

MS m/z (ESI): 362.6 [M+1]

Step 5

5-Methyl-2-(3-methyl-indan-5-yl)-2,4-dihydro-pyrazol-3-one

Di-tert-butyl 1-(3-methyl-inden-5-yl)hydrazine-1,2-dicarboxylate 38e (1.05 g, 2.9 mmol) was dissolved in 16 mL of a solvent mixture of ethanol and water (V:V=5:3) under stirring, followed by successive addition of ethyl acetoacetate (0.377 mL, 2.9 mmol) and 1.45 mL of 6 N hydrochloric acid. The reaction mixture was heated to reflux and reacted for 1.5 hours under nitrogen atmosphere. The mixture was cooled to room temperature and the mixture was concentrated under reduced pressure to remove ethanol. The aqueous layer was extracted with dichloromethane (15 mL×3). The combined organic extracts were dried over anhydrous sodium sulfate, filtered and concentrated under reduced pressure. The residue was purified by silica gel column chromatography to obtain the title compound 5-methyl-2-(3-methyl-indan-5-yl)-2,4-dihydro-pyrazol-3-one 38f (103 mg, yield 15.6%) as a yellow oil.

MS m/z (ESI): 229.3 [M+1]

Step 6

2'-Hydroxy-3'-{N'-[3-methyl-1-(3-methyl-indan-5-yl)-5-oxo-1,5-dihydro-pyrazol-4-ylidene]-hydrazino}-biphenyl-3-carboxylic acid 3'-Amino-2'-hydroxy-biphenyl-3-carboxylic acid hydrobromide 1f (344 mg, 1.11 mmol) was dissolved in 3.7 mL of hydrochloric acid (1 N) upon cooling by an ice-water bath, followed by addition of 1.5 mL of aqueous sodium nitrite (85 mg, 1.22 mmol) and 5-methyl-2-(3-methyl-indan-5-yl)-2,4-dihydro-pyrazol-3-one 38f (228 mg, 1 mmol). The mixture was adjusted to pH 8 with saturated aqueous sodium bicarbonate, followed by addition of 2 mL of ethanol. The reaction mixture was warmed up to room temperature overnight. The reaction was monitored by TLC until the disappearance of the starting materials. The mixture was filtered and 30 mL of water was added to the filter cake. The mixture was adjusted to pH 3~4 with concentrated hydrochloric acid and filtered. The filter cake was dried and then 10 mL of a solvent mixture of dichloromethane/methanol (V:V=50:1) was added. Upon completion of the addition, the mixture was stirred for 1 hour. Then the mixture was filtered and the filter cake was washed with dichloromethane (2 mL×3) and dried to obtain the title compound 2'-hydroxy-3'-{N'-[3-methyl-1-(3-methyl-indan-5-yl)-5-oxo-1,5-dihydro-pyrazol-4-ylidene]-hydrazino}-biphenyl-3-carboxylic acid 38 (300 mg, yield 64.1%) as a yellow solid.

MS m/z (ESI): 466.9 [M−1]

$^1$H NMR (400 MHz, DMSO-d$_6$): δ 1.25 (m, 3H), 1.58 (m, 1H), 2.30 (m, 1H), 2.33 (s, 3H), 2.80 (m, 2H), 3.19 (m, 1H), 7.13 (m, 2H), 7.26 (d, J=8.0 Hz, 1H), 7.62 (t, J=7.6 Hz, 1H), 7.69 (m, 3H), 7.80 (d, J=7.6 Hz, 1H), 7.97 (d, J=7.6 Hz, 1H), 8.43 (s, 1H), 9.69 (br, 1H), 13.06 (s, 1H), 13.76 (s, 1H)

Example 39

2'-Hydroxy-5'-methyl-3'-{N'-[3-methyl-1-(3-methyl-indan-5-yl)-5-oxo-1,5-dihydro-pyrazol-4-ylidene]-hydrazino}-biphenyl-3-carboxylic acid

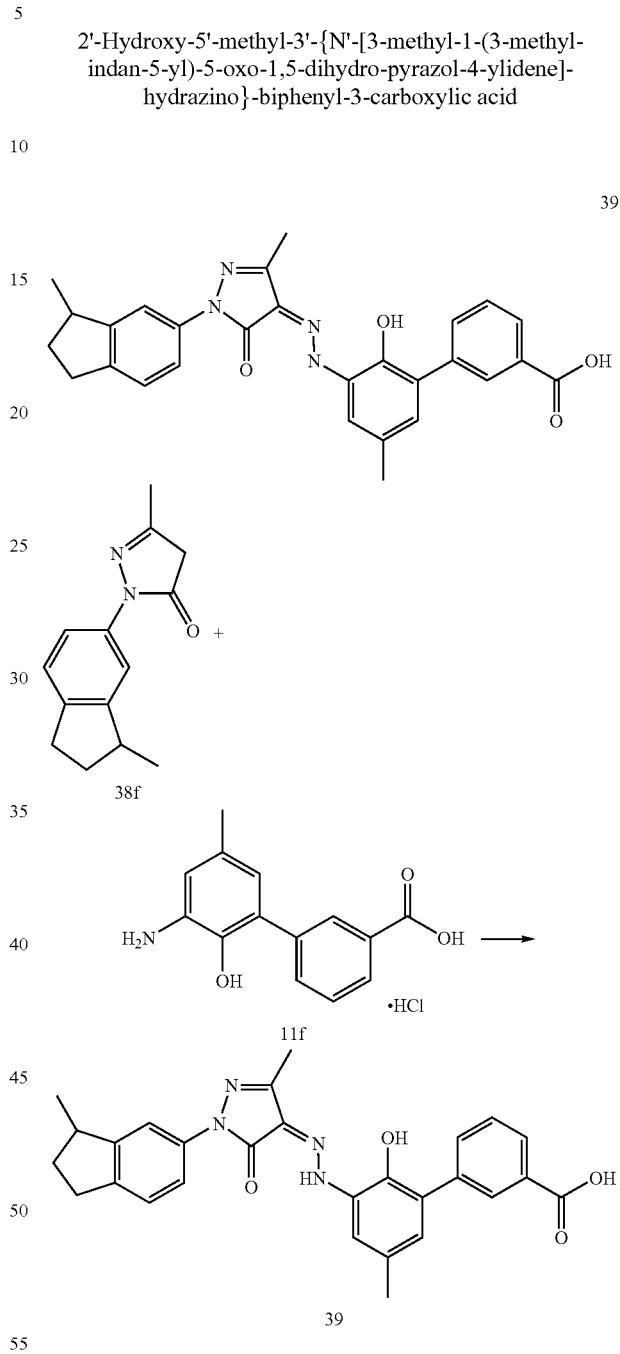

3'-Amino-2'-hydroxy-5'-methyl-biphenyl-3-carboxylic acid hydrochloride 11f (360 mg, 1.11 mmol) was dissolved in 3.7 mL of hydrochloric acid (1 N) upon cooling by an ice-water bath, followed by dropwise addition of 1.5 mL of aqueous sodium nitrite (85 mg, 1.22 mmol). After the mixture was stirred for 20 minutes, 5-methyl-2-(3-methyl-indan-5-yl)-2,4-dihydro-pyrazol-3-one 38f (228 mg, 1.0 mmol) was added. The mixture was adjusted to pH 8 with saturated aqueous sodium bicarbonate, followed by addition of 2 mL ethanol. The reaction mixture was warmed up to room temperature and reacted overnight. The reaction was monitored by TLC until the disappearance of the starting materials. The mixture was filtered and the filter cake was dissolved in 30 mL of water. After mixing well, the mixture was adjusted to pH 3~4 with concentrated hydrochloric acid. The mixture was filtered and the filter cake was dried followed by addition of 10 mL dichloromethane. The mixture was stirred for 1 hour and filtered. The filter cake was dried to obtain the title compound 2'-hydroxy-5'-methyl-3'-{N'-[3-methyl-1-methyl-indan-5-yl)-5-oxo-1,5-dihydro-pyrazol-4-ylidene]-hydrazino}-biphenyl-3-carboxylic acid 39 (240 mg, yield 49.8%) as a red solid.

MS m/z (ESI): 480.9 [M−1]

$^1$H NMR (400 MHz, DMSO-d$_6$): δ 1.29 (m, 3H), 1.56 (m, 1H), 2.28 (m, 1H), 2.34 (s, 3H), 2.36 (s, 3H), 2.80 (m, 2H), 3.18 (m, 1H), 7.00 (s, 1H), 7.27 (d, J=8.0 Hz, 1H), 7.54 (s, 1H), 7.61 (t, J=7.6 Hz, 1H), 7.70 (m, 2H), 7.80 (d, J=8.0 Hz, 1H), 7.95 (d, J=7.6 Hz, 1H), 8.14 (d, J=4.4 Hz, 1H), 9.40 (br, 1H), 13.03 (s, 1H), 13.76 (s, 1H)

Example 40

5-(2-Hydroxy-3-{N'-[3-methyl-1-(3-methyl-indan-5-yl)-5-oxo-1,5-dihydro-pyrazol-4-ylidene]-hydrazino}-phenyl)-thiophene-2-carboxylic acid

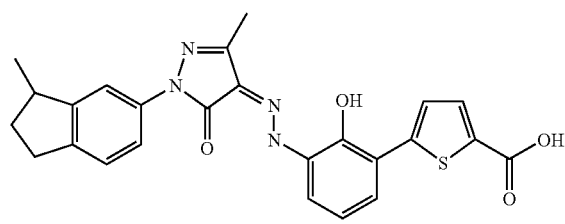

40

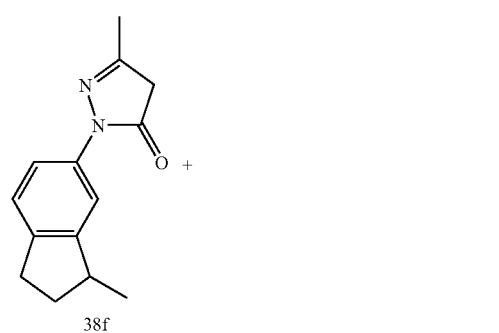

38f

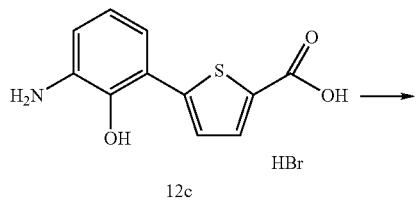

12c

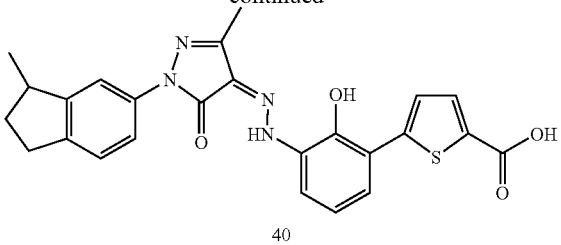

40

5-(3-Amino-2-hydroxy-phenyl)-thiophene-2-carboxylic acid hydrobromide 12c (351 mg, 1.11 mmol) was dissolved in 3.7 mL of hydrochloric acid (1 N) upon cooling by an ice-water bath, followed by dropwise addition of 1.5 mL of aqueous sodium nitrite (85 mg, 1.22 mmol). After the mixture was stirred for 20 minutes, 5-methyl-2-(3-methyl-indan-5-yl)-2,4-dihydro-pyrazol-3-one 38f (228 mg, 1 mmol) was added. The mixture was adjusted to pH 8 with saturated aqueous sodium bicarbonate. Then the generated bubbles were quenched with 2 mL of ethanol. The reaction mixture was warmed up to room temperature and reacted for 3 hours. The reaction was monitored by TLC until the disappearance of the starting materials. The mixture was filtered and 30 mL of water was added to the filter cake. The mixture was adjusted to pH 3~4 with concentrated hydrochloric acid. The mixture was filtered and the filter cake was dried, and then purified by silica gel column chromatography to obtain the title compound 5-(2-hydroxy-3-{N'-[3-methyl-1-(3-methyl-indan-5-yl)-5-oxo-1,5-dihydro-pyrazol-4-ylidene]-hydrazino}-phenyl)-thiophene-2-carboxylic acid 40 (90 mg, yield 19.0%) as a red solid.

MS m/z (ESI): 472.8 [M−1]

$^1$H NMR (400 MHz, DMSO-d$_6$): δ 1.26 (m, 3H), 1.58 (m, 1H), 2.30 (m, 1H), 2.32 (s, 3H), 2.82 (m, 2H), 3.18 (m, 1H), 7.16 (t, J=8.0 Hz, 1H), 7.27 (d, J=8.0 Hz, 1H), 7.54 (d, J=7.6 Hz, 1H), 7.70 (m, 5H), 10.09 (br, 1H), 13.71 (br, 1H)

Example 41

3'-{N'-[1-(3-Ethyl-indan-5-yl)-3-methyl-5-oxo-1,5-dihydro-pyrazol-4-ylidene]-hydrazino}-2'-hydroxy-biphenyl-3-carboxylic acid

41

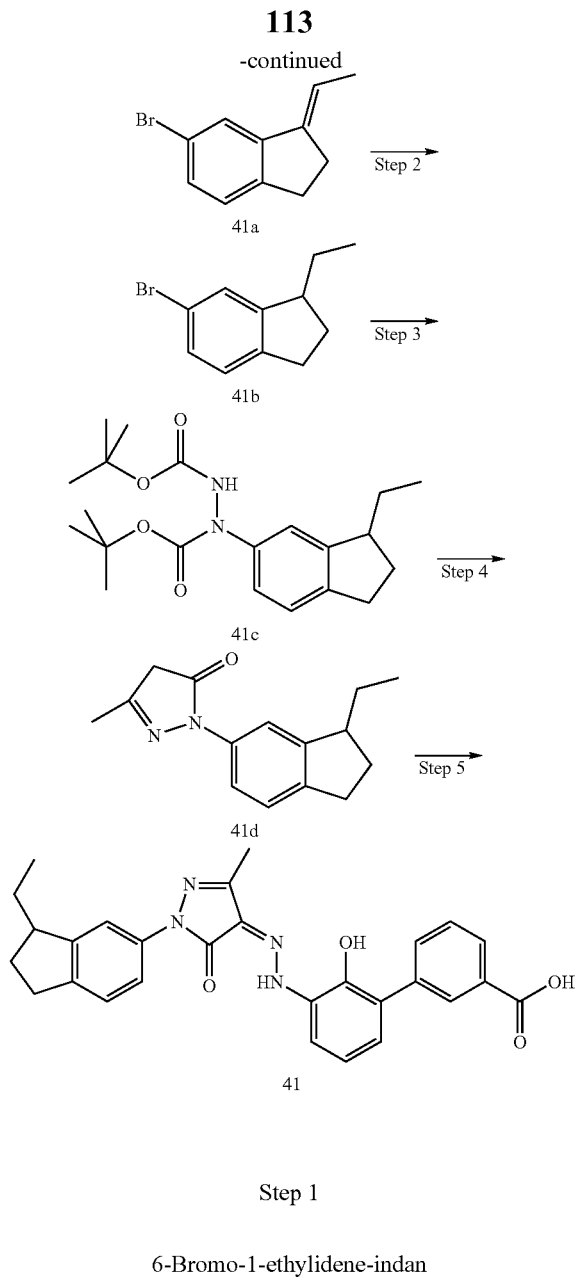

41a

41b

41c

41d

41

Step 1

6-Bromo-1-ethylidene-indan (Ethyl)triphenylphosphonium bromide (14.5 g, 39.1 mmol) was dissolved in 75 mL of tetrahydrofuran followed by addition of potassium tert-butoxide (5.29 g, 47.3 mmol) at room temperature. Upon completion of the addition, the reaction mixture was stirred for 1 hour. A solution of 6-bromo-indan-1-one 38b (3.39 g, 18.6 mmol) in 25 mL of tetrahydrofuran was added to above mixture and the mixture was stirred for another 1 hour. The reaction was monitored by TLC until the disappearance of the starting materials. The reaction was quenched with 150 mL of water and then the mixture was extracted with dichloromethane (50 mL×4). The combined organic extracts were washed with saturated brine (45 mL×2), dried over anhydrous sodium sulfate, filtered to remove the drying agent and concentrated under reduced pressure. The residue was purified by silica gel column chromatography to obtain the title compound 6-bromo-1-ethylidene-indan 41a (3.07 g, 74%) as a yellow oil.

MS m/z (ESI): 221.8 [M−1]

Step 2

6-Bromo-1-ethyl-indan

6-Bromo-1-ethylidene-indan 41a (3.07 g, 13.7 mmol) was dissolved in 80 mL of ethyl acetate followed by addition of palladium on carbon (0.61 g) at room temperature. The mixture was hydrogenated for 5 hours in a hydrogenator under 3 atm. of hydrogen. The reaction was monitored by TLC until the disappearance of the starting materials. The mixture was filtered to remove palladium on carbon and the filter cake was washed with ethyl acetate (10 mL×3). The filtrate was concentrated under reduced pressure and the residue was purified by silica gel column chromatography to obtain the title compound 6-bromo-1-ethyl-indan 41b (2.75 g, 88.7%) as a light yellow oil.

MS m/z (ESI): 224 [M−1]

Step 3

Di-tert-butyl 1-(3-ethyl-2,3-dihydro-1H-inden-5-yl)hydrazine-1,2-dicarboxylate Upon cooling by a dry ice-acetone bath, a solution of 6-bromo-1-ethyl-indan 41b (2.52 g, 11.2 mmol) in 15 mL of tetrahydrofuran was added dropwise to a solution of t-butyl-lithium in cyclohexane (18.1 mL, 1.3 N) under argon atmosphere. Upon completion of the addition, the mixture was stirred for 2 hours in the dry ice-acetone bath. A solution of di-tert-butyl azodicarboxylate in 15 mL of tetrahydrofuran was added dropwise to the above mixture at the same temperature. Upon completion of the addition, the reaction mixture was stirred for another 1.5 hours in the dry ice-acetone bath. Then the dry ice-ethanol bath was removed. The mixture was warmed up to room temperature and stirred for 18 hours. The reaction was monitored by TLC until the disappearance of the starting materials and quenched by addition of 25 mL of saturated ammonium chloride. The mixture was extracted with ethyl acetate (30 mL×3). The combined organic extracts were dried over anhydrous sodium sulfate, filtered to remove the drying agent and concentrated under reduced pressure. The residue was purified by silica gel column chromatography to obtain the title compound di-tert-butyl 1-(3-ethyl-2,3-dihydro-1H-inden-5-yl)hydrazine-1,2-dicarboxylate 41c (3.43 g, 81.5%) as a brown oil.

Step 4

2-(3-Ethyl-indan-5-yl)-5-methyl-2,4-dihydro-pyrazol-3-one

Di-tert-butyl 1-(3-ethyl-2,3-dihydro-1H-inden-5-yl)hydrazine-1,2-dicarboxylate 41c (3.43 g, 9.1 mmol) was dissolved in 50 mL of a solvent mixture of ethanol/water (V:V=3:2) followed by addition of 3-oxo-butanoic acid ethyl ester (1.18 g, 9.1 mmol) and 4.55 mL of hydrochloric acid (6 N). Upon completion of the addition, the reaction mixture was heated to reflux and reacted for 1 hour. The reaction was monitored by TLC until the disappearance of the starting materials. The mixture was concentrated under reduced pressure to remove ethanol and then extracted with dichloromethane (15 mL×3). The combined organic extracts were dried over anhydrous sodium sulfate, filtered to remove the drying agent and concentrated under reduced pressure. The residue was purified by silica gel column chromatography to obtain the title compound 2-(3-ethyl-indan-5-yl)-5-methyl-2,4-dihydro-pyrazol-3-one 41d (0.712 g, 39.8%) as a yellow oil.

MS m/z (ESI): 243.2 [M+1]

Step 5

3'-{N'-[1-(3-Ethyl-indan-5-yl)-3-methyl-5-oxo-1,5-dihydro-pyrazol-4-ylidene]-hydrazino}-2'-hydroxy-biphenyl-3-carboxylic acid 3'-Amino-2'-hydroxy-biphenyl-3-carboxylic acid hydrobromide 1f (285 mg, 0.92 mmol) was dissolved in 3.1 mL of hydrochloric acid (1 N) upon cooling by an ice-water bath, followed by dropwise addition of 1.2 mL of aqueous sodium nitrite (70 mg, 1.01 mmol). After the mixture was stirred for 20 minutes, 2-(3-ethyl-indan-5-yl)-5-methyl-2,4-dihydro-pyrazol-3-one 41d (200 mg, 0.83 mmol) was added. The mixture was adjusted to pH 8 with saturated aqueous sodium bicarbonate followed by addition of 2 mL of ethanol. The reaction mixture was warmed up to room temperature overnight. The reaction was monitored by TLC until the disappearance of the starting materials. The mixture was filtered and the filter cake was added to 20 mL of water. The mixture was adjusted to pH 3~4 with concentrated hydrochloric acid. The mixture was filtered and the filter cake was dried to obtain the title compound 3'-{N'-[1-(3-ethyl-indan-5-yl)-3-methyl-5-oxo-1,5-dihydro-pyrazol-4-ylidene]-hydrazino}-2'-hydroxy-biphenyl-3-carboxylic acid 41 (145 mg, yield 36.4%) as a red solid.

MS m/z (ESI): 480.9 [M−1]

$^1$H NMR (400 MHz, DMSO-$d_6$): δ 0.95 (m, 3H), 1.43 (m, 1H), 1.65 (m, 1H), 1.83 (m, 1H), 2.23 (m, 1H), 2.34 (s, 3H), 2.92 (m, 2H), 3.05 (m, 1H), 7.15 (s, 2H), 7.27 (d, J=8.0 Hz, 1H), 7.62 (t, J=8.0 Hz, 1H), 7.72 (m, 3H), 7.80 (d, J=7.6 Hz, 1H), 7.97 (d, J=8.0 Hz, 1H), 8.14 (s, 1H), 9.66 (s, 1H), 13.04 (s, 1H), 13.76 (s, 1H)

Example 42

3'-{N'-[1-(3-Ethyl-indan-5-yl)-3-methyl-5-oxo-1,5-dihydro-pyrazol-4-ylidene]-hydrazino}-2'-hydroxy-5'-methyl-biphenyl-3-carboxylic acid

42

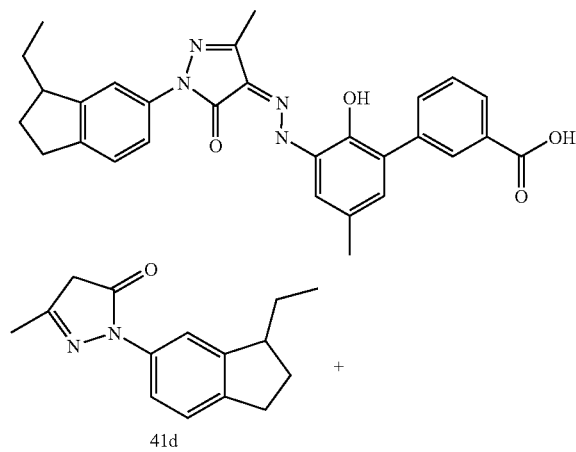

41d

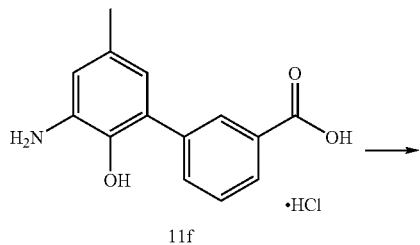

11f

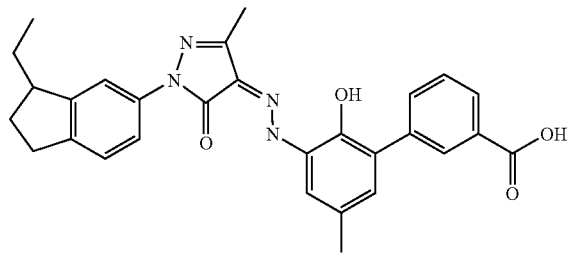

42

3'-Amino-2'-hydroxy-5'-methyl-biphenyl-3-carboxylic acid hydrochloride 11f (298 mg, 0.92 mmol) was dissolved in 3.1 mL of hydrochloric acid (1 N) upon cooling by an ice-water bath, followed by dropwise addition of 1.2 mL of aqueous sodium nitrite (70 mg, 1.01 mmol). After the mixture was stirred for 20 minutes, 2-(3-ethyl-indan-5-yl)-5-methyl-2,4-dihydro-pyrazol-3-one 41d (200 mg, 0.83 mmol) was added. The mixture was adjusted to pH 8 with saturated aqueous sodium bicarbonate followed by addition of 2 mL of ethanol. The reaction mixture was warmed up to room temperature overnight. The reaction was monitored by TLC until the disappearance of the starting materials. The mixture was filtered and 20 mL of water was added to the filter cake. The mixture was adjusted to pH 3~4 with concentrated hydrochloric acid. The mixture was filtered and the filter cake was dried to obtain the title compound 3'-{N'-[1-(3-ethyl-indan-5-yl)-3-methyl-5-oxo-1,5-dihydro-pyrazol-4-ylidene]-hydrazino}-2'-hydroxy-5'-methyl-biphenyl-3-carboxylic acid 42 (290 mg, yield 70.7%) as a red solid.

MS m/z (ESI): 494.9 [M−1]

$^1$H NMR (400 MHz, DMSO-$d_6$): δ 0.95 (m, 3H), 1.43 (m, 1H), 1.65 (m, 1H), 1.83 (m, 1H), 2.23 (m, 1H), 2.34 (s, 3H), 2.92 (m, 2H), 3.05 (m, 1H), 6.99 (s, 1H), 7.26 (d, J=8.0 Hz, 1H), 7.53 (s, 1H), 7.60 (t, J=8.0 Hz, 1H), 7.68 (m, 1H), 7.75

(s, 1H), 7.80 (d, J=7.6 Hz, 1H), 7.96 (d, J=7.6 Hz, 1H), 8.14 (s, 1H), 9.39 (s, 1H), 13.03 (s, 1H), 13.76 (s, 1H)

Example 43

5-(3-{N'-[1-(3,3-Dimethyl-indan-5-yl)-3-methyl-5-oxo-1,5-dihydro-pyrazol-4-ylidene]-hydrazino}-2-hydroxy-phenyl)-furan-2-carboxylic acid

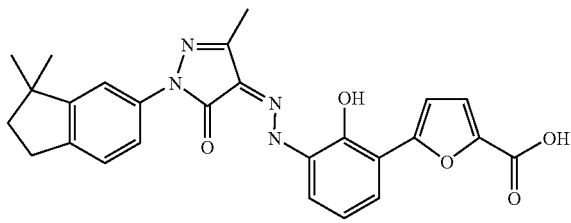

43

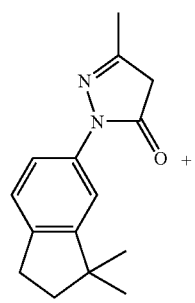

8i

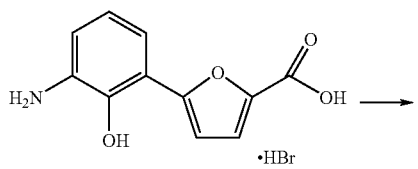

9c

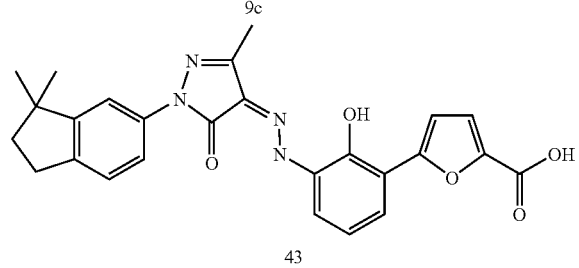

43

5-(3-Amino-2-hydroxy-phenyl)-furan-2-carboxylic acid hydrobromide 9c (333 mg, 1.1 mmol) was dissolved in hydrochloric acid (3.7 mL, 1 mol/L) upon cooling by an ice-water bath, followed by dropwise addition of 1.5 mL of aqueous sodium nitrite (85 mg, 1.22 mmol). After the mixture was reacted for 20 minutes, 2-(3,3-dimethyl-indan-5-yl)-5-methyl-2,4-dihydro-pyrazol-3-one 8i (242 mg, 1.0 mmol), sodium bicarbonate (1.4 g, 16.67 mmol) and 3 mL of ethanol were added successively. The reaction mixture was reacted overnight at room temperature. The reaction was monitored by TLC until the disappearance of the starting materials. The mixture was filtered and 20 mL of water was added to the filter cake. The mixture was adjusted to pH 3~4 with concentrated hydrochloric acid. The mixture was filtered and the filter cake was dried and purified by silica gel column chromatography to obtain the title compound 5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid 43 (190 mg, yield 40.3%) as a red solid.

MS m/z (ESI): 470.9 [M−1]

$^1$H NMR (400 MHz, DMSO-d$_6$): δ 1.26 (s, 6H), 1.92 (t, J=7.2 Hz, 2H), 2.33 (s, 3H), 2.86 (t, J=7.2 Hz, 2H), 7.15 (m, 1H), 7.20 (m, 2H), 7.37 (d, J=3.6 Hz, 1H), 7.55 (d, J=6.8 Hz, 1H), 7.71 (m, 3H), 9.99 (br, 1H), 13.15 (br, 1H), 13.74 (br, 1H)

Example 44

5-(2-Hydroxy-3-{N'-[3-methyl-1-(3-methyl-indan-5-yl)-5-oxo-1,5-dihydro-pyrazol-4-ylidene]-hydrazino}-phenyl)-furan-2-carboxylic acid

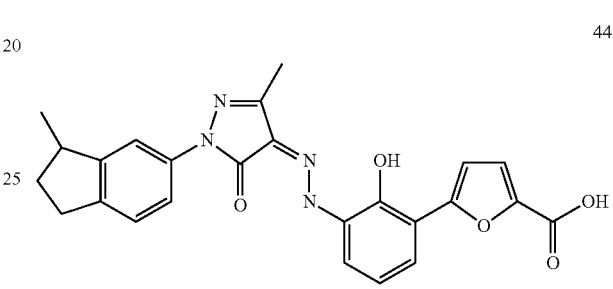

44

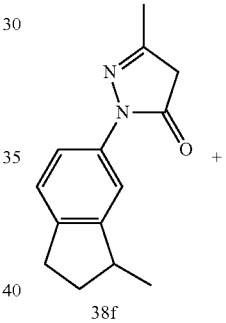

38f

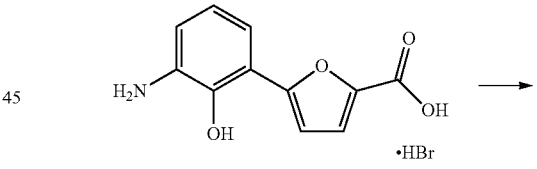

9c

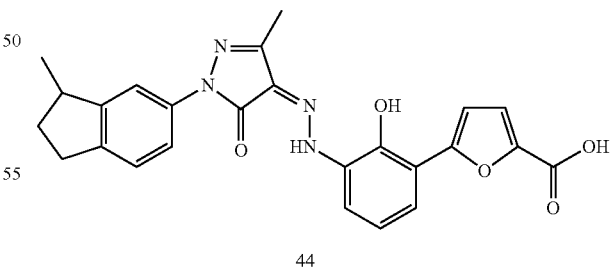

44

5-(3-Amino-2-hydroxy-phenyl)-furan-2-carboxylic acid hydrobromide 9c (333 mg, 1.1 mmol) was dissolved in hydrochloric acid (3.7 mL, 1 mol/L) upon cooling by an ice-water bath, followed by dropwise addition of 1.5 mL of aqueous sodium nitrite (85 mg, 1.22 mmol). After the mixture was reacted for 20 minutes, 5-methyl-2-(3-methyl-indan-5-yl)-2,4-dihydro-pyrazol-3-one 38c (228 mg, 1.0 mmol), sodium bicarbonate (1.4 g, 16.67 mmol) and 3 mL of ethanol were added successively. The reaction mixture was reacted overnight at room temperature. The reaction was monitored by TLC until the disappearance of the starting materials. The mixture was filtered and 20 mL of water was added to the filter cake. The mixture was adjusted to pH 3~4 with concentrated hydrochloric acid. The mixture was filtered and the filter cake was dried and purified by silica gel column chromatography to obtain the title compound 5-(2-hydroxy-3-{N'-[3-methyl-1-(3-methyl-indan-5-yl)-5-oxo-1,5-dihydro-pyrazol-4-ylidene]-hydrazino}-phenyl)-furan-2-carboxylic acid 44 (110 mg, yield 24.0%) as a red solid.

MS m/z (ESI): 457.0 [M−1]

$^1$H NMR (400 MHz, DMSO-$d_6$): δ 1.25 (m, 3H), 1.59 (m, 1H), 2.29 (m, 1H), 2.33 (s, 3H), 2.84 (m, 2H), 3.17 (m, 1H), 7.14 (d, J=3.2 Hz, 1H), 7.22 (t, J=8.0 Hz, 1H), 7.28 (d, J=8.0 Hz, 1H), 7.36 (d, J=3.2 Hz, 1H), 7.55 (d, J=8.0 Hz, 1H), 7.71 (m, 3H) 9.96 (br, 1H) 13.75 (br, 1H)

Example 45

5-(3-{N'-[1-(2,2-Dimethyl-indan-5-yl)-3-methyl-5-oxo-1,5-dihydro-pyrazol-4-ylidene]-hydrazino}-2-hydroxy-phenyl)-furan-2-carboxylic acid

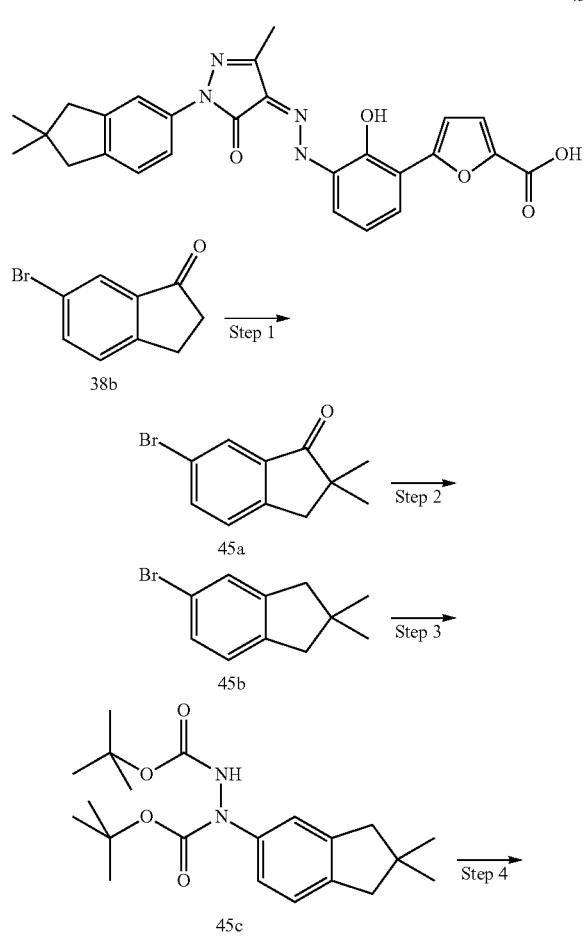

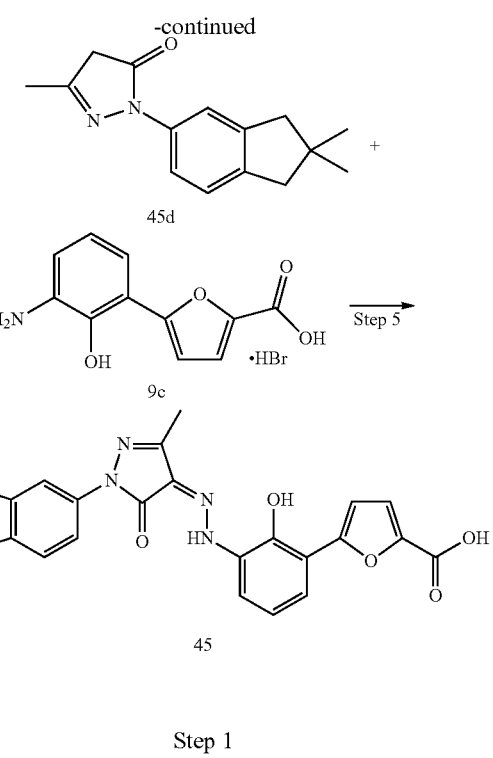

Step 1

6-Bromo-2,2-dimethyl-indan-1-one

6-Bromo-indan-1-one 38b (6.02 g, 28.5 mmol) and iodomethane (4.4 mL, 70 mmol) were dissolved in 200 mL of dry tetrahydrofuran. After the mixture was stirred at room temperature for 15 minutes, sodium hydride (2.73 g, 68.2 mmol) was added. The reaction mixture was stirred for another 2 hours. The reaction was monitored by TLC until the disappearance of the starting materials. The reaction was quenched with 150 mL of water and then extracted with ethyl acetate (150 mL×2). The combined organic extracts were washed with saturated brine, dried over anhydrous sodium sulfate, filtered to remove the drying agent and concentrated under reduced pressure. The residue was purified by silica gel column chromatography to obtain the title compound 6-bromo-2,2-dimethyl-indan-1-one 45a (5.36 g, yield 78.6%) as a brown solid.

$^1$H NMR (400 MHz, CDCl$_3$): δ 7.918 (d, J=1.6 Hz, 1H), 7.725 (dd, J$_1$=8 Hz, J$_2$=2 Hz, 1H), 7.352 (d, J=8 Hz, 1H), 2.979 (s, 2H), 1.273 (s, 6H)

Step 2

5-Bromo-2,2-dimethyl-indan

6-Bromo-2,2-dimethyl-indan-1-one 45a (7.23 g, 30.3 mmol) was dissolved in 150 mL of trifluoroacetic acid followed by addition of triethylsilane (12.1 mL, 75.6 mmol). The reaction mixture was stirred overnight at room temperature. The reaction was monitored by TLC until the disappearance of the starting materials and then quenched by addition of water. The mixture was concentrated under reduced pressure to remove trifluoroacetic acid. The mixture was adjusted to be basic with saturated aqueous sodium bicarbonate and then extracted with ethyl acetate (50 mL×3). The combined organic extracts were washed with saturated brine, dried over anhydrous sodium sulfate, filtered to remove the drying agent and concentrated under reduced pressure. The residue was purified by silica gel column chromatography to obtain the title compound 5-bromo-2,2-dimethyl-indan 45b (14 g) as a colourless oil, which was directly used in the next step.

¹H NMR (400 MHz, CDCl$_3$): δ 7.335 (s, 1H), 7.281 (d, J=8 Hz, 1H), 7.063 (s, J=8 Hz, 1H), 2.749 (s, 2H), 2.702 (s, 2H), 1.188 (s, 6H)

Step 3

Di-tert-butyl 1-(2,2-dimethyl-5-yl)hydrazine-1,2-dicarboxylate

5-Bromo-2,2-dimethyl-indan 45b (2.4 g, 10.7 mmol) was dissolved in 20 mL of dry tetrahydrofuran. Upon cooling by a dry ice-ethanol bath to −78° C., n-butyllithium (12.1 mL, 30.2 mmol) was added dropwise. Upon completion of the addition, the mixture was stirred for 2 hours. A solution of di-tert-butyl azodicarboxylate (3.27 g, 14.2 mmol) in 20 mL of dry tetrahydrofuran was added to the above mixture. The reaction mixture was reacted at the same temperature for 3 hours. The reaction was monitored by TLC until the disappearance of the starting materials and quenched by addition of 50 mL of water. The mixture was extracted with ethyl acetate (50 mL×2). The combined organic extracts were washed with saturated brine, dried over anhydrous sodium sulfate, filtered to remove the drying agent and concentrated under reduced pressure. The residue was purified by silica gel column chromatography to obtain the title compound di-tert-butyl 1-(2,2-dimethyl-inden-5-yl)hydrazine-1,2-dicarboxylate 45c (2.68 g, yield 66.8%) as a yellow oil.

Step 4

2-(2,2-Dimethyl-indan-5-yl)-5-methyl-2,4-dihydro-pyrazol-3-one

Di-tert-butyl 1-(2,2-dimethyl-1H-inden-5-yl)hydrazine-1,2-dicarboxylate 45c (3.3 g, 8.78 mmol) was dissolved in 12 mL of acetic acid followed by addition of 6 mL of trifluoroacetic acid and 3-oxo-butanoic acid methyl ester (1.5 mL, 13.8 mmol). Upon completion of the addition, the reaction mixture was stirred at 90° C. for 2 hours. The reaction was monitored by TLC until the disappearance of the starting materials. The mixture was concentrated under reduced pressure and the residue was diluted with 30 mL of water and 30 mL of ethyl acetate. After mixing well, the separated organic layer was washed with saturated brine, dried over anhydrous sodium sulfate, filtered to remove the drying agent and concentrated under reduced pressure. The residue was purified by silica gel column chromatography to obtain the title compound 2-(2,2-dimethyl-indan-5-yl)-5-methyl-2,4-dihydro-pyrazol-3-one 45d (464 mg, yield 22.1%) as a yellow oil.

MS m/z (ESI): 243.3 [M+1]

Step 5

5-(3-{N'-[1-(2,2-Dimethyl-indan-5-yl)-3-methyl-5-oxo-1,5-dihydro-pyrazol-4-ylidene]-hydrazino}-2-hydroxy-phenyl)-furan-2-carboxylic acid 5-(3-Amino-2-hydroxy-phenyl)-furan-2-carboxylic acid hydrobromide 9c (150 mg, 0.5 mmol) was dissolved in hydrochloric acid (1.7 mL, 1 mol/L) upon cooling by an ice-water bath, followed by dropwise addition of 0.6 mL of aqueous sodium nitrite (38 mg, 0.55 mmol). After the mixture was reacted for 20 minutes, 2-(2,2-dimethyl-indan-5-yl)-5-methyl-2,4-dihydro-pyrazol-3-one 45d (109 mg, 0.45 mmol), sodium bicarbonate (630 mg, 7.5 mmol) and 1 mL of ethanol were added successively. The reaction mixture was reacted overnight at room temperature. The reaction was monitored by TLC until the disappearance of the starting materials. The mixture was filtered and 15 mL of water was added to the filter cake. The mixture was adjusted to pH 3~4 with concentrated hydrochloric acid and filtered. The filter cake was washed with ethyl acetate (1 mL×3) and dried to obtain the title compound 5-(3-{N'-[1-(2,2-dimethyl-indan-5-yl)-3-methyl-5-oxo-1,5-dihydro-pyrazol-4-ylidene]-hydrazino}-2-hydroxy-phenyl)-furan-2-carboxylic acid 45 (67 mg, yield 31.6%) as a yellow solid.

MS m/z (ESI): 470.7 [M−1]

¹H NMR (400 MHz, DMSO-d$_6$): δ 1.13 (s, 6H), 2.32 (s, 3H), 2.70 (m, 4H), 7.14 (d, J=3.6 Hz, 1H), 7.21 (m, 2H), 7.36 (d, J=3.6 Hz, 1H), 7.54 (m, 1H), 7.62 (m, 1H), 7.69 (m, 2H)

Example 46

5-{2-Hydroxy-3-[N'-(1-indan-5-yl-3-methyl-5-oxo-1,5-dihydro-pyrazol-4-ylidene)-hydrazino]-5-methyl-phenyl}-furan-2-carboxylic acid

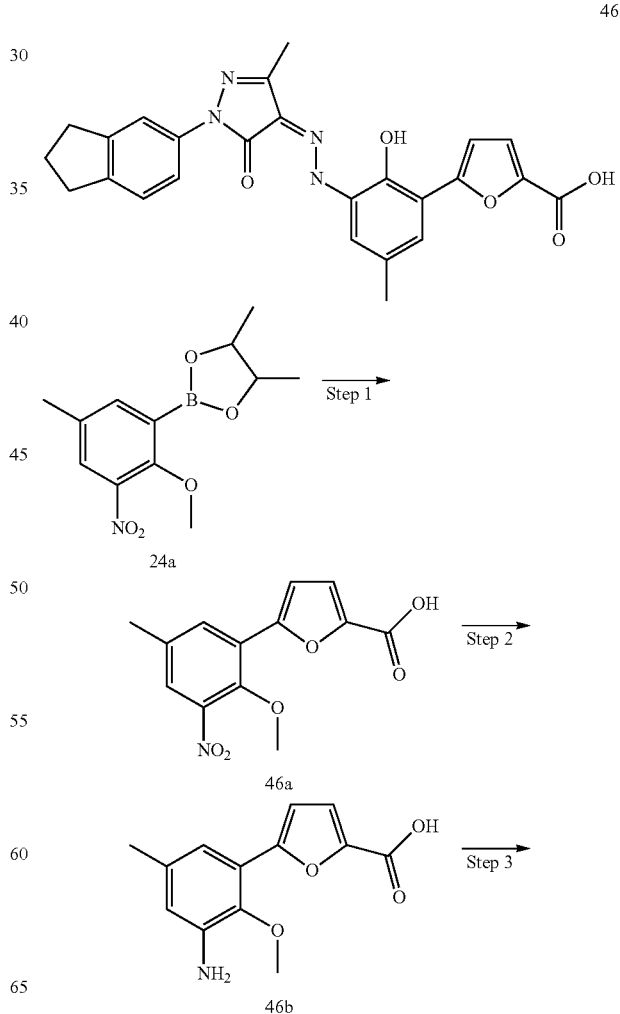

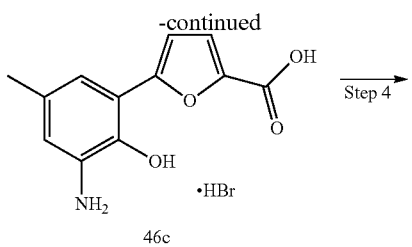

46c

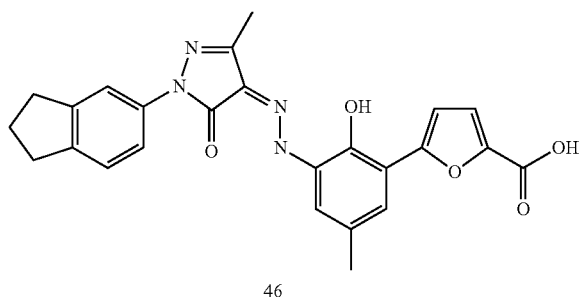

46

Step 1

5-(3-Nitro-2-methoxy-5-methyl-phenyl)-furan-2-carboxylic acid

To a solution of the solvent mixture of 30 mL of 1,4-dioxane and 15 mL of water was added 2-(2-methoxy-5-methyl-3-nitro-phenyl)-4,4,5,5-tetramethyl-1,3,2-dioxaborolane 24a (3.1 g, 7.5 mmol) followed by 5-bromofuran-2-carboxylic acid (1.3 g, 6.8 mmol), tetrakis(triphenylphosphine)palladium (0.43 g, 0.4 mmol) and sodium carbonate (1.6 g, 15.1 mmol). The reaction mixture was heated to reflux for 1 hour. The reaction was monitored by TLC until the disappearance of the starting materials. The mixture was cooled and filtered. The filtrate was washed with ethyl acetate and concentrated under reduced pressure. The resulting residue was diluted with 50 mL of water and adjusted to pH 3 with concentrated hydrochloric acid and filtered. The filter cake was washed with ethyl acetate and dried to obtain the title compound 5-(3-nitro-2-methoxy-5-methyl-phenyl)-furan-2-carboxylic acid 46a (522 mg, 29%) as a yellow solid.

MS m/z (ESI): 275.7 [M−1]

$^1$H NMR (400 MHz, DMSO-$d_6$): δ 13.31 (1H, br), 7.90 (1H, s), 7.78 (1H, s), 7.39 (1H, d, J=3.2 Hz), 7.16 (1H, d, J=3.6 Hz), 3.80 (3H, s), 2.42 (3H, s)

Step 2

5-(3-Amino-2-methoxy-5-methyl-phenyl)-furan-2-carboxylic acid 5-(3-Nitro-2-methoxy-5-methyl-phenyl)-furan-2-carboxylic acid 46a (410 mg, 1.48 mmol) was dissolved in 28 mL of ethyl acetate followed by addition of 61 mg of palladium on carbon and ammonium formate (658 mg, 10.44 mmol). Upon completion of the addition, the reaction mixture was heated to reflux for 3 hours. The reaction was monitored by TLC until the disappearance of the starting materials. The mixture was filtered to remove palladium on carbon. The filtrate was concentrated under reduced pressure and dried to obtain the title compound 5-(3-amino-2-methoxy-5-methyl-phenyl)-furan-2-carboxylic acid 46b (356 mg, yield 97.3%) as a white solid.

MS m/z (ESI): 246.0 [M−1]

$^1$H NMR (400 MHz, DMSO-$d_6$): δ 7.18 (1H, s), 6.98 (1H, m), 6.80 (1H, s), 6.56 (1H, s), 3.62 (3H, s), 2.20 (3H, s)

Step 3

5-(3-Amino-2-hydroxy-5-methyl-phenyl)-furan-2-carboxylic acid hydrobromide 5-(3-Amino-2-methoxy-5-methyl-phenyl)-furan-2-carboxylic acid 46b (248 mg, 1 mmol) was dissolved in 20 mL of dichloromethane followed by dropwise addition of a solution of boron tribromide in dichloromethane (3 mL, 1 mmol/L). The reaction mixture was reacted at room temperature for 2 hours. The reaction was monitored by TLC until the disappearance of the starting materials. The mixture was concentrated under reduced pressure. The resulting residue was washed with ethyl acetate (50 mL×3) and dried to obtain the title compound 5-(3-amino-2-hydroxy-5-methyl-phenyl)-furan-2-carboxylic acid hydrobromide 46c (172 mg, yield 54.7%) as a white solid.

MS m/z (ESI): 231.8 [M−1]

$^1$H NMR (400 MHz, DMSO-$d_6$): δ 7.46 (1H, m), 7.34 (1H, m), 7.10 (2H, m), 2.31 (3H, s)

Step 4

5-{2-Hydroxy-3-[N'-(1-indan-5-yl-3-methyl-5-oxo-1,5-dihydro-pyrazol-4-ylidene)-hydrazino]-5-methyl-phenyl}-furan-2-carboxylic acid 5-(3-Amino-2-hydroxy-5-methyl-phenyl)-furan-2-carboxylic acid hydrobromide 46c (219 mg, 0.70 mmol) was dissolved in 2.3 mL of 1 N hydrochloric acid upon cooling by an ice-water bath, followed by dropwise addition of 1.0 mL of aqueous sodium nitrite (53 mg, 0.77 mmol). After the mixture was reacted for 20 minutes, 2-indan-5-yl-5-methyl-2,4-dihydro-pyrazol-3-one 1i (134 mg, 0.63 mmol), sodium bicarbonate (878 mg, 10.45 mmol) and 2 mL of ethanol were added successively. The reaction mixture was reacted overnight at room temperature. The reaction was monitored by TLC until the disappearance of the starting materials. The mixture was filtered and the filter cake was added to 20 mL of water. The mixture was adjusted to pH 3~4 with concentrated hydrochloric acid upon cooling by an ice-water bath. The mixture was filtered and the filter cake was washed with 6 mL of dichloromethane and dried to obtain the title compound 5-{2-hydroxy-3-[N'-(1-indan-5-yl-3-methyl-5-oxo-1,5-dihydro-pyrazol-4-ylidene)-hydrazino]-5-methyl-phenyl}-furan-2-carboxylic acid 46 (170 mg, yield 59.2%) as a red solid.

MS m/z (ESI): 456.8 [M−1]

¹H NMR (400 MHz, DMSO-d₆): δ 2.05 (m, 2H), 2.32 (s, 3H), 2.37 (s, 3H), 2.88 (m, 4H), 7.13 (d, J=3.6 Hz, 1H), 7.28 (d, J=8.0 Hz, 1H), 7.35 (m, 2H), 7.51 (s, 1H), 7.68 (d, J=7.6 Hz, 1H), 7.78 (s, 1H)

Example 47

2-{2-Hydroxy-3-[N'-(1-indan-5-yl-3-methyl-5-oxo-1,5-dihydro-pyrazol-4-ylidene)-hydrazino]-phenyl}-5-methyl-thiazole-4-carboxylic acid

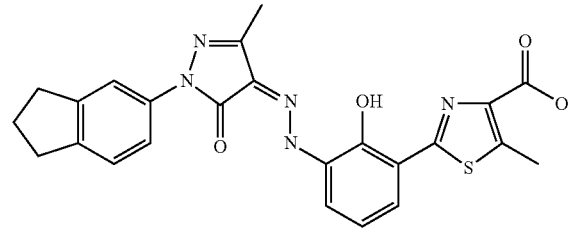

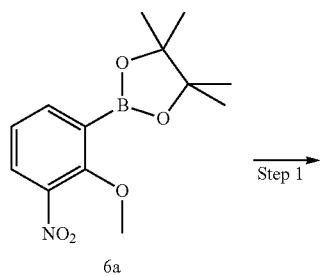

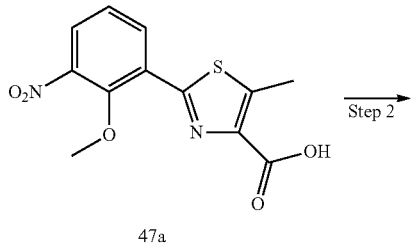

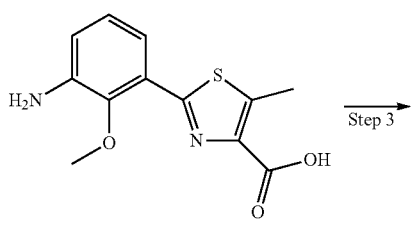

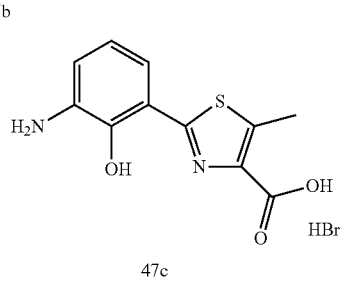

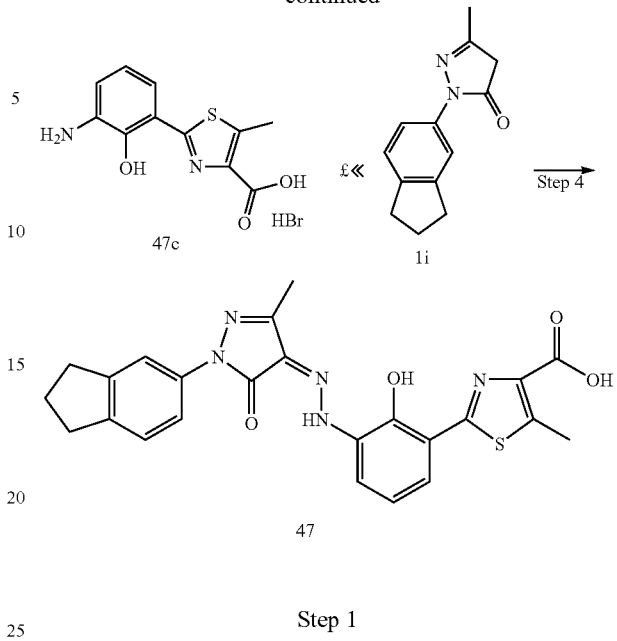

Step 1

2-(2-Methoxy-3-nitro-phenyl)-5-methyl-thiazole-4-carboxylic acid 2-(2-Methoxy-3-nitro-phenyl)-4,4,5,5-tetramethyl-1,3,2-dioxaborolane 6a (1.7 g, 6.08 mmol), 2-bromo-5-methyl-thiazole-4-carboxylic acid (900 mg, 4.05 mmol), tetrakis(triphenylphosphine)palladium (233 mg, 0.2 mmol) and sodium carbonate (1.29 g, 12.16 mmol) were dissolved in 30 mL of 1,4-dioxane. The reaction mixture was heated to reflux for 4 hours. The reaction was monitored by TLC until the disappearance of the starting materials. The mixture was filtered and the filtrate was concentrated under reduced pressure. The residue was diluted with 20 mL of hydrochloric acid (1 N) and 30 mL of ethyl acetate. The separated organic layer was washed with saturated brine, dried over anhydrous sodium sulfate, filtered to remove the drying agent and concentrated under reduced pressure. The residue was recrystallized from a solvent mixture of ethyl acetate and hexane to obtain the title compound 2-(2-methoxy-3-nitro-phenyl)-5-methyl-thiazole-4-carboxylic acid 47a (310 mg, yield 26%) as a yellow solid.

MS m/z (ESI): 292.6 [M−1]

¹H NMR (400 MHz, DMSO-d₆): δ 13.45 (br, 1H), 8.58 (dd, J=8.0 Hz, 1H), 8.14 (dd, J=8.0 Hz, 1H), 7.52 (t, J=8.0 Hz, 1H), 3.93 (s, 3H), 2.71 (s, 3H)

Step 2

2-(2-Methoxy-3-amino-phenyl)-5-methyl-thiazole-4-carboxylic acid 2-(2-Methoxy-3-nitro-phenyl)-5-methyl-thiazole-4-carboxylic acid 47a (300 mg, 1.02 mmol) was dissolved in 15 mL of methanol followed by addition of 30 mg of palladium on carbon. The reaction mixture was stirred for 24 hours under hydrogen atmosphere. The reaction was monitored by TLC until the disappearance of the starting materials. The mixture was filtered to remove palladium on carbon and the filtrate was concentrated under reduced pressure to obtain the title compound 2-(2-methoxy-3-amino-phenyl)-5-methyl-thiazole-4-carboxylic acid 47b (250 mg, yield 92%) as a yellow solid.

MS m/z (ESI): 262.8 [M−1]

Step 3

2-(2-Hydroxy-3-amino-phenyl)-5-methyl-thiazole-4-carboxylic acid hydrobromide 2-(2-Methoxy-3-amino-phenyl)-5-methyl-thiazole-4-carboxylic acid 47b (280 mg, 0.94 mmol) was dissolved in 5 mL of hydrogen bromide. The reaction mixture was stirred overnight at 80° C. The reaction was monitored by TLC until the disappearance of the starting materials. The mixture was filtered and the filter cake was washed with ethyl acetate and dried to obtain the title compound 2-(2-hydroxy-3-amino-phenyl)-5-methyl-thiazole-4-carboxylic acid hydrobromide 47c (200 mg, yield 64%) as a yellow solid.

MS m/z (ESI): 262.7 [M−1]

$^1$H NMR (400 MHz, DMSO-$d_6$): δ 7.88 (d, J=8.0 Hz, 1H), 7.51 (d, J=8.0 Hz, 1H), 7.09 (t, J=8.0 Hz, 1H), 2.73 (s, 3H)

Step 4

2-{2-Hydroxy-3-[N'-(1-indan-5-yl-3-methyl-5-oxo-1,5-dihydro-pyrazol-4-ylidene)-hydrazino]-phenyl}-5-methyl-thiazole-4-carboxylic acid 2-(2-Hydroxy-3-amino-phenyl)-5-methyl-thiazole-4-carboxylic acid hydrobromide 47c (200 mg, 0.60 mmol) was dissolved in 2 mL of hydrochloric acid (1 N) upon cooling by an ice-water bath, followed by dropwise addition of 0.82 mL of aqueous sodium nitrite (46 mg, 0.66 mmol). After the mixture was stirred for 20 minutes, 2-indan-5-yl-5-methyl-2,4-dihydro-pyrazol-3-one 1i (116 mg, 0.544 mmol) was added. The mixture was adjusted to pH 8~9 by batch addition of saturated aqueous sodium bicarbonate (781 mg, 9.3 mmol). Then the generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in 20 mL of water. The mixture was adjusted to pH 3~4 with concentrated hydrochloric acid. The mixture was filtered and the filter cake was dried and purified by HPLC to obtain the title compound 2-{2-hydroxy-3-[N'-(1-indan-5-yl-3-methyl-5-oxo-1,5-dihydro-pyrazol-4-ylidene)-hydrazino]-phenyl}-5-methyl-thiazole-4-carboxylic acid 47 (195 mg, yield 75.9%) as a red solid.

MS m/z (ESI): 473.7 [M−1]

$^1$H NMR (400 MHz, D$_2$O): δ 1.97 (m, 2H), 2.31 (s, 3H), 2.53 (s, 3H), 2.80 (m, 4H), 6.52 (t, J=8.0 Hz, 1H), 7.23 (m, 4H), 7.84 (d, J=8.0 Hz, 1H)

Example 48

5-{2-Hydroxy-3-[N'-(1-indan-5-yl-3-methyl-5-oxo-1,5-dihydro-pyrazol-4-ylidene)-hydrazino]-phenyl}-1,2,4-trimethyl-1H-pyrrole-3-carboxylic acid ethyl ester

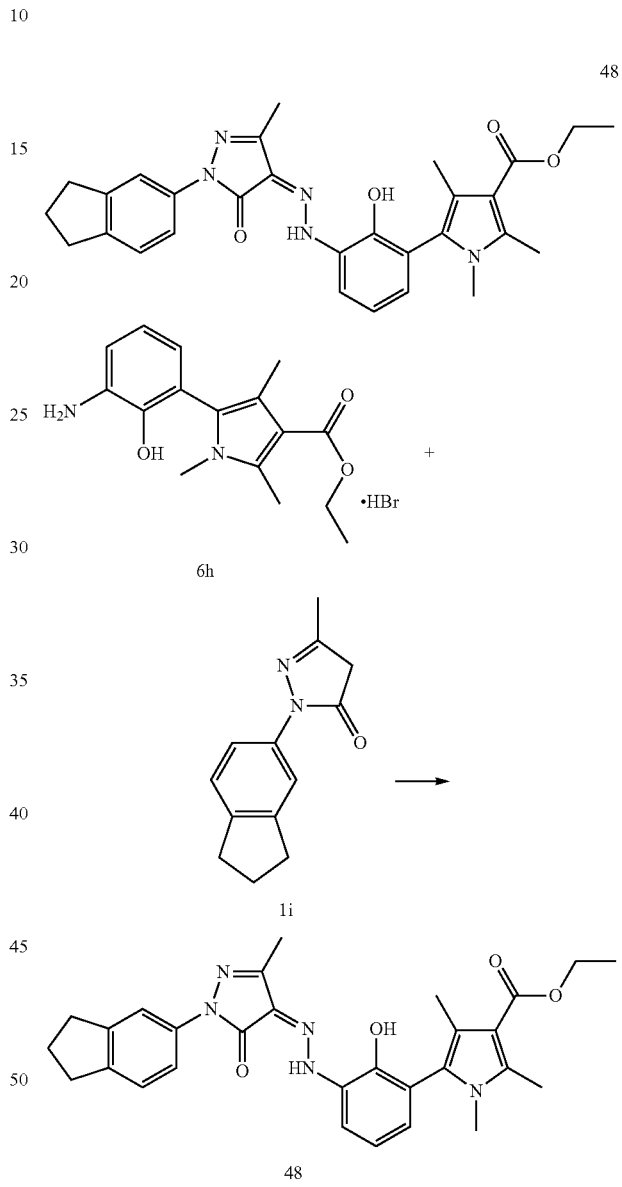

5-(3-Amino-2-hydroxy-phenyl)-1,2,4-trimethyl-1H-pyrrole-3-carboxylic acid ethyl ester hydrobromide 6h (180 mg, 0.66 mmol) was dissolved in 2.2 mL of hydrochloric acid (1 N) upon cooling by an ice-water bath, followed by dropwise addition of 0.8 mL of aqueous sodium nitrite (50 mg, 0.72 mmol). After the mixture was stirred for 20 minutes, 2-indan-5-yl-5-methyl-2,4-dihydro-pyrazol-3-one 1i (126 mg, 0.59 mmol) was added. The mixture was adjusted to pH 8~9 with saturated aqueous sodium bicarbonate. Then the generated bubbles were quenched with 2 mL of ethanol. The reaction mixture was warmed up to room temperature and reacted overnight. The reaction was monitored by TLC until the disappearance of the starting materials. The mixture was filtered and the filter cake was dissolved in a mixture of 20 mL of chloromethane and 20 mL of water. After mixing well, the mixture was adjusted to pH 3~4 with concentrated hydrochloric acid. The separated organic layer was washed with saturated brine, dried over anhydrous sodium sulfate, filtered to remove the drying agent and concentrated under reduced pressure. The resulting residue was purified by silica gel column chromatography to obtain the title compound 5-{2-hydroxy-3-[N'-(1-indan-5-yl-3-methyl-5-oxo-1,5-dihydro-pyrazol-4-ylidene)-hydrazino]-phenyl}-1,2,4-trimethyl-1H-pyrrole-3-carboxylic acid ethyl ester 48 (80 mg, yield 25.8%) as a red solid.

MS m/z (ESI): 514.0 [M+1]

$^1$H NMR (400 MHz, DMSO-$d_6$): δ 1.30 (m, 3H), 2.01 (m, 2H), 2.23 (s, 3H), 2.50 (s, 3H), 2.95 (m, 4H), 3.32 (s, 3H), 4.33 (m, 2H), 6.63 (m, 1H), 7.00 (m, 1H), 7.12 (m, 1H), 7.28 (m, 1H), 7.73 (m, 2H), 13.91 (br, 1H)

Example 49

5-(2-Hydroxy-3-{N'-[3-methyl-5-oxo-1-(1,1,3,3-tetramethyl-indan-5-yl)-1,5-dihydro-pyrazol-4-ylidene]-hydrazino}-phenyl)-thiophene-2-carboxylic acid

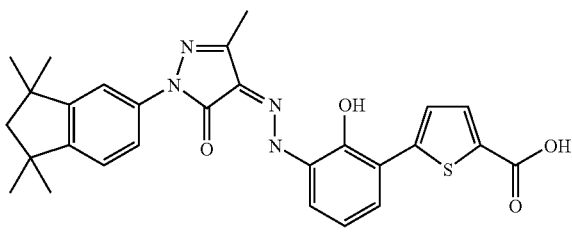

49

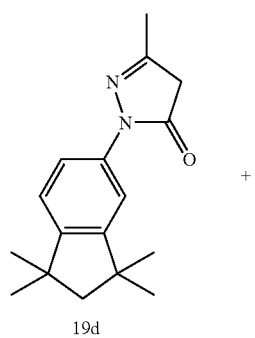

19d

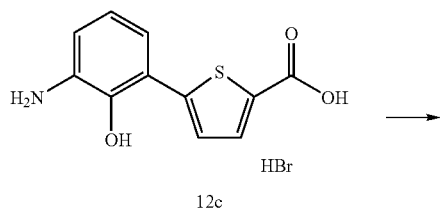

12c

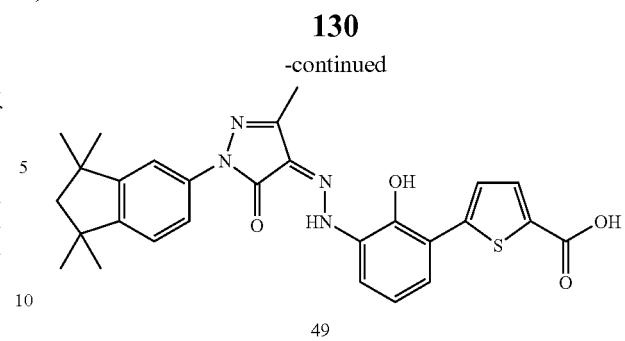

49

5-(3-Amino-2-hydroxy-phenyl)-thiophene-2-carboxylic acid hydrobromide 12c (260 mg, 0.823 mmol) was dissolved in 2.7 mL of hydrochloric acid (1 N) upon cooling by an ice-water bath, followed by dropwise addition of 1.1 mL of aqueous sodium nitrite (62 mg, 0.91 mmol). After the mixture was stirred for 20 minutes, 5-methyl-2-(1,1,3,3-tetramethyl-indan-5-yl)-2,4-dihydro-pyrazol-3-one 19d (200 mg, 0.74 mmol) was added. The mixture was adjusted to pH 8 with saturated aqueous sodium bicarbonate. Then the generated bubbles were quenched with 2 mL of ethanol. The reaction mixture was warmed up to room temperature and reacted for 3 hours. The reaction was monitored by TLC until the disappearance of the starting materials. The mixture was filtered and 20 mL of water was added to the filter cake. The mixture was adjusted to pH 3~4 with concentrated hydrochloric acid and filtered. The filter cake was dried and purified by silica gel column chromatography to obtain the title compound 5-(2-hydroxy-3-{N'-[3-methyl-5-oxo-1-(1,1,3,3-tetramethyl-indan-5-yl)-1,5-dihydro-pyrazol-4-ylidene]-hydrazino}-phenyl)-thiophene-2-carboxylic acid 49 (216 mg, yield 56.5%) as a red solid.

$^1$H NMR (400 MHz, DMSO-$d_6$): δ 1.30 (m, 12H), 1.93 (s, 2H), 2.34 (s, 3H), 7.19 (t, J=8.0 Hz, 1H), 7.25 (d, J=8.0 Hz, 1H), 7.57 (d, J=8.0 Hz, 1H), 7.66 (m, 2H), 7.71 (d, J=8.0 Hz, 1H), 7.77 (m, 2H), 10.10 (s, 1H), 13.06 (br, 1H), 13.72 (br, 1H)

Example 50

5-(2-Hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid

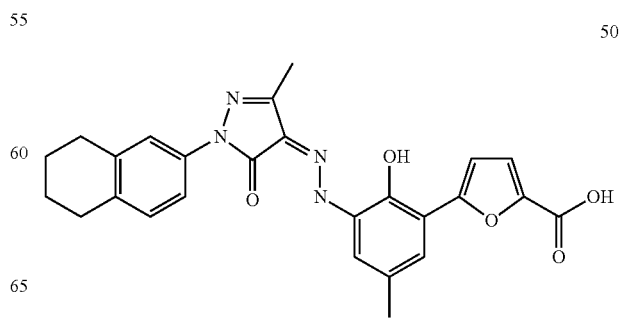

50

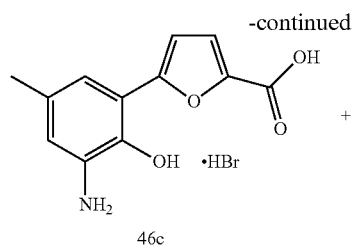

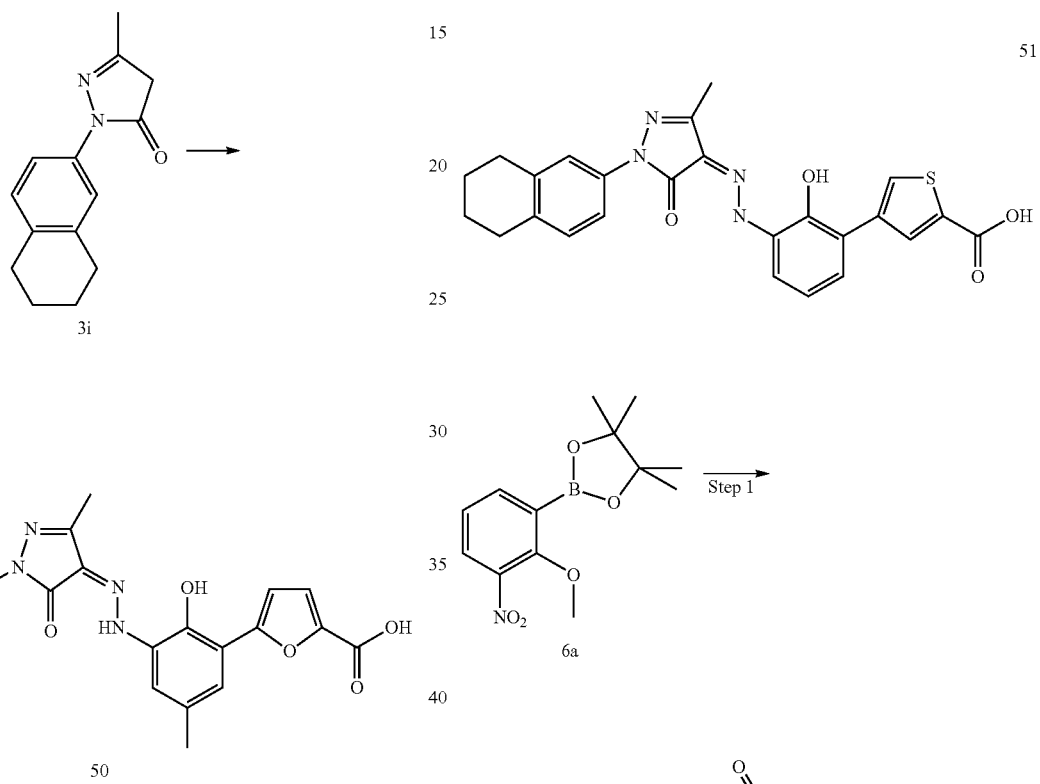

5-(3-Amino-2-hydroxy-5-methyl-phenyl)-furan-2-carboxylic acid hydrobromide 46c (120 mg, 0.38 mmol) was dissolved in 1.3 mL of 1 N hydrochloric acid upon cooling by an ice-water bath, followed by dropwise addition of 0.5 mL of aqueous sodium nitrite (29 mg, 0.42 mmol). After the mixture was reacted for 20 minutes, 5-methyl-2-(5,6,7,8-tetrahydro-naphthalen-2-yl)-2,4-dihydro-pyrazol-3-one 3i (78 mg, 0.34 mmol) was added. The mixture was adjusted to pH 8 with saturated aqueous sodium bicarbonate followed by addition of 2 mL of ethanol. The reaction mixture was reacted at room temperature overnight. The reaction was monitored by TLC until the disappearance of the starting materials. The mixture was filtered and the filter cake was added to 20 mL of water. The mixture was adjusted to pH 3~4 with concentrated hydrochloric acid. The mixture was filtered and the filter cake was dried and purified by silica gel column chromatography to obtain the title compound 5-(2-hydroxy-5-methyl-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 50 (56 mg, yield 34.8%) as a red solid.

MS m/z (ESI): 470.8 [M−1]

$^1$H NMR (400 MHz, DMSO-$d_6$): δ 1.75 (m, 4H), 2.31 (s, 3H), 2.37 (s, 3H), 2.73 (m, 4H), 7.13 (m, 2H), 7.35 (m, 2H), 7.50 (s, 1H), 7.62 (m, 2H)

Example 51

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid

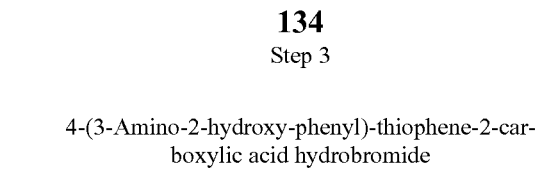

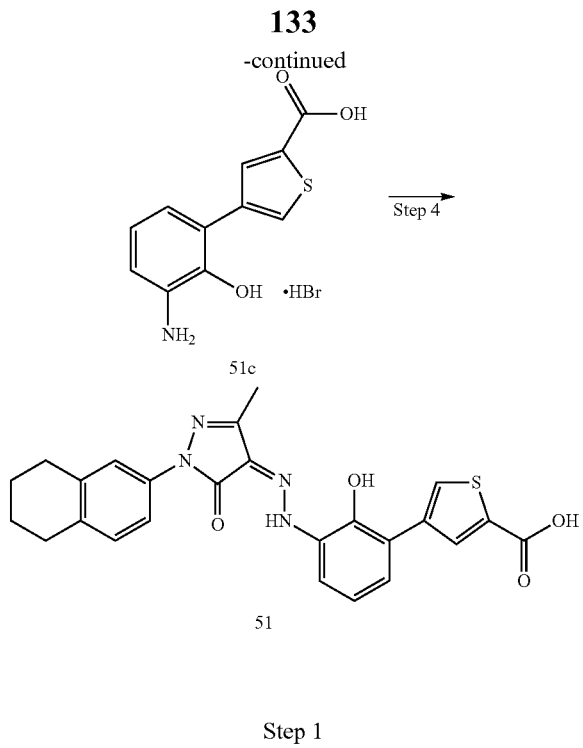

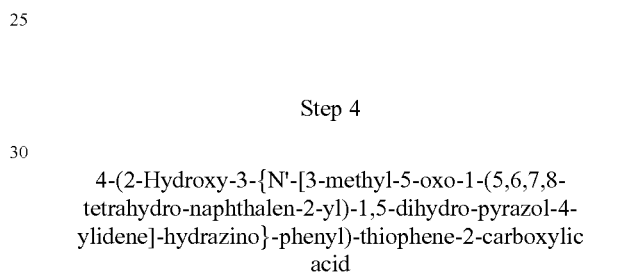

Step 1

4-(3-Nitro-2-methoxy-phenyl)-thiophene-2-carboxylic acid 2-(2-Methoxy-3-nitro-phenyl)-4,4,5,5-tetramethyl-1,3,2-dioxaborolane 6a (0.81 g, 2.9 mmol), 4-bromo-thiophene-2-carboxylic acid (0.3 g, 1.45 mmol), tetrakis(triphenylphosphine)palladium (80 mg, 0.073 mmol) and sodium carbonate (0.31 g, 2.9 mmol) were dissolved in a solvent mixture of 20 mL of 1,4-dioxane and 10 mL of water. The reaction was heated to reflux for 0.5 hours. The reaction was monitored by TLC until the disappearance of the starting materials. The mixture was adjusted to pH 3 with 1 N hydrochloric acid and extracted with ethyl acetate (20 mL×3). The combined organic extracts were concentrated under reduced pressure and the residue was purified by silica gel column chromatography to obtain the title compound 4-(3-nitro-2-methoxy-phenyl)-thiophene-2-carboxylic acid 51a (0.54 g) as a brown oil, which was directly used in the next step.

MS m/z (ESI): 277.6 [M−1]

Step 2

4-(3-Amino-2-methoxy-phenyl)-thiophene-2-carboxylic acid 4-(3-Nitro-2-methoxy-phenyl)-thiophene-2-carboxylic acid 51a (400 mg, 1.45 mmol) was dissolved in 30 mL of ethyl acetate followed by addition of 100 mg of palladium on carbon and ammonium formate (360 mg, 5.8 mmol). The mixture was heated to reflux for 3 hours. The reaction was monitored by TLC until the disappearance of the starting materials. The mixture was filtered to remove palladium on carbon and concentrated under reduced pressure to obtain the title compound 4-(3-amino-2-methoxy-phenyl)-thiophene-2-carboxylic acid 51b (410 mg) as a brown oil, which was directly used in the next step.

MS m/z (ESI): 247.8 [M−1]

Step 3

4-(3-Amino-2-hydroxy-phenyl)-thiophene-2-carboxylic acid hydrobromide 4-(3-Amino-2-methoxy-phenyl)-thiophene-2-carboxylic acid hydrobromide 51b (360 mg, 1.45 mmol) was dissolved in 5 mL of dichloromethane followed by dropwise addition of boron tribromide (2.8 mL, 5.6 mmol). The reaction mixture was reacted at room temperature for 4.5 hours. The reaction was monitored by TLC until the disappearance of the starting materials and quenched with 5 mL of methanol. The mixture was concentrated under reduced pressure. The residue was diluted with 10 mL of ethyl acetate and stirred for 0.5 hours. The mixture was filtered and the filter cake was dried to obtain the title compound 4-(3-amino-2-hydroxy-phenyl)-thiophene-2-carboxylic acid hydrobromide 51c (80 mg, yield 17.5%) as a grey solid.

MS m/z (ESI): 236.1 [M+1]

Step 4

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid 4-(3-Amino-2-hydroxy-phenyl)-thiophene-2-carboxylic acid hydrobromide 51c (80 mg, 0.25 mmol) was dissolved in 1 mL of 1 N hydrochloric acid upon cooling by an ice-water bath, followed by dropwise addition of 0.3 mL of aqueous sodium nitrite (19 mg, 0.28 mmol). After the mixture was reacted for 20 minutes, 5-methyl-2-(5,6,7,8-tetrahydro-naphthalen-2-yl)-2,4-dihydro-pyrazol-3-one 3i (52 mg, 0.23 mmol) was added. The mixture was adjusted to pH 8 with saturated aqueous sodium bicarbonate followed by addition of 2 mL of ethanol. The reaction mixture was reacted overnight at room temperature. The reaction was monitored by TLC until the disappearance of the starting materials. The mixture was filtered and the filter cake was added to 20 mL of water. The mixture was adjusted to pH 3~4 with concentrated hydrochloric acid. The mixture was filtered and 4 mL of ethyl acetate was added to the filter cake. The resulting mixture was stirred for 2 hours and filtered, the filter cake was dried to obtain the title compound 4-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-thiophene-2-carboxylic acid 51 (11 mg, yield 10.2%) as a black solid.

MS m/z (ESI): 472.8 [M−1]

$^1$H NMR (400 MHz, DMSO-$d_6$): δ 1.76 (m, 4H), 2.33 (s, 3H), 2.74 (m, 4H), 7.13 (m, 2H), 7.33 (m, 1H), 7.65 (m, 3H), 8.06 (d, J=1.6 Hz, 1H), 8.14 (d, J=1.6 Hz, 1H), 9.68 (s, 1H), 13.75 (s, 1H)

Example 52

4-{2-Hydroxy-3-[N'-(1-indan-5-yl-3-methyl-5-oxo-1,5-dihydro-pyrazol-4-ylidene)-hydrazino]-phenyl}-thiophene-2-carboxylic acid

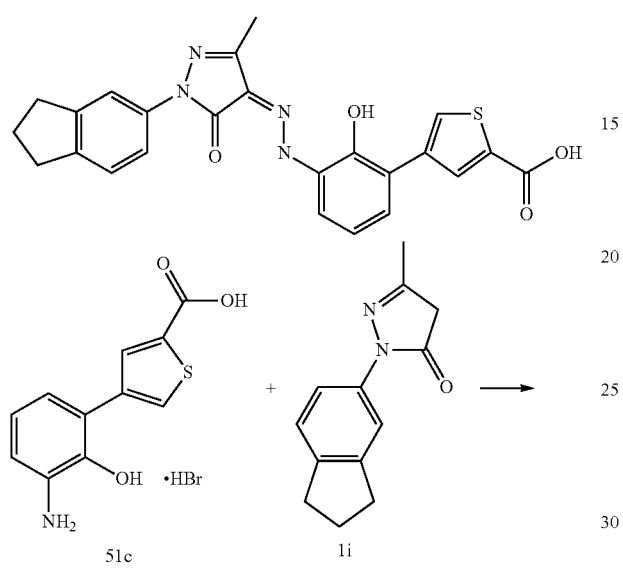

4-(3-Amino-2-hydroxy-phenyl)-thiophene-2-carboxylic acid hydrobromide 51c (120 mg, 0.38 mmol) was dissolved in 2.7 mL of 1 N hydrochloric acid upon cooling by an ice-water bath, followed by dropwise addition of 0.45 mL of aqueous sodium nitrite (29 mg, 0.42 mmol). After the mixture was reacted for 20 minutes, 2-indan-5-yl-5-methyl-2,4-dihydro-pyrazol-3-one 1i (73 mg, 0.34 mmol) was added. The mixture was adjusted to pH 8 with saturated aqueous sodium bicarbonate followed by addition of 2 mL of ethanol. The reaction mixture was reacted overnight at room temperature. The reaction was monitored by TLC until the disappearance of the starting materials. The mixture was filtered and the filter cake was added to 20 mL of water. The mixture was adjusted to pH 3~4 with concentrated hydrochloric acid and filtered. Then 5 mL of ethyl acetate was added to the filter cake and the mixture was stirred for 1 hour. The mixture was filtered and the filter cake was dried to obtain the title compound 4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 52 (45 mg, yield 28.7%) as a yellow solid.

MS m/z (ESI): 458.8 [M−1]

$^1$H NMR (400 MHz, DMSO-d$_6$): δ 2.05 (m, 2H), 2.32 (s, 3H), 2.87 (m, 4H), 7.13 (t, J=8.0 Hz, 1H), 7.32 (m, 2H), 7.67 (m, 2H), 7.78 (s, 1H), 8.05 (d, J=1.6 Hz, 1H), 8.13 (d, J=1.2 Hz, 1H), 9.68 (s, 1H), 13.79 (s, 1H)

Example 53

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-2-methyl-furan-3-carboxylic acid

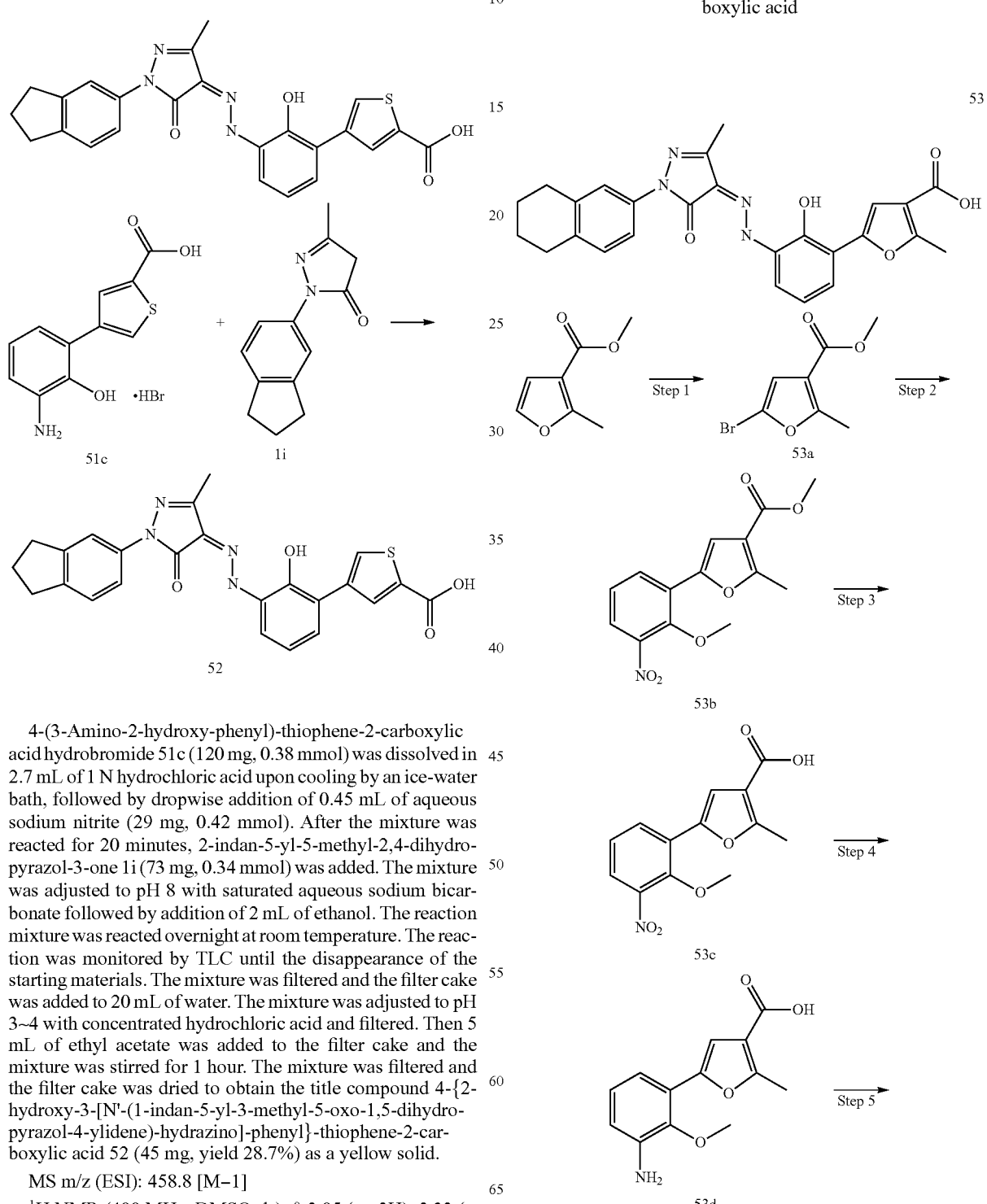

-continued

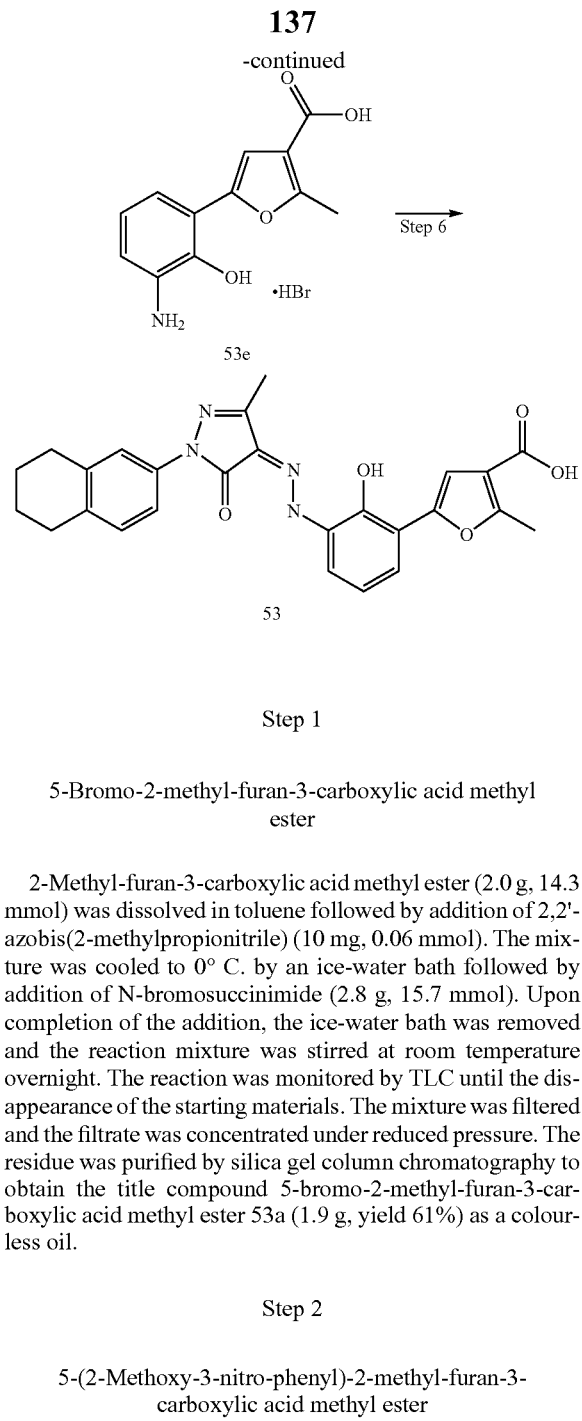

Step 1

5-Bromo-2-methyl-furan-3-carboxylic acid methyl ester

2-Methyl-furan-3-carboxylic acid methyl ester (2.0 g, 14.3 mmol) was dissolved in toluene followed by addition of 2,2'-azobis(2-methylpropionitrile) (10 mg, 0.06 mmol). The mixture was cooled to 0° C. by an ice-water bath followed by addition of N-bromosuccinimide (2.8 g, 15.7 mmol). Upon completion of the addition, the ice-water bath was removed and the reaction mixture was stirred at room temperature overnight. The reaction was monitored by TLC until the disappearance of the starting materials. The mixture was filtered and the filtrate was concentrated under reduced pressure. The residue was purified by silica gel column chromatography to obtain the title compound 5-bromo-2-methyl-furan-3-carboxylic acid methyl ester 53a (1.9 g, yield 61%) as a colourless oil.

Step 2

5-(2-Methoxy-3-nitro-phenyl)-2-methyl-furan-3-carboxylic acid methyl ester

5-Bromo-2-methyl-furan-3-carboxylic acid methyl ester 53a (0.65 g, 3.0 mmol) and 2-(2-methoxy-3-nitro-phenyl)-4,4,5,5-tetramethyl-1,3,2-dioxaborolane 6a (1.0 g, 3.58 mmol) were dissolved in 1,4-dioxane (15 mL) followed by addition of tetrakis(triphenylphosphine)palladium (173 mg, 0.15 mmol) and sodium carbonate (636 mg, 6.0 mmol). The reaction mixture was heated to reflux at 100° C. for 3 hours. The reaction was monitored by TLC until the disappearance of the starting materials. The mixture was cooled and filtered. The filtrate was concentrated under reduced pressure and the residue was purified by silica gel column chromatography to obtain the title compound 5-(2-methoxy-3-nitro-phenyl)-2-methyl-furan-3-carboxylic acid methyl ester 53b (659 mg, yield 75%) as a white solid.

Step 3

5-(2-Methoxy-3-nitro-phenyl)-2-methyl-furan-3-carboxylic acid 5-(2-Methoxy-3-nitro-phenyl)-2-methyl-furan-3-carboxylic acid methyl ester 53b (650 mg, 2.23 mmol) was dissolved in methanol, followed by addition of sodium hydroxide (268 mg, 6.7 mmol). Upon completion of the addition, the reaction mixture was stirred at 50° C. for 3 hours. The reaction was monitored by TLC until the disappearance of the starting materials. The mixture was concentrated under reduced pressure and adjusted to pH 3~4 with 1 N hydrochloric acid to form a copious amount of precipitates. The mixture was filtered and the filter cake was recrystallized from a solvent mixture of hexane/ethyl acetate (V:V=5:1) to obtain the title compound 5-(2-methoxy-3-nitro-phenyl)-2-methyl-furan-3-carboxylic acid 53c (450 mg, yield 84%) as a white solid.

MS m/z (ESI): 275.7 [M−1]

$^1$H NMR (400 MHz, DMSO-$d_6$): δ 12.80 (s, 1H), 8.03 (dd, J=8.0 Hz, 1H), 7.87 (dd, J=8.0 Hz, 1H), 7.44 (t, J=8.0 Hz, 1H), 7.13 (s, 1H), 3.83 (s, 3H), 2.64 (s, 3H)

Step 4

5-(2-Methoxy-3-amino-phenyl)-2-methyl-furan-3-carboxylic acid 5-(2-Methoxy-3-nitro-phenyl)-2-methyl-furan-3-carboxylic acid 53c (450 mg, 1.62 mmol) was dissolved in methanol, followed by addition of 45 mg of palladium on carbon. The reaction mixture was heated to reflux for 4 hours under hydrogen atmosphere. The reaction was monitored by TLC until the disappearance of the starting materials. The mixture was filtered and the filtrate was concentrated under reduced pressure to obtain the title compound 5-(2-methoxy-3-amino-phenyl)-2-methyl-furan-3-carboxylic acid 53d (370 mg, yield 92%) as a white solid.

MS m/z (ESI): 245.8 [M−1]

$^1$H NMR (400 MHz, CDCl$_3$): δ 6.97 (s, 1H), 6.87 (m, 2H), 6.68 (m, 1H), 5.06 (br, 2H), 3.63 (s, 3H), 2.59 (s, 3H)

Step 5

5-(2-Hydroxy-3-amino-phenyl)-2-methyl-furan-3-carboxylic acid hydrobromide 5-(2-Methoxy-3-amino-phenyl)-2-methyl-furan-3-carboxylic acid 53d (370 mg, 1.5 mmol) was dissolved in dichloromethane. The mixture was cooled to 0° C. by an ice-water bath followed by dropwise addition of a solution of boron tribromide in dichloromethane (1 N, 3.6 mL). Upon completion of the addition, the reaction mixture was reacted at room temperature for 2 hours. The reaction was monitored by TLC until the disappearance of the starting materials and quenched by addition of 0.5 mL of methanol. The mixture was stirred for 30 minutes and concentrated under reduced pressure. The resulting residue was diluted with 10 mL of ethyl acetate and stirred for 30 minutes. The mixture was filtered and the filter cake was dried to obtain the title compound 5-(2-hydroxy-3-amino-phenyl)-2-methyl-furan-3-carboxylic acid hydrobromide 53e (240 mg, yield 46%) as a grey solid.

MS m/z (ESI): 231.7 [M−1]

$^1$H NMR (400 MHz, CDCl$_3$): δ 7.57 (dd, J=8.0, 1H), 7.24 (dd, J=8.0, 1H), 7.05 (t, J=8.0, 1H), 2.61 (s, 3H)

Step 6

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-2-methyl-furan-3-carboxylic acid 5-(2-Hydroxy-3-amino-phenyl)-2-methyl-furan-3-carboxylic acid hydrobromide 53e (200 mg, 0.64 mmol) was dissolved in 2.2 mL of 1 N hydrochloric acid upon cooling by an ice-water bath, followed by dropwise addition of 0.9 mL of aqueous sodium nitrite (48 mg, 0.7 mmol). After the mixture was reacted for 20 minutes, 5-methyl-2-(5,6,7,8-tetrahydro-naphthalen-2-yl)-2,4-dihydro-pyrazol-3-one 3i (131 mg, 0.57 mmol) was added. The mixture was adjusted to pH 8 with saturated aqueous sodium bicarbonate followed by addition of 2 mL ethanol. The reaction mixture was reacted overnight at room temperature. The reaction was monitored by TLC until the disappearance of the starting materials. The mixture was filtered and the filter cake was added to 20 mL of water. The mixture was adjusted to pH 3~4 with concentrated hydrochloric acid. The mixture was filtered and 8 mL of ethyl acetate was added to the filter cake. After stirring for 1 hour, the mixture was filtered and the filter cake was dried to obtain the title compound 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-2-methyl-furan-3-carboxylic acid 53 (200 mg, yield 73.8%) as a red solid.

$^1$H NMR (400 MHz, DMSO-$d_6$): δ 1.75 (m, 4H), 2.31 (s, 3H), 2.62 (s, 3H), 2.77 (m, 4H), 7.14 (m, 3H), 7.47 (d, J=7.6 Hz, 1H), 7.65 (m, 3H), 9.79 (s, 1H), 12.73 (br, 1H), 13.76 (br, 1H)

Example 54

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid methyl ester

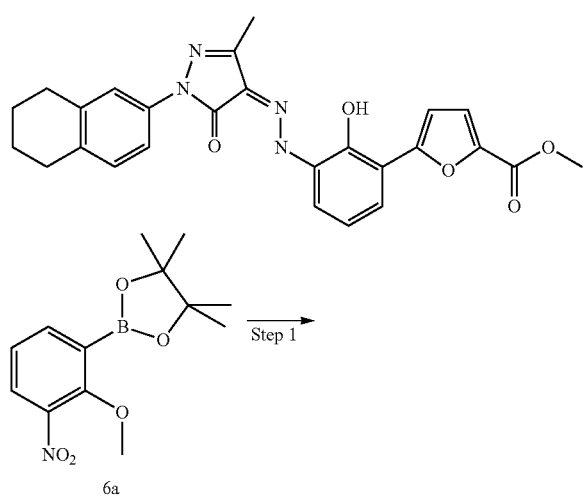

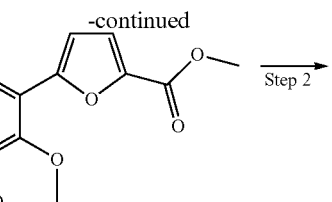

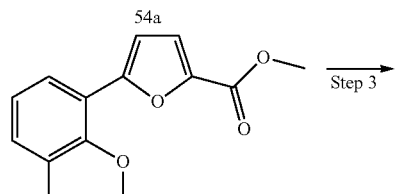

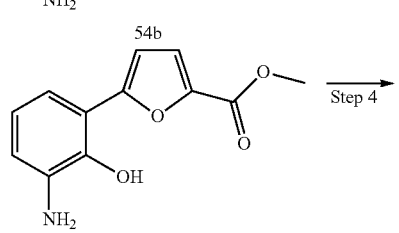

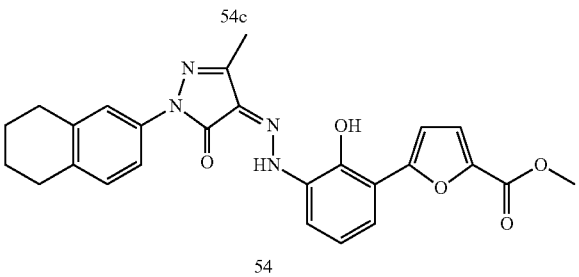

Step 1

5-(2-Methoxy-3-nitro-phenyl)-furan-2-carboxylic acid methyl ester 2-(2-Methoxy-3-nitro-phenyl)-4,4,5,5-tetramethyl-1,3,2-dioxaborolane 6a (3.6 g, 12 mmol), 5-bromofuran-2-carboxylic acid methyl ester (2.05 g, 10 mmol), tetrakis(triphenylphosphine)palladium (1.55 g, 0.5 mmol) and sodium carbonate (2.12 g, 20 mmol) were dissolved in 1,4-dioxane. The reaction mixture was heated to reflux for 3 hours. The reaction was monitored by TLC until the disappearance of the starting materials. The mixture was filtered and the filtrate was concentrated under reduced pressure. The residue was diluted with 30 mL of water and 50 mL of ethyl acetate. The separated organic layer was concentrated under reduced pressure and recrystallized from a solvent mixture of ethyl acetate and n-hexane to obtain the title compound 5-(2-methoxy-3-nitro-phenyl)-furan-2-carboxylic acid methyl ester 54a (500 mg, yield 18%) as a yellow solid.

$^1$H NMR (400 MHz, CDCl$_3$): δ 8.23 (dd, J=7.6 Hz, 1H), 7.83 (dd, J=7.6, 1H), 7.35 (m, 2H), 7.16 (d, J=4.0 Hz, 1H), 3.98 (s, 3H), 3.94 (s, 3H)

Step 2

5-(3-Amino-2-methoxy-phenyl)-furan-2-carboxylic acid methyl ester 5-(2-Methoxy-3-nitro-phenyl)-furan-2-carboxylic acid methyl ester 54a (500 mg, 1.8 mmol) was dissolved in methanol followed by addition of 50 mg of palladium on carbon. The reaction mixture was heated to reflux for 4 hours under hydrogen atmosphere. The reaction was monitored by TLC until the disappearance of the starting materials. The mixture was concentrated under reduced pressure. The resulting residue was recrystallized from a solvent mixture of ethyl acetate/n-hexane (V:V=1:5) and dried to obtain the title compound 5-(3-amino-2-methoxy-phenyl)-furan-2-carboxylic acid methyl ester 54b (370 mg, yield 83%) as a white solid.

Step 3

5-(3-Amino-2-hydroxy-phenyl)-furan-2-carboxylic acid methyl ester 5-(3-Amino-2-methoxy-phenyl)-furan-2-carboxylic acid methyl ester 54b (350 mg, 1.42 mmol) was dissolved in dichloromethane followed by dropwise addition of boron tribromide (3.3 mL, 2.0 mol/L). The reaction mixture was stirred at room temperature for 2 hours. The reaction was monitored by TLC until the disappearance of the starting materials and quenched with methanol. The mixture was adjusted to pH 5~6 with saturated aqueous sodium bicarbonate and extracted with ethyl acetate. The organic layers were concentrated and then the resulting residue was purified by silica gel column chromatography to obtain the title compound 5-(3-amino-2-hydroxy-phenyl)-furan-2-carboxylic acid methyl ester 54c (170 mg, yield 45.1%) as a grey solid.

MS m/z (ESI): 232.0 [M−1]

$^1$H NMR (400 MHz, DMSO-d$_6$): δ 7.32 (d, J=7.6 Hz, 1H), 7.05 (d, J=7.6 Hz, 1H), 6.82 (m, 3H), 3.96 (s, 3H)

Step 4

5-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid methyl ester 5-(3-Amino-2-hydroxy-phenyl)-furan-2-carboxylic acid methyl ester 54c (110 mg, 0.47 mmol) was dissolved in hydrochloric acid (1.6 mL, 1 mol/L) upon cooling by an ice-water bath, followed by dropwise addition of 0.6 mL of aqueous sodium nitrite (36 mg, 0.52 mmol). After the mixture was reacted for 10 minutes, 5-methyl-2-(5,6,7,8-tetrahydro-naphthalen-2-yl)-2,4-dihydro-pyrazol-3-one 3i (97 mg, 0.43 mmol) was added. The mixture was adjusted to pH 8~9 with saturated aqueous sodium bicarbonate. The reaction mixture was reacted at room temperature for 24 hours. The reaction was monitored by TLC until the disappearance of the starting materials. The mixture was filtered and the filter cake was dissolved in 15 mL of water. The mixture was adjusted to pH 3~4 with concentrated hydrochloric acid upon cooling by an ice-water bath. The mixture was filtered and the filter cake was purified by silica gel column chromatography to obtain the title compound 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid methyl ester 54 (48 mg, yield 23.9%) as a red solid.

MS m/z (ESI): 470.7 [M−1]

$^1$H NMR (400 MHz, DMSO-d$_6$): δ 1.76 (m, 4H), 2.31 (s, 3H), 2.73 (m, 4H), 3.86 (s, 3H), 7.12 (m, 1H), 7.17 (m, 1H), 7.22 (t, J=8.0 Hz, 1H), 7.46 (m, 1H), 7.56 (m, 1H), 7.65 (m, 2H), 7.72 (m, 1H), 10.02 (s, 1H), 13.72 (br, 1H)

Example 55

5-{2-Hydroxy-3-[N-(1-indan-5-yl-3-methyl-5-oxo-1,5-dihydro-pyrazol-4-ylidene)-hydrazino]-phenyl}-furan-2-carboxylic acid methyl ester

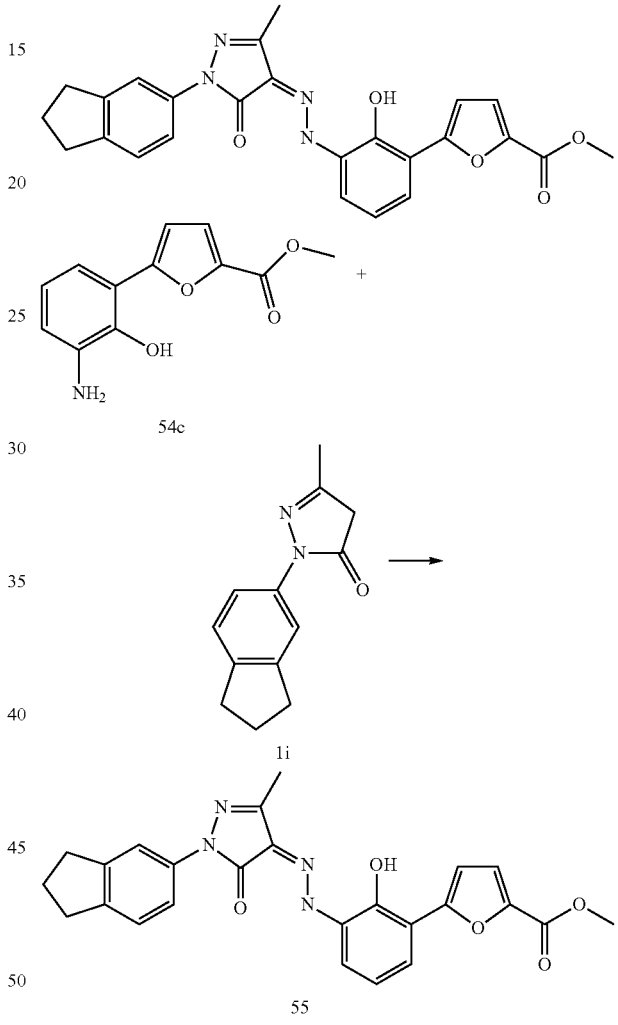

5-(3-Amino-2-hydroxy-phenyl)-furan-2-carboxylic acid methyl ester 54c (110 mg, 0.47 mmol) was dissolved in hydrochloric acid (1.6 mL, 1 mol/L) upon cooling by an ice-water bath, followed by dropwise addition of 0.6 mL of aqueous sodium nitrite (36 mg, 0.52 mmol). After the mixture was reacted for 20 minutes, 2-indan-5-yl-5-methyl-2,4-dihydro-pyrazol-3-one 1i (91 mg, 0.43 mmol) was added. The mixture was adjusted to pH 8~9 with saturated aqueous sodium bicarbonate. The reaction mixture was reacted at room temperature for 24 hours. The reaction was monitored by TLC until the disappearance of the starting materials and quenched with ethanol. The mixture was filtered and the filter cake was dissolved in 15 mL of water. The mixture was adjusted to pH 3-4 with concentrated hydrochloric acid upon cooling by an ice-water bath. The mixture was filtered and the filter cake was purified by silica gel column chromatography to obtain the title compound 5-{2-hydroxy-3-[N'-(1-indan-5-yl-3-methyl-5-oxo-1,5-dihydro-pyrazol-4-ylidene)-hydrazino]-phenyl}-furan-2-carboxylic acid methyl ester 55 (137 mg, yield 70.3%) as a red solid.

MS m/z (ESI): 456.7 [M−1]

$^1$H NMR (400 MHz, DMSO-d$_6$): δ 2.05 (m, 2H), 2.33 (s, 3H), 2.89 (m, 4H), 3.86 (s, 3H), 7.18 (m, 2H), 7.30 (d, J=8.4 Hz, 1H), 7.46 (d, J=3.6 Hz, 1H), 7.56 (m, 1H), 7.71 (m, 2H), 7.78 (s, 1H)

Example 56

3'-{N'-[1-(2,2-Dimethyl-indan-5-yl)-3-methyl-5-oxo-1,5-dihydro-pyrazol-4-ylidene]-hydrazino}-2'-hydroxy-biphenyl-3-carboxylic acid

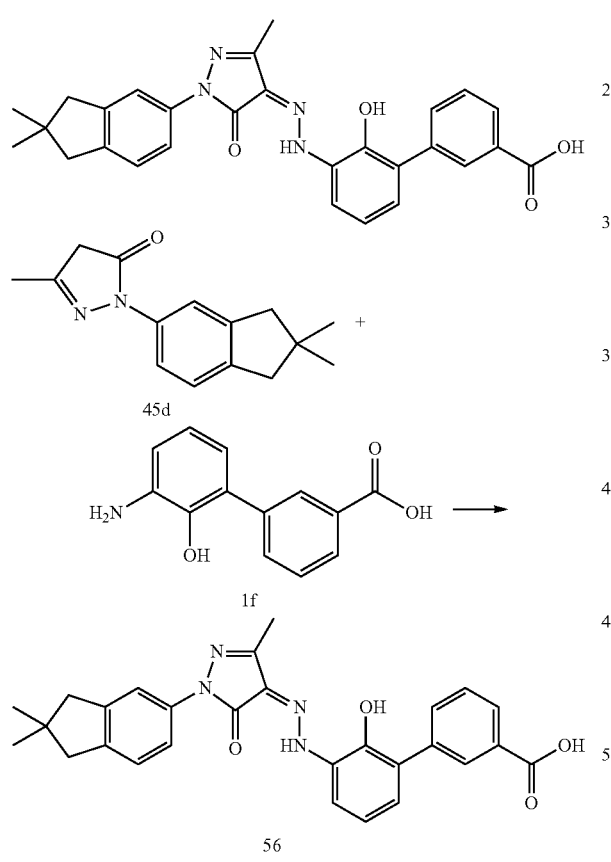

3'-Amino-2'-hydroxy-biphenyl-3-carboxylic acid hydrobromide 1f (150 mg, 0.5 mmol) was dissolved in hydrochloric acid (1.7 mL, 1 mol/L) upon cooling by an ice-water bath, followed by dropwise addition of 0.6 mL of aqueous sodium nitrite (38 mg, 0.55 mmol). After the mixture was reacted for 20 minutes, 2-(2,2-dimethyl-indan-5-yl)-5-methyl-2,4-dihydro-pyrazol-3-one 45d (109 mg, 0.45 mmol) was added. The mixture was adjusted to pH 8~9 with saturated aqueous sodium bicarbonate. Then the generated bubbles were quenched with ethanol. The reaction mixture was reacted overnight at room temperature. The reaction was monitored by TLC until the disappearance of the starting materials. The mixture was filtered and the filter cake was added to 15 mL of water. The mixture was adjusted to pH 3~4 with concentrated hydrochloric acid and filtered. The filter cake was washed with ethyl acetate (1 mL×3) and then dried to obtain the title compound 3'-{N'-[1-(2,2-dimethyl-indan-5-yl)-3-methyl-5-oxo-1,5-dihydro-pyrazol-4-ylidene]-hydrazino}-2'-hydroxy-biphenyl-3-carboxylic acid 56 (16 mg, yield 7.6%) as a yellow solid.

MS m/z (ESI): 480.7 [M−1]

$^1$H NMR (400 MHz, DMSO-d$_6$): δ 1.13 (s, 6H), 2.32 (s, 3H), 2.70 (m, 4H), 7.14 (m, 2H), 7.22 (d, J=8.8 Hz, 1H), 7.61 (t, J=8.0 Hz, 1H), 7.66 (d, J=7.6 Hz, 1H), 7.70 (m, 2H), 7.80 (d, J=7.6 Hz, 1H), 7.95 (d, J=8.0 Hz, 1H), 8.13 (s, 1H)

Example 57

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1H-pyrrole-2-carboxylic acid

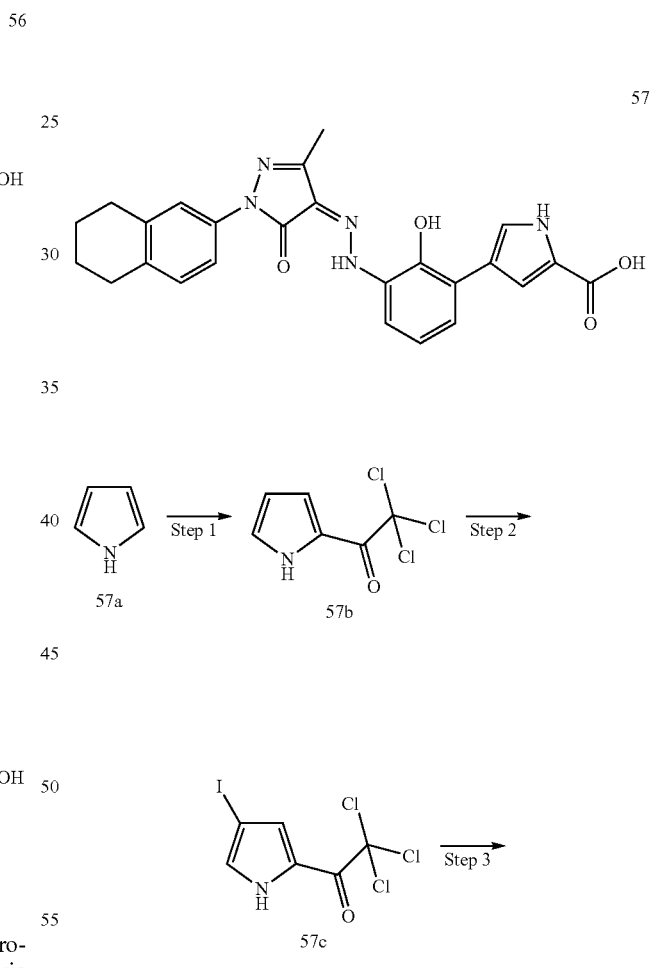

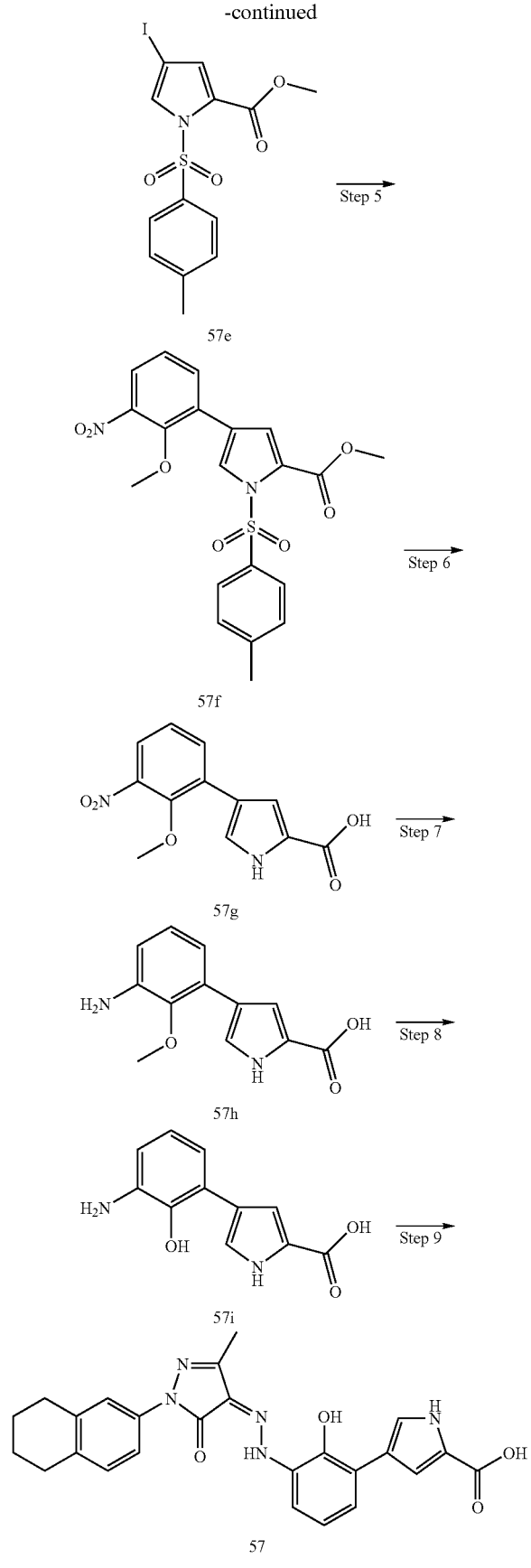

Step 1

2,2,2-Trichloro-1-(1H-pyrrol-2-yl)-ethanone

Trichloroacetyl chloride (45 g, 247 mmol) was dissolved in 100 mL of ether followed by dropwise addition of a solution of 1H-Pyrrole (15.4 g, 230 mmol) in 100 mL of ether and 200 mL of aqueous potassium carbonate (20 g, 145 mmol). Upon completion of the addition, the reaction mixture was stirred at room temperature for 1 hour. The reaction was monitored by TLC until the disappearance of the starting materials. The layers were separated and the organic layer was dried over anhydrous magnesium sulfate, filtered to remove the drying agent and concentrated under reduced pressure. The residue was purified by silica gel column chromatography to obtain the title compound 2,2,2-trichloro-1-(1H-pyrrol-2-yl)-ethanone 57b (38 g, yield 77.8%) as a white solid.

MS m/z (ESI): 210.3 [M−1]

Step 2

2,2,2-Trichloro-1-(4-iodo-1H-pyrrol-2-yl)-ethanone 2,2,2-Trichloro-1-(1H-pyrrol-2-yl)-ethanone 57b (32 g, 151.8 mmol) was dissolved in 250 mL of dichloromethane followed by dropwise addition of a solution of iodine monochloride (25 g, 153 mmol) in 125 mL of dichloromethane. Upon completion of the addition, the reaction mixture was stirred at room temperature for 2 hours. The reaction was monitored by TLC until the disappearance of the starting materials. The mixture was washed with saturated aqueous sodium carbonate, aqueous sodium thiosulfate (2 M) and saturated brine successively, dried over anhydrous magnesium sulfate, filtered to remove the drying agent and concentrated under reduced pressure. The residue was purified by silica gel column chromatography to obtain the title compound 2,2,2-trichloro-1-(4-iodo-1H-pyrrol-2-yl)-ethanone 57c (47 g, yield 92%) as a yellow solid.

MS m/z (ESI): 336.4 [M−1]

Step 3

4-Iodo-1H-pyrrole-2-carboxylic acid methyl ester 2,2,2-Trichloro-1-(4-iodo-1H-pyrrol-2-yl)-ethanone 57c (47 g, 136 mmol) was dissolved in 265 mL of methanol followed by dropwise addition of a solution of sodium methoxide (17.23 g, 163 mmol) in 200 mL of methanol. The reaction mixture was stirred at room temperature for 1 hour. The reaction was monitored by TLC until the disappearance of the starting materials. The mixture was concentrated under reduced pressure. The residue was diluted with 20 mL of water and then extracted with ethyl acetate (30 mL×3). The combined organic extracts were washed with saturated brine, dried over anhydrous sodium sulfate, filtered to remove the drying agent and concentrated under reduced pressure to obtain the title compound 4-iodo-1H-pyrrole-2-carboxylic acid methyl ester 57d (32.2 g, yield 92.5%) as a grey solid.

MS m/z (ESI): 250.1 [M−1]

Step 4

4-Iodo-1-(toluene-4-sulfonyl)-1H-pyrrole-2-carboxylic acid methyl ester

4-Iodo-1H-pyrrole-2-carboxylic acid methyl ester 57d (25.1 g, 100 mmol) was dissolved in 150 mL of dichloromethane followed by addition of triethylamine (30.6 mL, 220 mmol), 4-dimethylaminopyridine (1.22 g, 10 mmol) and p-toluenesulfonic acid (21 g, 110 mmol). The reaction mixture was reacted at 20° C. overnight. The reaction was monitored by TLC until the disappearance of the starting materials and quenched by addition of 30 mL of hydrochloric acid (1 N). The mixture was extracted with dichloromethane (50 mL×3). The combined organic extracts were washed with saturated aqueous sodium carbonate and saturated brine successively, dried over anhydrous sodium sulfate, filtered to remove the drying agent and concentrated under reduced pressure. The residue was purified by silica gel column chromatography to obtain the title compound 4-iodo-1-(toluene-4-sulfonyl)-1H-pyrrole-2-carboxylic acid methyl ester 57e (32.5 g, yield 80.2%) as a white solid.

MS m/z (ESI): 405.8 [M+1]

Step 5

4-(3-Nitro-2-methoxy-phenyl)-1-(p-tolylsulfonyl)-1H-pyrrole-2-carboxylic acid methyl ester To a solution of 15 mL of 1,4-dioxane and 5 mL of water was added 2-(2-methoxy-3-nitro-phenyl)-4,4,5,5-tetramethyl-1,3,2-dioxaborolane 6a (2.05 g, 5.5 mmol) followed by 4-iodo-1-(toluene-4-sulfonyl)-1H-pyrrole-2-carboxylic acid methyl ester 57e (2.03 g, 5 mmol), potassium carbonate (1.38 g, 10 mmol) and tetrakis(triphenylphosphine)palladium (144 mg, 0.125 mmol). Upon completion of the addition, the reaction mixture was reacted at 80° C. for 30 minutes under microwave. The reaction was monitored by TLC until the disappearance of the starting materials. The mixture was concentrated under reduced pressure and the residue was diluted with 20 mL of water. After mixing well, the mixture was extracted with ethyl acetate (20 mL×3). The combined organic extracts were washed with saturated brine, dried over anhydrous magnesium sulfate, filtered to remove the drying agent and concentrated under reduced pressure. The residue was purified by silica gel column chromatography to obtain the title compound 4-(3-nitro-2-methoxy-phenyl)-1-(p-tolylsulfonyl)-1H-pyrrole-2-carboxylic acid methyl ester 57f (1.04 g, yield 48%) as a grey solid.

MS m/z (ESI): 431.0 [M+1]

$^1$H NMR (400 MHz, CDCl$_3$): δ 8.225~8.231 (m, 1H), 7.979~8.00 (m, 2H), 7.710~7.765 (m, 1H), 7.452~7.457 (m, 1H), 7.389~7.409 (m, 2H), 7.271~7.311 (m, 2H), 3.839 (s, 3H), 3.829 (s, 2H), 2.488 (s, 3H)

Step 6

4-(3-Nitro-2-methoxy-phenyl)-1H-pyrrole-2-carboxylic acid 4-(3-Nitro-2-methoxy-phenyl)-1-(p-tolylsulfonyl)-1H-pyrrole-2-carboxylic acid methyl ester 57f (1.04 g, 2.42 mmol) and lithium hydroxide monohydrate (1.01 g, 24.19 mmol) were added to a solvent mixture of 10 mL of N,N-dimethylformamide and 5 mL of water. The reaction mixture was reacted at 100° C. for 30 minutes under microwave. The reaction was monitored by TLC until the disappearance of the starting materials. The mixture was adjusted to pH 3 with hydrochloric acid (1 N) to form a lot of precipitates. The mixture was filtered and the filter cake was dried to obtain the title compound 4-(3-nitro-2-methoxy-phenyl)-1H-pyrrole-2-carboxylic acid 57g (350 mg, yield 50%) as a yellow solid.

MS m/z (ESI): 260.8 [M−1]

Step 7

4-(3-Amino-2-methoxy-phenyl)-1H-pyrrole-2-carboxylic acid 4-(3-Nitro-2-methoxy-phenyl)-1H-pyrrole-2-carboxylic acid 57g (633 mg, 2.41 mmol) was dissolved in 15 mL of ethyl acetate followed by addition of 127 mg of palladium on carbon and ammonium formate (609 mg, 9.66 mmol). Upon completion of the addition, the reaction mixture was heated to reflux for 2 hours. The reaction was monitored by TLC until the disappearance of the starting materials. The mixture was filtered to remove palladium on carbon and the filtrate was concentrated under reduced pressure. The residue was purified by silica gel column chromatography to obtain the title compound 4-(3-amino-2-methoxy-phenyl)-1H-pyrrole-2-carboxylic acid 57h (130 mg, yield 23.2%) as a grey solid.

MS m/z (ESI): 230.8 [M−1]

$^1$H NMR (400 MHz, DMSO-d$_6$): δ 11.631 (s, 1H), 7.305 (s, 1H), 7.025 (s, 1H), 6.712~6.798 (m, 2H), 6.524~6.543 (m, 1H), 3.514 (s, 3H)

Step 8

4-(3-Amino-2-hydroxy-phenyl)-1H-pyrrole-2-carboxylic acid

To a solution of 4-(3-amino-2-methoxy-phenyl)-1H-pyrrole-2-carboxylic acid 57h (130 mg, 0.56 mmol) in 2 mL of dichloromethane was added boron tribromide (1.12 mL, 2.24 mmol). The reaction mixture was stirred at room temperature for 6 hours. The reaction was monitored by TLC until the disappearance of the starting materials and quenched with methanol. The mixture was concentrated under reduced pressure and the residue was purified by silica gel column chromatography to obtain the title compound 4-(3-amino-2-hydroxy-phenyl)-1H-pyrrole-2-carboxylic acid 57i (140 mg, yield 99%) as a grey solid.

$^1$H NMR (400 MHz, CD$_3$OD): δ 7.312 (s, 1H), 7.178 (s, 1H), 7.006~7.028 (m, 1H), 6.822~6.837 (m, 2H)

Step 9

4-(2-Hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-1H-pyrrole-2-carboxylic acid 4-(3-Amino-2-hydroxy-phenyl)-1H-pyrrole-2-carboxylic acid 57i (130 mg, 0.43 mmol) was dissolved in hydrochloric acid (1.5 mL, 1 mol/L) upon cooling by an ice-water bath, followed by dropwise addition of 0.6 mL of aqueous sodium nitrite (33 mg, 0.47 mmol). After the mixture was reacted for 10 minutes, 5-methyl-2-(5,6,7,8-tetrahydro-naphthalen-2-yl)-2,4-dihydro-pyrazol-3-one 3i (89 mg, 0.3 mmol) was added. The mixture was adjusted to pH 8~9 with saturated aqueous sodium bicarbonate. The reaction mixture was reacted at room temperature for 24 hours. The reaction was monitored by TLC until the disappearance of the starting materials. The mixture was filtered and the filter cake was dissolved in 15 mL of water. The mixture was adjusted to pH 3~4 with concentrated hydrochloric acid upon cooling by an ice-water bath. The mixture was filtered and the filter cake was washed with ethyl acetate and dried to obtain the title compound 4-(2-hydroxy-3-{N'-[3-methyl-5-oxo-1-(5,6,7,8- tetrahydro-naphthalen-2-yl)-1,5-dihydro-pyrazol-4-ylidene]-hydrazino}-phenyl)-1H-pyrrole-2-carboxylic acid 57 (38 mg, yield 21.3%) as a grey solid.

$^1$H NMR (400 MHz, DMSO-$d_6$): δ 11.74 (1H, br), 11.64 (1H, br), 7.60 (1H, d, J=8.2 Hz), 7.49 (1H, d, J=8.0 Hz), 7.32 (3H, m), 7.05 (3H, m), 2.67 (4H, m), 1.95 (3H, s), 1.13 (4H, m)

Example 58

4-{2-Hydroxy-3-[N'-(1-indan-5-yl-3-methyl-5-oxo-1,5-dihydro-pyrazol-4-ylidene)-hydrazino]-phenyl}-1H-pyrrole-2-carboxylic acid

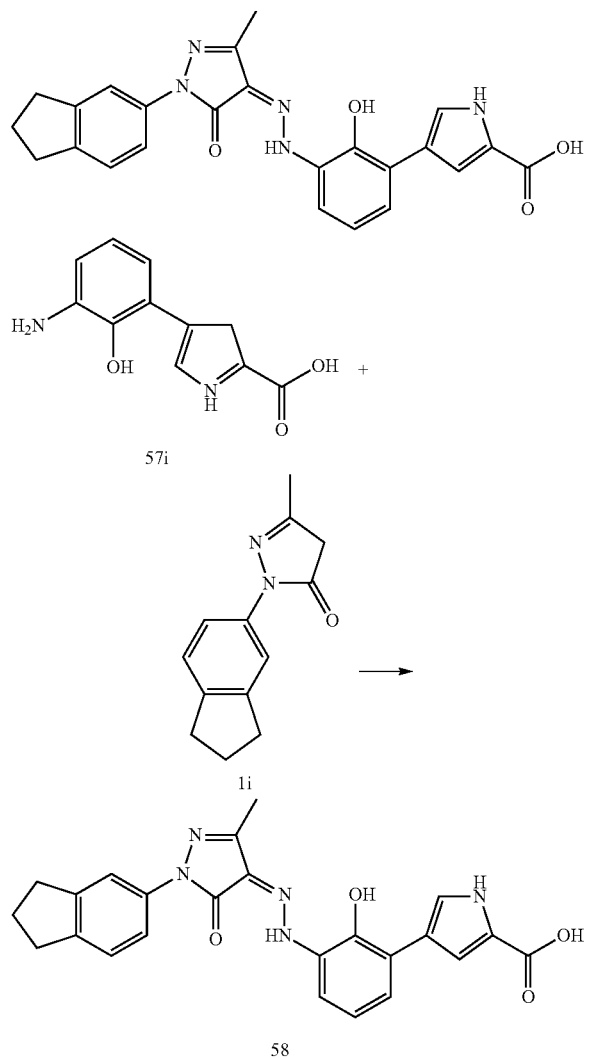

4-(3-Amino-2-hydroxy-phenyl)-1H-pyrrole-2-carboxylic acid 57i (240 mg, 0.8 mmol) was dissolved in hydrochloric acid (3 mL, 1 mol/L) upon cooling by an ice-water bath, followed by dropwise addition of 1.1 mL of aqueous sodium nitrite (61 mg, 0.88 mmol). After the mixture was reacted for 20 minutes, 2-indan-5-yl-5-methyl-2,4-dihydro-pyrazol-3-one 1i (154 mg, 0.72 mmol) was added. The mixture was adjusted to pH 8~9 with saturated aqueous sodium bicarbonate. The reaction mixture was reacted at room temperature for 24 hours. The reaction was monitored by TLC until the disappearance of the starting materials and quenched with ethanol. The mixture was filtered and the filter cake was dissolved in 15 mL of water. The mixture was adjusted to pH 3~4 with concentrated hydrochloric acid upon cooling by an ice-water bath. The mixture was filtered and the filter cake was purified by silica gel column chromatography to obtain the title compound 4-{2-hydroxy-3-[N'-(1-indan-5-yl-3-methyl-5-oxo-1,5-dihydro-pyrazol-4-ylidene)-hydrazino]-phenyl}-1H-pyrrole-2-carboxylic acid 58 (101 mg, yield 28.4%) as a red solid.

$^1$H NMR (400 MHz, DMSO-$d_6$): δ 11.83 (1H, br), 11.77 (1H, br), 7.57 (1H, d, J=7.2 Hz), 7.50 (1H, s), 7.37 (4H, m), 7.26 (1H, m), 7.10 (1H, m), 2.87 (4H, m), 2.32 (3H, s), 2.04 (2H, m)

Biological Assay

Test Example 1: pro-proliferation effect of a series of TPO compounds on BAF3-TPOR cell.

1. Material and Reagents.

a) RPMI Medium 1640, powder, 10*1 L, containing HEPES (Gibco Catalog No. 23400021).

b) Fetal Bovine Serum (Gibco Catalog No. 10099-141).

c) PENICILLIN STREPTOMYCIN SOL (Gibco Catalog No. 15140-122).

d) Geneticin (G418) (Gibco Catalog No. 11811-098).

e) Recombinant mouse IL-3 (chemicon Catalog No. IL015).

f) Human Thrombopoietin R Mab (TPO) (R&D Catalog No. MAB1016).

g) DMSO, (AppliChem Catalog No. A3672).

h) QuikChange® Multi Site Directed Mutagenesis Kit, 10 Runs (Stratagene ST200515).

i) Cell Counting Kit-8 (Dojindo, Catalog No. CK04-13)

j) BaF3 cell (Union cell culture center, Catalog No. 0095)

k) EX-EGFP-M02 (FulenGen Catalog No. EX-EGFP-M02 Control)

l) EX-B0010-M02 (FulenGen Catalog No. EX-B0010-M02)

2. Operating Process:

(1) Plasmid constructs: based on the TPOR sequence information from Entrez (Gene ID: 4325, Refseq: NM_005373), dual-site mutation was performed on EX-B0010-M02 plasmid by using QuikChange® Multi Site Directed Mutagenesis Kit (Stratagene). The sequence of primers which contains multi-sites mutation was designed as follows:

```
g491a:
5'-gggaacttcagatcagctgggaggagccg-3' g491a_antisense:
5'-cggctcctcccagctgatctgaagttccc-3';

c965t:
5'-caggaccatgctagctcccaaggcttcttct-3', c965t_antisense:
5'-agaagaagccttgggagctagcatggtcctg-3'.
```

The *E. coli* DH5α competent cell was transformed with mutated plasmid, and positive colonies were picked up through ampicillin selection. The mutation result was confirmed by sequence analysis.

(2) BAF3-TPOR stable transfected cell line: the following method was used to construct the BaF3 cell which stably over-expressed functional human TPO receptor. The successfully mutated EX-B0010-M02 plasmid (25 µg) which expressed human TPO receptor and screening gene neomycin was transfected into wild-type BaF3 cells ($1\times10^7$) by electroporation at 250V for 18 ms using an electric pulse generator (Electro Square Porator ECM830, BTX Division of Genetronic, Inc. US). The stable transfected cells BAF3-TPOR were selected with G418 (Gibco, US), then incubated with RPMI1640 medium plus 10% FBS (Gibco, US), 800 ng/mL G418, 5 ng/mL, rmIL-3 (Chemicon, US).

3. Screening Compounds Assay (1) Washing cells by centrifugation: a suitable amount of cell suspension was centrifuged at 1000 rpm for 5 minutes, and the supernatant was discarded. 10 mL of cell culture media without containing IL-3 was added. Then the resulting cell suspension was centrifuged at 1000 rpm for 5 minutes, and the supernatant was discarded.

(2) 1 mL of cell culture media without containing IL-3 was added to beat upon them to equality, and the number of a suitable amount of cell suspension was counted after dilution.

(3) According to the result of the cell counting, a cell suspension in a concentration of 100,000 cell/mL was prepared.

(4) 100 μL of cell suspension was transferred to each well of 96-well culture plate, and there were 3 parallel wells, that is, there were a blank control group (B), a negative control group (N), a positive control group of TPO (P) and a test compound group (S).

(5) The test compound was dissolved in DMSO to prepare a 10 mM stock solution, and then the solution was diluted with RPMI 1640 medium into a series of test samples at different concentration: 30 μM, 10 μM, 3 μM, 1 μM, 0.3 μM, 0.1 μM, 0.03 μM, 0.01 μM, 0.003 μM, 0.001 μM.

(6) 10 μL of test compound solution was transferred to each well respectively; 1 μL of rhTPO (10 μg/mL) was added to positive control well.

(7) The plates were incubated in an incubator at 5% $CO_2$ and 37° C. for 24 hours.

(8) After incubation, 10 μL of CCK-8 solution was added to each well and the plates were incubated in an incubator for 24 hours.

(9) OD value was detected at 450 nm by VICTOR3 (Perkin Elmer 1420-120) plate reader.

4. Analytical Calculation (1) The proliferation rate was calculated as follows:

Rate=[(S−B)/(P−B)]*100%

S: OD value of wells which contains test compound.
B: OD value of blank control wells
P: OD value of positive control wells (2) The $EC_{50}$ value was calculated by Origin 7.0 software.

5. Results:

| $EC_{50}$ of TPO activity of the compounds of the present disclosure | |
|---|---|
| Example No. | $EC_{50}$ (nM) |
| Eltrombopag | 299 |
| 1 | 200 |
| 3 | 310 |
| 4 | 283 |
| 5 | 354 |
| 7 | 265 |
| 9 | 100 |
| 11 | 257 |
| 13 | 141 |
| 15 | 21 |
| 16 | 160 |
| 20 | 89 |
| 22 | 15 |
| 25 | 60 |

| $EC_{50}$ of TPO activity of the compounds of the present disclosure | |
|---|---|
| Example No. | $EC_{50}$ (nM) |
| 28 | 42 |
| 29 | 124 |
| 31 | 27 |
| 37 | 90 |
| 43 | 32 |
| 44 | 50 |
| 45 | 130 |
| 46 | 56 |
| 50 | 126 |
| 51 | 55 |
| 52 | 43 |
| 54 | 133 |
| 55 | 71 |
| 56 | 60 |

Pharmacokinetics Assay

Test Example 1: Pharmacokinetics assay of the compounds of the present disclosure 1. Purpose The compounds of Example 1, Example 15 and Example 29 were administrated intragastrically to Sprague-Dawley (SD) rats to determine the drug concentration in plasma at different time points. The pharmacokinetics of the compounds of the present disclosure was studied and evaluated in rats.

2. Protocol 2.1 Samples

Compounds of Example 1, Example 15 and Example 29

2.2 Experimental Animals 24 healthy adult SD rats, male and female in half, were purchased from SINO-BRITSH SIPPR/BK LAB.ANIMAL LTD., CO, License number: SCXK (Shanghai) 2003-0002

2.3 Instrument

TSQ Quantum Ultra AM Triple Quadrupole Mass Spectrometer, Thermo Finnigan Corp., USA;

Agilent 1200 high performance liquid chromatograph, Agilent Corp., USA;

2.3 Preparation of Test Compounds

The test compound was diluted with 1% sodium carboxymethyl cellulose to 0.5 mg/mL (calculated as the free acid form) of suspension before use.

2.5 Administration 24 healthy adult SD rats, male and female in half, were divided into 5 groups. After an overnight fast, the rats were administered intragastrically at a dose of 5.0 mg/kg (calculated as the free acid form), at a volume of 10 mL/kg.

2.6 Sample Collection 24 healthy adult SD rats, male and female in half, were administered intragastrically at a dose of 5.0 mg/kg after an overnight fast. Blood samples (0.2 mL) were taken from eye socket at pre administration and at 0.5, 1.0, 2.0, 3.0, 4.0, 5.0, 6.0, 8.0, 11.0, 14.0, 24.0, 36.0 and 48.0 hours post administration, which were stored in heparinized tubes and centrifuged for 10 minutes at 3,500 rpm. The plasma samples were stored at −20° C. until analysis.

2.7 Analytical Methods

50 μL of rat plasma, obtained at various time points after administration, 20 μL of internal standard solution and 20 μL of a solvent mixture of methanol and water (80:20, v/v) were mixed well, and then 150 μL of methanol was added to result in protein precipitation. Then the mixture was mixed for 1 minute using a vortexer and centrifuged for 10 minutes at 13,000 rpm. 20 μL of the supernatant was analyzed by LC/MS/MS.

2.8 Preparation of Calibration Curve

50 μL of blank plasma was spiked with a series of standard solutions to produce final concentrations of 1.0, 5.0, 25.0, 50.0, 100.0, 250.0, 500.0 ng/mL, followed by addition of 20 μL of internal standard solution, which was treated according to plasma sample pretreatment protocol. A typical calibration curve equation was obtained with plasma concentration as the abscissa and the chromatographic peak area ratio of sample to internal standard as the ordinate, using weighted least squares method ($w=1/x^2$) for linear regression.

2.9 Calculation of Pharmacokinetic Parameters

The compartmental model of pharmacokinetics was fitted for the test compounds and the major pharmacokinetic parameters were calculated in which $C_{max}$ and $t_{max}$ were the actually measured values.

3. Results of Pharmacokinetic Parameters

Pharmacokinetic Parameters of the compounds of the present disclosure were shown as follows:

| Number | Pharmacokinetics Assay (5 mg/Kg) | | | | | |
|---|---|---|---|---|---|---|
| | Plasma Conc. $C_{max}$ (μg/mL) | Curve Area AUC (μg/mL *h) | Half-Life $t^{1/2}$(h) | Mean Residence Time MRT(h) | Clearance CL/F(l/h/kg) | Apparent Distribution Volume Vz/F(l/kg) |
| Example 1 | 29.05 ± 11.44 | 131.99 ± 46.95 | 5.39 ± 0.94 | 4.96 ± 1.16 | 0.049 ± 0.039 | 0.35 ± 0.18 |
| Example 15 | 6.63 ± 3.78 | 23.8 ± 17.26 | 3.47 ± 0.79 | 4.09 ± 0.99 | 0.28 ± 0.15 | 1.36 ± 0.70 |
| Example 29 | 12.95 ± 5.96 | 44.78 ± 19.45 | 4.01 ± 0.63 | 4.29 ± 0.80 | 0.14 ± 0.088 | 0.77 ± 0.39 |
| Eltrombopag | 8.47 ± 0.95 | 29.02 ± 3.82 | 6.11 ± 1.04 | 4.63 ± 1.03 | 0.18 ± 0.02 | 1.53 ± 0.26 |

The results of the current study indicate that the above test compounds of the present disclosure are well absorbed after an intragastric administration to rats.

The invention claimed is:

1. A compound of formula (I), tautomers, and pharmaceutically acceptable salts thereof:

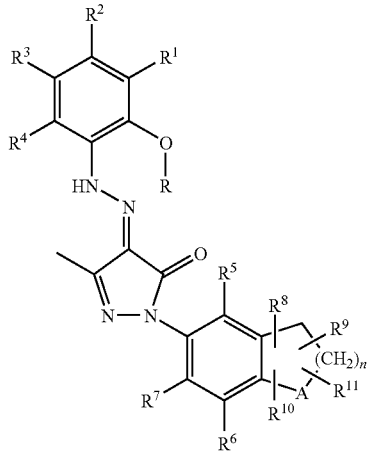

(I)

wherein:
A is carbon;
R is selected from hydrogen and alkyl;
$R^1$, $R^2$, $R^3$, and $R^4$ are each independently selected from the group consisting of: hydrogen, alkyl, alkoxy, halogen, aryl, and heteroaryl, wherein the aryl or heteroaryl is each independently either unsubstituted or substituted with one or more groups independently selected from the group consisting of: alkyl, halogen, hydroxyl, tetrazolyl, imidazolyl, dihydroimidazolyl, carboxylic acid, and carboxylic ester;
$R^5$, $R^6$, and $R^7$ are each independently selected from the group consisting of: hydrogen, alkyl, alkoxy, halogen, hydroxyl, amino, nitro, cyano, carboxylic acid, and carboxylic ester;
$R^8$, $R^9$, $R^{10}$, and $R^{11}$ are each independently selected from the group consisting of: hydrogen and alkyl, wherein $R^8$, $R^9$, $R^{10}$, and $R^{11}$ can substitute any open valence of the ring to which they attach; and
n is 0, 1, or 2.

2. The compound of formula (I), tautomers, and pharmaceutically acceptable salts thereof, wherein:
$R^1$ is selected from aryl and heteroaryl, each independently unsubstituted or substituted with one or more groups independently selected from the group consisting of: alkyl, halogen, hydroxyl, tetrazolyl, imidazolyl, dihydroimidazolyl, carboxylic acid, and carboxylic ester; and
$R^2$, $R^3$, and $R^4$ are each independently selected from the group consisting of: hydrogen, alkyl, alkoxy, and halogen.

3. The compound of formula (I), tautomers, and pharmaceutically acceptable salts thereof, selected from the group consisting of:

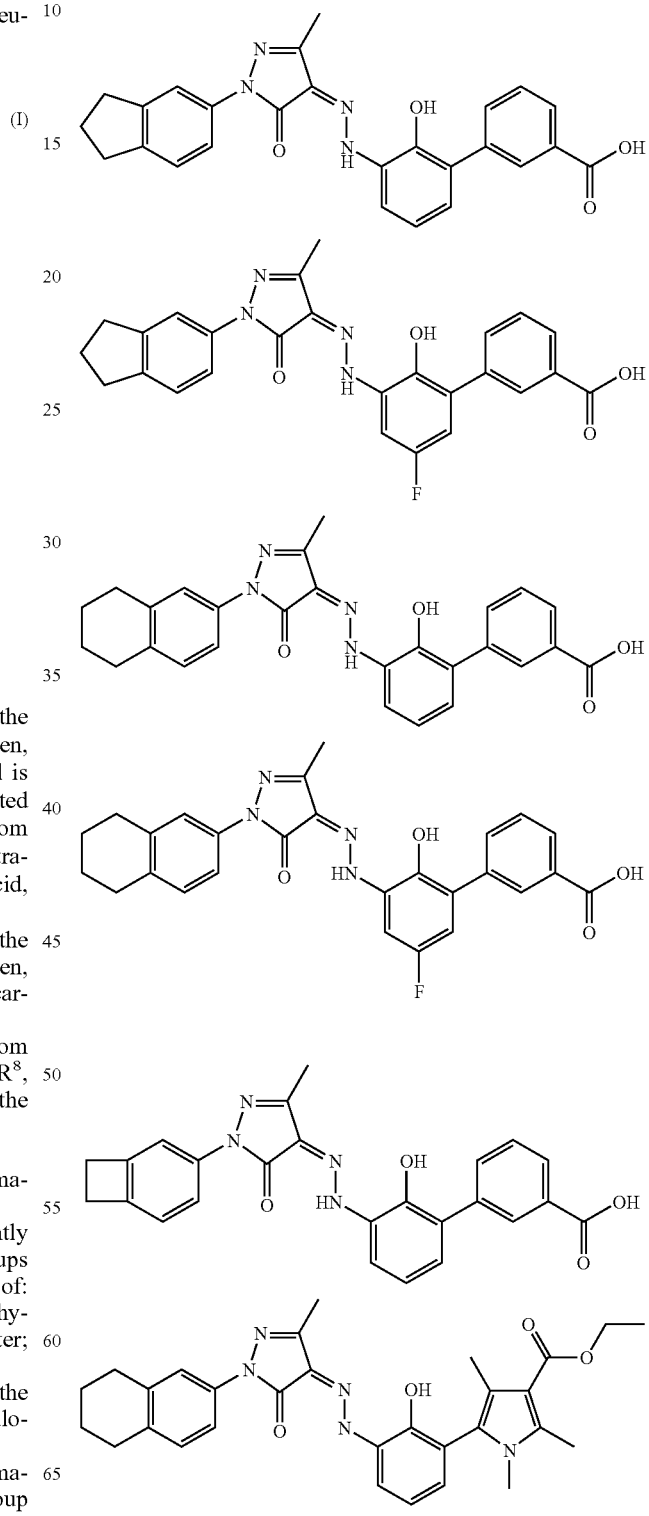

157
-continued
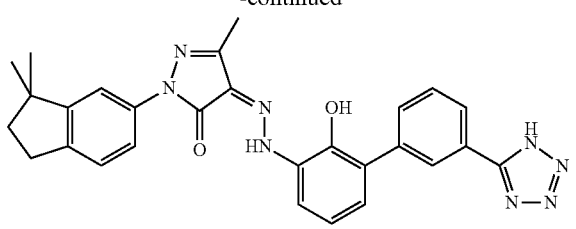
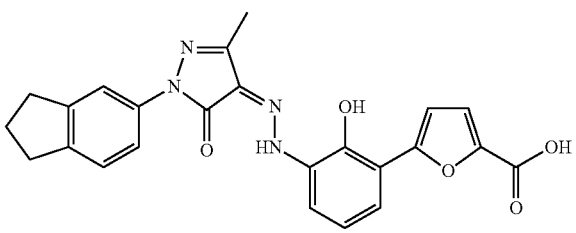
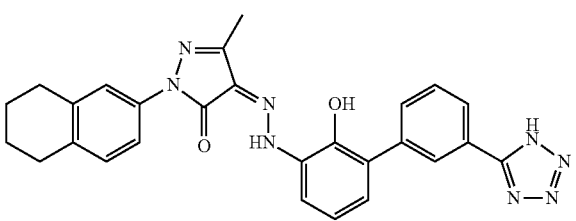
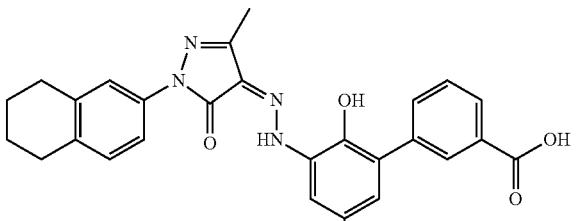
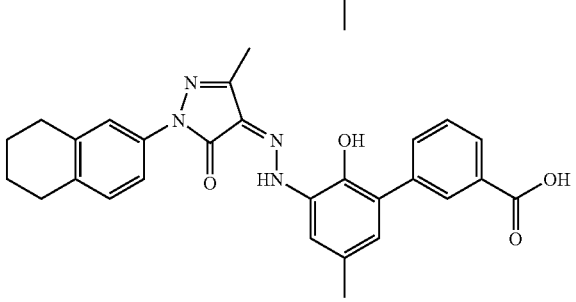
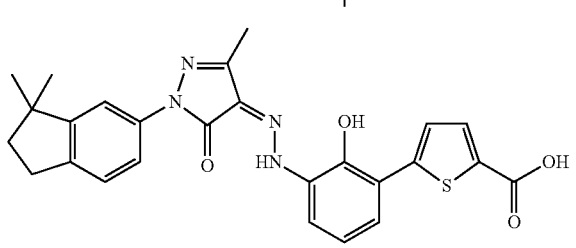
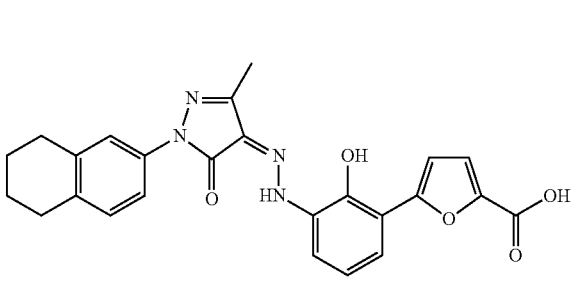
158
-continued
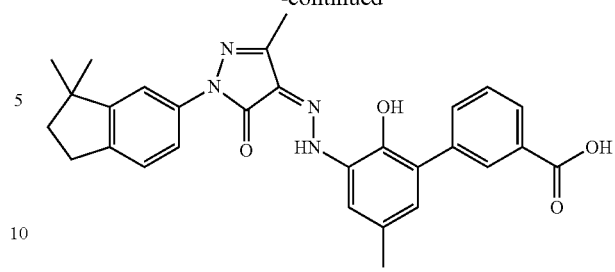
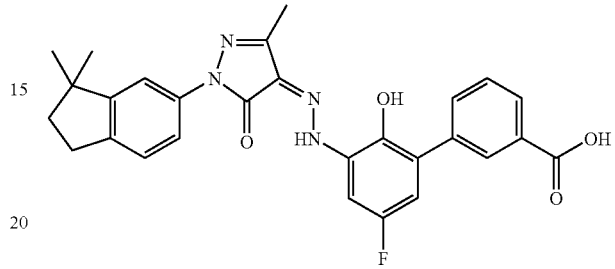
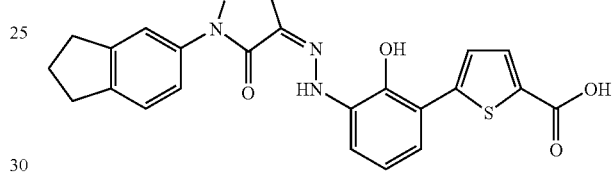
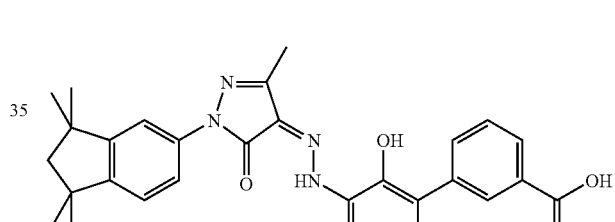
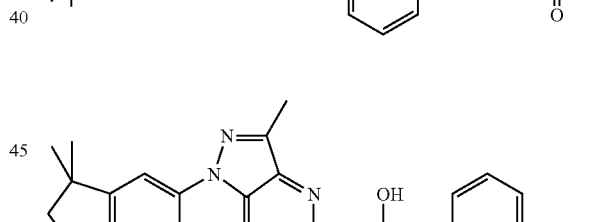
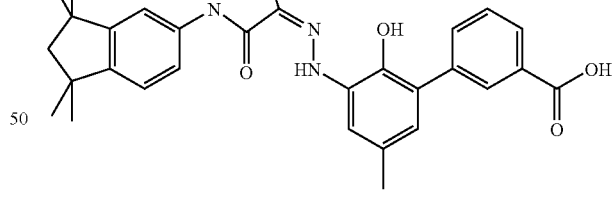
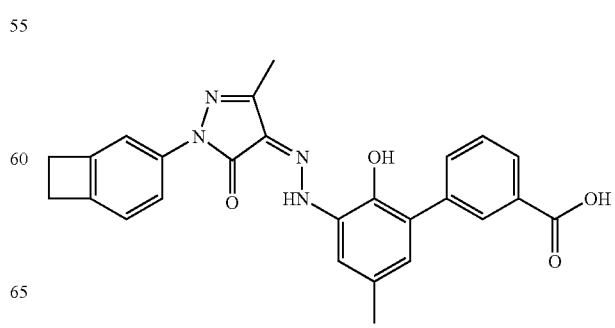

-continued
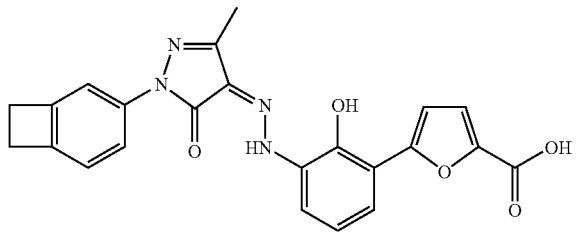
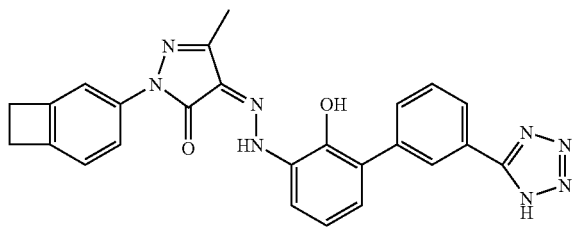
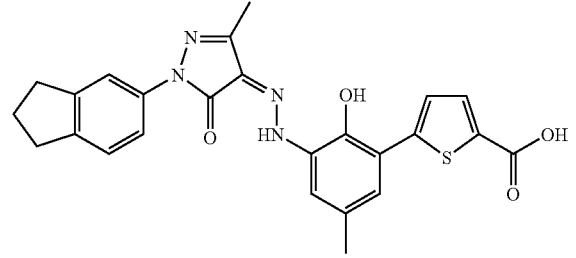
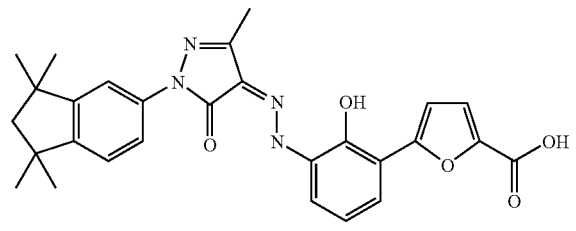
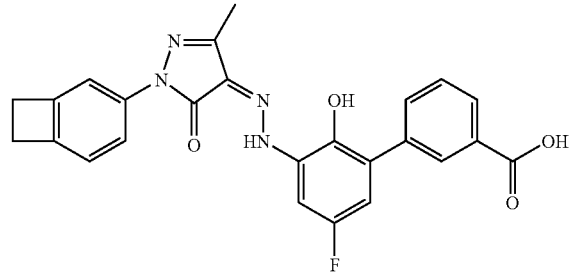
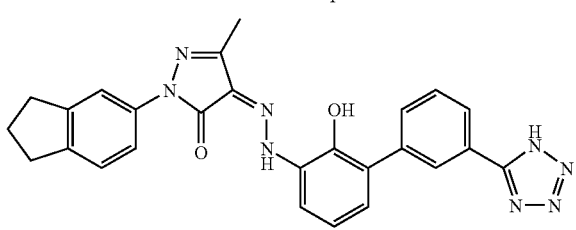
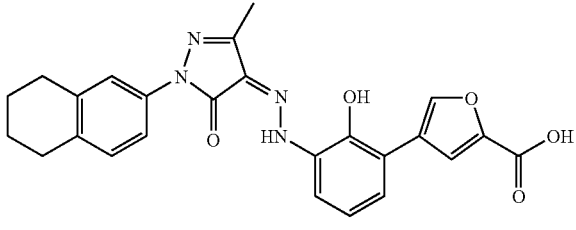
-continued
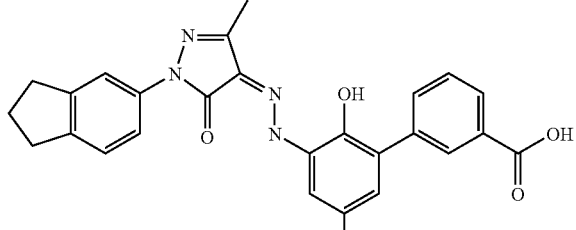
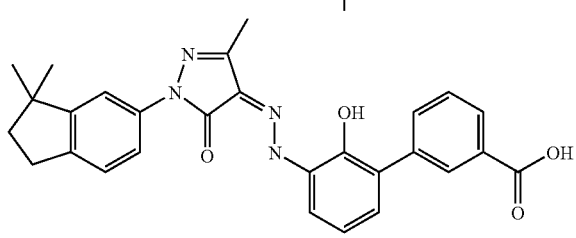
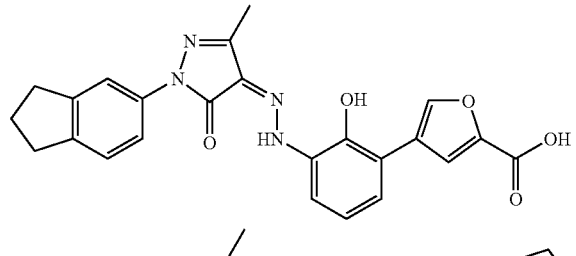
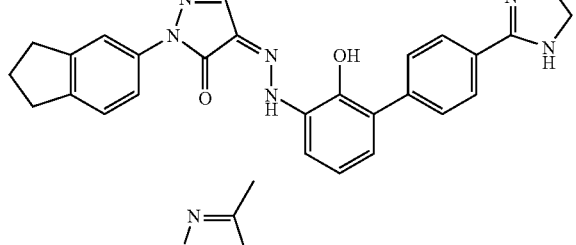
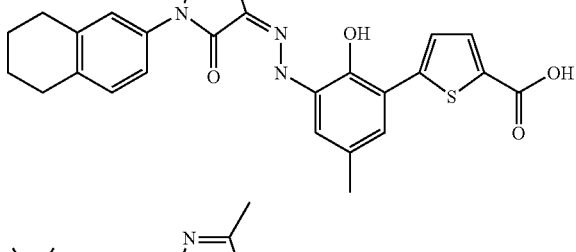
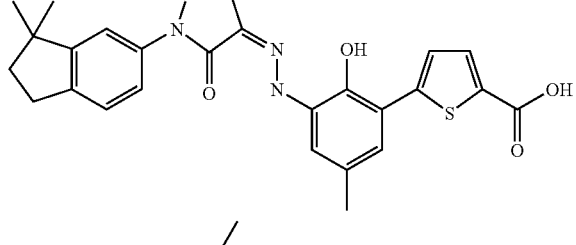
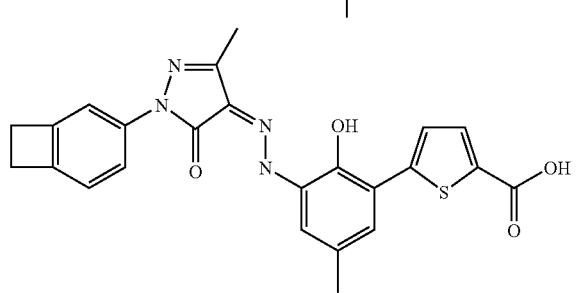

161
-continued
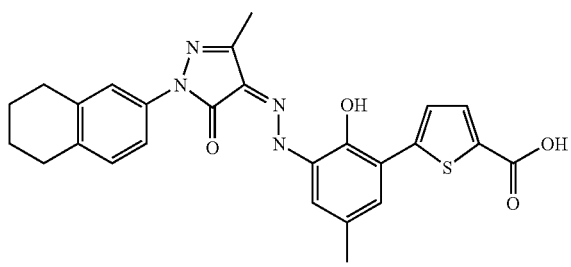
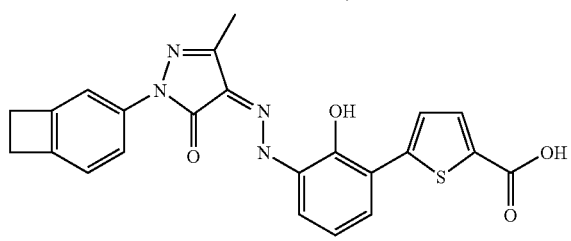
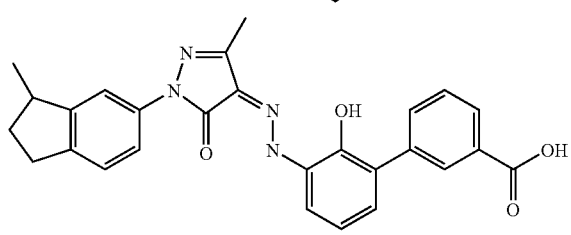
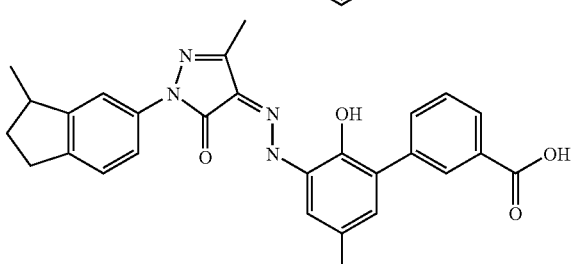
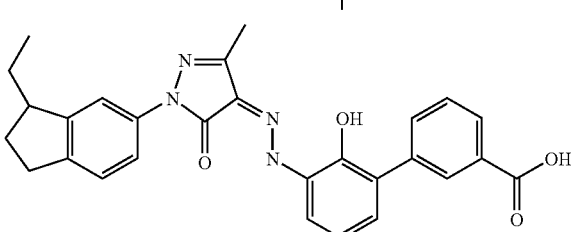
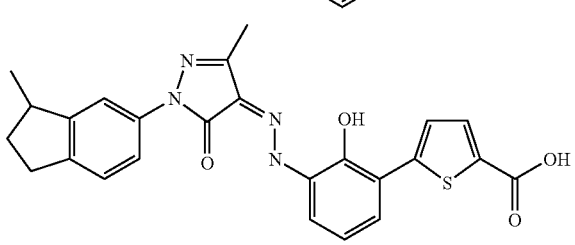
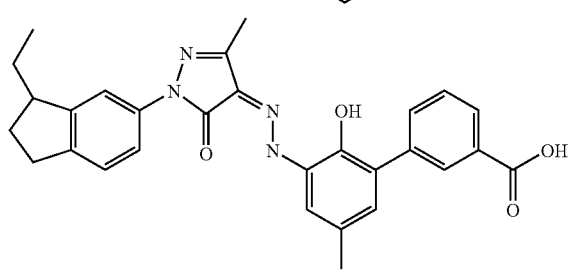
162
-continued
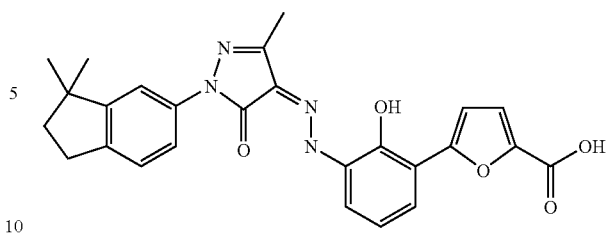
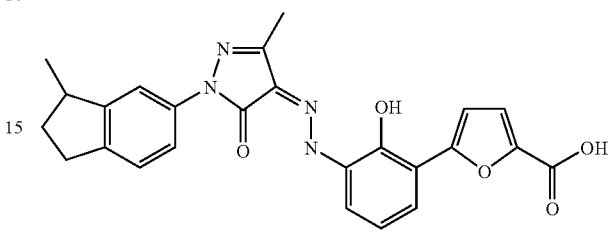
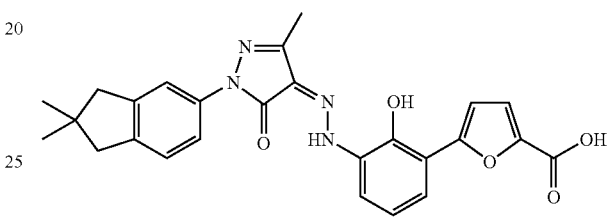
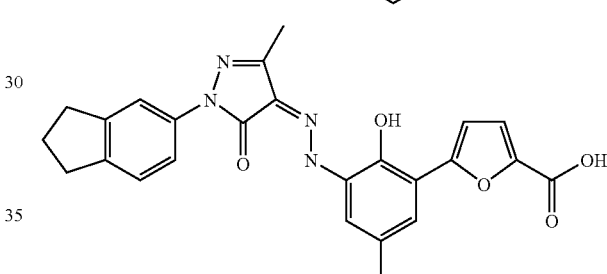
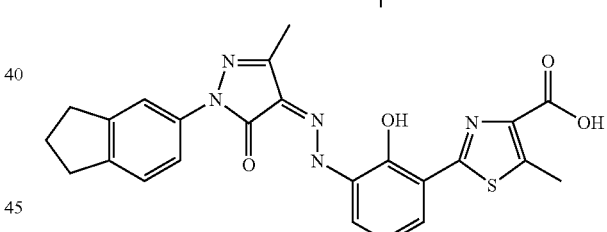
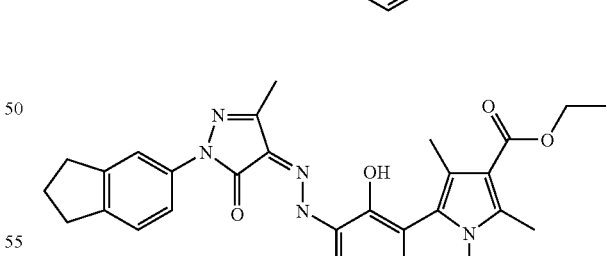
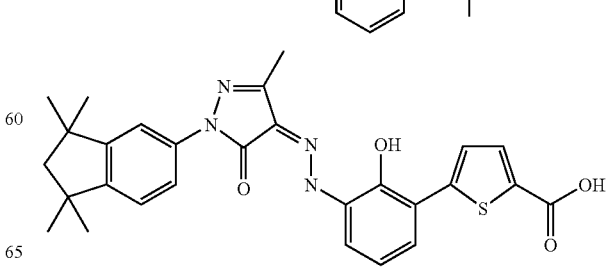

-continued
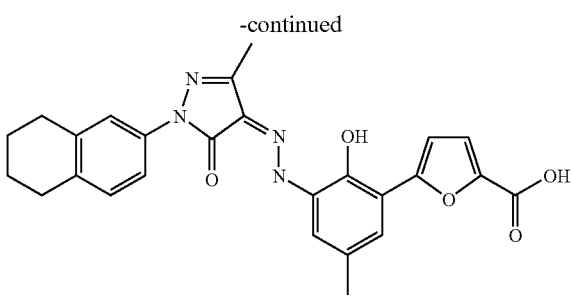
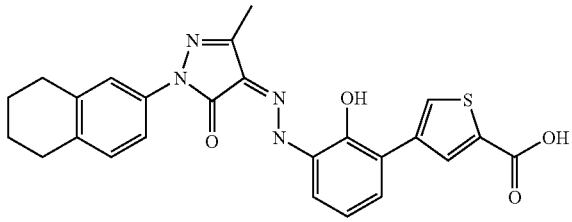
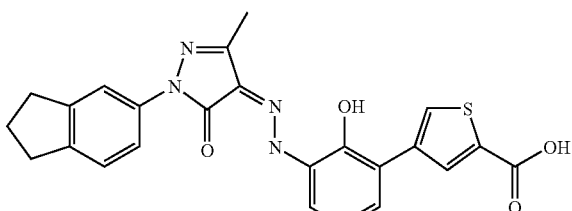
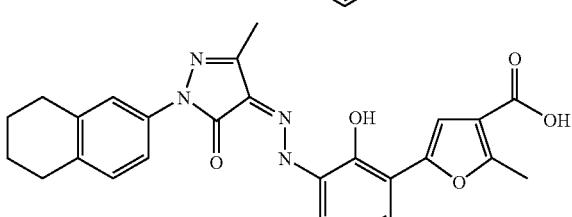
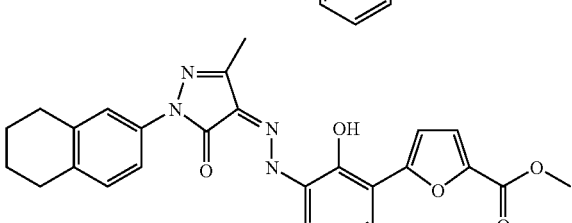
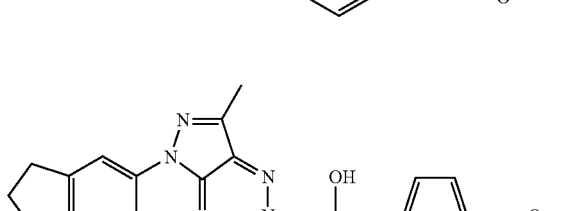
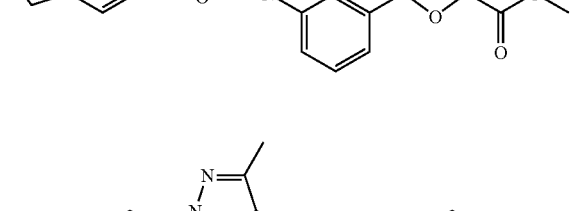
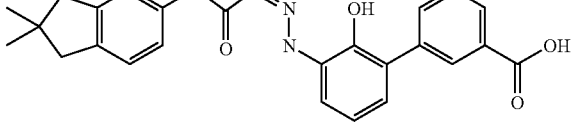
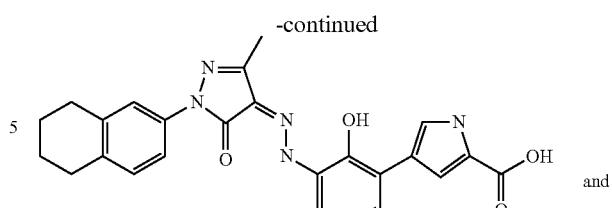
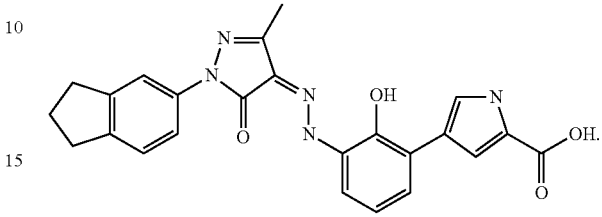
4. A process for preparing the compound according to claim 1 comprising:
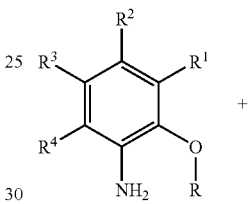
(IA_c)
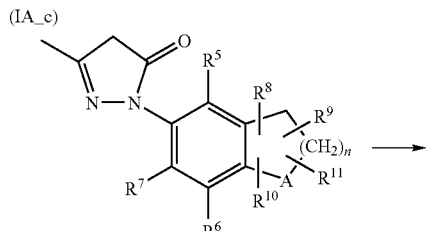
(IA)
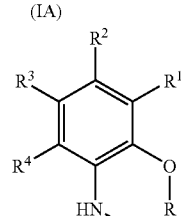
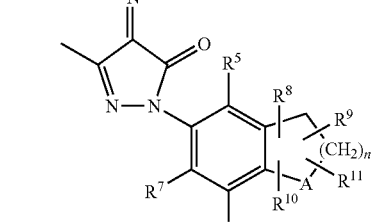
(I)
converting a substituted aniline compound of formula (IA_c) to the corresponding diazo-substituted compound; and
reacting the diazo substituted compound with the compound of formula (IA) to obtain the compound of formula (I).

5. A thrombopoietin (TPO) receptor agonist comprising a compound of claim 1, tautomers, and pharmaceutically acceptable salts thereof.

6. A medicament comprising a compound of claim 1, tautomers, and pharmaceutically acceptable salts thereof.

7. The medicament according to claim 6, co-administered with a drug selected from the group consisting of: a colony stimulating factor, a cytokine, a chemokine, an interleukin or cytokine receptor agonist or antagonist, a soluble receptor, a receptor agonist or antagonist antibody, and combinations thereof.

8. A pharmaceutical composition, comprising a therapeutically effective amount of the compound of claim 1, tautomers, and pharmaceutically acceptable salts thereof, and a pharmaceutically acceptable carrier.

9. The pharmaceutical composition according to claim 8, wherein the composition further comprising a drug selected from the group consisting of: a colony stimulating factor, a cytokine, a chemokine, an interleukin or cytokine receptor agonist and combinations thereof.

10. A method of treating thrombocytopenia comprising administering the pharmaceutical composition according to claim 8 to a patient.

11. The compound of claim 1, tautomers, and pharmaceutically acceptable salts thereof, wherein $R^1$ is a $-COOR^{12}$ substituted aryl or a $-COOR^{12}$ substituted heteroaryl, wherein $R^{12}$ is hydrogen or alkyl.

12. The compound of claim 11, tautomers, and pharmaceutically acceptable salts thereof, wherein $R^1$ is selected from the group consisting of:

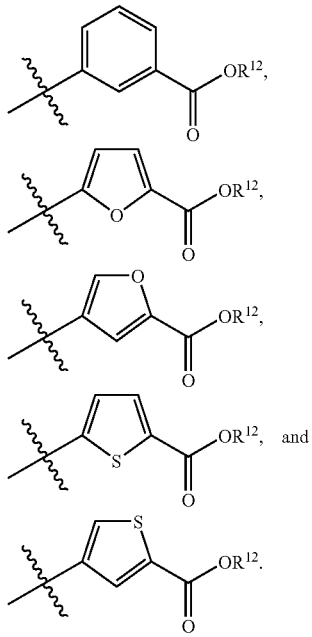

13. The compound of claim 1, tautomers, and pharmaceutically acceptable salts thereof, wherein $R^2$, $R^3$ and $R^4$ are each independently selected from the group consisting of: hydrogen, alkyl, alkoxy, and halogen.

14. The compound of claim 1, tautomers, and pharmaceutically acceptable salts thereof, wherein $R^2$ and $R^4$ are hydrogen.

15. The compound of claim 1, tautomers, and pharmaceutically acceptable salts thereof, wherein $R^3$ is hydrogen or alkyl.

16. The compound of claim 1, tautomers, and pharmaceutically acceptable salts thereof, wherein R is hydrogen.

17. The compound of claim 1, tautomers, and pharmaceutically acceptable salts thereof, wherein $R^5$, $R^6$, and $R^7$ are hydrogen.

18. The compound of claim 1, tautomers, and pharmaceutically acceptable salts thereof, wherein $R^8$, $R^9$, $R^{10}$, and $R^{11}$ are each independently selected from the group consisting of: hydrogen, methyl, and ethyl.

19. The compound of claim 1, tautomers, and pharmaceutically acceptable salts thereof, which is of the formula (II):

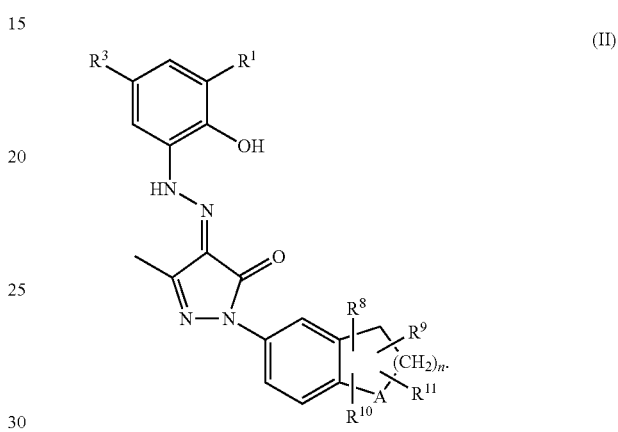

20. The compound of claim 1, tautomers, and pharmaceutically acceptable salts thereof, selected from the group consisting of:

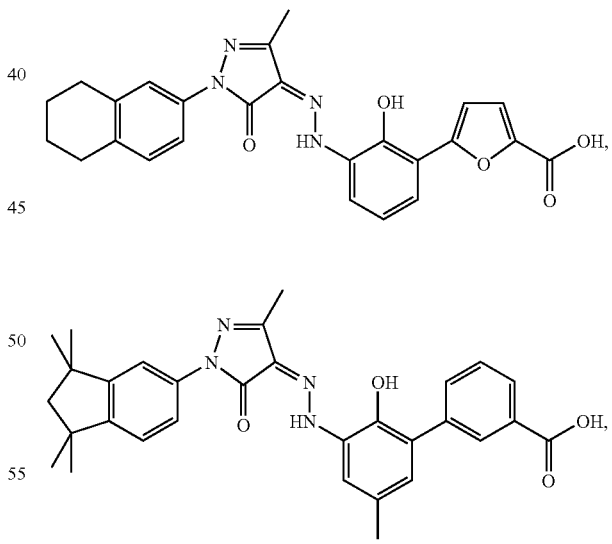

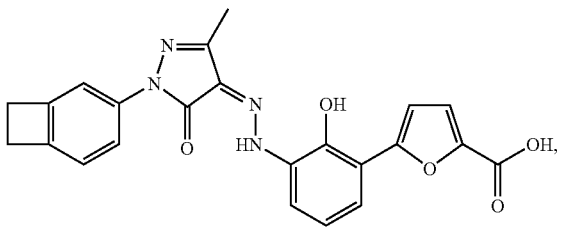

-continued

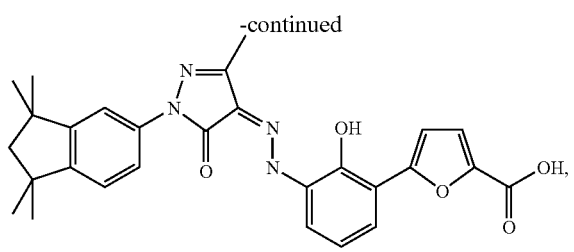
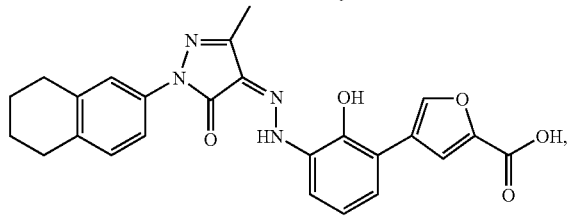
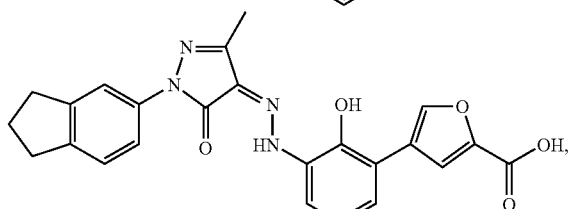
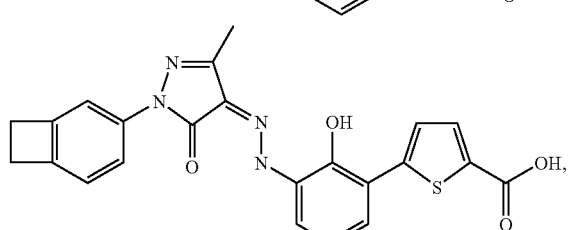
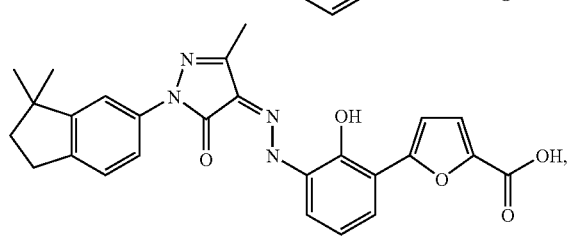
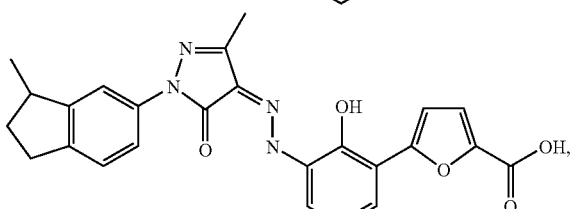
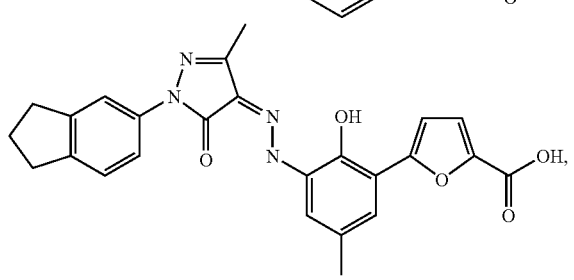

-continued

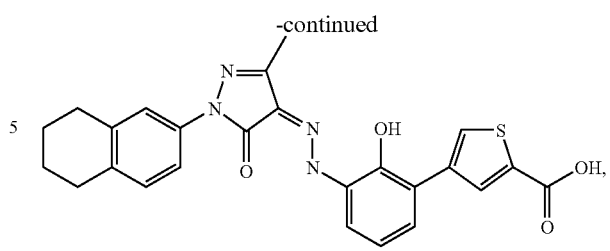
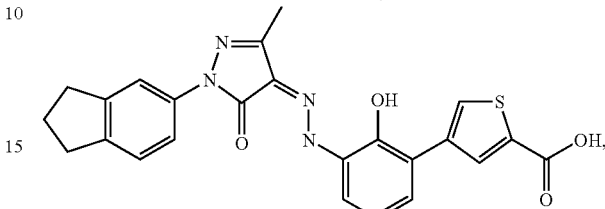
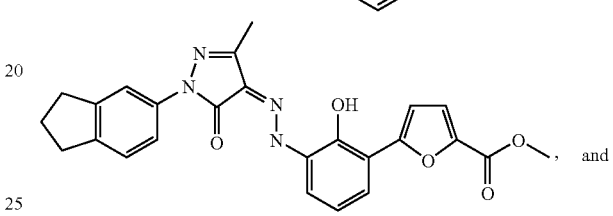, and
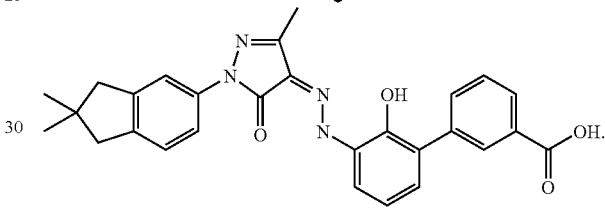

21. The method according to claim 10, further comprising co-administering a drug selected from the group consisting of: a colony stimulating factor, a cytokine, a chemokine, an interleukin or cytokine receptor agonist, and combinations thereof.

22. A method of treating thrombocytopenia comprising administering a therapeutically effective amount of the compound of claim 1, tautomers, and pharmaceutically acceptable salts thereof, to a patient.

23. The method according to claim 22, further comprising co-administering a drug selected from the group consisting of: a colony stimulating factor, a cytokine, a chemokine, an interleukin or cytokine receptor agonist, and combinations thereof.

24. A method of enhancing platelet production, comprising administering a therapeutically effective amount of the compound of claim 1, tautomers, and pharmaceutically acceptable salts thereof, to a patient.

25. A method of agonizing the TPO receptor, comprising administering a therapeutically effective amount of the compound of claim 1, tautomers, and pharmaceutically acceptable salts thereof, to a patient.

* * * * *

```
                        SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: g491a

<400> SEQUENCE: 1
gggaacttca gatcagctgg gaggagccg                                29

<210> SEQ ID NO 2
<211> LENGTH: 29
<212> TYPE: DNA
<213> ORGANISM: Artificial Sequence
<220> FEATURE:
<223> OTHER INFORMATION: g491a antisense

<400> SEQUENCE: 2
cggctcctcc cagctgatct gaagttccc                                29

<210> SEQ ID NO 3
<211> LENGTH: 31
<212> TYPE: DNA
<213> ORGANISM: Artificial Sequence
<220> FEATURE:
<223> OTHER INFORMATION: c965t

<400> SEQUENCE: 3
caggaccatg ctagctccca aggcttcttc t                             31

<210> SEQ ID NO 4
<211> LENGTH: 31
<212> TYPE: DNA
<213> ORGANISM: Artificial Sequence
<220> FEATURE:
```

<223> OTHER INFORMATION: c965t antisense

<400> SEQUENCE: 4
agaagaagcc ttgggagcta gcatggtcct g          31